(12) United States Patent
Narain et al.

(10) Patent No.: US 9,205,064 B2
(45) Date of Patent: Dec. 8, 2015

(54) METHODS FOR THE DIAGNOSIS OF ONCOLOGICAL DISORDERS USING EPIMETABOLIC SHIFTERS, MULTIDIMENSIONAL INTRACELLULAR MOLECULES, OR ENVIRONMENTAL INFLUENCERS

(75) Inventors: Niven Rajin Narain, Cambridge, MA (US); John Patrick McCook, Frisco, TX (US); Rangaprasad Sarangarajan, Rutland, MA (US)

(73) Assignee: Berg LLC, Nashville, TN (US)

( * ) Notice: Subject to any disclaimer, the term of this patent is extended or adjusted under 35 U.S.C. 154(b) by 0 days.

(21) Appl. No.: 12/778,029

(22) Filed: May 11, 2010

(65) Prior Publication Data

US 2011/0123987 A1 May 26, 2011

Related U.S. Application Data

(60) Provisional application No. 61/177,241, filed on May 11, 2009, provisional application No. 61/177,243, filed on May 11, 2009, provisional application No. 61/177,244, filed on May 11, 2009, provisional application No. 61/177,245, filed on May 11, 2009, provisional application No. 61/177,246, filed on May 11, 2009.

(51) Int. Cl.
*G01N 33/53* (2006.01)
*A61K 31/122* (2006.01)
*A61K 31/00* (2006.01)

(52) U.S. Cl.
CPC ............... *A61K 31/122* (2013.01); *A61K 31/00* (2013.01)

(58) Field of Classification Search
None
See application file for complete search history.

(56) References Cited

U.S. PATENT DOCUMENTS

| | | |
|---|---|---|
| 2006/0035981 A1 | 2/2006 | Mazzio et al. |
| 2008/0038736 A1 | 2/2008 | Llovet et al. |
| 2008/0299100 A1 | 12/2008 | Hsia et al. |
| 2011/0136231 A1 | 6/2011 | Narain et al. |
| 2012/0309086 A1 | 12/2012 | Narain et al. |

FOREIGN PATENT DOCUMENTS

| | | |
|---|---|---|
| EP | 2028492 A1 | 2/2009 |
| RU | 2007131900 | 1/2009 |
| WO | 2007095186 A2 | 8/2007 |

OTHER PUBLICATIONS

Scambia et al (Br J Cancer, 1991, 64(5): 965-967).*
Lockwood et al (Mol Aspects Med, 1994, 15 Suppl: Abstract).*
Tockman et al (Cancer Res., 1992, 52:2711s-2718s).*
Riethdorf et al (J Histochem Cytochem, 1997, 45(7): 957-963).*
Merlo et al (J Clin Oncol, 2009, 27(11): 1746-1752).*
Mohammed et al (Br J Cancer, 2007, 96(7): 1092-1100).*
Olopade et al (Cancer J Sci Am, 1997, 3(4): Abstract).*
Yagasaki et al (Int J Oncol, 1996, 9(4): 755-761).*
Lockwood et al (Mol Aspects Med, 1994, 15 Suppl:s231-240).*
Cheung et al (Clin Cancer Res, 2007, 13(23): 6978-6983).*
Johnson et al (Ann Surg, 2007, 145(4): 611-621).*
Aris et al (BMC Bioinformics, 2004, 5(185): 1-9).*
Chang et al (Journal of Clinical Oncology, 2005, 23(6): 1169-1177).*
Lockwood et al (Biochem Biophys Res Comm, 1994, 199(3): Abstract).*
O'Driscoll et al (Cancer Genomics Proteomics, 2008, 5(2): Abstract).*
Prayst et al (Crit Rev Food Sci Nutr, 2010, 50(4): Abstract).*
Garrel, R. et aL, "The diagnostic accuracy of reverse transcripton—PCR quantification of cytokeratin mRNA in the detection of sentinel lymph node invasion in oral and oropharyngeal squamous cell carcinoma: a comparison with immunohistochemistry", *Clin Cancer Res 2006*;12: 2498-2505.
Langer, R. et al., "Protein expression profiling in esophageal adenocarcinoma patients indicates association of heat-shock protein 27 expression and chemotherapy response," *Clin Cancer Res 2008*; 14: 8279-8287.
Okumura, Y. et al., "Identification of biomarkers in ductal carcinoma in situ of the breast with microinvasion", *BMC Cancer 2008*, 8: 287.
Todaro, M. et al., "Apoptosis resistance in epithelial tumors is mediated by tumor-cell-derived interleukin-4," *Cell Death & Differentiation, 2008*, 15: 762-772.
Rydberg, C. et al., "Toll-like receptor agonists induce inflammation and cell death in a model of head and neck squamous cell carcinomas," *Immunology*, 2009, 128: e600-e611.
Li, Y. et al., "Candidate genes responsible for human hepatocellular carcinoma identified from differentially expressed genes in hepatocarcinogenesis of the tree shrew (*Tupaia belangeri chinesis*)", *Hepatology Research* 2008; 38:85-95.
Antoneeva, et al: "Markers of Apoptosis and Proliferation of Tumor Cells in the Dynamic of Ovarian Cancer Progression", Oncologiya, vol. 10, No. 2 (2008), pp. 234-237.
Fernandez-Ayala D J et al: "Coenzyme Q protects cells against serum withdrawal-induced apoptosis by inhibition of ceramide release and caspase-3 activation.", Antioxidants & Redox Signaling Summer 2000, vol. 2, No. 2, Jul. 2000, pp. 263-275.
Gogvadze et al: "Mitochondria as targets for chemotherapy", Apoptosis ; An International Journal on Programmed Cell Death, Kluwer Academic Publishers, Bo, vol. 14, No. 4, Feb. 10, 2009, pp. 624-640.
Lockwood et al., "Partial and Complete Regression of Breast Cancer in Patients in Relation to Dosage of Coenzyme Q10" Biochem. and Biophys. Res. Comm. vol. 199(3): 1504-1508, 1994.
Perumal, et al., "Combined efficacy of tamoxifen and coenzyme Q10 on the status of lipid peroxidation and antioxidants in DMBA induced breast cancer " Mol Cell Biochem. 2005; 273(1-2):151-60.

\* cited by examiner

*Primary Examiner* — Sean Aeder
(74) *Attorney, Agent, or Firm* — McCarter & English, LLP; Elizabeth A. Hanley, Esq.; Jill Mello

(57) ABSTRACT

Methods and formulations for diagnosing oncological disorders in humans using epimetabolic shifters, multidimensional intracellular molecules or environmental influencers are described.

14 Claims, 25 Drawing Sheets

METHODS FOR THE DIAGNOSIS OF ONCOLOGICAL DISORDERS USING EPIMETABOLIC SHIFTERS, MULTIDIMENSIONAL INTRACELLULAR MOLECULES, OR ENVIRONMENTAL INFLUENCERS

RELATED APPLICATIONS

This application claims priority to U.S. Provisional Application Ser. No. 61/177,241, filed May 11, 2009, entitled "Methods for Treatment of Oncological Disorders Using an Epimetabolic Shifter (Coenzyme Q10)", U.S. Provisional Application Ser. No. 61/177,243, filed May 11, 2009, entitled "Methods for Treatment of Oncological Disorders Using Epimetabolic Shifters, Multidimensional Intracellular Molecules or Environmental Influencers", U.S. Provisional Application Ser. No. 61/177,244, filed May 11, 2009, entitled "Methods for the Diagnosis of Oncological Disorders Using Epimetabolic Shifters, Multidimensional Intracellular Molecules or Environmental Influencers", U.S. Provisional Application Ser. No. 61/177,245, filed May 11, 2009, entitled "Methods for Treatment of Metabolic Disorders Using Epimetabolic Shifters, Multidimensional Intracellular Molecules or Environmental Influencers", and U.S. Provisional Application Ser. No. 61/177,246, filed May 11, 2009, entitled "Methods for the Diagnosis of Metabolic Disorders Using Epimetabolic Shifters, Multidimensional Intracellular Molecules or Environmental Influencers". The entire contents of each of the foregoing applications are hereby incorporated herein by reference.

BACKGROUND OF THE INVENTION

Cancer is presently one of the leading causes of death in developed nations and is a serious threat to modern society. Cancer can develop in any tissue of any organ at any age. Worldwide, more than 10 million people are diagnosed with cancer every year and it is estimated that this number will grow to 15 million new cases every year by 2020. It is believed that cancer causes six million deaths every year or 12% of the deaths worldwide.

The etiology of cancer is not clearly understood. Cancer has been linked to or associated with many factors over the many years of ongoing research including genetic susceptibility, chromosome breakage disorders, viruses, environmental factors and immunologic disorders. Cancer encompasses a large category of medical conditions. Cancer cells can arise in almost any organ and/or tissue of the body. Cancer develops when cells in a part of the body begin to grow or differentiate out of control.

Although recent research has vastly increased our understanding of many of the molecular mechanisms of tumorigenesis and has provided numerous new avenues for the treatment of cancer, standard treatments for most malignancies remain gross resection, chemotherapy, and radiotherapy. While increasingly successful, each of these treatments may cause numerous undesired side effects. For example, surgery may result in pain, traumatic injury to healthy tissue, and scarring. Radiation therapy has the advantage of killing cancer cells but it also damages non-cancerous tissue at the same time. Chemotherapy involves the administration of various anti-cancer drugs to a patient. These standard treatments often are accompanied by adverse side effects, e.g., nausea, immune suppression, gastric ulceration and secondary tumorigenesis.

Over the years, many individuals and companies have conducted extensive research searching for improvements in the treatments for the wide array of cancers. Companies are developing bioactive agents including chemical entities, e.g., small molecules, and biologics, e.g., antibodies, with the desire of providing more beneficial therapies for cancer. Some of the bioactive agents tested have worked and provided beneficial therapeutic effects in some individuals or cancer types and others have failed or had minimal therapeutic effects in their testing protocols. Other bioactive agents studied to date have mechanisms of action that are not entirely understood.

Coenzyme Q10, also referred to herein as CoQ10, Q10, ubiquinone, or ubidecarenone, is a popular nutritional supplement and can be found in capsule form in nutritional stores, health food stores, pharmacies, and the like, as a vitamin-like supplement to help protect the immune system through the antioxidant properties of ubiquinol, the reduced form of CoQ10. CoQ10 is art-recognized and further described in International Publication No. WO 2005/069916, the entire disclosure of which is incorporated by reference herein.

CoQ10 is found throughout most tissues of the human body and the tissues of other mammals. The tissue distribution and redox state of CoQ10 in humans has been reviewed in a review article by Bhagavan H N, et al., *Coenzyme Q10: Absorption, tissue uptake, metabolism and pharmacokinetic*, Free Radical Research 40(5), 445-453 (2006) (hereinafter, Bhagavan, et al.). The authors report that "as a general rule, tissues with high-energy requirements or metabolic activity such as the heart, kidney, liver and muscle contain relatively high concentrations of CoQ10." The authors further report that "[a] major portion of CoQ10 in tissues is in the reduced form as the hydroquinone or uniquinol, with the exception of brain and lungs," which "appears to be a reflection of increased oxidative stress in these two tissues." In particular, Bhagavan et al. reports that in heart, kidney, liver, muscle, intenstine and blood (plasma), about 61%, 75%, 95%, 65%, 95% and 96%, respectively, of CoQ10 is in the reduced form. Similarly, Ruiz-Jiminez, et al., *Determination of the ubiquinol-10 and ubiquinone-10 (coenzyme Q10) in human serum by liquid chromatography tandem mass spectrometry to evaluate the oxidative stress*, J. Chroma A 1175(2), 242-248 (2007) (hereinafter Ruiz-Jiminez, et al.) reports that when human plasma was evaluated for Q10 and the reduced form of Q10 (Q10H2), the majority (90%) of the molecule was found in the reduced form.

CoQ10 is very lipophilic and, for the most part, insoluble in water. Due to its insolubility in water, limited solubility in lipids, and relatively large molecular weight, the efficiency of absorption of orally administered CoQ10 is poor. Bhagavan, et al. reports that "in one study with rats it was reported that only about 2-3% of orally-administered CoQ10 was absorbed." Bhagavan, et al. further reports that "[d]ata from rat studies indicate that CoQ10 is reduced to ubiquinol either during or following absorption in the intestine."

CoQ10 has been associated with cancer in the literature for many years. Described below are some representative but not all inclusive examples of the reported associations in the literature. Karl Folkers, et al., *Survival of Cancer Patients on Therapy with Coenzyme Q10*, Biochemical and Biophysical Research Communication 192, 241-245 (1993) (herein after "Folkers, et al.") describes eight case histories of cancer patients "on therapy with CoQ10" and their stories of survival . . . "for periods of 5-15 years." CoQ10 was orally administered to eight patients having different types of cancer, including pancreatic carcinoma, adenocarcinoma, laryngeal carcinoma, breast, colon, lung and prostate cancer. Folkers, et al. sets forth that "these results now justify systemic protocols." Lockwood, et al., *Progress on Therapy of Breast Cancer with Vitamin Q10 and the Regression of Metastases*, Biochemical and Biophysical Research Communication 212, 172-177 (1995) (hereinafter "Lockwood, et al.") is another review article that reports on the "[p]rogress on therapy of breast cancer with Vitamin Q10". Lockwood, et al. refers to Folkers, et al., which "covers 35 years of international research on animals and humans which revealed variable levels of vitamin Q10 in non-tumor and tumor tissues and includes data on vitamin Q10 which are intrinsic to the host defense system as based on increased survivors of treated mice with tumors". Lockwood, et al. further sets forth that "Mlle potential of vitamin Q10 therapy of human cancer became evident in 1961" relying on a study that determined the blood levels of CoQ10 in 199 Swedish and American cancer patients that revealed variable levels of deficiencies in cases of breast cancer. U.S. Pat. No. 6,417,233, issued Jul. 9, 2002 (hereinafter Sears, et al.) describes compositions containing lipid-soluble benzoquinones, e.g., coenzyme Q10, for the prevention and/or treatment of mitochondriopathies. Sears, et al. sets forth that "CoQ10 treatment has been reported to provide some benefits in cancer patients (see column 2, lines 30-31)."

As of the date of filing of this application, the National Cancer Institute reports that no well-designed clinical trials involving large numbers of patients of CoQ10 in cancer treatment have been conducted since "the way the studies were done and the amount of information reported made it unclear if the benefits were caused by the coenzyme Q10 or by something else." See The National Cancer Institute (NCI), available at www.cancer.gov/cancertopics/pdq/cam/coenzymeQ10/patient/allpages (Sep. 29, 2008). In particular, the NCI cites three small studies on the use of CoQ10 as an adjuvant therapy after standard treatment in breast cancer patients, in which some patients appeared to be helped by the treatment, and reiterates that "weaknesses in study design and reporting, however, made it unclear if benefits were caused by the coenzyme Q10 or by something else." The NCI specifies that "these studies had the following weaknesses: the studies were not randomized or controlled; the patients used other supplements in addition to coenzyme Q10; the patients received standard treatments before or during the coenzyme Q10 therapy; and details were not reported for all patients in the studies." The NCI further reports on "anecdotal reports that coenzyme Q10 has helped some cancer patients live longer, including patients with cancers of the pancreas, lung, colon, rectum and prostate," but states that 'the patients described in these reports, however, also received treatments other than coenzyme Q10 including chemotherapy, radiation therapy and surgery."

US Patent Application Publication 2006/0035981, published Feb. 16, 2006 (hereinafter "Mazzio 2006") describes methods and formulations for treating or preventing human and animal cancers using compositions that exploit the vulnerability of cancers with regards to its anaerobic requirement for non-oxidative phosphorylation of glucose to derive energy, which is opposite to the host. The formulations of Mazzio 2006 contain one or more compounds that synergistically promote oxidative metabolism and/or impede lactic acid dehydrogenase or anaerobic glucose metabolism and more particularly are described as containing "2,3-dimethoxy-5-methyl-1,4-benzoquinone (herein also termed "DMBQ") (quinoid base) and options for the entire ubiquinone series including corresponding hydroquinones, ubichromenols, ubichromanols or synthesized/natural derivatives and analogues. See Mazzio 2006 at page 3, paragraph 0010. Mazzio 2006 establishes "the short chain ubiquinones (CoQ<3) as anti-cancer agents and even further establishes that "2,3-dimethoxy-5-methyl-1,4-benzoquinone (DMBQ) is in excess of 1000 times more potent than CoQ10 as an anti-cancer agent." See Mazzio 2006 at page 3, paragraph 0011. Mazzio 2006 further set forth that the study "did not find CoQ10 to be as lethal as expected" and like "previous studies that have employed CoQ10 against cancer have been somewhat contradictory". See Mazzio 2006 at pages 3-4 for an extensive list of citations supporting this statement.

US Patent Application Publication 2007/0248693, published Oct. 25, 2007 (herein after "Mazzio 2007") also describes nutraceutical compositions and their use for treating or preventing cancer. Again, this published patent application focuses on the short chain ubiquinones and specifically sets forth that CoQ10 is not a critical component of this invention. According to Mazzio 2007 "while CoQ10 can increase the Vmax of mitochondrial complex II activity in cancer cells (Mazzio and Soliman, Biochem Pharmacol. 67:1167-84, 2004), this did not control the rate of mitochondrial respiration or O2 utilization through complex IV. And, CoQ10 was not as lethal as expected. Likewise, results of CoQ10 against cancer have been contradictory." See Mazzio 2007 at page 5, paragraph 0019.

SUMMARY OF THE INVENTION

Applicants have previously described topical formulations of CoQ10 and methods for reducing the rate of tumor growth in animal subjects (Hsia et al., WO 2005/069916 published Aug. 4, 2005). In the experiments described in Hsia et al., CoQ10 was shown to increase the rate of apoptosis in a culture of skin cancer cells but not normal cells. Moreover, treatment of tumor-bearing animals with a topical formulation of CoQ10 was shown to dramatically reduce the rate of tumor growth in the animals.

The present invention is based, at least in part, upon a more complete understanding of the role of CoQ10 within a human and/or cell. In particular, the methods and formulations of the present invention are based, at least in part, upon the knowledge gained about the therapeutic activity of CoQ10 for oncological disorders learned by designing and implementing human clinical trials and/or by administering CoQ10 to human subjects and observing the surprising and unexpected results that occur during these trials and/or treatment regimens. The methods and formulations of the present invention are further based, at least in part, upon insight gained into the therapeutic mechanism of CoQ10 from extensive studies of CoQ10 treatment of cells in vitro.

Specifically, in at least one embodiment, the methods and formulations of the present invention are based, at least in part, on the surprising discovery that application of Coenzyme Q10 (also referred to as CoQ10 or Q10 herein) to cells results in selective induction of an apoptotic response in cancer cells, with no effect or, in some cases, a positive effect on growth of normal cells. Moreover, in at least one additional embodiment, it was unexpectedly found that cell lines derived from aggressive cancers were more sensitive to CoQ10 (e.g., required lower concentrations and/or treatment time of CoQ10 for cytotoxicity and/or induction of apoptosis) as compared to cell lines derived from less aggressive or non-aggressive cancers. A time and dose response of mitochondrial Q10 levels was observed, wherein after 48 hours, the level of Q10 in cell mitochondria was increased by six fold. In at least one additional embodiment, the invention is further based on the surprising and unexpected discovery that the Q10 is maintained in the supplied oxidized form (pro-oxidant) and not converted to the reduced (anti-oxidant) form of Q10H2 in any significant amounts. In another embodiment, the invention is still further based on the discovery that the expression of a significant number of genes are modulated in cells treated with the oxidized from of Q10. These modulated proteins were found to be clustered into several cellular pathways, including apoptosis, cancer biology and cell growth, glycolysis and metabolism, molecular transport, and cellular signaling.

Taken together, the results described herein have provided insight into the therapeutic mechanism of Q10. For example, while not wishing to be bound by theory, Applicants' discoveries indicate that Q10 and, in particular, the oxidized form of Q10, induces a metabolic shift to the cell microenvironment. Differential metabolism is known to occur in cancer cells (the Warburg effect), whereby most cancer cells predominantly produce energy by glycolysis followed by lactic acid fermentation in the cytosol, rather than by oxidative phosphorylation (oxidation of pyruvate) in the mitochondria. Applicants' discoveries indicate that Q10 is capable of shifting the metabolic state of cancer cells from anaerobic use of glucose to mitochondrial oxidative phosphorylation.

Based on Applicants' data presented herein, CoQ10 has been identified as a Multidimensional Intracellular Molecule (MIM) and as an Epimetabolic Shifter (Epi-Shifter). The present invention provides MIMs, Epi-shifters and methods for diagnosing or prognosing an oncological disorder by using same.

Accordingly, in certain aspects, the present invention is directed to methods of assessing whether a subject is afflicted with an oncological disorder. Such methods include (1) determining the level of expression of a marker present in a biological sample obtained from the subject, wherein the marker is selected from the group consisting of the markers listed in Tables 2-4 & 6-29; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication that the subject is afflicted with an oncological disorder, thereby assessing whether the subject is afflicted with an oncological disorder.

In certain aspects, the present invention is directed to methods of assessing whether a subject is afflicted with an oncological disorder. Such methods include (1) determining the level of expression of a marker present in a biological sample obtained from the subject, wherein the expression of the marker is modulated, in a cancerous cell of the oncological disorder induced to undergo a cellular metabolic energy shift from glycolysis to mitochondrial oxidative phosphorylation towards levels observed in a normal cell of the subject under normal physiological conditions; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication that the subject is afflicted with an oncological disorder, thereby assessing whether the subject is afflicted with an oncological disorder.

In certain aspects, the present invention is directed to methods of prognosing whether a subject is predisposed to developing an oncological disorder. Such methods include (1) determining the level of expression of a marker present in a biological sample obtained from the subject, wherein the marker is selected from the group consisting of the markers listed in Tables 2-4 & 6-29; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication that the subject is predisposed to developing an oncological disorder, thereby prognosing whether the subject is predisposed to developing an oncological disorder.

In certain aspects, the present invention is directed to methods of prognosing whether a subject is predisposed to developing an oncological disorder. Such methods include (1) determining the level of expression of a marker present in a biological sample obtained from the subject, wherein the expression of the marker is modulated, in a cancerous cell of the oncological disorder induced to undergo a cellular metabolic energy shift from glycolysis to mitochondrial oxidative phosphorylation towards levels observed in a normal cell of the subject under normal physiological conditions; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication that the subject is predisposed to developing an oncological disorder, thereby prognosing whether the subject is predisposed to developing an oncological disorder.

In certain aspects, the present invention is directed to methods of prognosing the recurrence of an oncological disorder in a subject. Such methods include (1) determining the level of expression of a marker present in a biological sample obtained from the subject, wherein the marker is selected from the group consisting of the markers listed in Tables 2-4 & 6-29; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication of the recurrence of the oncological disorder, thereby prognosing the recurrence of an oncological disorder in the subject.

In certain aspects, the present invention is directed to methods of prognosing the recurrence of an oncological disorder in a subject. Such methods include (1) determining the level of expression of a marker present in a biological sample obtained from the subject, wherein the expression of the marker is modulated, in a cancerous cell of the oncological disorder induced to undergo a cellular metabolic energy shift from glycolysis to mitochondrial oxidative phosphorylation towards levels observed in a normal cell of the subject under normal physiological conditions; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication of the recurrence of the oncological disorder, thereby prognosing the recurrence of an oncological disorder in the subject.

In certain aspects, the present invention is directed to methods of prognosing the survival of a subject with an oncological disorder. Such methods include (1) determining the level of expression of a marker present in a biological sample obtained from the subject, wherein the marker is selected from the group consisting of the markers listed in Tables 2-4 & 6-29; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication of survival of the subject, thereby prognosing survival of the subject with an oncological disorder.

In certain aspects, the present invention is directed to methods of prognosing the survival of a subject with an oncological disorder. Such methods include (1) determining the level of expression of a marker present in a biological sample obtained from the subject, wherein the expression of the marker is modulated, in a cancerous cell of the oncological disorder induced to undergo a cellular metabolic energy shift from glycolysis to mitochondrial oxidative phosphorylation towards levels observed in a normal cell of the subject under normal physiological conditions; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication of survival of the subject, thereby prognosing survival of the subject with an oncological disorder.

In certain aspects, the present invention is directed to methods of prognosing the aggressiveness on an oncological disorder in a subject. Such methods include (1) determining the level of expression of a marker present in a biological sample obtained from the subject, wherein the marker is selected from the group consisting of the markers listed in Tables 2-4 & 6-29; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample indicates that the oncological disorder is aggressive, thereby prognosing the aggressiveness on an oncological disorder in the subject.

In certain aspects, the present invention is directed to methods of prognosing the aggressiveness on an oncological disorder in a subject. Such methods include (1) determining the level of expression of a marker present in a biological sample obtained from the subject, wherein the expression of the marker is modulated, in a cancerous cell of the oncological disorder induced to undergo a cellular metabolic energy shift from glycolysis to mitochondrial oxidative phosphorylation towards levels observed in a normal cell of the subject under normal physiological conditions; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample indicates that the oncological disorder is aggressive, thereby prognosing the aggressiveness on an oncological disorder in the subject.

In certain aspects, the present invention is directed to methods of monitoring the progression of an oncological disorder in a subject. Such methods include comparing the level of expression of a marker present in a first sample obtained from the subject prior to administering at least a portion of a treatment regimen to the subject and the level of expression of the marker present in a second sample obtained from the subject following administration of at least a portion of the treatment regimen, wherein the marker is selected from the group consisting of the markers listed in Tables 2-4 & 6-29, thereby monitoring the progression of an oncological disorder in the subject.

In certain aspects, the present invention is directed to methods of monitoring the progression of an oncological disorder in a subject. Such methods include comparing the level of expression of a marker present in a first sample obtained from the subject prior to administering at least a portion of a treatment regimen to the subject and the level of expression of the marker present in a second sample obtained from the subject following administration of at least a portion of the treatment regimen, wherein the expression of the marker is modulated, in a cancerous cell of the oncological disorder induced to undergo a cellular metabolic energy shift from glycolysis to mitochondrial oxidative phosphorylation towards levels observed in a normal cell of the subject under normal physiological conditions, thereby monitoring the progression of an oncological disorder in the subject.

In certain aspects, the present invention is directed to methods for assessing the efficacy of a therapy for treating an oncological disorder in a subject. Such methods include comparing the level of expression of a marker present in a first sample obtained from the subject prior to administering at least a portion of the treatment regimen to the subject, wherein the marker is selected from the group consisting of the markers listed in Tables 2-4 & 6-29; and the level of expression of the marker present in a second sample obtained from the subject following administration of at least a portion of the treatment regimen, wherein a modulation in the level of expression of the marker in the second sample as compared to the first sample is an indication that the therapy is efficacious for treating the oncological disorder in the subject.

In certain aspects, the present invention is directed to methods for assessing the efficacy of a therapy for treating an oncological disorder in a subject. Such methods include comparing the level of expression of a marker present in a first sample obtained from the subject prior to administering at least a portion of the treatment regimen to the subject, wherein the expression of the marker is modulated, in a cancerous cell of the oncological disorder induced to undergo a cellular metabolic energy shift from glycolysis to mitochondrial oxidative phosphorylation towards levels observed in a normal cell of the subject under normal physiological conditions; and the level of expression of the marker present in a second sample obtained from the subject following administration of at least a portion of the treatment regimen, wherein a modulation in the level of expression of the marker in the second sample as compared to the first sample is an indication that the therapy is efficacious for treating the oncological disorder in the subject.

In certain aspects, the present invention is directed to methods of assessing the efficacy of an environmental influencer compound for treating an oncological disorder in a subject in need thereof. Such methods include (1) determining the level of expression of one or more markers present in a biological sample obtained from the subject, wherein the biological sample is exposed to the environmental influencer compound, and wherein the marker is selected from the group consisting of the markers listed in Tables 2-4 & 6-29 with a positive fold change and/or with a negative fold change; (2) determining the level of expression of the one or more markers present in a second biological sample obtained from the subject, wherein the sample is not exposed to the environmental influencer compound; and (3) comparing the level of expression of the one of more markers in the biological sample exposed to the environmental influencer compound and the level of expression of the one or more markers in the biological sample not exposed to the environmental influencer compound, wherein a decrease in the level of expression of the one or more markers with a negative fold change present in the biological sample exposed to the environmental influencer compound relative to the level of expression of the one or more markers present in the second sample is an indication that the environmental influencer compound is efficacious for treating an oncological disorder to in the subject having an oncological disorder, and, wherein an increase in the level of expression of the one or more markers with a positive fold change present in the biological sample exposed to the environmental influencer compound relative to the level of expression of the one or more markers present in the second sample is an indication that the environmental influencer compound is efficacious for treating an oncological disorder to in the subject having an oncological disorder, thereby assessing the efficacy of the environmental influencer compound for treating an oncological disorder to in a subject having an oncological disorder.

In certain aspects, the present invention is directed to methods of assessing the efficacy of an environmental influencer compound for treating an oncological disorder in a subject in need thereof. Such methods include (1) determining the level of expression of one or more markers present in a biological sample obtained from the subject, wherein the biological sample is exposed to the environmental influencer compound, and wherein the expression of the marker is up- or down-regulated, in a cancerous cell of the oncological disorder induced to undergo a cellular metabolic energy shift from glycolysis to mitochondrial oxidative phosphorylation towards levels observed in a normal cell of the subject under normal physiological conditions; (2) determining the level of expression of the one or more markers present in a second biological sample obtained from the subject, wherein the sample is not exposed to the environmental influencer compound; and (3) comparing the level of expression of the one of more markers in the biological sample exposed to the environmental influencer compound and the level of expression of the one of more markers in the biological sample not exposed to the environmental influencer compound, wherein a decrease, in the biological sample exposed to the environmental influencer compound, in the level of expression of the one or more down-regulated markers relative to the level of expression of the one or more markers present in the second sample is an indication that the environmental influencer compound is efficacious for treating an oncological disorder to in the subject having an oncological disorder, and, wherein an increase, in the biological sample exposed to the environmental influencer compound, in the level of expression of the one or more up-regulated markers relative to the level of expression of the one or more markers present in the second sample is an indication that the environmental influencer compound is efficacious for treating an oncological disorder to in the subject having an oncological disorder, thereby assessing the efficacy of the environmental influencer compound for treating an oncological disorder to in a subject having an oncological disorder.

In certain aspects, the present invention is directed to methods of identifying a compound for treating an oncological disorder in a subject. Such methods include (1) obtaining a biological sample from the subject; (2) contacting the biological sample with a test compound; (3) determining the level of expression of one or more markers present in the biological sample obtained from the subject, wherein the marker is selected from the group consisting of the markers listed in Tables 2-4 & 6-29 with a positive fold change and/or with a negative fold change; (4) comparing the level of expression of the one of more markers in the biological sample with a control sample not contacted by the test compound; and (5) selecting a test compound that decreases the level of expression of the one or more markers with a negative fold change present in the biological sample and/or increases the level of expression of the one or more markers with a positive fold change present in the biological sample, thereby identifying a compound for treating an oncological disorder in a subject.

In certain aspects, the present invention is directed to methods of identifying a compound for treating an oncological disorder in a subject. Such methods include (1) obtaining a biological sample from the subject; (2) contacting the biological sample with a test compound; (3) determining the level of expression of one or more markers present in the biological sample obtained from the subject, wherein the expression of the marker is up- or down-regulated, in a cancerous cell of the oncological disorder induced to undergo a cellular metabolic energy shift from glycolysis to mitochondrial oxidative phosphorylation towards levels observed in a normal cell of the subject under normal physiological conditions; (4) comparing the level of expression of the one of more markers in the biological sample with a control sample not contacted by the test compound; and (5) selecting a test compound that decreases the level of expression, in the biological sample, of the one or more down-regulated markers, and/or increases the level of expression, in the biological sample, of the one or more up-regulated markers, thereby identifying a compound for treating an oncological disorder in a subject.

In certain embodiments, the term glycolysis optionally includes the associated lactate biosynthesis.

In some embodiments, the oncological disorder is an oncological disorder selected from the group consisting of: a leukemia, a lymphoma, a melanoma, a carcinoma and a sarcoma.

In some embodiments, the marker(s) selectively elicits, in a cancerous cell of the mammal, a cellular metabolic energy shift from glycolysis to mitochondrial oxidative phosphorylation, towards levels observed in a normal cell of the mammal under normal physiological conditions.

In some embodiments, the sample comprises a fluid obtained from the subject, e.g., a fluid selected from blood fluids, vomit, saliva, lymph, cystic fluid, urine, fluids collected by bronchial lavage, fluids collected by peritoneal rinsing, and gynecological fluids. In some embodiments, the sample is a blood sample or a component thereof. In some embodiments, the sample comprises a tissue or component thereof obtained from the subject, e.g., tissue selected from bone, connective tissue, cartilage, lung, liver, kidney, muscle tissue, heart, pancreas, and skin.

In some embodiments, the subject is a human.

In some embodiments, the level of expression of the marker in the biological sample is determined by assaying a transcribed polynucleotide or a portion thereof in the sample. In some embodiments, assaying the transcribed polynucleotide comprises amplifying the transcribed polynucleotide. In some embodiments, the level of expression of the marker in the subject sample is determined by assaying a protein or a portion thereof in the sample. In some embodiments, the protein is assayed using a reagent, e.g., a labeled reagent, which specifically binds with the protein. Reagents may include, for example, an antibody and an antigen-binding antibody fragment.

In some embodiments, the level of expression of the marker in the sample is determined using a technique selected from the group consisting of polymerase chain reaction (PCR) amplification reaction, reverse-transcriptase PCR analysis, single-strand conformation polymorphism analysis (SSCP), mismatch cleavage detection, heteroduplex analysis, Southern blot analysis, Northern blot analysis, Western blot analysis, in situ hybridization, array analysis, deoxyribonucleic acid sequencing, restriction fragment length polymorphism analysis, and combinations or sub-combinations thereof, of said sample. In some embodiments, the level of expression of the marker in the sample is determined using a technique selected from the group consisting of immunohistochemistry, immunocytochemistry, flow cytometry, ELISA and mass spectrometry.

In some embodiments, the marker is a marker selected from the group consisting of HNF4-alpha, Bcl-xl, Bcl-xS, BNIP-2, Bcl-2, Birc6, Bcl-2-L11 (Bim), XIAP, BRAF, Bax, c-Jun, Bmf, PUMA, cMyc, transaldolase 1, COQ1, COQ3, COQ6, prenyltransferase, 4-hydrobenzoate, neutrophil cytosolic factor 2, nitric oxide synthase 2A, superoxide dismutase 2, VDAC, Bax channel, ANT, Cytochrome c, complex 1, complex II, complex III, complex IV, Foxo 3a, DJ-1, IDH-1, Cpt1C and Cam Kinase II. In some embodiments, the marker is a marker associated with apoptosis. In some embodiments, the marker is a marker associated with oxidative stress. In some embodiments, the marker is a marker associated with heat shock. In some embodiments, the marker is a marker associated with angiogenesis. In some embodiments, the level of expression of a plurality of markers is determined.

In some embodiments, the subject is being treated with a therapy selected from an environmental influencer compound, surgery, radiation, hormone therapy, antibody therapy, therapy with growth factors, cytokines, and chemotherapy. In some embodiments, the therapy comprises an environmental influencer compound. Environmental influencer compounds can be, for example, multidimensional intracellular molecules (MIMs) or epimetabolic shifters (epishifters). In some embodiments, the environmental influencer compound is CoQ-10. In some embodiments, the environmental influencer compound is vitamin D3. In some embodiments, the environmental influencer compound is a compound selected from acetyl Co-A, palmityl, L-carnitine, tyrosine, phenylalanine, cysteine and a small molecule. In some embodiments, the environmental influencer compound is a compound selected from fibronectin, TNF-alpha, IL-5, IL-12, IL-23, an angiogenic factor and an apoptotic factor. In some embodiments, the therapy further comprises a treatment regimen selected from surgery, radiation, hormone therapy, antibody therapy, therapy with growth factors, cytokines, and chemotherapy.

In certain aspects, the present invention is directed to kits for assessing whether a subject is afflicted with an oncological disorder. Such kits include reagents for determining the level of expression of at least one marker selected from the group consisting of the markers listed in Tables 2-4 & 6-29 and instructions for use of the kit to assess whether the subject is afflicted with the oncological disorder.

In certain aspects, the present invention is directed to kits for prognosing whether a subject is predisposed to developing an oncological disorder. Such kits include reagents for determining the level of expression of at least one marker selected from the group consisting of the markers listed in Tables 2-4 & 6-29 and instructions for use of the kit to prognose whether the subject is predisposed to developing the oncological disorder.

In certain aspects, the present invention is directed to kits for prognosing the recurrence of an oncological disorder in a subject. Such kits include reagents for assessing the level of expression of at least one marker selected from the group consisting of the markers listed in Tables 2-4 & 6-29 and instructions for use of the kit to prognose the recurrence of the oncological disorder.

In certain aspects, the present invention is directed to kits for prognosing the recurrence of an oncological disorder. Such kits include reagents for determining the level of expression of at least one marker selected from the group consisting of the markers listed in Tables 2-4 & 6-29 and instructions for use of the kit to prognose the recurrence of the oncological disorder.

In certain aspects, the present invention is directed to kits for prognosing the survival of a subject with an oncological disorder. Such kits include reagents for determining the level of expression of at least one marker selected from the group consisting of the markers listed in Tables 2-4 & 6-29 and instructions for use of the kit to prognose the survival of the subject with the oncological disorder.

In certain aspects, the present invention is directed to kits for prognosing the aggressiveness on an oncological disorder in a subject. Such kits include reagents for determining the level of expression of at least one marker selected from the group consisting of the markers listed in Tables 2-4 & 6-29 and instructions for use of the kit to prognose the aggressiveness on the oncological disorder in the subject.

In certain aspects, the present invention is directed to kits for monitoring the progression of an oncological disorder in a subject. Such kits include reagents for determining the level of expression of at least one marker selected from the group consisting of the markers listed in Tables 2-4 & 6-29 and instructions for use of the kit to prognose the progression of the oncological disorder in a subject.

In certain aspects, the present invention is directed to kits for assessing the efficacy of a therapy for treating an oncological disorder. Such kits include reagents for determining the level of expression of at least one marker selected from the group consisting of the markers listed in Tables 2-4 & 6-29 and instructions for use of the kit to assess the efficacy of the therapy for treating the oncological disorder.

In certain aspects, the present invention is directed to kits for assessing the efficacy of an environmental influencer compound for treating an oncological disorder to in a subject having an oncological disorder. Such kits include reagents for determining the level of expression of at least one marker selected from the group consisting of the markers listed in Tables 2-4 & 6-29 and instructions for use of the kit to assess the efficacy of the environmental influencer compound for treating the oncological disorder to in the subject having the oncological disorder.

In some embodiments, the kit further comprises means for obtaining a biological sample from a subject. In some embodiments, the kit further comprises a control sample. In some embodiments, the kit further comprises an environmental influencer compound. In some embodiments, the kit comprises reagents for determining the level of expression of a plurality of markers.

In some embodiments, the means for determining the level of expression of at least one marker comprises means for assaying a transcribed polynucleotide or a portion thereof in the sample. In other embodiments, the means for determining the level of expression of at least one marker comprises means for assaying a protein or a portion thereof in the sample.

In certain aspects, the present invention is directed to methods of assessing whether a subject is afflicted with a CoQ10 responsive state. Such methods include (1) determining the level of expression of a marker present in a biological sample obtained from the subject, wherein the marker is selected from the group consisting of the markers listed in Tables 2-4 & 6-29; and (2) comparing the level of expression of the marker present in the biological sample obtained from the subject with the level of expression of the marker present in a control sample, wherein a modulation in the level of expression of the marker in the biological sample obtained from the subject relative to the level of expression of the marker in the control sample is an indication that the subject is afflicted with the CoQ10 responsive state, thereby assessing whether the subject is afflicted with the CoQ10 responsive state. In some embodiments, the CoQ10 responsive state is an oncological disorder.

DETAILED DESCRIPTION OF THE INVENTION

Definitions

Figure 1:
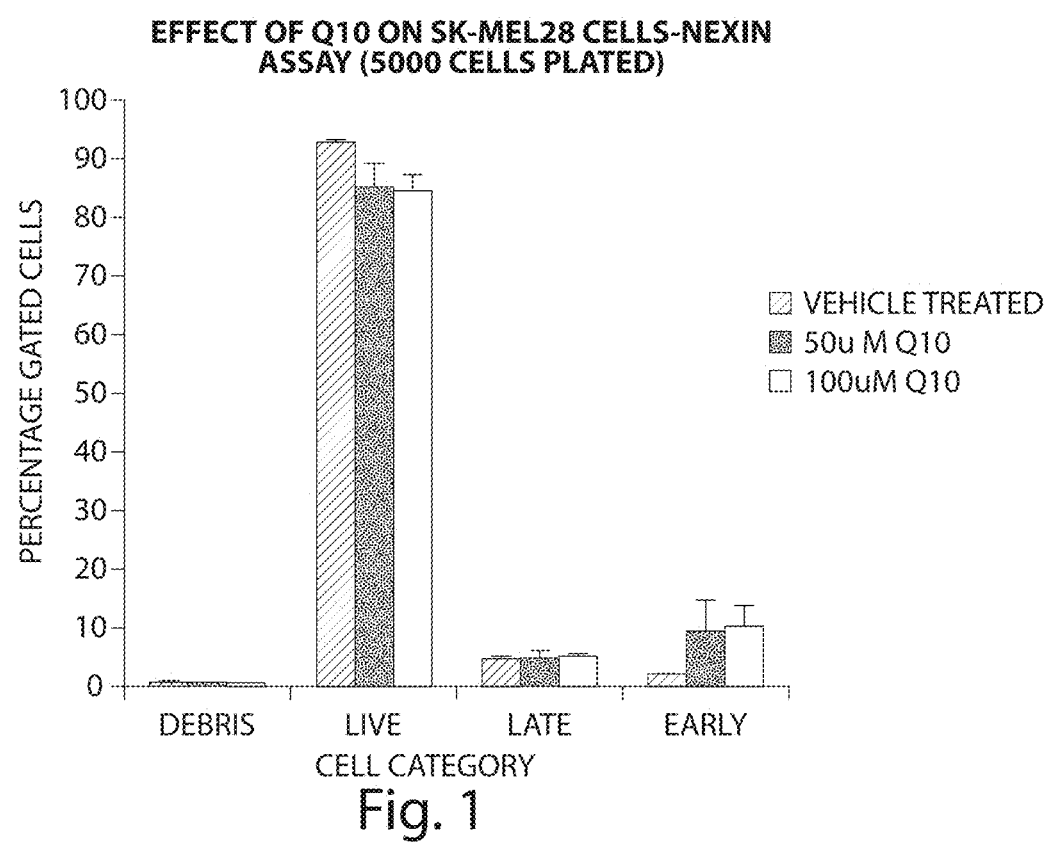
FIG. 1: Sensitivity of SK-MEL-28 to 24 hours of Q10 treatment measured by the amount of early and late apoptotic cells.
Figure 2:
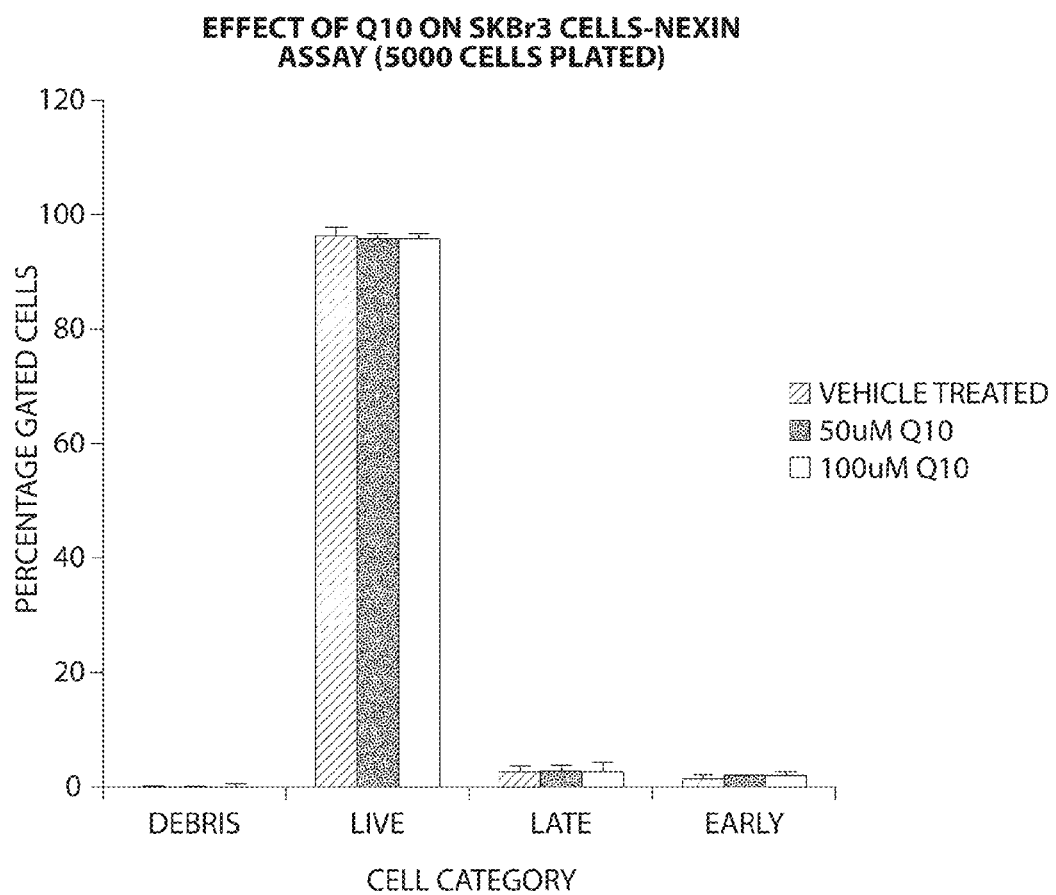
FIG. 2: Sensitivity of SKBR3 to 24 hours of Q10 treatment measured by the amount of early and late apoptotic cells.
Figure 3:
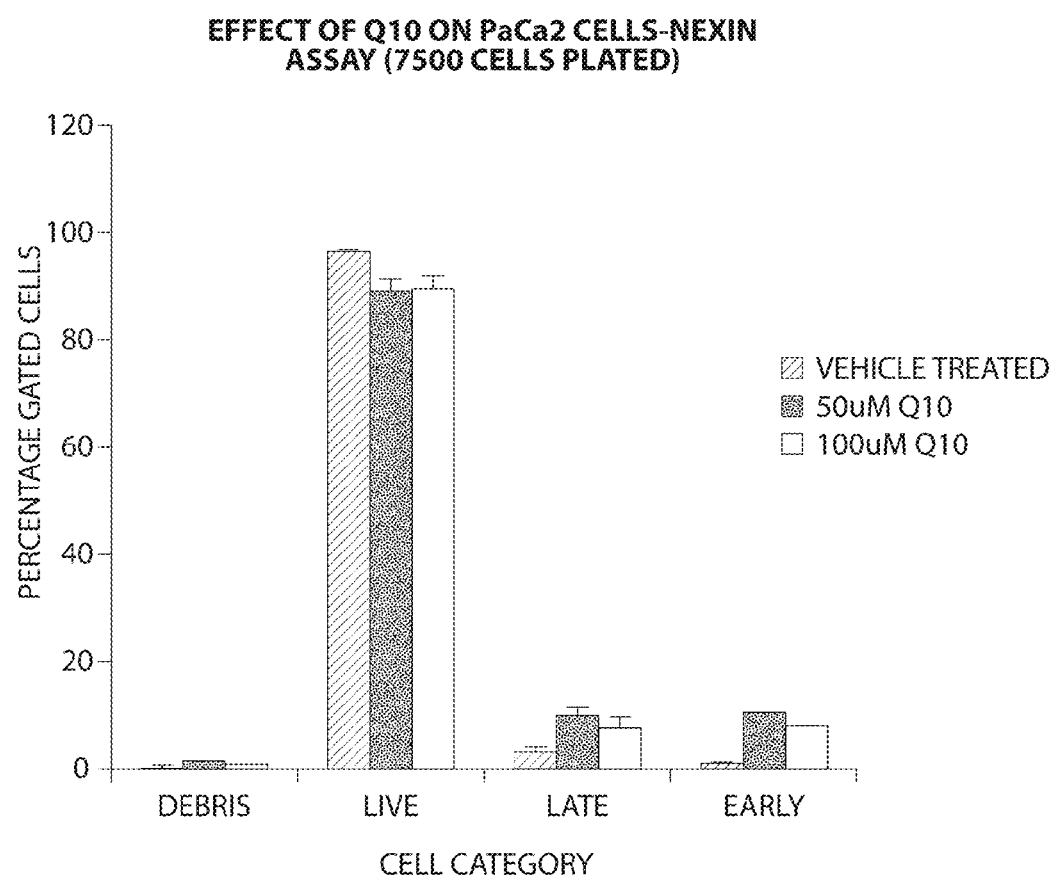
FIG. 3: Sensitivity of PaCa2 to 24 hours of Q10 treatment measured by the amount of early and late apoptotic cells.
Figure 4:
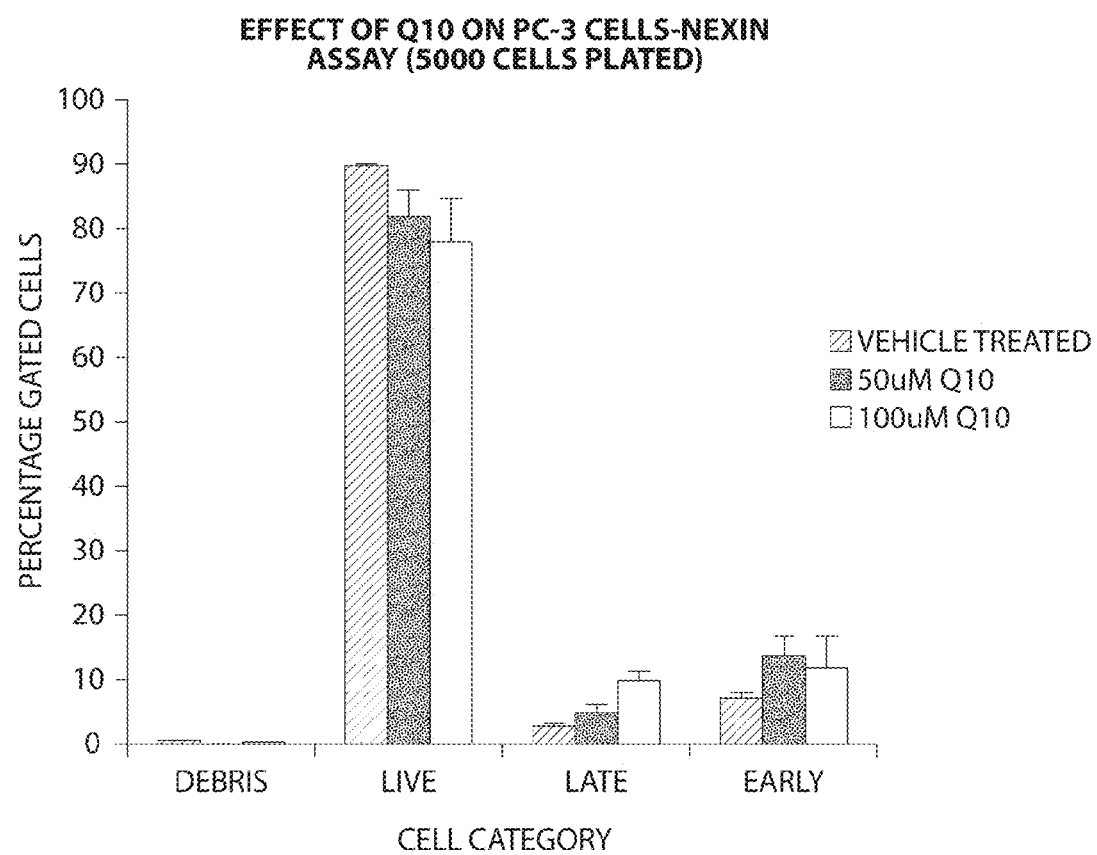
FIG. 4: Sensitivity of PC-3 to 24 hours of Q10 treatment measured by the amount of early and late apoptotic cells.
Figure 5:
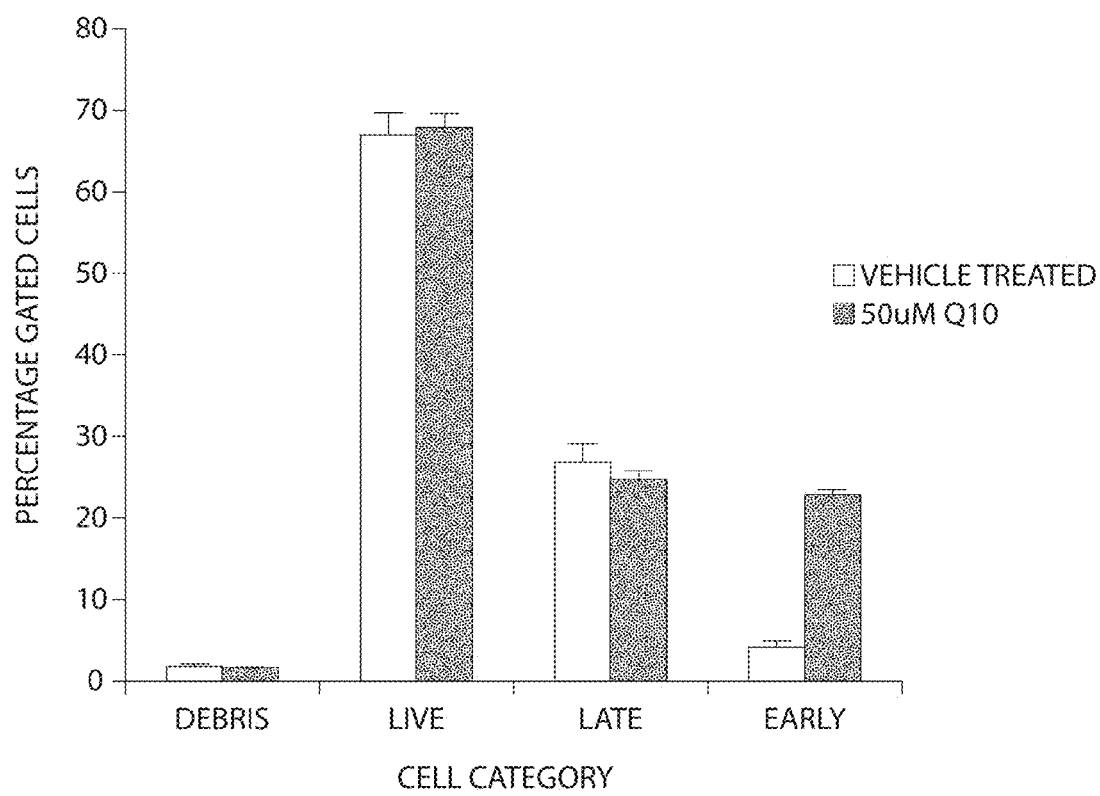
FIG. 5: Sensitivity of HepG2 to 24 hours of Q10 treatment measured by the amount of early and late apoptotic cells.
Figure 6:
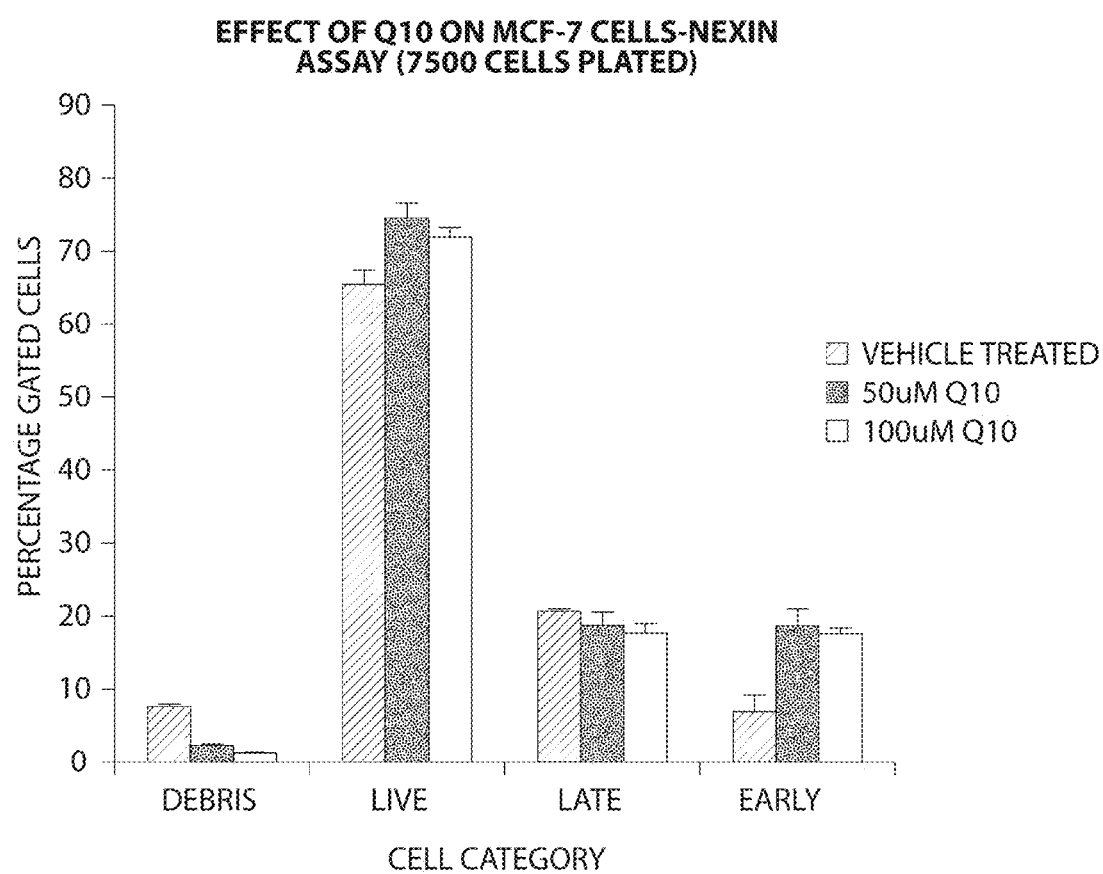
FIG. 6: Sensitivity of MCF-7 to 24 hours of Q10 treatment measured by the amount of early and late apoptotic cells.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

A "patient" or "subject" to be treated by the method of the invention can mean either a human or non-human animal, preferably a mammal. As used herein, a "subject" or a "patient" includes, without limitation, any animal (e.g., a human), including horses, dogs, cats, pigs, goats, rabbits, hamsters, monkeys, guinea pigs, rats, mice, lizards, snakes, sheep, cattle, fish, and birds.

As used herein, "survival" refers to the continuation of life of a subject which has been treated for an oncological disorder. In one embodiment, survival refers to the failure of an oncological disorder to recur.

As used herein, the terms "recur" or "recurrence" refer to the re-growth of a tumor or cancerous cells in a subject in whom primary treatment for the tumor has been administered. The tumor may recur in the original site or in another part of the body. In one embodiment a tumor that recurs is of the same type as the original tumor for which the subject was treated. For example, if a subject had a pancreatic tumor, was treated and subsequently developed another pancreatic tumor, the tumor has recurred. In addition, an oncologic disorder can recur in a different organ or tissue than the one where it originally occurred. For example, if a subject had a pancreatic tumor, was treated and subsequently developed a liver tumor, the tumor has also recurred.

As used herein, the term "aggressive", with respect to an oncological disorder, refers to a tumor having a predisposition to recur in a subject, or a cell derived from such an aggressive tumor.

As used herein, the term "amount", refers to either (a) an absolute amount as measured in molecules, moles or weight per unit volume or cell or (b) a relative amount as designated, for example, by a numerical rating from 0 to 5.

The term "control amount", as used herein, refers to the amount of marker in a cell or a sample derived from a subject not afflicted with an oncological disorder, a cell or a sample derived from an aggressive tumor, or a cell or sample derived from a non-aggressive tumor. The "control amount" may, for example, be determined by calculating the average amount of marker present in cells or tissues that are known to express the marker, e.g., express these proteins at high levels, intermediate levels and low levels.

"Therapeutically effective amount" means the amount of a compound that, when administered to a patient for treating a disease, is sufficient to effect such treatment for the disease. When administered for preventing a disease, the amount is sufficient to avoid or delay onset of the disease. The "therapeutically effective amount" will vary depending on the compound, the disease and its severity and the age, weight, etc., of the patient to be treated.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

The term "prophylactic" or "therapeutic" treatment refers to administration to the subject of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like. For example, certain compounds discovered by the methods of the present invention may be administered in a sufficient amount to produce a reasonable benefit/risk ratio applicable to such treatment.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

The terms "level of expression of a gene in a cell" or "gene expression level" refer to the level of mRNA, as well as pre-mRNA nascent transcript(s), transcript processing intermediates, mature mRNA(s) and degradation products, encoded by the gene in the cell.

The term "modulation" refers to upregulation (i.e., activation or stimulation), downregulation (i.e., inhibition or suppression) of a response, or the two in combination or apart. A "modulator" is a compound or molecule that modulates, and may be, e.g., an agonist, antagonist, activator, stimulator, suppressor, or inhibitor.

A "higher level of expression", "higher level of activity", "increased level of expression" or "increased level of activity" refers to an expression level and/or activity in a test sample that is greater than the standard error of the assay employed to assess expression and/or activity, and is preferably at least twice, and more preferably three, four, five or ten or more times the expression level and/or activity of the marker in a control sample (e.g., a sample from a healthy subject not afflicted with an oncological disorder) and preferably, the average expression level and/or activity of the marker in several control samples.

A "lower level of expression", "lower level of activity", "decreased level of expression" or "decreased level of activity" refers to an expression level and/or activity in a test sample that is greater than the standard error of the assay employed to assess expression and/or activity, but is preferably at least twice, and more preferably three, four, five or ten or more times less than the expression level of the marker in a control sample (e.g., a sample that has been calibrated directly or indirectly against a panel of oncological disorders with follow-up information which serve as a validation standard for prognostic ability of the marker) and preferably, the average expression level and/or activity of the marker in several control samples.

As used herein, "antibody" includes, by way of example, naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

As used herein, "known standard" or "control" refers to one or more of an amount and/or mathematical relationship, as applicable, with regard to a marker of the invention, and the presence or absence of an oncological disorder. A known standard preferably reflects such amount and/or mathematical relationship characteristic of a recurrent tumor and a non-recurrent tumor and/or an aggressive or a non-aggressive tumor. Reagents for generating a known standard include, without limitation, tumor cells from a tumor known to be aggressive, tumor cells from a tumor known to be non-aggressive, and optionally labeled antibodies. Known standards may also include tissue culture cell lines (including, but not limited to, cell lines that have been manipulated to express specific marker proteins or to not express specific marker proteins, or tumor xenografts that either constitutively contain constant amounts of marker protein, or can be manipulated (e.g., by exposure to a changed environment, where such changed environment may include but not limited to growth factors, hormones, steroids, cytokines, antibodies, various drugs and anti-metabolites, and extracellular matrices) to express a marker protein. Cell lines may be mounted directly on glass slides for analysis, fixed, embedded in paraffin directly as a pellet, or suspended in a matrix such as agarose, then fixed, embedded in paraffin, sectioned and processed as tissue samples. The standards must be calibrated directly or indirectly against a panel of gastrointestinal or breast cancers with follow-up information which serve as a validation standard for prognostic ability of the marker proteins.

"Primary treatment" as used herein, refers to the initial treatment of a subject afflicted with an oncological disorder. Primary treatments include, without limitation, surgery, radiation, hormone therapy, chemotherapy, immunotherapy, angiogenic therapy, and therapy via biomodulators.

An oncological disorder is "treated" if at least one symptom of the oncological disorder is expected to be or is alleviated, terminated, slowed, or prevented. As used herein, an oncological disorder is also "treated" if recurrence or metastasis of the oncological disorder is reduced, slowed, delayed, or prevented.

A kit is any manufacture (e.g. a package or container) comprising at least one reagent, e.g. a probe, for specifically detecting a marker of the invention, the manufacture being promoted, distributed, or sold as a unit for performing the methods of the present invention.

"Metabolic pathway" refers to a sequence of enzyme-mediated reactions that transform one compound to another and provide intermediates and energy for cellular functions. The metabolic pathway can be linear or cyclic.

"Metabolic state" refers to the molecular content of a particular cellular, multicellular or tissue environment at a given point in time as measured by various chemical and biological indicators as they relate to a state of health or disease.

The term "microarray" refers to an array of distinct polynucleotides, oligonucleotides, polypeptides (e.g., antibodies) or peptides synthesized on a substrate, such as paper, nylon or other type of membrane, filter, chip, glass slide, or any other suitable solid support.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

In some embodiments, the compounds of the present invention, e.g., the MIMs or epi-shifters described herein, may be used to treat a Coenzyme Q10 responsive state in a subject in need thereof. The language "Coenzyme Q10 responsive state," or "CoQ10 responsive state," includes diseases, disorders, states and/or conditions which can be treated, prevented, or otherwise ameliorated by the administration of Coenzyme Q10. Without wishing to be bound by any particular theory, and as described further herein, it is believed that CoQ10 functions, at least partially, by inducing a metabolic shift to the cell microenvironment, such as a shift towards the type and/or level of oxidative phosphorylation in normal state cells. Accordingly, in some embodiments, CoQ10 responsive states are states that arise from an altered metabolism of cell microenvironment. Coenzyme Q10 responsive states include, for example, oncological disorders, which, for example, may be biased towards glycolysis and lactate biosynthesis. In some embodiments, CoQ10 responsive oncological disorders include liver cancer, pancreatic cancer, breast cancer, prostate cancer, liver cancer, or bone cancer, squamous cell carcinomas, basal cell carcinomas, melanomas, and actinic keratosis, among others. Coenzyme Q10 responsive states further include other oncological disorders as described herein.

Coenzyme Q10 responsive states also include, for example, metabolic disorders such as obesity, diabetes, pre-diabetes, Metabolic Syndrome, satiety, and endocrine abnormalities. Coenzyme Q10 responsive states further include other metabolic disorders as described herein.

In some embodiments, the compounds of the present invention, e.g., the MIMs or epi-shifters described herein, share a common activity with Coenzyme Q10. As used herein, the phrase "share a common activity with Coenzyme Q10" refers to the ability of a compound to exhibit at least a portion of the same or similar activity as Coenzyme Q10. In some embodiments, the compounds of the present invention exhibit 25% or more of the activity of Coenzyme Q10. In some embodiments, the compounds of the present invention exhibit up to and including about 130% of the activity of Coenzyme Q10. In some embodiments, the compounds of the present invention exhibit about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, or 130% of the activity of Coenzyme Q10. It is to be understood that each of the values listed in this paragraph may be modified by the term "about." Additionally, it is to be understood that any range which is defined by any two values listed in this paragraph is meant to be encompassed by the present invention. For example, in some embodiments, the compounds of the present invention exhibit between about 50% and about 100% of the activity of Coenzyme Q10. In some embodiments, the activity shared by Coenzyme Q10 and the compounds of the present invention is the ability to induce a shift in cellular metabolism. In certain embodiments, the activity shared by of CoQ10 and the compounds of the present invention is measured by OCR (Oxygen Consumption Rate) and/or ECAR (ExtraCellular Acidification Rate).

As used herein, "oncological disorder" refers to all types of cancer or neoplasm or malignant tumors found in humans, including, but not limited to: leukemias, lymphomas, melanomas, carcinomas and sarcomas. As used herein, the terms or language "oncological disorder", "cancer," "neoplasm," and "tumor," are used interchangeably and in either the singular or plural form, refer to cells that have undergone a malignant transformation that makes them pathological to the host organism. In some embodiments the oncological disorder is a Coenzyme Q10 responsive state.

In some embodiments, the oncological disorder or cancer is characterized by a lack of apoptosis. In other embodiments, the oncological disorder or cancer is characterized by increased angiogenesis. In other embodiments, the oncological disorder or cancer is characterized by extracellular matrix (ECM) degradation. In yet other embodiments, the oncological disorder or cancer is characterized by loss of cell cycle control. In still other embodiments, the oncological disorder or cancer is characterized by a shift in metabolic governance from mitochondrial oxidative phosphorylation to increased utilization and/or dependency on lactate and glycolytic flux. In further embodiments, the oncological disorder or cancer is characterized by adapted immunomodulatory mechanisms that have evaded immunosurveillance. In one embodiment, the oncological disorder or cancer is characterized by at least two of the above features, e.g., increased angiogenesis and ECM degradation. In one embodiment, the oncological disorder or cancer is characterized by at least three of the above features. In one embodiment, the oncological disorder or cancer is characterized by at least four of the above features. In one embodiment, the oncological disorder or cancer is characterized by at least five of the above features. In one embodiment, the oncological disorder or cancer is characterized by all six of the above features.

Accordingly, in some embodiments, the compounds of the present invention function by restoring the capacity for apoptosis or inducing apoptosis. In other embodiments, the compounds of the present invention function by reducing, decreasing or inhibiting angiogenesis. In still other embodiments, the compounds of the present invention function by restoring or re-establishing extracellular matrix. In other embodiments, the compounds of the present invention function by restoring cell cycle control. In still other embodiments, the compounds of the present invention function by shifting metabolic governance back from glycolysis to mitochondrial oxidative phosphorylation. In further embodiments, the compounds of the present invention function by restoring immunosurveillance or restoring the body's ability to recognize the cancer cell as foreign.

Without wishing to be bound by any particular theory, it is believed that there is typically a coordinated cascade of events that aggregate to develop into cancer. That is, in some embodiments, cancer is not singularly dependent on a 1 gene-1 protein-root causality. In some embodiments, cancer is a physiologic disease state that manifests into tissue changes and alterations that become tumors, altered tissue states, e.g., energetics, compromised extracellular matrix integrity that allows for metastatic potential, lack of immunosurveillance and/or altered state of angiogenesis.

Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

The term "sarcoma" generally refers to a tumor which is made up of a substance like the embryonic connective tissue and is generally composed of closely packed cells embedded in a fibrillar or homogeneous substance. Examples of sarcomas which can be treated with an environmental influencer of the invention include, but are not limited to, a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with an environmental influencer of the invention include, but are not limited to, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with an environmental influencer of the invention include, but are not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

In general, an environmental influencer may be used to prophylactically or therapeutically treat any neoplasm. In one embodiment, the environmental influencers of the invention are used to treat solid tumors. In various embodiments of the invention, an environmental influencer (e.g., CoQ10) is used for treatment, of various types of skin cancer (e.g., Squamous cell Carcinoma or Basal Cell Carcinoma), liver cancer, pancreatic cancer, breast cancer, prostate cancer, liver cancer, or bone cancer. In one embodiment, an environmental influencer, e.g., CoQ10, is used for treatment of a skin oncological disorder including, but not limited to, squamous cell carcinomas (including SCCIS (in situ) and more aggressive squamous cell carcinomas), basal cell carcinomas (including superficial, nodular and infiltrating basal cell carcinomas), melanomas, and actinic keratosis. However, treatment using an environmental influencer is not limited to the foregoing types of cancers. Examples of cancers amenable to treatment with an environmental influencer include, but are not limited to, cancer of the brain, head and neck, prostate, breast, testicular, pancreas, liver, colon, bladder, kidney, lung, non-small cell lung, melanoma, mesothelioma, uterus, cervix, ovary, sarcoma, bone, stomach and Medulloblastoma.

Additional cancers which can be treated with an environmental influencer of the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer. In one embodiment, the oncological disorder or cancer which can be treated with the environmental influencer, e.g., CoQ10, is not melanoma.

The definition of a cancer cell, as used herein, is intended to include a cancer cell that produces energy by anaerobic glycolysis (e.g., glycolysis followed by lactic acid fermantion in the cytosol), aerobic glycolysis (e.g., glycolysis followed by oxidation of pyruvate in the mitochondria), or a combination of anaerobic glycolysis and aerobic glycolysis. In one embodiment, a cancer cell produces energy predominantly by anaerobic glycolysis (e.g., at least 50%, 60%, 70%, 80%, 90%, 95% or more of the cell's energy is produced by anaerobic glycolysis). In one embodiment, a cancer cell produces energy predominantly by aerobic glycolysis (e.g., at least 50%, 60%, 70%, 80%, 90%, 95% or more of the cell's energy is produced by anaerobic glycolysis). The definition of cancer cells, as used herein, is also intended to include a cancer cell population or mixture of cancer cells comprising cells that produce energy by anaerobic glycolysis and cells that produce energy by aerobic glycolysis. In one embodiment, a cancer cell population comprises predominantly cells that produce energy by anaerobic glycolysis (e.g., at least 50%, 60%, 70%, 80%, 90%, 95% or more of the cells in the population produce energy by anaerobic glycolysis). In one embodiment, a cancer cell population comprises predominantly cells that produce energy by aerobic glycolysis (e.g., at least 50%, 60%, 70%, 80%, 90%, 95% or more of the cells in the population).

As used herein, the phrase "anaerobic use of glucose" or "anaerobic glycolysis" refers to cellular production of energy by glycolysis followed by lactic acid fermentation in the cytosol. For example, many cancer cells produce energy by anaerobic glycolysis.

As used herein, the phrase "aerobic glycolysis" or "mitochondrial oxidative phosphorylation" refers to cellular production of energy by glycolysis followed by oxidation of pyruvate in mitochondria.

As used herein, the phrase "capable of blocking anaerobic use of glucose and augmenting mitochondrial oxidative phosphorylation" refers to the ability of an environmental influencer (e.g., an epitmetabolic shifter) to induce a shift or change in the metabolic state of a cell from anaerobic glycolysis to aerobic glycolysis or mitochondrial oxidative phosphorylation.

The present invention also provides a method for diagnosing an aggressive oncological disorder in a human, comprising administering an environmental infuencer to the human at a selected lower dose than the dosage regimen used or selected for less aggressive or non-aggressive oncological disorders, thereby diagnosing the aggressive oncological disorder. In a related aspect, the invention provides a method for diagnosing a non-aggressive oncological disorder in a human, comprising administering an environmental influencer to the human at a selected higher dose over the dosage regimen used or selected for aggressive oncological disorders, thereby diagnosing the non-aggressive oncological disorder.

As used herein, the term "aggressive oncological disorder" refers to an oncological disorder involving a fast-growing tumor. An aggressive oncological disorder typically does not respond or responds poorly to therapeutic treatment. Examples of an aggressive oncological disorder include, but are not limited to, pancreatic carcinoma, hepatocellular carcinoma, Ewing's sarcoma, metastatic breast cancer, metastatic melanoma, brain cancer (astrocytoma, glioblastoma), neuroendocrine cancer, colon cancer, lung cancer, osteosarcoma, androgen-independent prostate cancer, ovarian cancer and non-Hodgkin's Lymphoma.

As used herein, the term "non-aggressive oncological disorder" refers to an oncological disorder involving a slow-growing tumor. A non-aggressive oncological disorder typically responds favorably or moderately to therapeutic treatment. Examples of a non-aggressive oncological disorder include, but are not limited to, non-metastatic breast cancer, androgen-dependent prostate cancer, small cell lung cancer and acute lymphocytic leukemia. In one embodiment, non-aggressive oncological disorders include any oncological disorder that is not an aggressive oncological disorder.

I. Environmental Influencers

The present invention provides methods of treating oncological disorders by administration of an Environmental influencer. "Environmental influencers" (Env-influencers) are molecules that influence or modulate the disease environment of a human in a beneficial manner allowing the human's disease environment to shift, reestablish back to or maintain a normal or healthy environment leading to a normal state. Env-influencers include both Multidimensional Intracellular Molecules (MIMs) and Epimetabolic shifters (Epi-shifters) as defined below.

1. Multidimensional Intracellular Molecule (MIM)

The term "Multidimensional Intracellular Molecule (MIM)", is an isolated version or synthetically produced version of an endogenous molecule that is naturally produced by the body and/or is present in at least one cell of a human. A MIM is characterized by one or more, two or more, three or more, or all of the following functions. MIMs are capable of entering a cell, and the entry into the cell includes complete or partial entry into the cell, as long as the biologically active portion of the molecule wholly enters the cell. MIMs are capable of inducing a signal transduction and/or gene expression mechanism within a cell. MIMs are multidimensional in that the molecules have both a therapeutic and a carrier, e.g., drug delivery, effect. MIMs also are multidimensional in that the molecules act one way in a disease state and a different way in a normal state. For example, in the case of CoQ-10, administration of CoQ-10 to a melanoma cell in the presence of VEGF leads to a decreased level of Bcl2 which, in turn, leads to a decreased oncogenic potential for the melanoma cell. In contrast, in a normal fibroblast, co-administration of CoQ-10 and VEFG has no effect on the levels of Bcl2. Preferably, MIMs selectively act in cells of a disease state, and have substantially no effect in (matching) cells of a normal state. Preferably, MIMs selectively renders cells of a disease state closer in phenotype, metabolic state, genotype, mRNA/protein expression level, etc. to (matching) cells of a normal state.

In one embodiment, a MIM is also an epi-shifter. In another embodiment, a MIM is not an epi-shifter. The skilled artisan will appreciate that a MIM of the invention is also intended to encompass a mixture of two or more endogenous molecules, wherein the mixture is characterized by one or more of the foregoing functions. The endogenous molecules in the mixture are present at a ratio such that the mixture functions as a MIM.

MIMs can be lipid based or non-lipid based molecules. Examples of MIMs include, but are not limited to, CoQ10, acetyl Co-A, palmityl Co-A, L-carnitine, amino acids such as, for example, tyrosine, phenylalanine, and cysteine. In one embodiment, the MIM is a small molecule. In one embodiment of the invention, the MIM is not CoQ10. MIMs can be routinely identified by one of skill in the art using any of the assays described in detail herein.

In some embodiments, MIMs include compounds in the Vitamin B family, or nucleosides, mononucleotides or dinucleotides that comprise a compound in the Vitamin B family. Compounds in the vitamin B family include, for example, thiamine (vitamin B1), niacin (also known as nicotinic acid or Vitamin B3), or pyridoxine (vitamin B6) as well as provitamins such as panthenol (provitamin B5). In some embodiments, the MIM is selected from thiamine, niacin and pyridoxine. Nucleosides, mononucleotides or dinucleotides that comprise a compound in the vitamin B family include, for example, nucleosides, mononucleotides or dinucleotides which include an adenine or a niacin (nicotinic acid) molecule. In some embodiments, the MIM is selected from adenosine, adenosine diphosphate (ADP), flavin adenosine dinucleotide (FAD, which comprises parts of vitamin B2 and ADP) and nicotinic acid dinucleotide.

In other embodiments, the MIMs include amino acids. Examples of amino acids include, for example, tyrosine (e.g., L-tyrosine), cysteine, phenylalanine (e.g., L-phenylalanine) and alanine. In some embodiments, the amino acid is phenylalanine or alanine. In some embodiments, the MIMs include amino acid derivatives such as 4-hydroxyphenylpyruvate or acetylglycine.

In some embodiment, the MIM is a glucose analog, e.g., a glucose molecule wherein one —OH or —CH$_2$OH substituent has been replaced with a —COOH, a —COO$^-$ or an —NH$_2$ substituent. Examples of glucose analogs include glucosamine, glucuronic acid, glucuronide and glucuronate.

In some embodiments, the MIM is selected from compounds of formula (I):

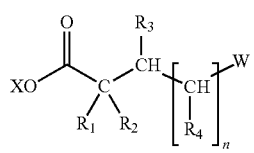

(I)

wherein
n is an integer of 0 or 1;
$R^1$, $R^2$, $R^3$ and $R^4$, when present, are each independently selected from hydrogen and hydroxyl or $R^1$ and $R^2$ are taken together with the carbon on which they are attached to form a carbonyl (C=O) group;
W is —COOH or —N(CH$_3$)$_3^+$; and X is hydrogen, a negative charge or a alkali metal cation, such as Na$^+$ or.

It is to be understood that when n is 0, the CHR$^3$ group is bonded to the W substituent.

In some embodiments, W is —N(CH$_3$)$_3^+$. In some embodiments, the MIM is a carnitine, such as L-carnitine.

In some embodiments, the MIM is a dicarboxylic acid. In some embodiments, W is —COOH. In some embodiments, $R^3$ is hydrogen. In some embodiments, n is 0. In some embodiments, $R^1$ and $R^2$ are each independently hydrogen. In some embodiments, W is —COOH, $R^3$ is hydrogen, n is 0 and $R^1$ and $R^2$ are each independently hydrogen. In some embodiments, n is 1. In some embodiments $R^1$ and $R^2$ are taken together with the carbon on which they are attached to form a carbonyl (C=O) group. In some embodiments, $R^4$ is hydrogen. In some embodiments, $R^4$ is hydroxyl. In some embodiments, W is —COOH, $R^3$ is hydrogen, n is 1 and $R^1$ and $R^2$ are taken together with the carbon on which they are attached to form a carbonyl (C=O) group.

In some embodiments, the MIM is an intermediate of the Krebs Cycle, the excess of which drives the Krebs Cycle towards productive oxidative phosphorylation. Exemplary Krebs Cycle intermediates that are MIMs include succinic acid or succinate, malic acid or malate, and α-ketoglutaric acid or α-ketoglutarate.

In some embodiments, the MIM is a building block of CoQ10, which has the following structure:

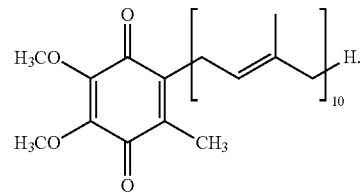

Thus, building blocks of CoQ10 include, but are not limited to, phenylalanine, tyrosine, 4-hydroxyphenylpyruvate, phenylacetate, 3-methoxy-4-hydroxymandelate, vanillic acid, 4-hydroxybenzoate, mevalonic acid, farnesyl, 2,3-dimethoxy-5-methyl-p-benzoquinone, as well as the corresponding acids or ions thereof. In some embodiments, the MIM is selected from phenylalanine, tyrosine, 4-hydroxyphenylpyruvate, phenylacetate and 4-hydroxybenzoate.

(i) Methods of Identifying MIMS

The present invention provides methods for identifying a MIM. Methods for identifying a MIM involve, generally, the exogenous addition to a cell of an endogenous molecule and evaluating the effect on the cell, e.g., the cellular microenvironment profile, that the endogenous molecule provides. Effects on the cell are evaluated at one or more of the cellular, mRNA, protein, lipid, and/or metabolite level to identify alterations in the cellular microenvironment profile. In one embodiment, the cells are cultured cells, e.g., in vitro. In one embodiment, the cells are present in an organism. The endogenous molecule may be added to the cell at a single concentration or may be added to the cell over a range of concentrations. In one embodiment, the endogenous molecule is added to the cells such that the level of the endogenous molecule in the cells is elevated (e.g., is elevated by 1.1 fold, 1.2 fold, 1.3 fold, 1.4 fold, 1.5 fold, 1.6 fold, 1.7 fold, 1.8 fold, 1.9 fold, 2.0 fold, 3.0 fold, 4.0 fold, 5.0 fold, 10 fold, 15 fold, 20 fold, 25 fold, 30 fold, 35 fold, 40 fold, 45 fold, 50 fold or greater) as compared to the level of the endogenous molecule in a control, untreated cell.

Molecules that induce a change in the cell as detected by alterations in, for example, any one or more of morphology, physiology, and/or composition (e.g., mRNA, protein, lipid, metabolite) may be evaluated further to determine if the induced changes to the cellular microenvironment profile are different between a disease cellular state and a normal cellular state. Cells (e.g., cell culture lines) of diverse tissue origin, cell type, or disease state may be evaluated for comparative evaluation. For example, changes induced in the cellular microenvironment profile of a cancer cell may be compared to changes induced to a non-cancerous or normal cell. An endogenous molecule that is observed to induce a change in the microenvironment profile of a cell (e.g., induces a change in the morphology, physiology and/or composition, e.g., mRNA, protein, lipid or metabolite, of the cell) and/or to differentially (e.g., preferentially) induce a change in the microenvironment profile of a diseased cell as compared to a normal cell, is identified as a MIM.

MIMs of the invention may be lipid based MIMs or non-lipid based MIMs. Methods for identifying lipid based MIMs involve the above-described cell based methods in which a lipid based endogenous molecule is exogenously added to the cell. In a preferred embodiment, the lipid based endogenous molecule is added to the cell such that the level of the lipid based endogenous molecule in the cell is elevated. In one embodiment, the level of the lipid based endogenous molecule is elevated by 1.1 fold, 1.2 fold, 1.3 fold, 1.4 fold, 1.5 fold, 1.6 fold, 1.7 fold, 1.8 fold, 1.9 fold, 2.0 fold, 3.0 fold, 4.0 fold, 5.0 fold, 10 fold, 15 fold, 20 fold, 25 fold, 30 fold, 35 fold, 40 fold, 45 fold, 50 fold or greater as compared to the level in an untreated control cell. Formulation and delivery of the lipid based molecule to the cell is dependent upon the properties of each molecule tested, but many methods are known in the art. Examples of formulation and delivery of lipid based molecules include, but are not limited to, solubilization by co-solvents, carrier molecules, liposomes, dispersions, suspensions, nanoparticle dispersions, emulsions, e.g., oil-in-water or water-in-oil emulsions, multiphase emulsions, e.g., oil-in-water-in-oil emulsions, polymer entrapment and encapsulation. The delivery of the lipid based MIM to the cell can be confirmed by extraction of the cellular lipids and quantification of the MIM by routine methods known in the art, such as mass spectrometry.

Methods for identifying non-lipid based MIMs involve the above-described cell based methods in which a non-lipid based endogenous molecule is exogenously added to the cell. In a preferred embodiment, the non-lipid based endogenous molecule is added to the cell such that the level of the non-lipid based endogenous molecule in the cell is elevated. In one embodiment, the level of the non-lipid based endogenous molecule is elevated by 1.1 fold, 1.2 fold, 1.3 fold, 1.4 fold, 1.5 fold, 1.6 fold, 1.7 fold, 1.8 fold, 1.9 fold, 2.0 fold, 3.0 fold, 4.0 fold, 5.0 fold, 10 fold, 15 fold, 20 fold, 25 fold, 30 fold, 35 fold, 40 fold, 45 fold, 50 fold or greater as compared to the level in an untreated control cell. Formulation and delivery of the non-lipid based molecule to the cell is dependent upon the properties of each molecule tested, but many methods are known in the art. Examples of formulations and modes of delivery of non-lipid based molecules include, but are not limited to, solubilization by co-solvents, carrier molecules, active transport, polymer entrapment or adsorption, polymer grafting, liposomal encapsulation, and formulation with targeted delivery systems. The delivery of the non-lipid based MIM to the cell may be confirmed by extraction of the cellular content and quantification of the MIM by routine methods known in the art, such as mass spectrometry.

2. Epimetabolic Shifters (Epi-Shifters)

As used herein, an "epimetabolic shifter" (epi-shifter) is a molecule (endogenous or exogenous) that modulates the metabolic shift from a healthy (or normal) state to a disease state and vice versa, thereby maintaining or reestablishing cellular, tissue, organ, system and/or host health in a human. Epi-shifters are capable of effectuating normalization in a tissue microenvironment. For example, an epi-shifter includes any molecule which is capable, when added to or depleted from a cell, of affecting the microenvironment (e.g., the metabolic state) of a cell. The skilled artisan will appreciate that an epi-shifter of the invention is also intended to encompass a mixture of two or more molecules, wherein the mixture is characterized by one or more of the foregoing functions. The molecules in the mixture are present at a ratio such that the mixture functions as an epi-shifter. Examples of epi-shifters include, but are not limited to, coQ-10; vitamin D3; ECM components such as fibronectin; immunomodulators, such as TNFa or any of the interleukins, e.g., IL-5, IL-12, IL-23; angiogenic factors; and apoptotic factors.

In some embodiments, the epi-shifter is an enzyme, such as an enzyme that either directly participates in catalyzing one or more reactions in the Krebs Cycle, or produces a Krebs Cycle intermediate, the excess of which drive the Krebs Cycle. In some embodiments, the enzyme is an enzyme of the non-oxidative phase of the pentose phosphate pathway, such as transaldolase, or transketolase. In other embodiments, the enzyme is a component enzyme or enzyme complex that facilitates the Krebs Cycle, such as a synthase or a ligase. Exemplary enzymes include succinyl CoA synthase (Krebs Cycle enzyme) or pyruvate carboxylase (a ligase that catalyzes the reversible carboxylation of pyruvate to form oxaloacetate (OAA), a Krebs Cycle intermediate).

In some embodiments, the epi-shifter is a building block of CoQ10. Building blocks of CoQ10 include, but are not limited to, phenylalanine, tyrosine, 4-hydroxyphenylpyruvate, phenylacetate, 3-methoxy-4-hydroxymandelate, vanillic acid, 4-hydroxybenzoate, mevalonic acid, farnesyl, 2,3-dimethoxy-5-methyl-p-benzoquinone, as well as the corresponding acids or ions thereof. In some embodiments, the epi-shifter is selected from phenylalanine, tyrosine, 4-hydroxyphenylpyruvate, phenylacetate and 4-hydroxybenzoate.

In some embodiments, the epi-shifter is a compound in the Vitamin B family. Compounds in the vitamin B family include, for example, riboflavin (vitamin B2), or analogs thereof. Epi-shifters also include any analogs or pro-drugs that may be metabolized in vivo to any of the endogenous MIMs, such as those described herein.

In one embodiment, the epi-shifter also is a MIM. In one embodiment, the epi-shifter is not CoQ10. Epi-shifters can be routinely identified by one of skill in the art using any of the assays described in detail herein.

(i) Methods of Identifying Epi-Shifters

Epimetabolic shifters (epi-shifter) are molecules capable of modulating the metabolic state of a cell, e.g., inducing a metabolic shift from a healthy (or normal) state to a disease state and vice versa, and are thereby capable of maintaining or reestablishing cellular, tissue, organ, system and/or host health in a human. Epi-shifters of the invention thus have utility in the diagnostic evaluation of a diseased state. Epi-shifters of the invention have further utility in therapeutic applications, wherein the application or administration of the epi-shifter (or modulation of the epi-shifter by other therapeutic molecules) effects a normalization in a tissue microenvironment and the disease state.

The identification of an epimetabolic shifter involves, generally, establishing a molecular profile, e.g., of metabolites, lipids, proteins or RNAs (as individual profiles or in combination), for a panel of cells or tissues that display differential disease states, progression, or aggressiveness A molecule from the profile(s) for which a change in level (e.g., an increased or decreased level) correlates to the disease state, progression or aggressiveness is identified as a potential epi-shifter.

In one embodiment, an epi-shifter is also a MIM. Potential epi-shifters may be evaluated for their ability to enter cells upon exogenous addition to a cell by using any number of routine techniques known in the art, and by using any of the methods described herein. For example, entry of the potential epi-shifter into a cell may be confirmed by extraction of the cellular content and quantification of the potential epi-shifter by routine methods known in the art, such as mass spectrometry. A potential epi-shifter that is able to enter a cell is thereby identified as a MIM.

To identify an epi-shifter, a potential epi-shifter is next evaluated for the ability to shift the metabolic state of a cell. The ability of a potential epi-shifters to shift the metabolic state of the cell microenvironment is evaluated by introducing (e.g., exogenously adding) to a cell a potential epi-shifter and monitoring in the cell one or more of: changes in gene expression (e.g., changes in mRNA or protein expression), concentration changes in lipid or metabolite levels, changes in bioenergetic molecule levels, changes in cellular energetics, and/or changes in mitochondrial function or number. Potential epi-shifters capable of shifting the metabolic state of the cell microenvironment can be routinely identified by one of skill in the art using any of the assays described in detail herein. Potential epi-shifters are further evaluated for the ability to shift the metabolic state of a diseased cell towards a normal healthy state (or conversely, for the ability to shift the metabolic state of a normal cell towards a diseased state). A potential epi-shifter capable of shifting the metabolic state of a diseased cell towards a normal healthy state (or of shifting the metabolic state of healthy normal cell towards a diseased state) is thus identified as an Epi-shifter. In a preferred embodiment, the epi-shifter does not negatively impact the health and/or growth of normal cells.

Epimetabolic shifters of the invention include, but are not limited to, small molecule metabolites, lipid-based molecules, and proteins and RNAs. To identify an epimetabolic shifter in the class of small molecule endogenous metabolites, metabolite profiles for a panel of cells or tissues that display differential disease states, progression, or aggressiveness are established. The metabolite profile for each cell or tissue is determined by extracting metabolites from the cell or tissue and then identifying and quantifying the metabolites using routine methods known to the skilled artisan, including, for example, liquid-chromatography coupled mass spectrometry or gas-chromatography couple mass spectrometry methods. Metabolites for which a change in level (e.g., an increased or decreased level) correlates to the disease state, progression or aggressiveness, are identified as potential epi-shifters.

To identify epimetabolic shifters in the class of endogenous lipid-based molecules, lipid profiles for a panel of cells or tissues that display differential disease states, progression, or aggressiveness are established. The lipid profile for each cell or tissue is determined by using lipid extraction methods, followed by the identification and quantitation of the lipids using routine methods known to the skilled artisan, including, for example, liquid-chromatography coupled mass spectrometry or gas-chromatography couple mass spectrometry methods. Lipids for which a change in level (e.g., an increase or decrease in bulk or trace level) correlates to the disease state, progression or aggressiveness, are identified as potential epi-shifters.

To identify epimetabolic shifters in the class of proteins and RNAs, gene expression profiles for a panel of cells or tissues that display differential disease states, progression, or aggressiveness are established. The expression profile for each cell or tissue is determined at the mRNA and/or protein level(s) using standard proteomic, mRNA array, or genomic array methods, e.g., as described in detail herein. Genes for which a change in expression (e.g., an increase or decrease in expression at the mRNA or protein level) correlates to the disease state, progression or aggressiveness, are identified as potential epi-shifters.

Once the molecular profiles described above are established (e.g., for soluble metabolites, lipid-based molecules, proteins, RNAs, or other biological classes of composition), cellular and biochemical pathway analysis is carried out to elucidate known linkages between the identified potential epi-shifters in the cellular environment. This information obtained by such cellular and/or biochemical pathway analysis may be utilized to categorize the pathways and potential epi-shifters.

The utility of an Epi-shifter to modulate a disease state can be further evaluated and confirmed by one of skill in the art using any number of assays known in the art or described in detail herein. The utility of an Epi-shifter to modulate a disease state can be evaluated by direct exogenous delivery of the Epi-shifter to a cell or to an organism. The utility of an Epi-shifter to modulate a disease state can alternatively be evaluated by the development of molecules that directly modulate the Epi-shifter (e.g., the level or activity of the Epi-shifter). The utility of an Epi-shifter to modulate a disease state can also be evaluated by the development of molecules that indirectly modulate the Epi-shifter (e.g., the level or activity of the Epi-shifter) by regulating other molecules, such as genes (e.g., regulated at the RNA or protein level), placed in the same pathway as the Epi-shifter.

The Epimetabolomic approach described herein facilitates the identification of endogenous molecules that exist in a cellular microenvironment and the levels of which are sensed and controlled through genetic, mRNA, or protein-based mechanisms. The regulation response pathways found in normal cells that are triggered by an Epi-shifter of the invention may provide a therapeutic value in a misregulated or diseased cellular environment. In addition, the epimetabolic approach described herein identifies epi-shifters that may provide a diagnostic indication for use in clinical patient selection, a disease diagnostic kit, or as a prognostic indicator.

II. Assays Useful for Identifying MIMs/Epi-Shifters

Techniques and methods of the present invention employed to separate and identify molecules and compounds of interest include but are not limited to: liquid chromatography (LC), high-pressure liquid chromatography (HPLC), mass spectroscopy (MS), gas chromatography (GC), liquid chromatography/mass spectroscopy (LC-MS), gas chromatography/mass spectroscopy (GC-MS), nuclear magnetic resonance (NMR), magnetic resonance imaging (MRI), Fourier Transform InfraRed (FT-IR), and inductively coupled plasma mass spectrometry (ICP-MS). It is further understood that mass spectrometry techniques include, but are not limited to, the use of magnetic-sector and double focusing instruments, transmission quadrapole instruments, quadrupole ion-trap instruments, time-of-flight instruments (TOF), Fourier transform ion cyclotron resonance instruments (FT-MS) and matrix-assisted laser desorption/ionization time-of-flight mass spectrometry (MALDI-TOF MS).

Quantification of Bioenergetic Molecule Levels:

Environmental influencers (e.g., MIMs or Epi-shifters) may be identified by changes in cellular bioenergetic molecule levels (e.g., ATP, pyruvate, ADP, NADH, NAD, NADPH, NADP, acetylCoA, FADH2) of cells to which a candidate epi-shifter has been applied. Exemplary assays of bioenergetic molecule levels use colorometric, fluorescence, and/or bioluminescent-based methods. Examples of such assays are provided below.

Levels of ATP within cells can be measured with a number of assays and systems known in the art. For example, in one system, cytoplasmic ATP released from lysed cells reacts with luciferin and the enzyme luciferase to produce light. This bioluminescence is measured by a bioluminometer and the intracellular ATP concentration of the lysed cells can be calculated (EnzyLight™ ATP Assay Kit (EATP-100), BioAssay Systems, Hayward, Calif.). In another system, for example, both ATP and its dephosphorylated form, ADP, are calculated via bioluminescence; after ATP levels are calculated, ADP is transformed into ATP and then detected and calculated using the same luciferase system (ApoSENSOR™ ADP/ATP Ratio Assay Kit, BioVision Inc., Mountain View, Calif.).

Pyruvate is an important intermediate in cellular metabolic pathways. Pyruvate may be converted into carbohydrate via gluconeogenesis, converted into fatty acid or metabolized via acetyl CoA, or converted into alanine or ethanol, depending upon the metabolic state of a cell. Thus detection of pyruvate levels provides a measure of the metabolic activity and state of a cell sample. One assay to detect pyruvate, for example, uses both a colorimetric and fluorimetric to detect pyruvate concentrations within different ranges (EnzyChrom™ Pyruvate Assay Kit (Cat #EPYR-100), BioAssay Systems, Hayward, Calif.).

Environmental influencers (e.g., MIMs or Epi-shifters) may influence the process of oxidative phosphorylation carried out by mitochondria in cells, which are involved in the generation and maintenance of bioenergetic molecules in cells. In addition to assays that detect changes in cellular energetics in cell cultures and samples directly (described below), assays exist that detect and quantify the effects of compounds on discrete enzymes and complexes of mitochondria in cells. For example, the MT-OXC MitoTox™ Complete OXPHOS Activity Assay (MitoSciences Inc., Eugene, Oreg.) can detect and quantify the effects of compounds applied directly to complexes I to V extracted from mitochondria. Assays for the detection and quantification of effects on individual mitochondrial complexes such as NADH dehydrogenase (Complex I), cytochrome c oxidase (Complex IV) and ATP synthase (Complex V) are also available (MitoSciences Inc., Eugene, Oreg.).

Measurement of Cellular Energetics:

Environmental influencers (e.g., MIMs or Epi-shifters) may also be identified by changes in cellular energetics. One example of the measurement of cellular energetics are the real-time measures of the consumption of molecular oxygen and/or the change in pH of the media of a cell culture. For example, the ability of a potential epi-shifter to modulate the metabolic state of a cell may be analyzed using, for example, the XF24 Analyzer (Seahorse, Inc.). This technology allows for real time detection of oxygen and pH changes in a monolayer of cells in order to evaluate the bioenergetics of a cell microenvironment. The XF24 Analyzer measures and compares the rates of oxygen consumption (OCR), which is a measure of aerobic metabolism, and extracellular acidification (ECAR), which is a measure of glycolysis, both key indicators of cellular energetics.

Measurement of Oxidative Phosphorylation and Mitochondrial Function

Oxidative Phosphorylation is a process by which ATP is generated via the oxidation of nutrient compounds, carried out in eukaryotes via protein complexes embedded in the membranes of mitochondria. As the primary source of ATP in the cells of most organisms, changes in oxidative phosphorylation activity can strongly alter metabolism and energy balance within a cell. In some embodiments of the invention, environmental influencers (e.g., MIMs or Epi-shifters) may be detected and/or identified by their effects on oxidative phosphorylation. In some embodiments, environmental influencers (e.g., MIMs or Epi-shifters) may be detected and/or identified by their effects on specific aspects of oxidative phosphorylation, including, but not limited to, the electron transport chain and ATP synthesis.

The membrane-embedded protein complexes of the mitochrondria that carry out processes involved in oxidative phosphorylation perform specific tasks and are numbered I, II, III and IV. These complexes, along with the trans-inner membrane ATP synthase (also known as Complex V), are the key entities involved in the oxidative phosphorylation process. In addition to assays that can examine the effects of environmental influencers (e.g., MIMs or Epi-shifters) on mitochondrial function in general and the oxidative phosphorylation process in particular, assays are available that can be used to examine the effects of an epi-shifter on an individual complex separately from other complexes.

Complex I, also known as NADH-coenzyme Q oxidoreductase or NADH dehydrogenase, is the first protein in the electron transport chain. In some embodiments, the detection and quantification of the effect of an epi-shifter on the production of $NAD^+$ by Complex I may be performed. For example, the complex can be immunocaptured from a sample in a 96-well plate; the oxidation of NADH to $NAD^+$ takes place concurrently with the reduction of a dye molecule which has an increased absorbance at 450 nM (Complex I Enzyme Activity Microplate Assay Kit, MitoSciences Inc., Eugene, Oreg.).

Complex IV, also known as cytochrome c oxidase (COX), is the last protein in the electron transport chain. In some embodiments, the detection and quantification of the effect of an epi-shifter on the oxidation of cytochrome c and the reduction of oxygen to water by Complex IV may be performed. For example, COX can be immunocaptured in a microwell plate and the oxidation of COX measured with a colorimetric assay (Complex IV Enzyme Activity Microplate Assay Kit, MitoSciences Inc., Eugene, Oreg.).

The final enzyme in the oxidative phosphorylation process is ATP synthase (Complex V), which uses the proton gradient created by the other complexes to power the synthesis of ATP from ADP. In some embodiments, the detection and quantification of the effect of an epi-shifter on the activity of ATP synthase may be performed. For example, both the activity of ATP synthase and the amount of ATP synthase in a sample may be measured for ATP synthase that has been immunocaptured in a microwell plate well. The enzyme can also function as an ATPase under certain conditions, thus in this assay for ATP synthase activity, the rate at which ATP is reduced to ADP is measured by detecting the simultaneous oxidation of NADH to $NAD^+$. The amount of ATP is calculated using a labeled antibody to ATPase (ATP synthase Duplexing (Activity+Quantity) Microplate Assay Kit, MitoSciences Inc., Eugene, Oreg.). Additional assays for oxidative phosphorylation include assays that test for effects on the activity of Complexes II and III. For example, the MT-OXC MitoTox™ Complete OXPHOS System (MitoSciences Inc., Eugene, Oreg.) can be used to evaluate effects of a compound on Complex II and III as well as Complex I, IV and V, to provide data on the effects of a compound on the entire oxidative phosphorylation system.

As noted above, real-time observation of intact cell samples can be made using probes for changes in oxygen consumption and pH in cell culture media. These assays of cell energetics provide a broad overview of mitochondrial function and the effects of potential environmental influencers (e.g., MIMs or Epi-shifters) on the activity of mitochondria within the cells of the sample.

Environmental influencers (e.g., MIMs or Epi-shifters) may also affect mitochondrial permeability transition (MPT), a phenomena in which the mitochondrial membranes experience an increase in permeability due to the formation of mitochondrial permeability transition pores (MPTP). An increase in mitochondrial permeability can lead to mitochondrial swelling, an inability to conduct oxidative phosphorylation and ATP generation and cell death. MPT may be involved with induction of apoptosis. (See, for example, Halestrap, A. P., Biochem. Soc. Trans. 34:232-237 (2006) and Lena, A. et al. Journal of Translational Med. 7:13-26 (2009), hereby incorporated by reference in their entirety.)

In some embodiments, the detection and quantification of the effect of an environmental influencer (e.g., MIM or epi-shifter) on the formation, discontinuation and/or effects of MPT and MPTPs are measured. For example, assays can detect MPT through the use of specialized dye molecules (calcein) that are localized within the inner membranes of mitochondria and other cytosolic compartments. The application of another molecule, $CoCl_2$, serves to squelch the fluorescence of the calcein dye in the cytosol. $CoCl_2$ cannot access, however, the interior of the mitochondria, thus the calcein fluorescence in the mitochondria is not squelched unless MPT has occurred and $CoCl_2$ can access the interior of the mitochondra via MPTPs. Loss of mitochondrial-specific fluorescence signals that MPT has occurred. Flow cytometry can be used to evaluate cellular and organelle fluorescence (MitoProbe™ Transition Pore Assay Kit, Molecular Probes, Eugene, Oreg.). Additional assays utilize a fluorescence microscope for evaluating experimental results (Image-iT™ LIVE Mitochondrial Transition Pore Assay Kit, Molecular Probes, Eugene, Oreg.).

Measurement of Cellular Proliferation and Inflammation

In some embodiments of the invention, environmental influencers (e.g., MIMs or Epi-shifters) may be identified and evaluated by their effects on the production or activity of molecules associated with cellular proliferation and/or inflammation. These molecules include, but are not limited to, cytokines, growth factors, hormones, components of the extra-cellular matrix, chemokines, neuropeptides, neurotransmitters, neurotrophins and other molecules involved in cellular signaling, as well as intracellular molecules, such as those involved in signal transduction.

Vascular endothelial growth factor (VEGF) is a growth factor with potent angiogenic, vasculogenic and mitogenic properties. VEGF stimulates endothelial permeability and swelling and VEGF activity is implicated in numerous diseases and disorders, including rheumatoid arthritis, metastatic cancer, age-related macular degeneration and diabetic retinopathy.

In some embodiments of the invention, an environmental influencer (e.g., MIM or Epi-shifter) may be identified and characterized by its effects on the production of VEGF. For example, cells maintained in hypoxic conditions or in conditions mimicking acidosis will exhibit increased VEGF production. VEGF secreted into media can be assayed using an ELISA or other antibody-based assays, using available anti-VEGF antibodies (R&D Systems, Minneapolis, Minn.). In some embodiments of the invention, an Epi-shifter may be identified and/or characterized based on its effect(s) on the responsiveness of cells to VEGF and/or based on its effect(s) on the expression or activity of the VEGF receptor.

Implicated in both healthy immune system function as well as in autoimmune diseases, tumor necrosis factor (TNF) is a key mediator of inflammation and immune system activation. In some embodiments of the invention, an Epi-shifter may be identified and characterized by its effects on the production or the activity of TNF. For example, TNF produced by cultured cells and secreted into media can be quantified via ELISA and other antibody-based assays known in the art. Furthermore, in some embodiments an environmental influencer may be identified and characterized by its effect(s) on the expression of receptors for TNF (Human TNF RI Duoset, R&D Systems, Minneapolis, Minn.).

The components of the extracellular matrix (ECM) play roles in both the structure of cells and tissues and in signaling processes. For example, latent transforming growth factor beta binding proteins are ECM components that create a reservoir of transforming growth factor beta (TGFβ) within the ECM. Matrix-bound TGFβ can be released later during the process of matrix remodeling and can exert growth factor effects on nearby cells (Dallas, S. Methods in Mol. Biol. 139:231-243 (2000)).

In some embodiments, an environmental influencer (e.g., MIM or Epi-shifter) may be identified or characterized by its effect(s) on the creation of ECM by cultured cells. Researchers have developed techniques with which the creation of ECM by cells, as well as the composition of the ECM, can be studied and quantified. For example, the synthesis of ECM by cells can be evaluated by embedding the cells in a hydrogel before incubation. Biochemical and other analyses are performed on the ECM generated by the cells after cell harvest and digestion of the hydrogel (Strehin, I. and Elisseeff, J. Methods in Mol. Bio. 522:349-362 (2009)).

In some embodiments, the effect of environmental influencer (e.g., MIM or epi-shifter) on the production, status of or lack of ECM or one of its components in an organism may be identified or characterized. Techniques for creating conditional knock-out (KO) mice have been developed that allow for the knockout of particular ECM genes only in discrete types of cells or at certain stages of development (Brancaccio, M. et al. Methods in Mol Bio. 522:15-50 (2009)). The effect of the application or administration of an epi-shifter or potential epi-shifter on the activity or absence of a particular ECM component in a particular tissue or at a particular stage of development may thus be evaluated.

Measurement of Plasma Membrane Integrity and Cell Death

Environmental influencers (e.g., MIMs or Epi-shifters) may be identified by changes in the plasma membrane integrity of a cell sample and/or by changes in the number or percentage of cells that undergo apoptosis, necrosis or cellular changes that demonstrate an increased or reduced likelihood of cell death.

An assay for lactate dehydrogenase (LDH) can provide a measurement of cellular status and damage levels. LDH is a stable and relatively abundant cytoplasmic enzyme. When plasma membranes lose physical integrity, LDH escapes to the extracellular compartment. Higher concentrations of LDH correlate with higher levels of plasma membrane damage and cell death. Examples of LDH assays include assays that use a colorimetric system to detect and quantify levels of LDH in a sample, wherein the reduced form of a tetrazolium salt is produced via the activity of the LDH enzyme (QuantiChrom™ Lactate Dehydrogenase Kit (DLDH-100), BioAssay Systems, Hayward, Calif.; LDH Cytotoxicity Detection Kit, Clontech, Mountain View, Calif.).

Apoptosis is a process of programmed cell death that may have a variety of different initiating events. A number of assays can detect changes in the rate and/or number of cells that undergo apoptosis. One type of assay that is used to detect and quantify apoptosis is a capase assay. Capases are aspartic acid-specific cysteine proteases that are activated via proteolytic cleavage during apoptosis. Examples of assays that detect activated capases include PhiPhiLux® (OncoImmunin, Inc., Gaithersburg, Md.) and Caspase-Glo® 3/7 Assay Systems (Promega Corp., Madison, Wis.). Additional assays that can detect apoptosis and changes in the percentage or number of cells undergoing apoptosis in comparative samples include TUNEL/DNA fragmentation assays. These assays detect the 180 to 200 base pair DNA fragments generated by nucleases during the execution phase of apoptosis. Exemplary TUNEL/DNA fragmentation assays include the In Situ Cell Death Detection Kit (Roche Applied Science, Indianapolis, Ind.) and the DeadEnd™ Colorimetric and Fluorometric TUNEL Systems (Promega Corp., Madison, Wis.).

Some apoptosis assays detect and quantify proteins associated with an apoptotic and/or a non-apoptotic state. For example, the MultiTox-Fluor Multiplex Cytotoxicity Assay (Promega Corp., Madison, Wis.) uses a single substrate, fluorimetric system to detect and quantify proteases specific to live and dead cells, thus providing a ratio of living cells to cells that have undergone apoptosis in a cell or tissue sample.

Additional assays available for detecting and quantifying apoptosis include assays that detect cell permeability (e.g., APOPercentage™ APOPTOSIS Assay, Biocolor, UK) and assays for Annexin V (e.g., Annexin V-Biotin Apoptosis Detection Kit, BioVision Inc., Mountain View, Calif.).

III. Uses of the Invention

The invention provides methods for diagnosing oncological disorders. The methods of the present invention can be practiced in conjunction with any other method used by the skilled practitioner to prognose the recurrence of an oncologic disorder and/or the survival of a subject being treated for an oncologic disorder. For example, the methods of the invention may be performed in conjunction with a morphological or cytological analysis of the sample obtained from the subject. Cytological methods would include immunohistochemical or immunofluorescence detection (and quantitation if appropriate) of any other molecular marker either by itself, in conjunction with other markers, and/or in conjunction with the Shc markers. Other methods would include detection of other markers by in situ PCR, or by extracting tissue and quantitating other markers by real time PCR. PCR is defined as polymerase chain reaction.

Methods for assessing the efficacy of a treatment regimen, e.g., chemotherapy, radiation therapy, surgery, hormone therapy, or any other therapeutic approach useful for treating an oncologic disorder in a subject are also provided. In these methods the amount of marker in a pair of samples (a first sample not subjected to the treatment regimen and a second sample subjected to at least a portion of the treatment regimen) is assessed.

The invention also provides a method for determining whether an oncologic disorder is aggressive. The method comprises determining the amount of marker present in a cell and comparing the amount to a control amount of marker present in a control sample, defined in Definitions, thereby determining whether an oncologic disorder is aggressive.

The methods of the invention may also be used to select a compound that is capable of modulating, i.e., decreasing, the aggressiveness of an oncologic disorder. In this method, a cancer cell is contacted with a test compound, and the ability of the test compound to modulate the expression and/or activity of a marker in the invention in the cancer cell is determined, thereby selecting a compound that is capable of modulating aggressiveness of an oncologic disorder.

Using the methods described herein, a variety of molecules, particularly including molecules sufficiently small to be able to cross the cell membrane, may be screened in order to identify molecules which modulate, e.g., increase the expression and/or activity of a marker of the invention. Compounds so identified can be provided to a subject in order to inhibit the aggressiveness of an oncologic disorder in the subject, to prevent the recurrence of an oncologic disorder in the subject, or to treat an oncologic disorder in the subject.

IV. Markers of the Invention

The invention relates to markers (hereinafter "biomarkers", "markers" or "markers of the invention"), which are listed in Tables 2-4 & 6-29. The invention provides nucleic acids and proteins that are encoded by or correspond to the markers (hereinafter "marker nucleic acids" and "marker proteins," respectively). These markers are particularly useful in screening for the presence of an oncologic disorder, in assessing aggressiveness and metastatic potential of an oncologic disorder, assessing whether a subject is afflicted with an oncological disorder, identifying a composition for treating an oncological disorder, assessing the efficacy of an environmental influencer compound for treating an oncological disorder, monitoring the progression of an oncological disorder, prognosing the aggressiveness of an oncological disorder, prognosing the survival of a subject with an oncological disorder, prognosing the recurrence of an oncological disorder and prognosing whether a subject is predisposed to developing an oncological disorder.

In some embodiments of the present invention, one or more biomarkers is used in connection with the methods of the present invention. As used herein, the term "one or more biomarkers" is intended to mean that at least one biomarker in a disclosed list of biomarkers is assayed and, in various embodiments, more than one biomarker set forth in the list may be assayed, such as two, three, four, five, ten, twenty, thirty, forty, fifty, more than fifty, or all the biomarkers in the list may be assayed.

A "marker" is a gene whose altered level of expression in a tissue or cell from its expression level in normal or healthy tissue or cell is associated with a disease state, such as an oncologic disorder. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence encoding any of the markers of the invention or the complement of such a sequence. The marker nucleic acids also include RNA comprising the entire or a partial sequence encoding a marker of the invention or the complement of such a sequence, wherein all thymidine residues are replaced with uridine residues. A "marker protein" is a protein encoded by or corresponding to a marker of the invention. A marker protein comprises the entire or a partial sequence of a marker protein. The terms "protein" and "polypeptide' are used interchangeably.

A "marker associated with apoptosis" is a marker involved in an apoptotic pathway. For example, markers associated with apoptosis include, but are not limited to, the markers listed in Tables 6A, 6B, 7-9, 25 and 28. Specifically, markers associated with apoptosis include Bcl-xl, Bcl-xS, BNIP-2, Bcl-2, Birc6, Bcl-2-L11 (Bim), XIAP, BRAF, Bax, c-Jun, Bmf, PUMA, and cMyc.

A "marker associated with oxidative stress" is a marker involved in an oxidative stress pathway. For example, markers associated with oxidative stress include, but are not limited to, the markers listed in Tables 10-12. Specifically, markers associated with oxidative stress include Neutrophil cytosolic factor 2, nitric oxide synthase 2A, and superoxide dismutase 2 (mitochondrial).

A "marker associated with heat shock" is a marker involved in heat shock. For example, markers associated with heat shock include, but are not limited to, the markers listed in Table 13.

A "marker associated with angiogenesis" is a marker involved in an angiogenesis pathway. For example, markers associated with angiogenesis include, but are not limited to, the markers listed in Tables 24 and 27.

An "oncological disorder-associated" body fluid is a fluid which, when in the body of a patient, contacts or passes through oncological cells or into which cells or proteins shed from oncological cells are capable of passing. Exemplary oncological disorder-associated body fluids include blood fluids (e.g. whole blood, blood serum, blood having platelets removed therefrom), and are described in more detail below. Many oncological disorder-associated body fluids can have oncological cells therein, particularly when the cells are metastasizing. Cell-containing fluids which can contain oncological cells include, but are not limited to, whole blood, blood having platelets removed therefrom, lymph, prostatic fluid, urine and semen.

The "normal" level of expression of a marker is the level of expression of the marker in cells of a human subject or patient not afflicted with an oncological disorder.

An "over-expression" or "higher level of expression" of a marker refers to an expression level in a test sample that is greater than the standard error of the assay employed to assess expression, and is preferably at least twice, and more preferably three, four, five, six, seven, eight, nine or ten times the expression level of the marker in a control sample (e.g., sample from a healthy subject not having the marker associated disease, i.e., oncological disorder) and preferably, the average expression level of the marker in several control samples.

A "lower level of expression" of a marker refers to an expression level in a test sample that is at least twice, and more preferably three, four, five, six, seven, eight, nine or ten times lower than the expression level of the marker in a control sample (e.g., sample from a healthy subjects not having the marker associated disease, i.e., an oncological disorder) and preferably, the average expression level of the marker in several control samples.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

"Proteins of the invention" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

The invention further provides antibodies, antibody derivatives and antibody fragments which specifically bind with the marker proteins and fragments of the marker proteins of the present invention. Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In some embodiments, the biomarker is involved in apoptosis, e.g., pro- or anti-apoptotic. In some embodiments, the biomarker is an apoptosis related gene. Apoptosis related genes include, for example, the genes listed in Table 24. In some embodiments, the biomarker is a transcription factor. In some embodiments, the biomarker is involved in oxidative stress. In some embodiments, the biomarker is a caspase modulator, e.g., a caspase activator or a caspase inhibitor. In some embodiments, the biomarker is involved in cell growth. In other embodiments, the biomarker is involved in cell cycle regulation and DNA synthesis. In still other embodiments, the biomarker is involved in glycolysis and metabolism, e.g., pentose phosphate pathway and mitochondrial oxidative metabolism. In further embodiments, the biomarker is involved in molecular transport. In some embodiments, the biomarker is involved in cell signaling. In still other embodiments, the biomarker is involved in 14-3-3 mediated signaling. In further embodiments, the biomarker is involved in ceramide signaling. In some embodiments, the biomarker is involved in mitochondrial protein transport. In other embodiments, the biomarker is involved in adipocyte differentiation. In still other embodiments, the biomarker is involved in lipid and cholesterol metabolism. In further embodiments, the biomarker is involved in angiogenesis. In some embodiments, the biomarker is involved in membrane fluidity. In other embodiments, the biomarker is involved in immunomodulation. In still other embodiments, the biomarker is involved in genomic stability. In further embodiments, the biomarker is involved in extracellular matrix protein integrity. In some embodiments, the biomarker is involved in membrane transport. In other embodiments, the biomarker is involved in oxidative control. In some embodiments, the biomarker is involved in the pentose phosphate pathway. In some embodiments, the biomarker is a member of the tumor necrosis factor receptor superfamily. In some embodiments, the biomarker is involved in arachidonic acid metabolism. In some embodiments, the biomarker is involved in two or more of the pathways indicated hereinabove. In some embodiments, the biomarker is involved in three or more, four or more, five or more, etc. of the pathways indicated hereinabove. In some embodiments, more than one biomarker is utilized in connection with the present invention. In these embodiments, the biomarkers may each individually be involved in one or more, two or more, three or more, four or more, five or more, etc. of the pathways indicated hereinabove.

In certain embodiments, where a particular listed gene is associated with more than one treatment conditions, such as at different time periods after a treatment, or treatment by different concentrations of a potential environmental influencer (e.g., CoQ10), the fold change for that particular gene refers to the longest recorded treatment time. In other embodiments, the fold change for that particular gene refers to the shortest recorded treatment time. In other embodiments, the fold change for that particular gene refers to treatment by the highest concentration of env-influencer (e.g., CoQ10). In other embodiments, the fold change for that particular gene refers to treatment by the lowest concentration of env-influencer (e.g., CoQ10). In yet other embodiments, the fold change for that particular gene refers to the modulation (e.g., up- or down-regulation) in a manner that is consistent with the therapeutic effect of the env-influencer.

In certain embodiments, the positive or negative fold change refers to that of any gene listed in any of the Tables 2-4 & 6-29. In certain embodiments, the positive or negative fold change refers to that of any gene listed in any of the Tables 2-4 & 6-29, except for one of the tables (e.g., except for Table 1, except for Table 5, etc.). In certain embodiments, the positive or negative fold change refers to that of any gene listed in any of the Tables 2-4 & 6-29, except for any two of the tables (e.g., except for Tables 1 and 5, except for Table 2 & 16, etc.). In certain embodiments, the positive or negative fold change refers to that of any gene listed in any of the Tables 2-4 & 6-29, except for any three of the tables; or except for any four of the tables; or except for any 5, 6, 7, 8, 9, 10, or more of the tables. In certain embodiments, the positive or negative fold change refers to that of any gene listed in any of the Tables 2-4 & 6-29, except for tables 1, 5, 9, 12.

As used herein, "positive fold change" refers to "up-regulation" or "increase (of expression)" of a gene that is listed in the relevant tables.

As used herein, "negative fold change" refers to "down-regulation" or "decrease (of expression)" of a gene that is listed in the relevant tables.

Various aspects of the invention are described in further detail in the following subsections.

1. Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. In one embodiment, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. In another embodiment, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule that is substantially free of cellular material includes preparations having less than about 30%, 20%, 10%, or 5% of heterologous nucleic acid (also referred to herein as a "contaminating nucleic acid").

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a marker protein, and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a variant marker protein that contain changes in amino acid residues that are not essential for activity. Such variant marker proteins differ in amino acid sequence from the naturally-occurring marker proteins, yet retain biological activity. In one embodiment, such a variant marker protein has an amino acid sequence that is at least about 40% identical, 50%, 60%, 70%, 80%, 90%, 91%, 92%, 93%, 94%, 95%, 96%, 97%, 98% or 99% identical to the amino acid sequence of a marker protein.

An isolated nucleic acid molecule encoding a variant marker protein can be created by introducing one or more nucleotide substitutions, additions or deletions into the nucleotide sequence of marker nucleic acids, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded marker cDNA molecule or complementary to a marker mRNA sequence. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a marker protein. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a marker protein to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into an oncological disorder-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a marker protein can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a marker of the invention can be inhibited by targeting nucleotide sequences complementary to the regulatory region of the gene encoding the marker nucleic acid or protein (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

2. Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences comprising a sequence encoding any of the makers listed in Tables 2-4, 6-29 and 64-69. Other useful proteins are substantially identical (e.g., at least about 40%, preferably 50%, 60%, 70%, 80%, 90%, 91%, 92%, 93%, 94%, 95%, 96%, 97%, 98% or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. Preferably, the percent identity between the two sequences is calculated using a global alignment. Alternatively, the percent identity between the two sequences is calculated using a local alignment. The percent identity between the two sequences is a function of the number of identical positions shared by the sequences (i.e., % identity=# of identical positions/total # of positions (e.g., overlapping positions)×100). In one embodiment the two sequences are the same length. In another embodiment, the two sequences are not the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See http://www.ncbi.nlm.nih.gov. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins comprising a marker protein or a segment thereof. As used herein, a "chimeric protein" or "fusion protein" comprises all or part (preferably a biologically active part) of a marker protein operably linked to a heterologous polypeptide (i.e., a polypeptide other than the marker protein). Within the fusion protein, the term "operably linked" is intended to indicate that the marker protein or segment thereof and the heterologous polypeptide are fused in-frame to each other. The heterologous polypeptide can be fused to the amino-terminus or the carboxyl-terminus of the marker protein or segment.

One useful fusion protein is a GST fusion protein in which a marker protein or segment is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a marker protein can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a marker protein is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a marker protein Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a marker protein in a subject, to purify ligands and in screening assays to identify molecules which inhibit the interaction of the marker protein with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of marker proteins. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to marker proteins, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a protein of interest, such as a marker protein or a segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the marker proteins. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a marker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of segments of a marker protein can be used to generate a variegated population of polypeptides for screening and subsequent selection of variant marker proteins or segments thereof. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized protein or peptide. The preparation can further include an adjuvant, such as Freund's complete or incomplete adjuvant, or a similar immunostimulatory agent. Preferred immunogen compositions are those that contain no other human proteins such as, for example, immunogen compositions made using a non-human host cell for recombinant expression of a protein of the invention. In such a manner, the resulting antibody compositions have reduced or no binding of human proteins other than a protein of the invention.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof.

Polyclonal antibodies can be prepared by immunizing a suitable subject with a protein of the invention as an immunogen The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) Nature 256:495-497, the human B cell hybridoma technique (see Kozbor et al., 1983, Immunol. Today 4:72), the EBV-hybridoma technique (see Cole et al., pp. 77-96 In Monoclonal Antibodies and Cancer Therapy, Alan R. Liss, Inc., 1985) or trioma techniques. The technology for producing hybridomas is well known (see generally Current Protocols in Immunology, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734.

The invention also provides recombinant antibodies that specifically bind a protein of the invention. In preferred embodiments, the recombinant antibodies specifically binds a marker protein or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptide. They can be produced by techniques known in the art, for example using methods described in Ladner et. al U.S. Pat. No. 4,946,778 (which is incorporated herein by reference in its entirety); Bird et al., (1988) Science 242:423-426; Whitlow et al., (1991) Methods in Enzymology 2:1-9; Whitlow et al., (1991) Methods in Enzymology 2:97-105; and Huston et al., (1991) Methods in Enzymology Molecular Design and Modeling: Concepts and Applications 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) Proc. Natl. Acad. Sci. USA 90:6444-6448; Whitlow et al., (1994) Protein Eng. 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) Int. Rev. Immunol. 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

In a preferred embodiment, the substantially purified antibodies of the invention may specifically bind to a signal peptide, a secreted sequence, an extracellular domain, a transmembrane or a cytoplasmic domain or cytoplasmic membrane of a protein of the invention. In a particularly preferred embodiment, the substantially purified antibodies of the invention specifically bind to a secreted sequence or an extracellular domain of the amino acid sequences of a protein of the invention. In a more preferred embodiment, the substantially purified antibodies of the invention specifically bind to a secreted sequence or an extracellular domain of the amino acid sequences of a marker protein.

An antibody directed against a protein of the invention can be used to isolate the protein by standard techniques, such as affinity chromatography or immunoprecipitation. Moreover, such an antibody can be used to detect the marker protein or fragment thereof (e.g., in a cellular lysate or cell supernatant) in order to evaluate the level and pattern of expression of the marker. The antibodies can also be used diagnostically to monitor protein levels in tissues or body fluids (e.g. in an oncological disorder-associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention may also be used as therapeutic agents in treating cancers. In a preferred embodiment, completely human antibodies of the invention are used for therapeutic treatment of human cancer patients, particularly those having a cancer. In another preferred embodiment, antibodies that bind specifically to a marker protein or fragment thereof are used for therapeutic treatment. Further, such therapeutic antibody may be an antibody derivative or immunotoxin comprising an antibody conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugated antibodies of the invention can be used for modifying a given biological response, for the drug moiety is not to be construed as limited to classical chemical therapeutic agents. For example, the drug moiety may be a protein or polypeptide possessing a desired biological activity. Such proteins may include, for example, a toxin such as ribosome-inhibiting protein (see Better et al., U.S. Pat. No. 6,146,631, the disclosure of which is incorporated herein in its entirety), abrin, ricin A, pseudomonas exotoxin, or diphtheria toxin; a protein such as tumor necrosis factor, .alpha.-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Accordingly, in one aspect, the invention provides substantially purified antibodies, antibody fragments and derivatives, all of which specifically bind to a protein of the invention and preferably, a marker protein. In various embodiments, the substantially purified antibodies of the invention, or fragments or derivatives thereof, can be human, non-human, chimeric and/or humanized antibodies. In another aspect, the invention provides non-human antibodies, antibody fragments and derivatives, all of which specifically bind to a protein of the invention and preferably, a marker protein. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies. In still a further aspect, the invention provides monoclonal antibodies, antibody fragments and derivatives, all of which specifically bind to a protein of the invention and preferably, a marker protein. The monoclonal antibodies can be human, humanized, chimeric and/or non-human antibodies.

The invention also provides a kit containing an antibody of the invention conjugated to a detectable substance, and instructions for use. Still another aspect of the invention is a pharmaceutical composition comprising an antibody of the invention. In one embodiment, the pharmaceutical composition comprises an antibody of the invention and a pharmaceutically acceptable carrier.

3. Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing an oncological disorder. Such assays can be used for prognostic or predictive purposes to thereby prophylactically treat an individual prior to the onset of the disorder.

Yet another aspect of the invention pertains to monitoring the influence of agents (e.g., drugs or other compounds administered either to inhibit an oncological disorder or to treat or prevent any other disorder {i.e. in order to understand any carcinogenic effects that such treatment may have}) on the expression or activity of a marker of the invention in clinical trials. These and other agents are described in further detail in the following sections.

A. Diagnostic Assays

An exemplary method for detecting the presence or absence of a marker protein or nucleic acid in a biological sample involves obtaining a biological sample (e.g. an oncological disorder-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a marker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S, and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from non-cancer cells. The choice of the cell source is dependent on the use of the relative expression level. Using expression found in normal tissues as a mean expression score aids in validating whether the marker assayed is cancer specific (versus normal cells). In addition, as more data is accumulated, the mean expression value can be revised, providing improved relative expression values based on accumulated data. Expression data from cancer cells provides a means for grading the severity of the cancer state.

In another embodiment of the present invention, a marker protein is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether cells express a marker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cancer cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a marker protein or nucleic acid in a biological sample. Such kits can be used to determine if a subject is suffering from or is at increased risk of developing an oncological disorder. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

B. Pharmacogenomics

The markers of the invention are also useful as pharmacogenomic markers. As used herein, a "pharmacogenomic marker" is an objective biochemical marker whose expression level correlates with a specific clinical drug response or susceptibility in a patient (see, e.g., McLeod et al. (1999) *Eur. J. Cancer* 35(12): 1650-1652). The presence or quantity of the pharmacogenomic marker expression is related to the predicted response of the patient and more particularly the patient's oncological disorder to therapy with a specific drug or class of drugs. By assessing the presence or quantity of the expression of one or more pharmacogenomic markers in a patient, a drug therapy which is most appropriate for the patient, or which is predicted to have a greater degree of success, may be selected. For example, based on the presence or quantity of RNA or protein encoded by specific tumor markers in a patient, a drug or course of treatment may be selected that is optimized for the treatment of the specific tumor likely to be present in the patient. The use of pharmacogenomic markers therefore permits selecting or designing the most appropriate treatment for each cancer patient without trying different drugs or regimes.

Another aspect of pharmacogenomics deals with genetic conditions that alters the way the body acts on drugs. These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

C. Monitoring Clinical Trials

Monitoring the influence of agents (e.g., drug compounds) on the level of expression of a marker of the invention can be applied not only in basic drug screening, but also in clinical trials. For example, the effectiveness of an agent to affect marker expression can be monitored in clinical trials of subjects receiving treatment for an oncological disorder. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased expression of the marker gene(s) during the course of treatment may indicate ineffective dosage and the desirability of increasing the dosage. Conversely, decreased expression of the marker gene(s) may indicate efficacious treatment and no need to change dosage.

D. Arrays

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of an oncological disorder, progression of an oncological disorder, and processes, such a cellular transformation associated with an oncological disorder.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

V. Methods for Obtaining Samples

Samples useful in the methods of the invention include any tissue, cell, biopsy, or bodily fluid sample that expresses a marker of the invention. In one embodiment, a sample may be a tissue, a cell, whole blood, serum, plasma, buccal scrape, saliva, cerebrospinal fluid, urine, stool, or bronchoalveolar lavage. In preferred embodiments, the tissue sample is an oncological disorder sample, including a tumor sample.

Body samples may be obtained from a subject by a variety of techniques known in the art including, for example, by the use of a biopsy or by scraping or swabbing an area or by using a needle to aspirate bodily fluids. Methods for collecting various body samples are well known in the art.

Tissue samples suitable for detecting and quantitating a marker of the invention may be fresh, frozen, or fixed according to methods known to one of skill in the art. Suitable tissue samples are preferably sectioned and placed on a microscope slide for further analyses. Alternatively, solid samples, i.e., tissue samples, may be solubilized and/or homogenized and subsequently analyzed as soluble extracts.

In one embodiment, a freshly obtained biopsy sample is frozen using, for example, liquid nitrogen or difluorodichloromethane. The frozen sample is mounted for sectioning using, for example, OCT, and serially sectioned in a cryostat. The serial sections are collected on a glass microscope slide. For immunohistochemical staining the slides may be coated with, for example, chrome-alum, gelatine or poly-L-lysine to ensure that the sections stick to the slides. In another embodiment, samples are fixed and embedded prior to sectioning. For example, a tissue sample may be fixed in, for example, formalin, serially dehydrated and embedded in, for example, paraffin.

Once the sample is obtained any method known in the art to be suitable for detecting and quantitating a marker of the invention may be used (either at the nucleic acid or at the protein level). Such methods are well known in the art and include but are not limited to western blots, northern blots, southern blots, immunohistochemistry, ELISA, e.g., amplified ELISA, immunoprecipitation, immunofluorescence, flow cytometry, immunocytochemistry, mass spectrometrometric analyses, e.g., MALDI-TOF and SELDI-TOF, nucleic acid hybridization techniques, nucleic acid reverse transcription methods, and nucleic acid amplification methods. In particular embodiments, the expression of a marker of the invention is detected on a protein level using, for example, antibodies that specifically bind these proteins.

Samples may need to be modified in order to make a marker of the invention accessible to antibody binding. In a particular aspect of the immunocytochemistry or immunohistochemistry methods, slides may be transferred to a pretreatment buffer and optionally heated to increase antigen accessibility. Heating of the sample in the pretreatment buffer rapidly disrupts the lipid bi-layer of the cells and makes the antigens (may be the case in fresh specimens, but not typically what occurs in fixed specimens) more accessible for antibody binding. The terms "pretreatment buffer" and "preparation buffer" are used interchangeably herein to refer to a buffer that is used to prepare cytology or histology samples for immunostaining, particularly by increasing the accessibility of a marker of the invention for antibody binding. The pretreatment buffer may comprise a pH-specific salt solution, a polymer, a detergent, or a nonionic or anionic surfactant such as, for example, an ethyloxylated anionic or nonionic surfactant, an alkanoate or an alkoxylate or even blends of these surfactants or even the use of a bile salt. The pretreatment buffer may, for example, be a solution of 0.1% to 1% of deoxycholic acid, sodium salt, or a solution of sodium laureth-13-carboxylate (e.g., Sandopan LS) or and ethoxylated anionic complex. In some embodiments, the pretreatment buffer may also be used as a slide storage buffer.

Any method for making marker proteins of the invention more accessible for antibody binding may be used in the practice of the invention, including the antigen retrieval methods known in the art. See, for example, Bibbo, et al. (2002) *Acta. Cytol.* 46:25-29; Saqi, et al. (2003) *Diagn. Cytopathol.* 27:365-370; Bibbo, et al. (2003) *Anal. Quant. Cytol. Histol.* 25:8-11, the entire contents of each of which are incorporated herein by reference.

Following pretreatment to increase marker protein accessibility, samples may be blocked using an appropriate blocking agent, e.g., a peroxidase blocking reagent such as hydrogen peroxide. In some embodiments, the samples may be blocked using a protein blocking reagent to prevent non-specific binding of the antibody. The protein blocking reagent may comprise, for example, purified casein. An antibody, particularly a monoclonal or polyclonal antibody that specifically binds to a marker of the invention is then incubated with the sample. One of skill in the art will appreciate that a more accurate prognosis or diagnosis may be obtained in some cases by detecting multiple epitopes on a marker protein of the invention in a patient sample. Therefore, in particular embodiments, at least two antibodies directed to different epitopes of a marker of the invention are used. Where more than one antibody is used, these antibodies may be added to a single sample sequentially as individual antibody reagents or simultaneously as an antibody cocktail. Alternatively, each individual antibody may be added to a separate sample from the same patient, and the resulting data pooled.

Techniques for detecting antibody binding are well known in the art. Antibody binding to a marker of the invention may be detected through the use of chemical reagents that generate a detectable signal that corresponds to the level of antibody binding and, accordingly, to the level of marker protein expression. In one of the immunohistochemistry or immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Enzymes of particular interest include, but are not limited to, horseradish peroxidase (HRP) and alkaline phosphatase (AP).

In one particular immunohistochemistry or immunocytochemistry method of the invention, antibody binding to a marker of the invention is detected through the use of an HRP-labeled polymer that is conjugated to a secondary antibody. Antibody binding can also be detected through the use of a species-specific probe reagent, which binds to monoclonal or polyclonal antibodies, and a polymer conjugated to HRP, which binds to the species specific probe reagent. Slides are stained for antibody binding using any chromagen, e.g., the chromagen 3,3-diaminobenzidine (DAB), and then counterstained with hematoxylin and, optionally, a bluing agent such as ammonium hydroxide or TBS/Tween-20. Other suitable chromagens include, for example, 3-amino-9-ethylcarbazole (AEC). In some aspects of the invention, slides are reviewed microscopically by a cytotechnologist and/or a pathologist to assess cell staining, e.g., fluorescent staining (i.e., marker expression). Alternatively, samples may be reviewed via automated microscopy or by personnel with the assistance of computer software that facilitates the identification of positive staining cells.

Detection of antibody binding can be facilitated by coupling the anti-marker antibodies to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, $^{14}C$, or $^{3}H$.

In one embodiment of the invention frozen samples are prepared as described above and subsequently stained with antibodies against a marker of the invention diluted to an appropriate concentration using, for example, Tris-buffered saline (TBS). Primary antibodies can be detected by incubating the slides in biotinylated anti-immunoglobulin. This signal can optionally be amplified and visualized using diaminobenzidine precipitation of the antigen. Furthermore, slides can be optionally counterstained with, for example, hematoxylin, to visualize the cells.

In another embodiment, fixed and embedded samples are stained with antibodies against a marker of the invention and counterstained as described above for frozen sections. In addition, samples may be optionally treated with agents to amplify the signal in order to visualize antibody staining. For example, a peroxidase-catalyzed deposition of biotinyl-tyramide, which in turn is reacted with peroxidase-conjugated streptavidin (Catalyzed Signal Amplification (CSA) System, DAKO, Carpinteria, Calif.) may be used.

Tissue-based assays (i.e., immunohistochemistry) are the preferred methods of detecting and quantitating a marker of the invention. In one embodiment, the presence or absence of a marker of the invention may be determined by immunohistochemistry. In one embodiment, the immunohistochemical analysis uses low concentrations of an anti-marker antibody such that cells lacking the marker do not stain. In another embodiment, the presence or absence of a marker of the invention is determined using an immunohistochemical method that uses high concentrations of an anti-marker antibody such that cells lacking the marker protein stain heavily. Cells that do not stain contain either mutated marker and fail to produce antigenically recognizable marker protein, or are cells in which the pathways that regulate marker levels are dysregulated, resulting in steady state expression of negligible marker protein.

One of skill in the art will recognize that the concentration of a particular antibody used to practice the methods of the invention will vary depending on such factors as time for binding, level of specificity of the antibody for a marker of the invention, and method of sample preparation. Moreover, when multiple antibodies are used, the required concentration may be affected by the order in which the antibodies are applied to the sample, e.g., simultaneously as a cocktail or sequentially as individual antibody reagents. Furthermore, the detection chemistry used to visualize antibody binding to a marker of the invention must also be optimized to produce the desired signal to noise ratio.

In one embodiment of the invention, proteomic methods, e.g., mass spectrometry, are used for detecting and quantitating the marker proteins of the invention. For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) Expert Rev Mol Diagn 2:549; Li, J., et al. (2002) Clin Chem 48:1296; Laronga, C., et al. (2003) Dis Markers 19:229; Petricoin, E. F., et al. (2002) 359:572; Adam, B. L., et al. (2002) Cancer Res 62:3609; Tolson, J., et al. (2004) Lab Invest 84:845; Xiao, Z., et al. (2001) Cancer Res 61:6029) can be used to detect and quantitate the PY-Shc and/or p66-Shc proteins. Mass spectrometric methods are described in, for example, U.S. Pat. Nos. 5,622,824, 5,605,798 and 5,547,835, the entire contents of each of which are incorporated herein by reference.

In other embodiments, the expression of a marker of the invention is detected at the nucleic acid level. Nucleic acid-based techniques for assessing expression are well known in the art and include, for example, determining the level of marker mRNA in a sample from a subject. Many expression detection methods use isolated RNA. Any RNA isolation technique that does not select against the isolation of mRNA can be utilized for the purification of RNA from cells that express a marker of the invention (see, e.g., Ausubel et al., ed., (1987-1999) Current Protocols in Molecular Biology (John Wiley & Sons, New York). Additionally, large numbers of tissue samples can readily be processed using techniques well known to those of skill in the art, such as, for example, the single-step RNA isolation process of Chomczynski (1989, U.S. Pat. No. 4,843,155).

The term "probe" refers to any molecule that is capable of selectively binding to a marker of the invention, for example, a nucleotide transcript and/or protein. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the marker mRNA. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to marker genomic DNA.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in detecting the level of marker mRNA.

An alternative method for determining the level of marker mRNA in a sample involves the process of nucleic acid amplification, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, marker expression is assessed by quantitative fluorogenic RT-PCR (i.e., the TaqMan™ System). Such methods typically utilize pairs of oligonucleotide primers that are specific for a marker of the invention. Methods for designing oligonucleotide primers specific for a known sequence are well known in the art.

The expression levels of a marker of the invention may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of marker expression may also comprise using nucleic acid probes in solution.

In one embodiment of the invention, microarrays are used to detect the expression of a marker of the invention. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

The amounts of phosphorylated marker, and/or a mathematical relationship of the amounts of a marker of the invention may be used to calculate the risk of recurrence of an oncologic disorder in a subject being treated for an oncologic disorder, the survival of a subject being treated for an oncological disorder, whether an oncologic disorder is aggressive, the efficacy of a treatment regimen for treating an oncologic disorder, and the like, using the methods of the invention, which may include methods of regression analysis known to one of skill in the art. For example, suitable regression models include, but are not limited to CART (e.g., Hill, T, and Lewicki, P. (2006) "STATISTICS Methods and Applications" StatSoft, Tulsa, Okla.), Cox (e.g., www.evidence-based-medicine.co.uk), exponential, normal and log normal (e.g., www.obgyn.cam.ac.uk/mrg/statsbook/stsurvan.html), logistic (e.g., www.en.wikipedia.org/wiki/Logistic_regression or http://faculty.chass.ncsu.edu/garson/PA765/logistic.htm), parametric, non-parametric, semi-parametric (e.g., www.socserv.mcmaster.ca/jfox/Books/Companion), linear (e.g., www.en.wikipedia.org/wiki/Linear_regression or http://www.curvefit.com/linear_regression.htm), or additive (e.g., www.en.wikipedia.org/wiki/Generalized_additive_model or http://support.sas.com/rnd/app/da/new/dagam.html).

In one embodiment, a regression analysis includes the amounts of phosphorylated marker. In another embodiment, a regression analysis includes a marker mathematical relationship. In yet another embodiment, a regression analysis of the amounts of phosphorylated marker, and/or a marker mathematical relationship may include additional clinical and/or molecular co-variates. Such clinical co-variates include, but are not limited to, nodal status, tumor stage, tumor grade, tumor size, treatment regime, e.g., chemotherapy and/or radiation therapy, clinical outcome (e.g., relapse, disease-specific survival, therapy failure), and/or clinical outcome as a function of time after diagnosis, time after initiation of therapy, and/or time after completion of treatment.

In another embodiment, the amounts of phosphorylated marker, and/or a mathematical relationship of the amounts of a marker may be used to calculate the risk of recurrence of an oncologic disorder in a subject being treated for an oncologic disorder, the survival of a subject being treated for an oncologic disorder, whether an oncologic disorder is aggressive, the efficacy of a treatment regimen for treating an oncologic disorder, and the like, using the methods of the invention, which may include methods of regression analysis known to one of skill in the art. For example, suitable regression models include, but are not limited to CART (e.g., Hill, T, and Lewicki, P. (2006) "STATISTICS Methods and Applications" StatSoft, Tulsa, Okla.), Cox (e.g., www.evidence-based-medicine.co.uk), exponential, normal and log normal (e.g., www.obgyn.cam.ac.uk/mrg/statsbook/stsurvan.html), logistic (e.g., www.en.wikipedia.org/wiki/Logistic_regression or http://faculty.chass.ncsu.edu/garson/PA765/logistic.htm), parametric, non-parametric, semi-parametric (e.g., www.socserv.mcmaster.ca/jfox/Books/Companion), linear (e.g., www.en.wikipedia.org/wiki/Linear_regression or http://www.curvefit.com/linear_regression.htm), or additive (e.g., www.en.wikipedia.org/wiki/Generalized_additive_model or http://support.sas.com/rnd/app/da/new/dagam.html).

In one embodiment, a regression analysis includes the amounts of phosphorylated marker. In another embodiment, a regression analysis includes a marker mathematical relationship. In yet another embodiment, a regression analysis of the amounts of phosphorylated marker, and/or a marker mathematical relationship may include additional clinical and/or molecular co-variates. Such clinical co-variates include, but are not limited to, nodal status, tumor stage, tumor grade, tumor size, treatment regime, e.g., chemotherapy and/or radiation therapy, clinical outcome (e.g., relapse, disease-specific survival, therapy failure), and/or clinical outcome as a function of time after diagnosis, time after initiation of therapy, and/or time after completion of treatment.

VI. Kits

The invention also provides compositions and kits for prognosing an oncologic disorder, recurrence of an oncologic disorder, or survival of a subject being treated for an oncologic disorder. These kits include one or more of the following: a detectable antibody that specifically binds to a marker of the invention, a detectable antibody that specifically binds to a marker of the invention, reagents for obtaining and/or preparing subject tissue samples for staining, and instructions for use.

The kits of the invention may optionally comprise additional components useful for performing the methods of the invention. By way of example, the kits may comprise fluids (e.g., SSC buffer) suitable for annealing complementary nucleic acids or for binding an antibody with a protein with which it specifically binds, one or more sample compartments, an instructional material which describes performance of a method of the invention and tissue specific controls/ standards.

VII. Screening Assays

Targets of the invention include, but are not limited to, the genes subsequently listed in Tables 1-28 herein. Based on the results of experiments described by Applicants herein, the key proteins modulated by Q10 are associated with or can be classified into different pathways or groups of molecules, including transcription factors, apoptotic response, pentose phosphate pathway, biosynthetic pathway, oxidative stress (pro-oxidant), membrane alterations, and oxidative phosphorylation metabolism. The key proteins modulated by CoQ10, based on the results provided herein, are summarized as follows. A key protein modulated by CoQ10 and which is a transcription factor is HNF4alpha. Key proteins that are modulated by CoQ10 and associated with the apoptotic response include Bcl-xl, Bcl-xl, Bcl-xS, BNIP-2, Bcl-2, Birc6, Bcl-2-L11 (Bim), XIAP, BRAF, Bax, c-Jun, Bmf, PUMA, and cMyc. A key protein that is modulated by CoQ10 and associated with the pentose phosphate pathway is transaldolase 1. Key proteins that are modulated by CoQ10 and associated with a biosynthetic pathway include COQ1, COQ3, COQ6, prenyltransferase and 4-hydroxybenzoate. Key proteins that are modulated by CoQ10 and associated with oxidative stress (pro-oxidant) include Neutrophil cytosolic factor 2, nitric oxide synthase 2A and superoxide dismutase 2 (mitochondrial). Key proteins that are modulated by CoQ10 and associated with oxidative phosphorylation metabolism include Cytochrome c, complex I, complex II, complex III and complex IV. Further key proteins that are directly or indirectly modulated by CoQ10 include Foxo 3a, DJ-1, IDH-1, Cpt1C and Cam Kinase II.

Accordingly, in one embodiment of the invention, a marker may include HNF4-alpha, Bcl-xl, Bcl-xS, BNIP-2, Bcl-2, Birc6, Bcl-2-L11 (Bim), XIAP, BRAF, Bax, c-Jun, Bmf, PUMA, cMyc, transaldolase 1, COQ1, COQ3, COQ6, prenyltransferase, 4-hydrobenzoate, neutrophil cytosolic factor 2, nitric oxide synthase 2A, superoxide dismutase 2, VDAC, Bax channel, ANT, Cytochrome c, complex 1, complex II, complex III, complex IV, Foxo 3a, DJ-1, IDH-1, Cpt1C and Cam Kinase II. In a preferred embodiment, a marker may include HNF4A, Transaldolase, NM23 and BSCv. In one embodiment, the marker is TNF4A. In one embodiment, the marker is transaldolase. In one embodiment, the marker is NM23. In one embodiment, the marker is BSCv. Screening assays useful for identifying modulators of identified markers are described below.

The invention also provides methods (also referred to herein as "screening assays") for identifying modulators, i.e., candidate or test compounds or agents (e.g., proteins, peptides, peptidomimetics, peptoids, small molecules or other drugs), which modulate the aggressiveness of a cancer cell by modulating the expression and/or activity of a marker of the invention. Such assays typically comprise a reaction between a marker of the invention and one or more assay components. The other components may be either the test compound itself, or a combination of test compounds and a natural binding partner of a marker of the invention. Compounds identified via assays such as those described herein may be useful, for example, for modulating, e.g., inhibiting, ameliorating, treating, or preventing aggressiveness of a cancer cell.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

The screening methods of the invention comprise contacting a cancer cell with a test compound and determining the ability of the test compound to modulate the expression and/ or activity of a marker of the invention in the cell. The expression and/or activity of a marker of the invention can be determined as described herein.

In another embodiment, the invention provides assays for screening candidate or test compounds which are substrates of a marker of the invention or biologically active portions thereof. In yet another embodiment, the invention provides assays for screening candidate or test compounds which bind to a marker of the invention or biologically active portions thereof. Determining the ability of the test compound to directly bind to a marker can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{131}I$, $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

This invention further pertains to novel agents identified by the above-described screening assays. Accordingly, it is within the scope of this invention to further use an agent identified as described herein in an appropriate animal model. For example, an agent capable of modulating the expression and/or activity of a marker of the invention identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment as described above.

This invention is further illustrated by the following examples which should not be construed as limiting. The contents of all references and published patents and patent applications cited throughout the application are hereby incorporated by reference.

EXEMPLIFICATION OF THE INVENTION

Example 1

Identification of CoQ10 as a MIM

In order to evaluate CoQ10 as a potential MIM, CoQ10 in oxidized form was exogenously added to a panel of cell lines, including both cancer cell lines and normal control cell lines, and the changes induced to the cellular microenvironment profile for each cell line in the panel were assessed. Changes to cell morphology/physiology, and to cell composition, including both mRNA and protein levels, were evaluated and compared for the diseased cells as compared to normal cells. The results of these experiments identified CoQ10 and, in particular, the oxidized form of CoQ10, as a MIM.

In a first set of experiments, changes to cell morphology/physiology were evaluated by examining the sensitivity and apoptotic response of cells to CoQ10. A panel of skin cell lines including a control cell lines (primary culture of keratinocytes and melanocytes) and several skin cancers cell lines (SK-MEL-28, a non-metastatic skin melanoma; SK-MEL-2, a metastatic skin melanoma; or SCC, a squamous cell carcinoma; PaCa2, a pancreatic cancer cell line; or HEP-G2, a liver cancer cell line) were treated with various levels of Coenzyme Q10. The results of these experiments demonstrated that the cancer cell lines exhibited an altered dose dependent response as compared to the control cell lines, with an induction of apoptosis and cell death in the cancer cells only. Exemplary experiments are described in detail in Example 3 below.

Assays were next employed to assess changes in the composition of the cell following treatment with CoQ10. Changes in gene expression at the mRNA level were analyzed using Real-Time PCR array methodology. Exemplary experiments are described in detail in Examples 6 and 9-13 below. In complementary experiments, changes in gene expression at the protein level were analyzed by using antibody microarray methodology, 2-dimensional gel electrophoresis followed by protein identificuation using mass spectrometry characterization, and by western blot analysis. Exemplary experiments are described in detail below in Examples 4, 7 and 8, respectively. The results from these assays demonstrated that significant changes in gene expression, both at the mRNA and protein levels, were induced in the cell lines examined due to the addition of the oxidized form of CoQ10. Genes modulated by CoQ10 treatment were found to be clustered into several cellular pathways, including apoptosis, cancer biology and cell growth, glycolysis and metabolism, molecular transport, and cellular signaling.

Experiments were carried out to confirm the entry of CoQ10 into cells and to determine the level and form of CoQ10 present in the cells. In particular, the level of Coenzyme Q10, as well as the form of CoQ10 (i.e., oxidized or reduced), present in the mitochondria was determined by analyzing mitochondrial enriched preparations from cells treated with CoQ10. The level of Coenzyme Q10 present in the mitochondria was confirmed to increase in a time and dose dependent manner with the addition of exogenous Q10. In a surprising and unexpected result, CoQ10 was determined to be present in the mitochondria primarily in oxidized form. In addition, changes in levels of proteins from mitochondria enriched samples were analyzed by using 2-D gel electrophoresis and protein identification by mass spectrometry characterization. The results from these experiments demonstrated that the levels of the oxidized form of CoQ10 in the mitochondria over the time course examined correlated with a wide variety of cellular changes, as evidenced by the modulation of mRNA and protein levels for specific proteins related to metabolic and apoptotic pathways. Exemplary experiments are described in detail in Example 5 below.

The results described by Applicants herein identified the endogenous molecule CoQ10 and, in particular, the oxidized form of CoQ10, as a MIM. For example, the results identified CoQ10 as a MIM, since CoQ10 was observed to induce changes in gene expression at both the mRNA and protein level. The results identified CoQ10 as having multidimentional character, since CoQ10 induced differential changes in cell morphology/physiology and cell composition (e.g., differential changes in gene expression at both the mRNA and protein level), in a disease state (e.g., cancer) as compared to a normal (e.g., non-cancerous) state. Moreover, the results identified CoQ10 as having multidimensional character in that CoQ10 was capable of entering a cell, and thus exhibited both therapeutic and carrier effects.

Example 2

Methods for Identifying Disease Relevant Processes and Biomarkers for Oncological Disorders From the cell based assays in which cell lines were treated with a molecule of interest, the differences in treated vs non-treated cells is evaluated by mRNA arrays, protein antibody arrays, and 2D gel electrophoresis. The proteins identified from comparative sample analysis to be modulated by the MIM or Epi-shifter, are evaluated from a Systems Biology perspective with pathway analysis (Ingenuity IPA software) and a review of the known literature. Proteins identified as potential therapeutic or biomarker targets are submitted to confirmatory assays such as Western blot analysis, siRNA knock-down, or recombinant protein production and characterization methods.

Materials and Methods for Examples 3-8
Coenzyme Q10 Stock

A 500 μM Coenzyme Q10 (5% isopropanol in cell growth media) was prepared as follows. A 10 mL 500 μM Coenzyme Q10 stock was made fresh every time. Molecular Weight: 863.34

(0.0005 mol/L)(0.010 L)(863.34 g/mol)=0.004317 g

To make 10 mL of 500 μM stock, 4.32 mg Coenzyme Q10 was weighted out in a 15 mL falcon tube, and 500 μL isopropanol was added. The solution was warmed in a 50-60° C. water bath while swirling to dissolve completely. To this solution, 9.5 mL of media (the same media in which the cells are grown) was added.

Cell Culture

Cells were obtained from the American Type Culture Collection or Gibco. Cells were grown in DMEM/F-12 media supplemented with 5% fetal bovine serum, 0.25 ug/mL Amphotericin, 100 ug/mL Streptomycin, and 100 U mL-1 penicillin. Cells were maintained in an atmosphere of 95% air and 5% CO2 at 37 degrees C.

Coenzyme Q10 Treatment and Total Protein Isolation

Cells were grown to 85% confluency prior to exposure with Q10. Supplemented media was conditioned with Q10 to 50 and 100 micro molar concentrations. Flasks were treated with control, 50 µM Q10, and 100 µM Q10 in triplicate. Protein was isolated from the treated and control flask after 4, 8, 12, and 24 hours. For isolation of proteins, cells were washed three times with 5 mL of ice cold PBS at a pH of 7.4. The cells were then scraped in 3 mL of PBS, pelleted by centrifuge, and re-suspended in a lysis buffer at pH 7.4 (80 mM TRIS-HCl, 1% SDS, with protease and phosphotase inhibitors). Protein concentrations were quantified using the BCA method.

Cell Lines

The cell lines listed below were propagated and a cell bank established for each. Large scale production of cells for various assays were performed and the material harvested for analysis. In general, when a cell specific media was not required for maintenance of cell lines, the media used for cell growth was DMEMF-12 with 5% serum. Cells were typically grown to 75-80% confluence (clear spacing) prior to splitting and use in cell assays and standard practice methods followed. The following cell lines were established for experiments:

SK-MEL-28 (non-metastatic skin melanoma)
SK-MEL-2 (metastatic skin melanoma)
HEKa (kerantinocytes, skin control)
HEMa (melanocyte, skin control)
nFIB (neonatal fibroblasts)
HEP-G2 (liver cancer) [SBH cell line]
SkBr-3 (breast cancer, Her2 overexpressed)
MCF-7 (breast cancer, p53 mutation)
PC-3 (prostate cancer) [SBH cell line]
SkBr-3 (human breast adenocarcinoma)
NCI-ES-0808
SCC (squamous cell carcinoma)
PaCa-2
NIH-3T3

Cell Culture:

Cells were obtained for the American Type Culture Collection or Gibco. Cells were grown in DMEM/F-12 media supplemented with 5% fetal bovine serum, 0.25 ug/mL Amphotericin, 100 ug/mL Streptomycin, and 100 U mL-1 penicillin. Cells were maintained in an atmosphere of 95% air and 5% CO2 at 37 degrees C.

Skin malignant melanoma SK-MEL28 cells were grown and maintained in DMEM/F12 with Glutamax (Invitrogen, Carlsbad Calif.) supplemented with 5% FBS, amphotericin and penicillin/streptomycin. Cells were grown at 37° C. with 5% CO2. Details of additional cell line and growth conditions are outlined in the table below.

TABLE 1

Cell lines analyzed for sensitivity to Q10.

| Cell Line | Description | Growth Conditions |
| --- | --- | --- |
| PaCa2 | Pancreatic Carcinoma | DMEM/F12 with Glutamax + 10% FBS, 2.5% Horse Serum, amphotericin, penicillin/streptomycin. |
| HepG2 | Hepatocellular Carcinoma | MEM with Earles Salts supplemented with 10% FBS, amphotericin, penicillin/streptomycin, sodium pyruvate and non-essential amino acids. |
| PC3 | Prostate Adenocarcinoma | DMEM/F12 with Glutamax, supplemented with 5% FBS, amphotericin and penicillin/streptomycin. |
| SKBr3 | Breast Cancer | DMEM/F12 with Glutamax supplemented with 5% FBS and amphotericin, penicillin/streptomycin. |

TABLE 1-continued

Cell lines analyzed for sensitivity to Q10.

| Cell Line | Description | Growth Conditions |
| --- | --- | --- |
| MCF-7 | Breast Cancer | DMEM/F12 with Glutamax supplemented with 5% FBS and amphotericin, penicillin/streptomycin. |

Q10 Treatment of SKMEL28 Cells:

SK-MEL28 cells were treated with 100 µM Q10 or the control vehicle. The formulation of the Q10 was as follows. In a 15 mL capped tube, 4.32 mg of Q10 (supplied by Cytotech) was transferred and then dissolved by the addition of 500 µL of isopropanol. The resulting solution was warmed in a 65° C. water bath and vortexed at high speed. The Q10/isopropanol solution was made to a volume of 10 mL with the addition of equilibrated cell culture media. The stock solution was then vortexed to ensure maximum solubility of Q10. The stock solution was diluted (2 mL of stock with 8 mL of media) to obtain a final concentration of 100 µM Q10. For the control vehicle, 9.5 mL of media was added to 500 µL of isopropanol. The control stock was further diluted (2 mL of stock) with 8 mL of media. Cells were harvested 6, 16, 24, 48 or 72 hours after the start of the treatment.

Q10 Treatment of SCC Cells:

SCC cells were treated with 100 µM Q10 (prepared as described above) either for 6 hours or 24 hours. The control cells were untreated cells. Cells were harvested and pelleted at the different times after treatment and the pellets were flash frozen and stored at −80° C. until the RNA was isolated at XTAL as described below.

RNA Isolation:

Cells were lysed for RNA isolation at different treatment times using the RNeasy Mini kit (Qiagen, Inc., Valencia Calif.) kit following the manufacturer's instructions. RNA was quantified by measuring Optical Density at 260 nm.

First Strand Synthesis:

First strand cDNA was synthesized from 1 µg of total RNA using the RT2 First Strand Synthesis kit (SABiosciences, Frederick Md.) as per manufacturer's recommendations.

Real-Time PCR:

Products from the first strand synthesis were diluted with water, mixed with the SYBR green master mix (SABiosciences, Frederick Md.) and loaded onto PCR arrays. Real time PCR was run on the PCR Arrays (Apoptosis Arrays, Diabetes Arrays, Oxidative stress and Antioxidant defense Arrays and Heat Shock Protein Arrays.) (SABiosciences, Frederick Md.) on a Biorad CFX96.

Determining Cell Line Sensitivity to Coenzyme Q10 by Nexin Assay for Apoptosis:

The percentage of cells in early and late apoptosis was quantified following 24 hours of Coenzyme Q10 treatment. Early and late apoptosis was used as a marker to understand the differences in sensitivity of various cancer cell lines to Coenzyme Q10. The different cell lines tested were PaCa2, HepG2, PC-3, SKBr3, MCF-7 and SK-MEL28. Cells were allowed to adhere overnight in 96-well plates. These cells were treated with either control vehicle, 50 µM Q10 or 100 µM Coenzyme Q10. After 24 hours, the presence of apoptotic cells was estimated on a PCA96 flow cytometer (Guava Technologies, Hayward, Calif.). In addition, some cells were treated with 4 µM Staurosporine for 2 hours as a positive control for apoptosis. Cells were first washed with PBS and detached with 50 µL of Accumax (Innovative Cell Technologies, San Diego, Calif.) at room temperature. The dissociation was stopped by addition of culture medium containing 1% Pluronic F-68 (Sigma-Aldrich, St. Louis, Mo.). Then 100 μL of Nexin reagent (Guava Technologies, Hayward, Calif.) was added to each of the wells. After 20 minutes of incubation in the dark, the assay was performed in low binding plates to minimize reattachment of cells to the substrate. The Nexin Reagent contains two dyes. Annexin-V-PE which detects phosphotidyl serine on the outside of a cell; a characteristic of early apoptotic cells. The second dye, 7-AAD permeates only late apoptotic cells while being excluded from live (healthy) and early apoptotic cells. The percentage of four populations of cells; live, early apoptotic, late apoptotic and debris was determined using the Cytosoft 2.5.7 software (Guava Technologies, Hayward, Calif.).

Immunoblotting

Approximately 50 μg of protein were assayed per sample by immunoblotting. All treatments were run in triplicate with controls. Proteins were separated on 12% TRIS-HCl gels, transferred via electrophoresis to nitro-cellulose membranes and blocked using a 5% milk and TBST solution prior to incubation with primary antibodies. The primary antibodies were incubated overnight at 4 degrees C. in a 5% BSA and TBST solution. Secondary antibodies were incubated for one hour at 4 degrees. All antibodies were purchased from Cell Signaling Technology. Antibodies were used at a ratio of 1:1000, with the exception of βActin at a ratio of 1:5000. Blots were developed and results were quantified using the NIH Java based densitometer analysis software Image J. All blots were also probed for and normalized to their respective βActin expression.

Two-Dimensional Electrophoresis

Before isoelectric focusing (IEF), samples were solubilized in 40 mM Tris, 7 M urea, 2 M thiourea, and 1% C7 zwitterionic detergent, reduced with tributylphosphine, and alkylated with 10 mM acrylamide for 90 min at room temperature. After the sample was run through a 10-kDa cutoff Amicon Ultra device with at least 3 volumes of the resuspension buffer, consisting of 7 M urea, 2 M thiourea, and 2% CHAPS to reduce the conductivity of the sample. One hundred micrograms of protein were subjected to IEF on 11-cm pH 3 to 10, pH 4 to 7 or pH 6 to 11 immobilized pH gradient strips (GE, Amersham, USA) to 100,000 volts hour. After IEF, immobilized pH gradient strips were equilibrated in 6 M urea, 2% SDS, 50 mM Tris-acetate buffer, pH 7.0, and 0.01% bromphenol blue and subjected to SDS-polyacrylamide gel electrophoresis on 8 to 16% Tris-HCl Precast Gel, 1 mm (Bio-Rad, USA). The gels were run in duplicate. They were either fixed, stained in SYPRO Ruby, 80 mL/gel (Invitrogen, USA) and imaged on Fuji FLA-5100 laser scanner or transferred onto PVDF membrane.

Additional information was obtained for a control sample to test the utility of protein identification through the use of methods that utilize dPC (Protein Forest Inc.) selective pI fractionation, followed by trypsin digestion of the dPC plug with mass spec identification and semi-quantization (Nanomate or LC/LTQ/MS). The dPC analysis performed with a control sample demonstrated its utility in identifying a large subset of proteins. The materials produced during the studies were archived so that they may be utilized as a resource should the future need arise 2D Gel Image Analysis:

Analysis of all gel images was performed using Progenesis Discovery and Pro (Nonlinear Dynamics Inc., Newcastle upon Tyne, UK). After spot detection, matching, background subtraction, normalization, and filtering, data for SYPRO Ruby gel images was exported. Pairwise comparisons between groups were performed using the Student's t test in Progenesis Discovery to identify spots whose expression was significantly altered ($p>0.05$).

Antibody Array:

An antibody microarray (Panorama XP725 Antibody Array, Sigma) was utilized to screen over 700 protein antibodies to assess changes at the protein concentration level in Q10 treated cells (SK-MEL-28, SCC). The expression of a protein in a cell extract is detected when it is bound by a corresponding antibody spotted on the slide. Prior to binding, the proteins are directly labeled with a fluorescent dye which is used for fluorescent visualization and quantitative analysis. The array is used for comparing protein expression profiles of two samples (test versus reference samples), each labeled with a different CyDye (Cy3 or Cy5) and the two samples are applied simultaneously at equal protein concentrations on the array. Fluorescent signal intensity for each sample is then recorded individually at the wavelength corresponding to the dye label of the sample and compared.

High doses of Coenzyme Q10 regulates expression of genes involved in the apoptotic, diabetic and oxidative stress pathways in cultured SKMEL-28 cells. Experimental details: SKMEL-28 cells (ATCC Catalog #HTB-72) are non metastatic, skin melanoma cells that were cultured in DMEM-F12 containing Glutamax (Invitrogen Cat #10565-042) supplemented with 5% FBS, Penicillin, Streptomycin and Amphotericin, were treated with the vehicle or 100 uM Coenzyme Q10 for varying amounts of time. Any changes in gene expression consequent to Coenzyme Q10 treatment were quantified using Real time PCR Arrays (Apoptosis Cat #PAHS-12, Diabetes Cat #PAHS-023 and Oxidative Stress Cat #PAHS-065). (SABiosciences, Frederick, Md.).

A stock concentration of 500 uM Coenzyme Q10 was prepared by dissolving 4.32 mg in 500 ul of isopropanol which was further diluted to 10 ml by addition of media. Alternate vortexing and heating to 65° C. dissolved the Coenzyme Q10. 2 ml of the stock solution was diluted to 10 ml with media to get a 100 uM Q10 containing media that was used to treat cells. A vehicle was prepared in parallel with a similar protocol except that the Coenzyme Q10 was not added.

SKMEL-28 cells were plated at a density of $1\times10^5$ cells/well in a 6-well plate. After 24 hours, when cells had attached and were at 50% confluence, either the vehicle or 100 uM Q10 was added. Cells were harvested by at 6, 16, 24, 48 or 72 hours after Q10 treatment while the vehicle treated cells were harvested after 24 hours. Cells were lysed for RNA isolation at different treatment times using the RNeasy Mini kit (Qiagen, Inc., Valencia Calif. Cat #74104) kit following the manufacturer's instructions using a spin column and on-column DNase treatment. RNA was quantified by measuring absorbance at 260 nm.

Real time PCR was preceded by first strand cDNA synthesis using 0.4-1 ug of total RNA as the template using the RT2 First Strand Synthesis kit (SABiosciences, Frederick Md. Cat #C-03) with a genomic DNA elimination step as per manufacturer's recommendations. Products from the first strand synthesis were diluted with water, mixed with the SYBR green master mix (SABiosciences, Frederick Md. Cat #PA-010-12) and loaded onto PCR arrays that contain primer assays for 84 different genes linked within a common pathway, 5 housekeeping genes used for normalization, reverse transcription and PCR controls. Real time PCR was run on a Biorad Cfx96. The amplification was initiated with a hot start to activate the enzyme, followed by 40 cycles each of (95° C.-15 second denaturation step and 60° C.-1 minute annealing and extension step) followed by a melting curve program. Ct values, the output from the PCR thermocycler for all treatment groups were organized on an excel spreadsheet and loaded onto the comparative analysis software available at http://www.sabiosciences.com/pcdarrayanalysis.php.

Purification of Mitochondria Enriched Samples:

Experimental details: SKMEL-28, NCI-ES0808 and NIH-3T3 cells that were treated with 100 μM Q10 for 24 or 48 hours along with cells that were harvested at t=0 were harvested by washing and scraping from T160 flasks. Cells were centrifuged, pelleted, flash frozen and stored at −80° C. until the mitochondria were isolated. Cell pellets were thawed, resuspended and ruptured in Dounce homogenizer. The homogenate was centrifuged and mitochondria were isolated using reagents and the protocol recommended by the Mitochondria Isolation kit for Cultured cells (MitoSciences, Eugene Oreg., Cat #MS852). The mitochondrial fraction was aliquoted and stored at −80° C.

Coenzyme Q10 and Ubiquinol-10 Quantification Method:

A method for the simultaneous determination of Coenzyme Q10 (Q10) and the reduced form ubiquinol-10 (Q10H2) was implemented based upon a recently published method (Ruiz-Jimenez, 2007, J. Chromatogr. A, 1175, 242-248) through the use of LC-MS/MS with electrospray ionization (ESI) in the positive ion mode. The highly selective identification and sensitive quantitation of both Q10 and Q10H2 is possible, along with the identification of other selected lipids. An aliquot of the mitochondrial enriched samples from SK-MEL-28 treated with 100 µM Q10 was subjected to a conventional pre-treatment based on protein precipitation (100 µl of packed cells sonicated in 300 µl of 1-propanol), liquid-liquid extraction (add 100 µl of water to supernatant and extract X3 with 200 µl of n-hexane), evaporation of combined hexane extracts to dryness and reconstitution in 50 µl of 95:5 methanol/hexane (v/v). Analysis was by LC-MS/MS on a Waters Quattro II triple quadrupole mass spectrometer with a Prism RP 1×100 mm, 5 µm particle size column (Keystone Scientific). Isocratic elution with 4 mM ammonium formate in 20% isopropyl alcohol 80% methanol at a flow rate of 50 µl/min. Ten µl of each sample was injected. MRM analysis was performed using m/z 882.7>197.00 (Q10H2) and m/z 880.80>197.00 (Q10) transitions with cone voltage of 40 and collision energy of 30.

Example 3

Sensitivity of Cell Lines to CoQ10

A number of cell lines were tested for their sensitivity to Q10 after 24 hours of application by using a reagent (Nexin reagent) that contains a combination of two dyes, 7AAD and Annexin-V-PE. The 7AAD dye will enter into cells with permeabilized cell membranes; primarily those cells that are in late apoptosis. Annexin-V-PE is a dye that binds to Phosphotidyl serine, which is exposed on the outer surface of the plasma membrane in early apoptotic cells. The Nexin reagent thus can be used to differentiate between different populations of apoptotic cells in a flow cytometer.

PaCa2 cells showed an increase in both early and late apoptotic cells (between 5-10% of gated cells) with 50 µM Q10 and 100 µM Q10 after 24 hours of Q10 application. PC-3 cells also showed an increase in both early and late apoptotic population with 50 µM and 100 µM Q10, although the increase was less when compared to PaCa2 cells. MCF-7 and SK-MEL28 cells showed an increase only in early apoptotic population with 50 µM and 100 µM Q10. HepG2 cells were also sensitive to 50 µM Q10 treatment, where there was an increase of about 20% of the gated populated in the late apoptotic and early apoptotic stages. SKBr3 was the only cell line tested that did not show any significant increases of early and late apoptosis with either 50 µM or 100 µM Q10 treatment. The results are depicted in FIGS. 1-6.

Figure 7:
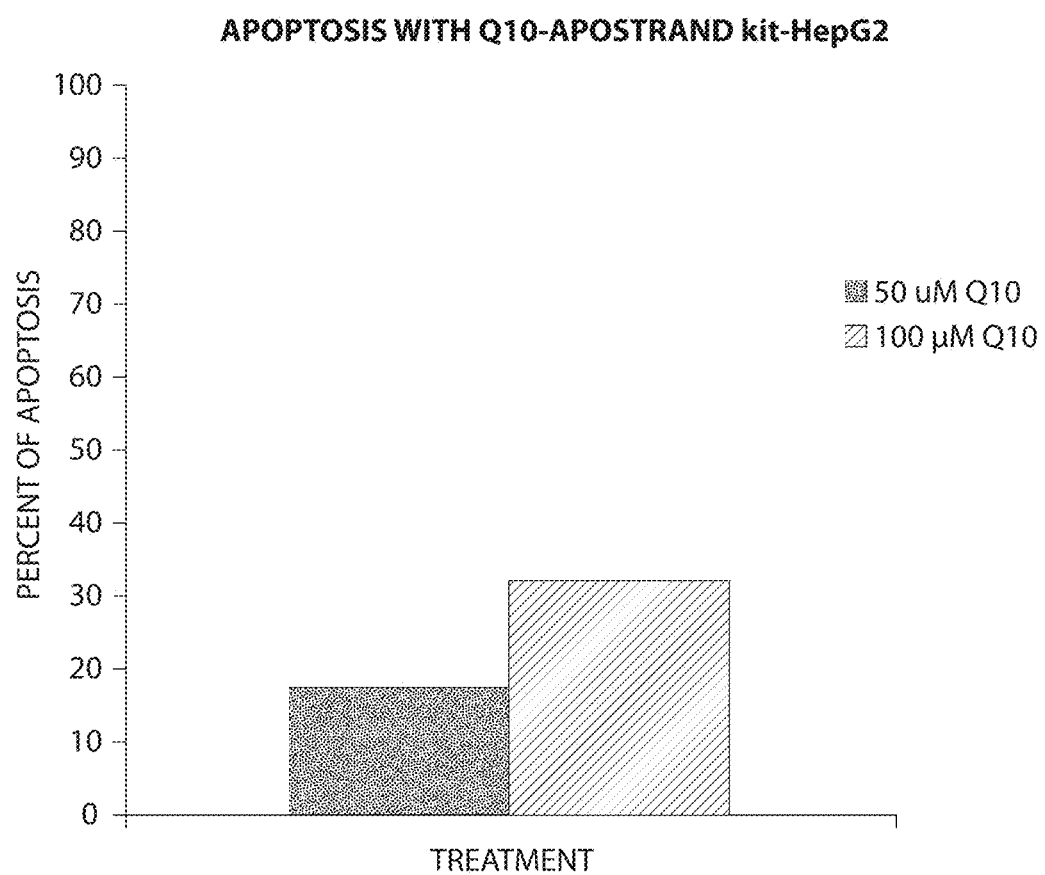
FIG. 7: Measurement of apoptotic cells upon 24 hour treatment with Q10, as measured by Apostrand ELISA method.

To provide additional confirmation that Q10 treatment causes an apoptotic response in HepG2 liver cancer cells, a second apoptosis assay was evaluated using the ApoStrand™ ELISA based method that measures single-stranded DNA. The ApoStrand™ ELISA is based on the sensitivity of DNA in apoptotic cells to formamide denaturation and the detection of the denatured DNA with a monoclonal antibody to single-stranded DNA (ssDNA). Treatment of the liver cancer cell line HepG2 with 50 and 100 µM Q10 resulted in detectable apoptosis, with a dose-response of 17% and 32%, respectively (FIG. 7). These results are consistent with the observation of Q10 inducing apoptosis in other cancer cell lines from other tissues (e.g., SCC, SKMEL-28, MCF-7, and PC-3).

Example 4

Proteomic Analysis of Cells Treated with Q10

Cell pellets of samples treated with Q10 were analyzed using proteomic methods. The cell pellets were lysed and treated for use in 2-D gel and Western blot analysis. Three cell types (SKMEL-28, SCC, and nFib) were treated with Q10 and submitted to proteomic characterization by 2-D gel electrophoresis.

Proteomic Analysis of SKMEL-28 Cells Treated with Q10

The first experimental set processed and evaluated by Western blot and 2-D gel electrophoresis was the skin cancer cell line SKMEL-28. This experimental set involved SK-MEL-28 cells treated at 3, 6, 12, and 24 hours with 0, 50 or 100 µM Q10.

Figure 8:
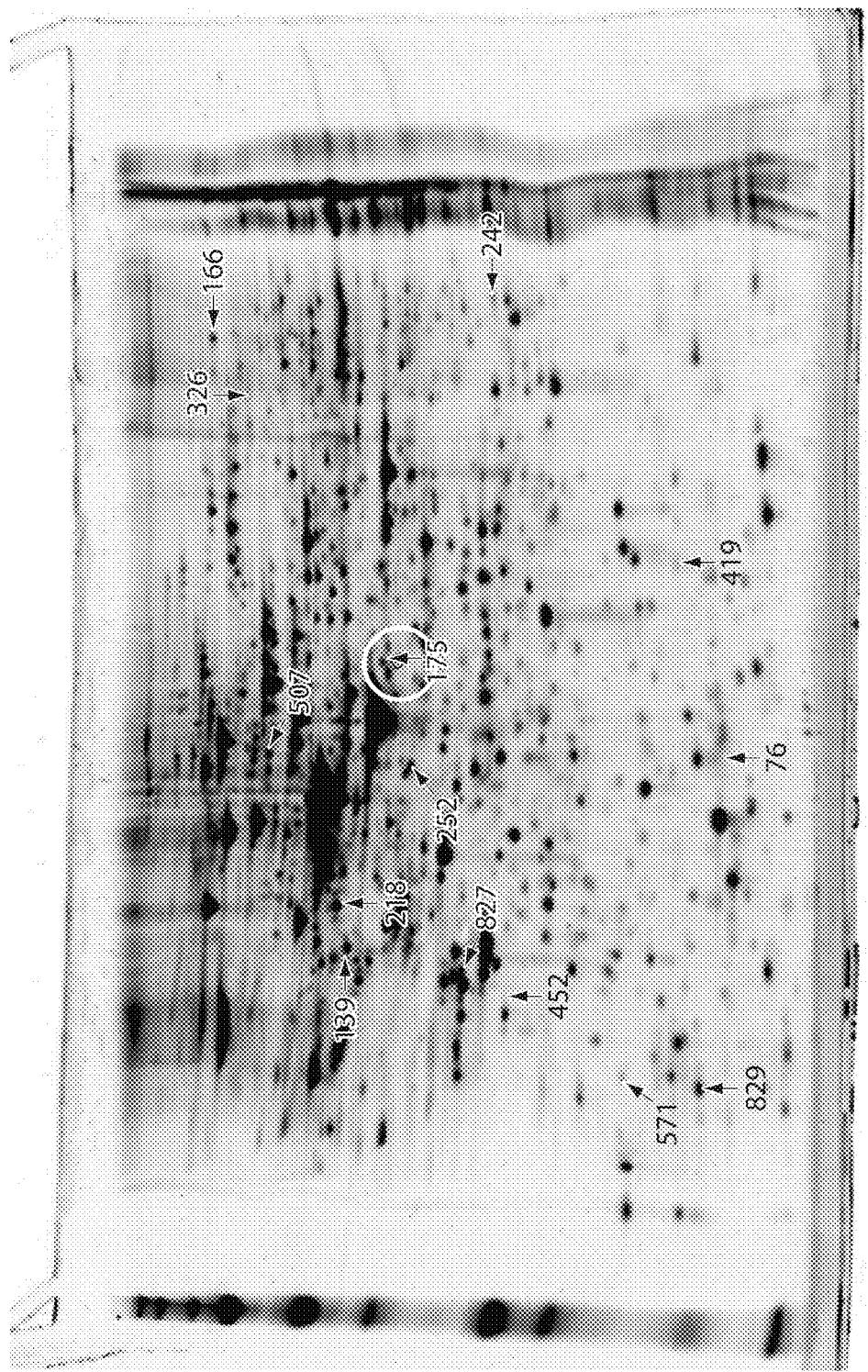
FIG. 8: Example gel analysis of 2-D gel electrophoresis. Spots excised for identification are marked.

The set of Q10 treated SK-MEL-28 samples were subjected to 2-D gel electrophoreses (FIG. 8) and were analyzed to identify protein-level changes relative to the control samples. A comparative analysis of 943 spots across all twenty-four gels was performed, comparing the control sample against all of the treated samples. The analysis included the identification of spot changes over the time course due to increase, decrease, or post-translational modification.

The analysis found thirty-two statistically significant differential spot changes. From this, twenty non-redundant spots were excised and submitted for protein identification by trypsin digestion and mass spectrometry characterization. The characterized peptides were searched against protein databases with Mascot and MSRAT software analysis to identify the protein (Table 2).

TABLE 2

Proteins identified to have a differential response to Q10 treatment in SKMEL-28 cell.

| Time (hr) | Q10 Conc. (uM) | 2D Spot # | Expression | Difference | Protein | Name | Type |
|---|---|---|---|---|---|---|---|
| 3 | 50 | 528 | down | 1.234 | cathepsin D | CTSD | peptidase |
| 3 | 50 | 702 | down | 1.575 | chaperonin containing TCP1, subunit 3 | CCT3 | other |

TABLE 2-continued

Proteins identified to have a differential response to Q10 treatment in SKMEL-28 cell.

| Time (hr) | Q10 Conc. (uM) | 2D Spot # | Expression | Difference | Protein | Name | Type |
|---|---|---|---|---|---|---|---|
| 3 | 50 | 74 | down | 1.383 | eukaryotic translation initiation factor 3 | EIF3G | translation regulator |
| 3 | 50 | 829 | down | 1.074 | Ribosomal protein P2 | RPLP2 | other |
| 3 | 50 | 368 | down | 1.121 | transaldolase 1 | TALDO1 | enzyme |
| 6 | 50 | 452 | up | −1.464 | eukaryotic translation initiation factor 6 | EIF6 | translation regulator |
| 6 | 50 | 175 | up | −1.32 | Stomatin; HSPC322 | STOM | other |
| 6 | 50 | 827 | up | −1.457 | Tyrosine 3/Tryptophan 5-monooxygenase activation protein | YWHAZ | enzyme |
| 6 | 50 | 139 | up | −1.628 | Vimentin | VIM | other |
| 6 | 50 | 218 | up | −1.416 | Vimentin | VIM | other |
| 6 | 50 | 218 | up | −1.212 | Vimentin | VIM | other |
| 6 | 50 | 139 | up | −1.036 | Vimentin | VIM | other |
| 6 | 50 | 507 | down | 1.379 | Lamin B1 | LMNB1 | other |
| 6 | 50 | 571 | down | 1.832 | mitochandrial import receptor Tom22 | TOMM22 | transporter |
| 12 | 50 | 166 | up | −1.171 | ALG-2 interacting protein 1 | PDCD6IP | other |
| 12 | 50 | 550 | up | −1.747 | peptidylprolyl isomerase A | PPIA | enzyme |
| 12 | 50 | 613 | down | 1.802 | galectin-1 | LGALS1 | other |
| 12 | 50 | 242 | down | 1.373 | Phosphoglycerate mutase; Posphomannomutase 2 | PGAM2 | phosphatase |
| 24 | 50 | 326 | down | 1.385 | glycyl-tRNA synthase | GARS | enzyme |
| 24 | 50 | 419 | down | 1.451 | Mago-nashi homolog | MAGOH | other |
| 3 | 100 | 528 | down | −1.036 | cathepsin D | CTSD | peptidase |
| 3 | 100 | 702 | down | 1.151 | chaperonin containing TCP1, subunit 3 | CCT3 | other |
| 3 | 100 | 74 | down | 1.122 | Eukaryotic translation initiation factor 3 | EIF3G | translation regulator |
| 3 | 100 | 829 | down | 1.145 | Ribosomal protein P2 | RPLP2 | other |
| 3 | 100 | 368 | down | 1.209 | transaldolase 1 | TALDO1 | enzyme |
| 6 | 100 | 139 | up | −1.829 | Vimentin | VIM | other |
| 6 | 100 | 218 | up | −1.761 | Vimentin | VIM | other |
| 6 | 100 | 452 | down | 1.134 | eukaryotic translation initiation factor 6 | EIF6 | translation regulator |
| 6 | 100 | 252 | down | 1.4 | Sec 13 protein, Keratin II | ? | |
| 6 | 100 | 827 | down | 1.12 | Tyrosine 3/Tryptophan 5-monooxygenase activation protein | YWHAZ | enzyme |
| 12 | 100 | 76 | up | −1.679 | galectin-1; keratin II | LGALS1 | other |

A key finding in this experiment was the decrease of Transaldolase 1, which supports the premise that Q10 acts by altering the metabolic state within the cancer cell. Transaldolase 1 is an enzyme in the pentose phosphate pathway (also known as the hexose monophosphate shunt). Transaldolase (EC:2.2.1.2) catalyses the reversible transfer of a three-carbon ketol unit from sedoheptulose 7-phosphate to glyceraldehyde 3-phosphate to form erythrose 4-phosphate and fructose 6-phosphate. This enzyme, together with transketolase, provides a link between the glycolytic and pentose-phosphate pathways. This is relevant to nucleotide and NADPH synthesis, to facilitate production of reducing equivalents for biosynthetic reactions and maintenance of a reducing environment.

A recent publication (Basta, P., et. al. August 2008, Cancer Detect Prevention, 32, 200-208) provided evidence of genetic polymorphism in Transaldolase and was linked to squamous cell carcinoma of the head and neck. Another recent publication (Qian, Y., et. al. May 2008, Biochem J, 415, 123-134) identified transaldolase deficiency as a modulator of mitochondrial homoeostasis, Ca2+ fluxing and apoptosis.

Figure 9:
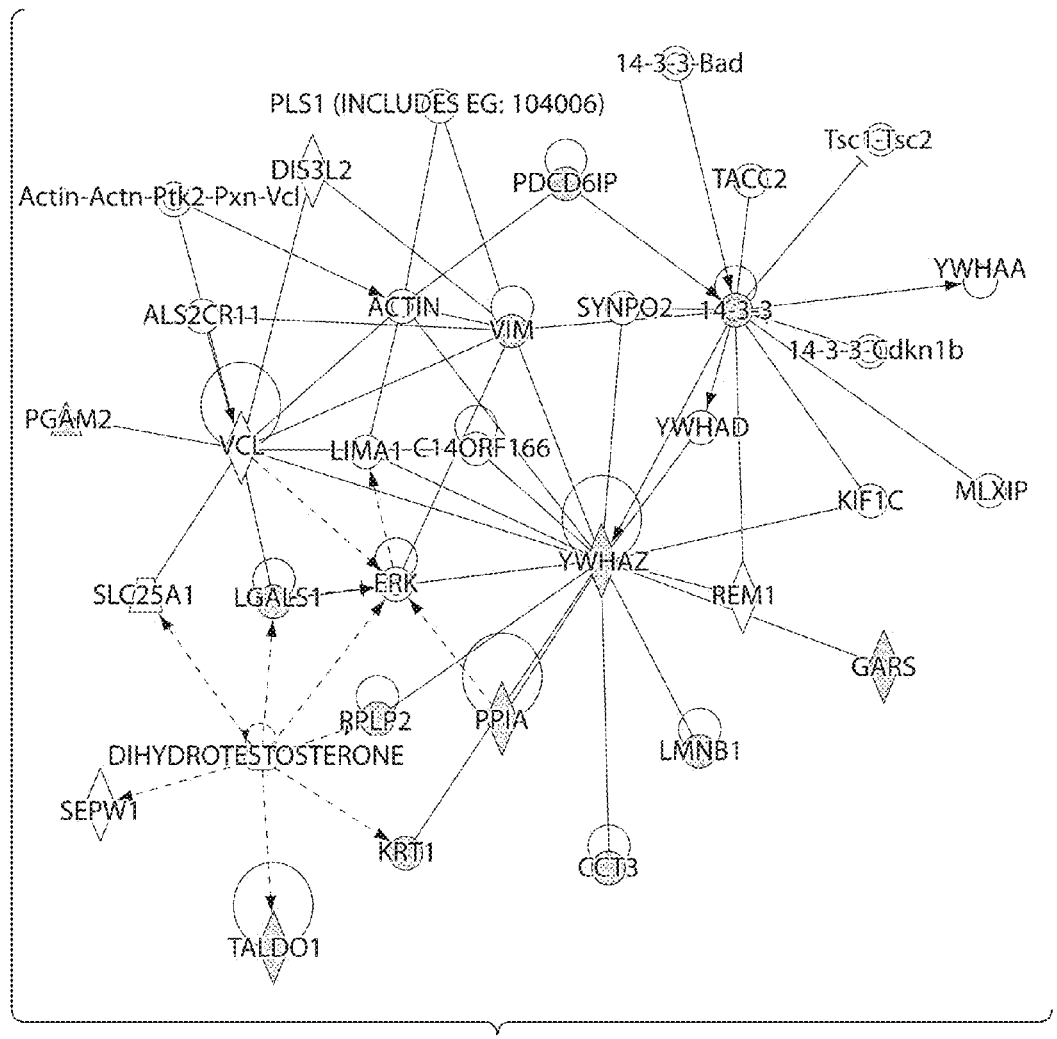
FIG. 9: Network of interaction between proteins identified by 2-D gel electrophoresis as being modulated by Q10 in SK-MEL-28 cells.

From these initial results, the other proteins identified by 2-D gel electrophoresis as being modulated by Q10 in SK-MEL-28 were analyzed for known relationships (FIG. 9). A functional evaluation of these proteins revealed that there was a group involved in 14-3-3-mediated signaling (PDCP6IP, YWHAZ, and VIM), along with individual proteins linked to a variety of processes [cell cycle; pentose phosphate pathway (TALDO1); ceramide signaling (CTSD); aminoacyl-tRNA biosynthesis (GARS), and mitochondrial protein import (TOM22)].

Proteomic Analysis of SCC Cells Treated with Q10

Another skin cancer cell line, Squamous Cell Carcinoma (SCC), was also prepared and analyzed by 2-D gel electrophoreses as a follow-up experiment the previous SK-MEL-28 analysis The SCC cells were treated with 100 μM Q10 for 6 hour or 24 hours before harvesting. A control of untreated cells was also harvested. The cell pellets were lysed and the samples were subjected to 2-D electrophoresis (in duplicate). Analysis of over six hundred protein spots in the comparative study was performed, comparing the control sample against the six hour and twenty-four hour treatments.

The top twenty-five statistically significant differential spot changes were evaluated from the comparative analysis of the 2-D electrophoresis gels. From this, twelve spots were excised and submitted for identification by trypsin digestion and mass spectrometry characterization (results summarized in Table 3 below).

TABLE 3

Proteins identified to have a differential response to 100 μM Q10 treatment in SCC cells at 6 and 24 hours.

| Spot # | Protein | Name | Cellular localization | Function | Response (fold change) |
|---|---|---|---|---|---|
| 331 | Transaldolase 1 | TALDO1 | Cytoplasm | Enzyme | Decrease (1.5) at 6 and 14 hr |
| 23 | Human BSCv (chromosome 20 reading frame 3) | C20ORF3 | Plasma membrane | strictosidine synthase | Decrease (2.1) at 6 and 24 hr |
| 54 | NM23 protein | NME1 | Nucleus, (mitochondria?) | Kinase | Increase (−1.2) at 6 hr, decrease at 24 hr |
| 116 | two Human ESTs from MCF7 breast cancer cell line (HSP 70) | | | HSP70 | Decrease (2.6) at 6 hr, further decrease at 24 hr |
| 176 | Heat shock 27 kDa protein 1 | HSPB1 | Cytoplasm | Response to environmental stresses | Increase (−1.9) at 6 and 24 hr |
| 135 | Keratin I | KRT1 | Cytoplasm | intermediate filaments | Decrease (2.3) at 6 and 24 hr |
| 50 | Keratin 14 | KRT14 | Cytoplasm | intermediate filaments | Increase (−1.6) at 6 and 24 hr |
| 68 | Keratin 13 | KRT13 | Cytoplasm | intermediate filaments | Increase (−1.5) at 6 and 24 hr |
| 49 | Proteasome Beta 7 | PSMB7 | Cytoplasm | Proteasome subunit | Decrease (1.6) at 24 hr only |
| 93 | Proteasome activator subunit 3 | PSME3 | Cytoplasm | Proteasome peptidase | Decrease (1.3) at 24 hr only |
| 66 | Rho GDP dissociation inhibitor (GDI) alpha | ARHGDIA | Cytoplasm | Inhibitor | Decrease (1.5) at 6 hr only |
| 1 | Unknown? | | | | Decrease (9.5) |

Transaldolase 1:

As previously observed in the SKMEL-28 cells treated with Q10, the enzyme Transaldolase 1 was modulated with a decrease in levels. This provides an independent confirmation of the previously observation of a linkage between Q10 and alterations in transaldolase (and thus the metabolic state of the cell).

Figure 10:
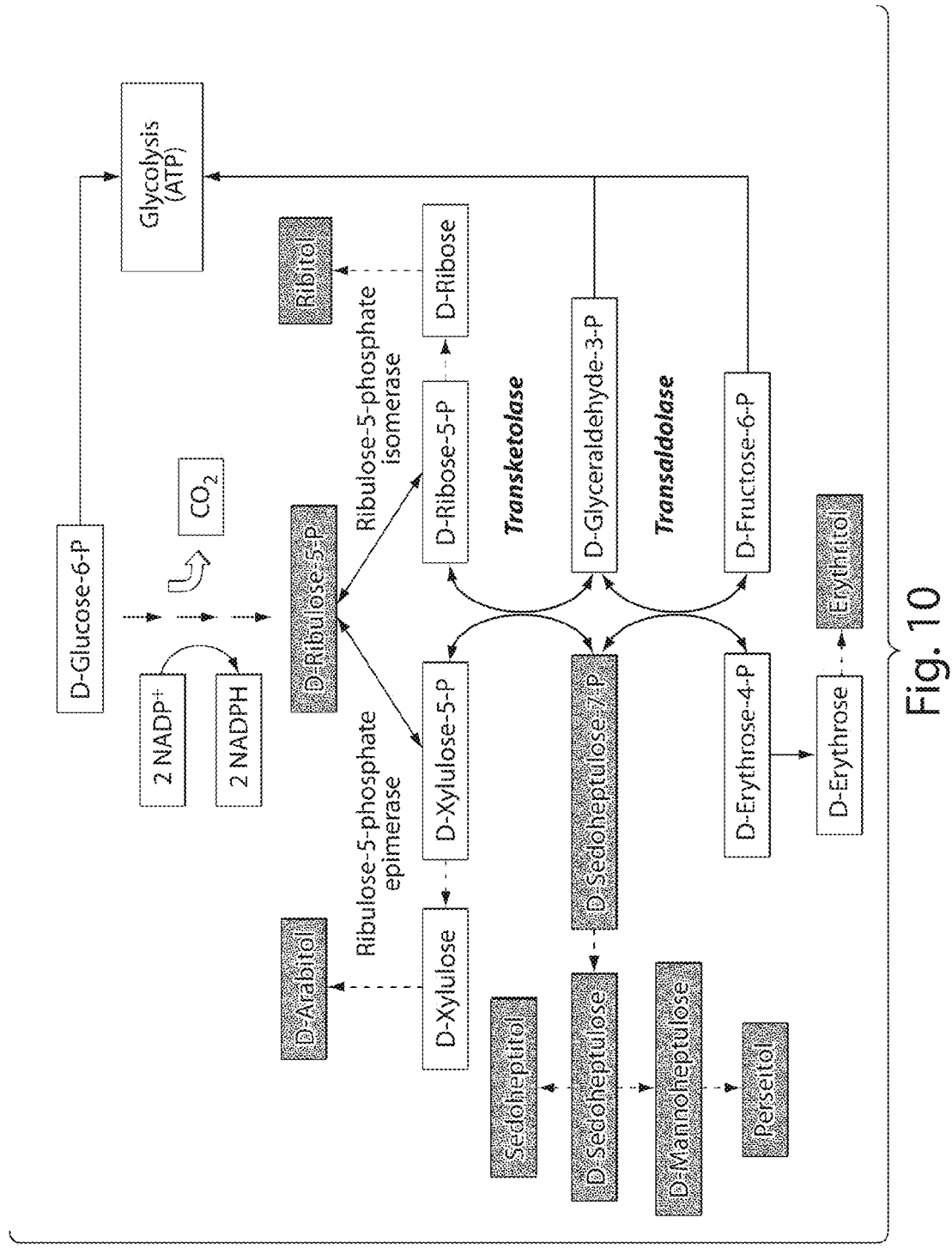
FIG. 10: The pentose phosphate pathway adapted from Verhoeven et al. (Am. J. Hum. Genet. 2001 68(5):1086-1092).

Transaldolase is an enzyme in the non-oxidative phase of the pentose phosphate pathway (FIG. 10). The pentose phosphate pathway is critical in the metabolic state of cells for the generation of nicotinamide adenine dinucleotide phosphate (reduced NADH), for reductive biosynthesis, and in the formation of ribose which is an essential component of ATP, DNA, and RNA. Transaldolase also links the pentose phosphate pathway to glycolysis. Glycolysis is the metabolic pathway by which cancer cells obtain the energy needed for cell survival, as the mitochondrial process of oxidative phosphorylation is not utilized. Q10 is an essential coenzyme factor required for oxidatative phosphorylation and mitochondrial ATP production.

BSCv:

Spot 23 was a novel human protein from Chromosome 20 named BSCv. BSCv protein is also known as Adipocyte plasma membrane-associated protein (Gene names: APMAP or C20orf3) and is predicted to be a single-pass type II membrane protein with sequence similarity to the strictosidine synthase family of proteins. Q10 treatment caused a reduction in the levels of this protein. This protein is not well characterized, nor has its homology with strictosidine synthases been confirmed. Interestingly, this protein has been associated with a role in adipocyte differentiation (Albrektsen et al., 2001). Recent proteomic studies of human omental adipose tissue identified BSCv as one of nine proteins with differential expression for polcystic ovary syndrome (PCOS) from morbidly obese women (Corton, 2008 Hum. Reprod. 23: 651-661). As a cell surface protein that responds to Q10, an antibody against BSCv would be useful as a biomarker. Based on the current results and the literature available, BSCv may a have a potential role in cancer and diabetes.

NM23A:

Non-metastatic cells 1, protein (NM23A, also known as NME1) is thought to be a metastasis suppressor. This gene (NME1) was identified because of its reduced mRNA transcript levels in highly metastatic cells. The protein has activity as a nucleoside diphosphate kinase (NDK) and exists as a hexamer composed of 'A' (encoded by this gene) and 'B' (encoded by NME2) isoforms. Mutations in this gene have been identified in aggressive neuroblastomas. NDK activities maintain an equilibrium between the concentrations of different nucleoside triphosphates such as, for example, when GTP produced in the citric acid (Krebs) cycle is converted to ATP. The NDK complex is associated with p53 through interaction with STRAP. It is noteworthy that STRAP is linked to HNF4A. Thus, NM23A is a potential protein involved in pathways important for cell control and disease treatment.

Rho GDP Dissociation Inhibitor (GDI) Alpha:

GDI Regulates the GDP/GTP exchange reaction of the Rho proteins by inhibiting the dissociation of GDP from them, and the subsequent binding of GTP to them. The protein is upregulated in cancer cells.

Example 5

Mitochondrial Enrichment Analysis

Several lines of evidence suggested that a closer evaluation of the role of mitochondrial proteins and cancer biology and Q10 response was warranted. First, there is the essential role of Q10 in the mitochondrial oxidative phosphorylation process for energy production in normal cells. However, the metabolic shift that occurs in cancer cells is to energy production through the alternative pathway of glycolysis, which does not require Q10. Second, the apoptotic response of cells requires mitochondrial proteins to occur. Q10 has been established as stimulating apoptosis in cancer cells (Bcl-2 family proteins, cytochrome c). Finally, new mitochondrial proteins were identified as being modulated by Q10 treatment, as exemplified by the modulation in protein levels of the mitochondrial import receptor protein TOM22 (see experiments described herein).

Production of Mitochondrial Enriched Samples

The skin cancer SKMEL-28 cells were treated with 100 µM Q10 or a mock vehicle for 6, 19, or 48 hours. The cells were harvested by washing and scraping the cells from T-160 flasks (4 for each time point). The cells were collected by centrifugation and the pellets flash frozen and stored at −80° C. The cell pellets were resuspended and ruptured using a 2 mL Dounce homogenizer. The reagents and method were obtained from a Mitochondria Isolation Kit for Cultured Cells (MitoSciences, Cat #MS852). The resultant mitochondria samples were divided into 75 µL aliquots (4-5 aliquots per sample) and stored at −80° C.

Proteomic Analysis of Mitochondria Enriched Samples Isolated from SK-MEL-28 Cells Treated with Q10

Figure 11:
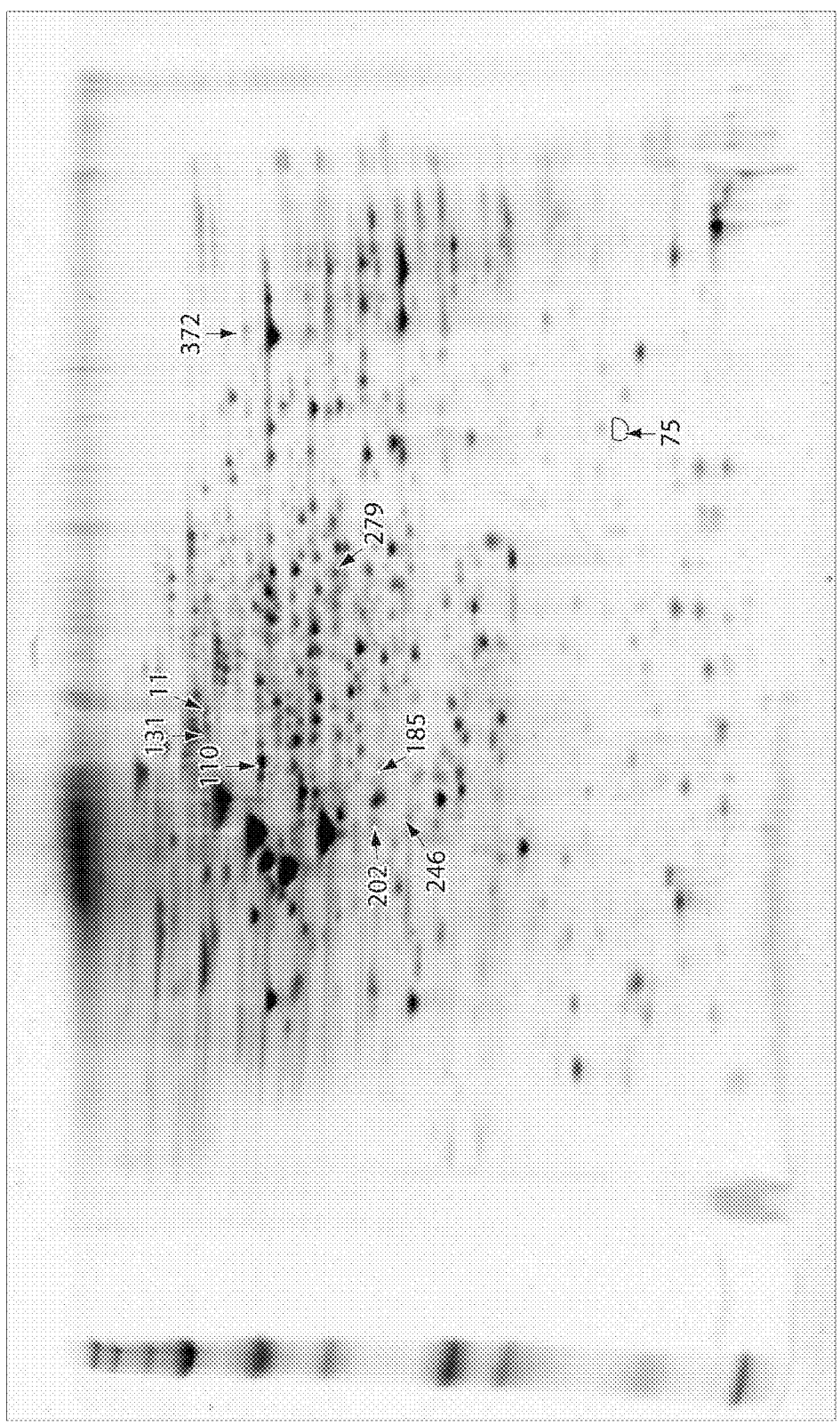
FIG. 11: 2-D gel of the mitochondrial enriched material of SK-MEL-28 cells. Spots excised and identified by mass spectrometry characterization are marked.

2-D gel electrophoresis was performed on proteins solubilized from two aliquots of the SK-MEL-28 mitochondria enriched samples treated with 100 µM Q10 for 6, 19, and 48 hours (along with the corresponding mock vehicle controls). The samples were subjected to 2-D electrophoresis (in duplicate). Analysis of 525 protein spots in the comparative study was performed, comparing the control samples against the other time point samples (FIG. 11).

The nine statistically significant differential spot changes were selected from the comparative analysis of the 2-D electrophoresis gels. From these, 9 spots were excised and submitted for identification by trypsin digestion and mass spectrometry characterization

TABLE 4

Proteins identified to have a differential response to Q10 treatment in SKMEL-28 mitochondria.

| Spot # | Protein | Name | Function | Response (fold change) |
|---|---|---|---|---|
| 11 | Unknown protein | ? | ? | Up (1.3) at 6 hr, drop to low levels after this |
| 131 | Unknown, same as spot #11, modified | ? | ? | Down (1.3) at 6 hr, drops more for 19 and 48 hr |
| 279 | acyl-CoA thioesterase 7 isoform hBACHb | ACOT7 | Cleaves fatty acyl-CoA's into free fatty acids and CoA | Down (1.3) at 6 hr, back to normal at 48 hr |
| 372 | Pyruvate kinase | PKM2 | catalyzes the production of phosphoenolpyruvate from pyruvate and ATP | Up (1.5) at 6 hr, back to normal at 48 hr |
| 110 | ER60 protein | PDIA3 | Protein disulfide isomerase | Up at 19 and 48 hr |
| 185 | Keratin 10 | KRT10 | intermediate filament | Up only at 19 hr |
| 202 | Beta-Actin | | Structural protein | Up only at 19 hr |
| 246 | Malectin | MLEC | carbohydrate-binding protein of the endoplasmic reticulum and a candidate player in the early steps of protein N-glycosylation | Up only at 19 hr |
| 75 | Coiled-coil domain containing 58 | CCDC58 | Conserved hypothetical protein - nuclear pore forming | Up at 48 hr |

Acyl-CoA Thioesterase 7:

Acyl-CoA thioesterase 7 (ACOT7) is a member of the enzyme family that catalyzes the hydrolysis of fatty acyl-CoA to free fatty acid and CoA. This enzyme thus has a role in the regulation of lipid metabolism and cellular signaling. ACOT7 has a preference for long-chain acyl-CoA substrates with fatty acid chains of 8-16 carbon atoms (C8-C16). The exact cellular function is ACOT7 is not fully understood. The transcription of this gene is activated by sterol regulatory element-binding protein 2, thus suggesting a function in cholesterol metabolism.

The results in this Example indicate that ACOT7 is potentially involved in the metabolism of Q10, either directly or indirectly. Thus, targeting ACOT7 could facilitate modulation of intercellular levels of Q10 and thus impact cellular Q10 effects.

Pyruvate Kinase:

Pyruvate kinase is an enzyme involved in the last step of glycolysis. It catalyzes the transfer of a phosphate group from phosphoenolpyruvate (PEP) to ADP, yielding one molecule of pyruvate and one molecule of ATP.

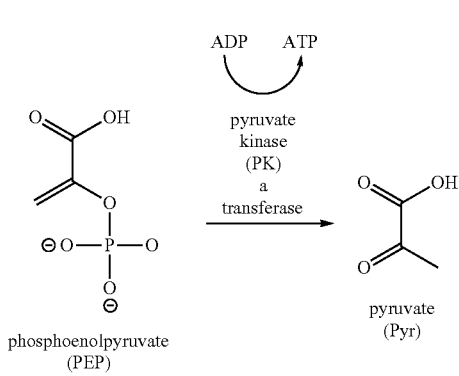

The protein is presumably that of PKM2, the type 2 isoform, as this was identified from the mitochondria enriched SK-MEL-28 sample. This isoform is well known to be involved in tumor cell formation and regulation.

Quantification of Q10 Levels in Mitochondria

A method for the simultaneous determination of Coenzyme Q10, (Q10) and the reduced form ubiquinol-10 (Q10H2) was implemented based upon a recently published method (Ruiz-Jimenez, 2007, J. Chroma A, 1175, 242-248) through the use of LC-MS-MS with electrospray ionization (ESI) in the positive mode. The highly selective identification and sensitive quantitation of both Q10 and Q10H2 is possible, along with the identification of other selected lipids. An aliquot of the mitochondrial enriched samples from SK-MEL-28 treated with 100 μM Q10 were subject to a conventional pretreatment based on protein precipitation, liquid-liquid extraction, evaporation to dryness and reconstitution with 95:5 methanol/hexane (v/v).

Figure 12:
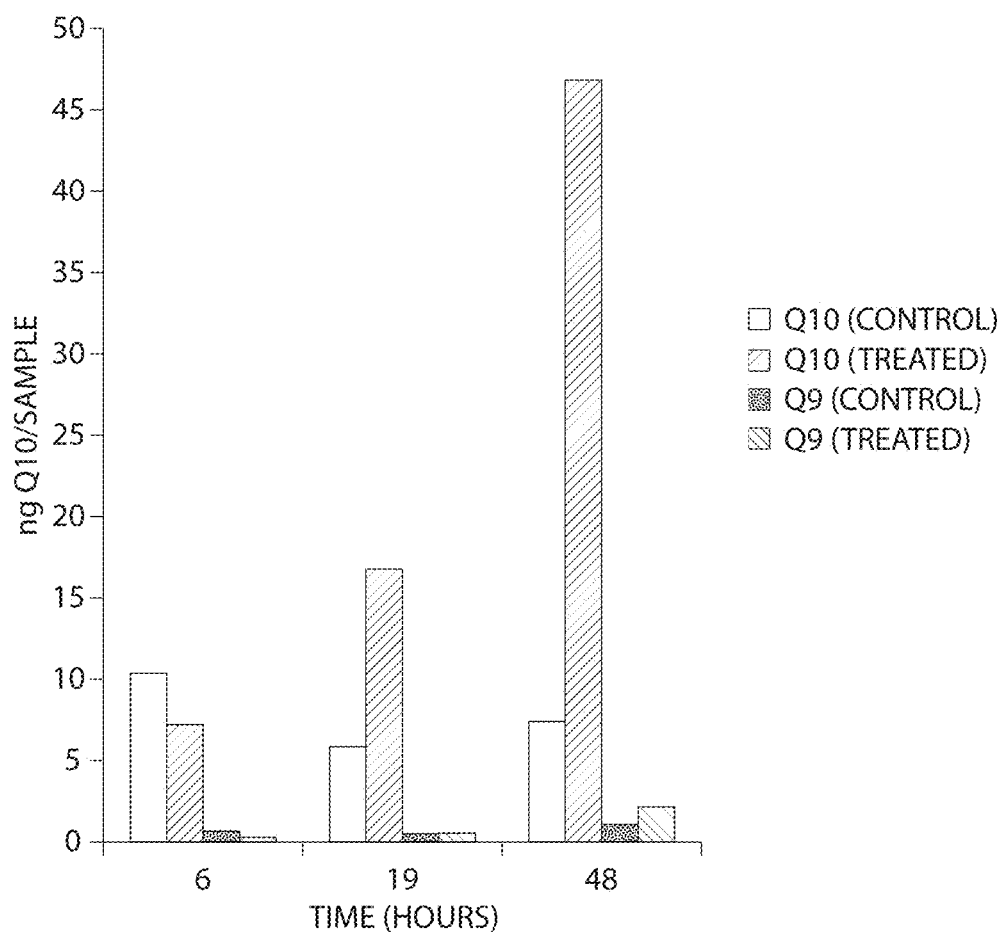
FIG. 12: Comparative plot of the relative amounts of Q10 present in SK-MEL-28 mitochondria following the exogenous addition of 100 μM Q10 into the culture medium.

In this analysis, Q10, Q10H2, and Q9 were quantitated (Table 5). The levels of the related molecule Q9 were low, and near the level of detection. The level of the untreated samples were relatively consistent, with the 6 hour Q10 treated sample having this same level. To control for sample variance in total material, the levels of cholesterol was also measured to confirm that the differences were not due to sample size errors. When the Q10 levels were corrected against total protein values obtained by protein extraction other aliquots of the same mitochondrial preps, the relative ratios were comparative. Thus, a significant increase in Q10 levels was obtained at 19 hours (~3-fold) with an even larger increase by the 48 hour time point (~6-fold) (FIG. 12).

A surprising result from this study was the finding that the Q10 was supplied to the cells as the oxidized form. For the 48 hour samples, the reduced form Q10H2 was also measured and found to be present in significantly lower amounts (0.28 ng/sample of CoQ10H2 as compared to 46.63 ng/sample of CoQ10). There was a general increase (3-fold) in the levels of Q10H2 in the Q10 treated 48 hour sample, although the levels were near the presumed detection limit of the assay. Interestingly, the oxidized form (Q10) can act as a pro-oxidant in biological systems. According to the literature, when human plasma was evaluated for Q10 and Q10H2, the majority (90%) of the molecule was found in the reduced form of Q10H2 (Ruiz-Jimenez, 2007, J. Chroma A, 1175, 242-248) which can act as an anti-oxidant.

Thus, these results confirm and quantitate that the levels of Q10 increase in the mitochondria upon the exogenous addition of Q10 to the media. A surprising and unexpected discovery was that Q10 was maintained in the supplied oxidized form (pro-oxidant) and not converted to the reduced (anti-oxidant) form of Q10H2 in any significant amounts.

Example 6

Real-Time PCR Arrays

Experiment 1

Apoptosis Array

As discussed above in Example 3, exposure of cancer cells to Q10 induces a portion of these cells to die due to apoptotic processes. To identify proteins that were involved in the Q10 response, real-time polymerase chain reaction (RT-PCR) methods were employed to identify changes in the level of mRNA for genes/proteins involved in targeted pathway arrays for apoptosis.

Using PCR arrays as a screening tool, a spectrum of molecular targets that would potentially offer an insight to the mode of biological action of Q10 within the cells were thus evaluated. Changes in mRNA levels were evaluated using real-time PCR quantification to assess mRNA levels in preselected subsets containing 80 pathway specific targets.

For the interpretation of mRNA results, the genes that were altered in their mRNA transcription by a two-fold level were identified and evaluated. The level of gene transcription to produce mRNA only provides a rough estimate of potential changes in the level of the expressed protein. The skilled

TABLE 5

HPLC-MS Quantification results for the levels of Q10 present in mitochondrial enriched samples from SK-MEL-28 cells treated with 100 μM Q10 in the media.

| | | | Peak Area | | ng/Sample | | | μg/sample |
| --- | --- | --- | --- | --- | --- | --- | --- | --- |
| File | Sample | Injection | Q9 | Q10 | Q9 | Q10 | Q10H$_2$ | Cholesterol |
| 081204-05 | 100 ng Std | | 245,342 | 352792 | | | | |
| 081204-06 | 6 hr mock#1 | 10% | 2560 | 32649 | 1.04 | 9.25 | | |
| 081204-07 | Solvent Blank#1 | 5 ul | 3781 | 3174 | 1.54 | 0.9 | | |
| 081204-08 | Solvent Blank#2 | 5 ul | 2396 | 4399 | 0.98 | 1.25 | | |
| 081204-09 | 6 hr mock#2 | 20% | 1572 | 36328 | 0.64 | 10.3 | | |
| 081204-10 | Solvent Blank#3 | 10 ul | 1722 | 2504 | 0.7 | 0.71 | | |
| 081204-11 | 48 hr Q10 treated | 20% | 4879 | 164496 | 1.99 | 46.63 | 0.28 | 13.86 |
| 081204-12 | 48 hr mock | 20% | 2412 | 25552 | 0.98 | 7.24 | 0.09 | 13.04 |
| 081204-13 | 6 hr Q10 treated | 20% | 692 | 25427 | 0.28 | 7.21 | | |
| 081204-14 | 19 hr Q10 treated | 20% | 1161 | 59164 | 0.47 | 16.27 | | |
| 081204-15 | 19 hr mock | 20% | 901 | 19999 | 0.37 | 5.67 | | | artisan will appreciate that each mRNA may have different rates at which it is degraded or its translation inefficiently, thus resulting in differing amounts of protein.

SkBr-3 Cells Treated with 50 um Q10 for 24 Hours

The assay method of RT-PCR was utilized to provide a measure of mRNA level changes to a total of 84 apoptotic pathway related proteins. The experiments with the real-time PCR apoptosis analysis on SkBr3 with Q10 (24 hr) identified the following mRNA's being affected: Bcl2, Bcl2L1, Bcl2L11, Birc6, Bax, Xiap, Hprt1, Apaf1, Ab11, Braf. These results again provided supporting evidence for the apoptotic response of cancer cells to Q10 treatment.

TABLE 6A

| Symbol | Up-Down Regulation | Unigene | Refseq | Description | Gname |
|---|---|---|---|---|---|
| BCL2L1 | 13.1957 | Hs.516966 | NM_138578 | BCL2-like 1 | BCL-XL/S |
| BNIP2 | 6.3291 | Hs.646490 | NM_004330 | BCL2/adenovirus E1B 19 kDa interacting protein 2 | BNIP-2/NIP2 |
| BCL2 | 5.4717 | Hs.150749 | NM_000633 | B-cell CLL/lymphoma 2 | Bcl-2 |
| BIRC6 | 4.7966 | Hs.150107 | NM_016252 | Baculoviral IAP repeat-containing 6 (apollon) | APOLLON/BRUCE |
| BCL2L11 | 4.6012 | Hs.469658 | NM_006538 | BCL2-like 11 (apoptosis facilitator) | BAM/BIM |
| XIAP | 4.3832 | Hs.356076 | NM_001167 | X-linked inhibitor of apoptosis | API3/BIRC4 |
| BRAF | 4.3832 | Hs.550061 | NM_004333 | V-raf murine sarcoma viral oncogene homolog B1 | B-raf 1/BRAF1 |
| BAX | 3.896 | Hs.631546 | NM_004324 | BCL2-associated X protein | Bax zeta |
| APAF1 | 2.6244 | Hs.708112 | NM_001160 | Apoptotic peptidase activating factor 1 | CED4/DKFZp 781B1145 |
| HPRT1 | −160.6748 | Hs.412707 | NM_000194 | Hypoxanthine phosphoribosyltransferase 1 (Lesch-Nyhan syndrome) | HGPRT/HPRT |

Results that are consistent from three independent experiments from SK-MEL-28 cells are summarized below in Table 6B. Many genes are regulated in SCC cells as well with 100 µM Q10 treatment. The genes in the Apoptosis array that appear to be regulated in SCC cells are described in Table 7. We find that many genes are regulated at 6 hours, both in SK-MEL-28 cells and in SCC cells. By 24 hours, the regulation is decreased. Genes that appear to be regulated in both SK-MEL-28 cells and in SCC cells are described in Table 8.

TABLE 6B

Genes in SK-MEL-28 cells regulated by 100 µM Q10 treatment when analyzed by the Apoptosis Array.

| Symbol | Description | Regulation | Location | Possible Functions |
|---|---|---|---|---|
| ABL1 | C-abl oncogene 1, receptor tyrosine kinase | Down Regulated at 72 hours | Nucleus | Tyrosine Kinase |
| BAG1 | BCL2-associated athanogene | Up Regulated at 48 hours | Cytoplasm | Anti-apoptotic, glucocorticoid receptor pathway |
| BCL2 | B-cell CLL/lymphoma 2 | Down Regulated at 48 hours | Cytoplasm | Cell death |
| BCL2A1 | BCL2-related protein A1 | Down Regulated at 48 hours | Cytoplasm | Regulates Caspases, phosphorylates TP73 |
| BCL2L1 | BCL2-like 1 | Down Regulated at 72 hours | Cytoplasm | Caspase Inhibitor |
| BCL2L10 | BCL2-like 10 (apoptosis facilitator) | Down Regulated at 48 hours | Cytoplasm | Caspase Activator |
| BCL2L11 | BCL2-like 11 (apoptosis facilitator) | Down Regulated at 48 hours | Cytoplasm | Pro-Apoptotic, Caspase3 Activator |
| BIRC3 | Baculoviral IAP repeat-containing 3 | Down Regulated at 6 hours | Cytoplasm | Anti-apoptotic |
| BIRC8 | Baculoviral IAP repeat-containing 8 | Down Regulated at 48 hours | Cytoplasm | Activates Caspase |
| CARD8 | Caspase recruitment domain family, member 8 | Down Regulated at 48 hours | Nucleus | Caspase Activator |
| CASP14 | Caspase 14, apoptosis-related cysteine peptidase | Down Regulated at 48 hours | Cytoplasm | Apoptosis related cysteine peptidase |

TABLE 6B-continued

Genes in SK-MEL-28 cells regulated by 100 μM Q10 treatment when analyzed by the Apoptosis Array.

| Symbol | Description | Regulation | Location | Possible Functions |
| --- | --- | --- | --- | --- |
| CASP5 | Caspase 5, apoptosis-related cysteine peptidase | Down Regulated at 48 hours | Cytoplasm | Apoptosis related cysteine peptidase |
| CD40LG | CD40 ligand (TNF superfamily, member 5, hyper-IgM syndrome) | Down Regulated at 48 hours | Extracellular Space | CD40 receptor binding |
| CIDEA | Cell death-inducing DFFA-like effector a | Up Regulated at 48 hours | Cytoplasm | Pro-Apoptotic |
| FADD | Fas (TNFRSF6)-associated via death domain | Down Regulated at 6 hours | Cytoplasm | Pro-Apoptotic |
| FAS | Fas (TNF receptor superfamily, member 6) | Up Regulated at 48 hours | Plasma Membrane | Pro-Apoptotic |
| FASLG | Fas ligand (TNF superfamily, member 6) | Down Regulated at 48 hours | Extracellular Space | Pro-Apoptotic |
| GADD45A | Growth arrest and DNA-damage-inducible, alpha | Up Regulated at 48 hours | Nucleus | Growth Arrest |
| HRK | Harakiri, BCL2 interacting protein (contains only BH3 domain) | Down Regulated at 48 hours | Cytoplasm | Pro-Apoptotic |
| PYCARD | PYD and CARD domain containing | Down Regulated at 6 hours | Cytoplasm | Apoptotic Protease Activator |
| TNF | Tumor necrosis factor (TNF superfamily, member 2) | Up Regulated at 48 hours then down regulated | Extracellular Space | TNF receptor binding |
| TNFRSF10A | Tumor necrosis factor receptor superfamily, member 10a | Up Regulated at 48 hours then down regulated | Plasma Membrane | Caspase Activator |
| TNFRSF10B | Tumor necrosis factor receptor superfamily, member 10b | Down Regulated at 72 hours | Plasma Membrane | p53 signaling, caspase activation. |
| TNFRSF1A | Tumor necrosis factor receptor superfamily, member 1A | Down Regulated at 72 hours | Plasma Membrane | Pro-apoptotic |
| TNFRSF21 | Tumor necrosis factor receptor superfamily, member 21 | Down Regulated at 48 hours | Plasma Membrane | Activates Caspase |
| CD27 | CD27 molecule | Down Regulated at 48 hours | Plasma Membrane | Caspase Inhibitor |
| TNFRSF9 | Tumor necrosis factor receptor superfamily, member 9 | Down Regulated at 48 hours | Plasma Membrane | Pro-apoptotic |
| TNFSF10 | Tumor necrosis factor (ligand) superfamily, member 10 | Upregulated at 48 hours | Extracellular Space | Pro-apoptotic |
| TP73 | Tumor protein p73 | Down Regulated at 48 hours | Nucleus | Transcription factor |
| TRAF3 | TNF receptor-associated factor 3 | Down Regulated at 48 hours | Cytoplasm | Zinc-finger domain |
| TRAF4 | TNF receptor-associated factor 4 | Down Regulated at 48 hours | Cytoplasm | Zinc-finger domain |

TABLE 7

Genes in SCC cells that are regulated by 100 μM Q10 treatment when analyzed by the Apoptosis Array.

| Symbol | Description | Regulation. |
| --- | --- | --- |
| AKT1 | V-akt murine thymoma viral oncogene homolog 1 | Down regulated at 6 hours and then up regulated at 24 hours. |
| BAG4 | BCL2-associated athanogene 4 | Up regulated at 24 hours. |
| BAX | BCL2-associated X protein | Up regulated at 24 hours. |
| BCL2 | B-cell CLL/lymphoma 2 | Up regulated at 24 hours. |
| BCL2L1 | BCL2-like 1 | Down regulated at 6 hours and then up regulated at 24 hours. |
| BIRC3 | Baculoviral IAP repeat-containing 3 | Down regulated at 6 hours. |
| BNIP3 | BCL2/adenovirus E1B 19 kDa interacting protein 3 | Down regulated at 24 hours. |
| CARD6 | Caspase recruitment domain family, member 6 | Down regulated at 6 hours. |

TABLE 7-continued

Genes in SCC cells that are regulated by 100 µM Q10 treatment when analyzed by the Apoptosis Array.

| Symbol | Description | Regulation. |
|---|---|---|
| CASP6 | Caspase 6, apoptosis-related cysteine peptidase | Up regulated at 24 hours. |
| CASP7 | Caspase 7, apoptosis-related cysteine peptidase | Up regulated at 24 hours. |
| CD40 | CD40 molecule, TNF receptor superfamily member 5 | Down regulated at 6 hours. |
| FADD | Fas (TNFRSF6)-associated via death domain | Up regulated at 24 hours. |
| GADD45A | Growth arrest and DNA-damage-inducible, alpha | Up regulated at 24 hours. |
| HRK | Harakiri, BCL2 interacting protein (contains only BH3 domain) | Up regulated at 24 hours. |
| TNFRSF21 | Tumor necrosis factor receptor superfamily, member 21 | Down regulated at 6 hours. |
| TNFRSF25 | Tumor necrosis factor receptor superfamily, member 25 | Down regulated at 6 hours and then up regulated at 24 hours. |
| CD27 | CD27 molecule | Down regulated at 6 hours. |
| TNFRSF9 | Tumor necrosis factor receptor superfamily, member 9 | Down regulated at 6 hours. |
| TNFSF10 | Tumor necrosis factor (ligand) superfamily, member 10 | Up regulated at 24 hours. |
| CD70 | CD70 molecule | Down regulated at 6 hours. |
| TP53 | Tumor protein p53 | Up regulated at 24 hours. |
| TP73 | Tumor protein p73 | Down regulated at 6 hours and then up regulated at 24 hours. |
| TRAF2 | TNF receptor-associated factor 2 | Up regulated at 24 hours. |

TABLE 8

Genes from the apoptosis array regulated with 100 µM Q10 treatment in both SK-MEL-28 and SCC cells.

| Symbol | Description |
|---|---|
| BCL2 | B-cell CLL/lymphoma 2 |
| BCL2L1 | BCL2-like 1 (Bcl-xl) |
| BIRC3 | Baculoviral IAP repeat-containing 3 |
| FADD | Fas (TNFRSF6)-associated via death domain |
| GADD45A | Growth arrest and DNA-damage-inducible, alpha |
| TNFRSF21 | Tumor necrosis factor receptor superfamily, member 21 |
| CD27 | CD27 molecule |
| TNFRSF9 | Tumor necrosis factor receptor superfamily, member 9 |
| TNFSF10 | Tumor necrosis factor (ligand) superfamily, member 10 |
| TP73 | Tumor protein p73 |
| TRAF2 | TNF receptor-associated factor 2 |

Interestingly, the altered mRNA levels showed a significant up-regulation in a series of apoptitic proteins, with Bcl-xl one of the highest. This was also observed in the protein array experiments on SK-MEL-28 cells.

Bcl-xl is a transmembrane molecule in the mitochondria (Bcl-xl stands for "Basal cell lymphoma-extra large"). It is involved in the signal transduction pathway of the FAS-L and is one of several anti-apoptotic proteins which are members of the Bcl-2 family of proteins. It has been implicated in the survival of cancer cells. However, it is known that alternative splicing of human Bcl-x mRNA may result in at least two distinct Bcl-x mRNA species, Bcl-xL and Bcl-xS. The predominant protein product (233 amino acids) is the larger Bcl-x mRNA, Bcl-xL, which inhibits cell death upon growth factor withdrawal (Boise et al., 1993. Cell 74, 597-608). Bcl-xS, on the other hand, inhibits the ability of Bcl-2 to inhibit cell death and renders cells more susceptible to apoptotic cell death. The employed assays utilized do not distinguish which isoform of Bcl-x is being upregulated. The Bcl-x isoform being upregulated by CoQ10 in these studies may be determined by routine methods known in the art, e.g., by using RT-PCR methods to evaluate the ratio of the two mRNA splicing isoforms (Bcl-xL vs Bcl-sL).

From the survey of apoptotic related proteins it was observed multiple pro- and anti-apoptotic factors were in the BCL-2 family or that interact with these factors have modulated expression levels (BCL2L11, BNIP2, BAG1, HRK, BAK1, BCL2, BCL2L1). These proteins govern mitochondrial outer membrane permeabilization.

An early marker for apoptotic response is observed with the upregulation of Caspase-9 (16 hour) which is consistent with previous observations of apoptosis with caspase 3/7 proteins. Induction of stress signaling pathways causes release of cytochrome c from mitochondria and activation of apaf-1 (apoptosome), which in turn cleaves the pro-enzyme of caspase-9 into the active form. Once intiated caspase-9 goes on to cleave procaspase-3 & procaspase-7 to trigger additional apoptotic pathways.

There is also a consistent linkage to the tumor necrosis factor receptor family of proteins being modulated.

Figure 13A:
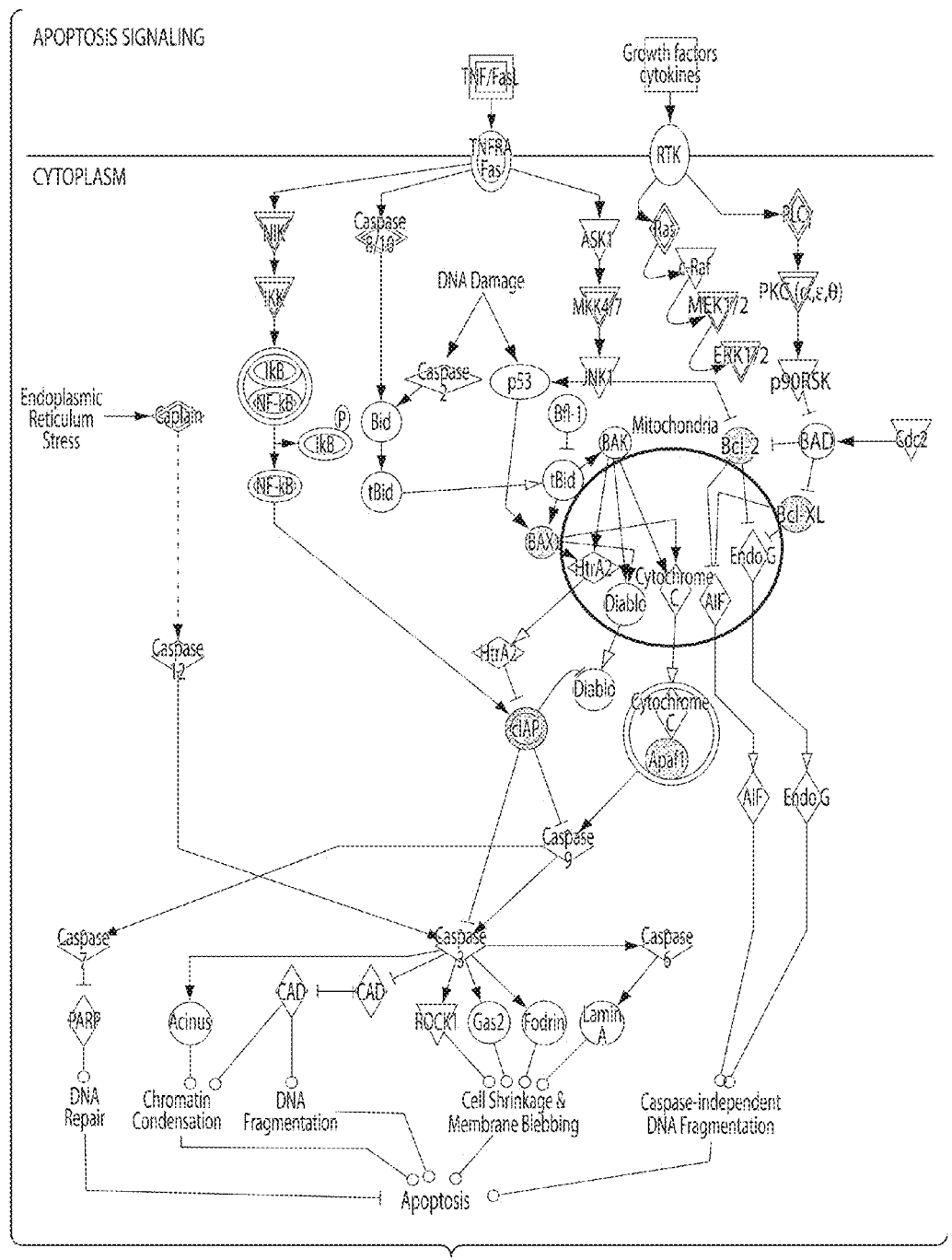
FIG. 13: Apoptosis pathway mapping known processes.
Figure 13B:
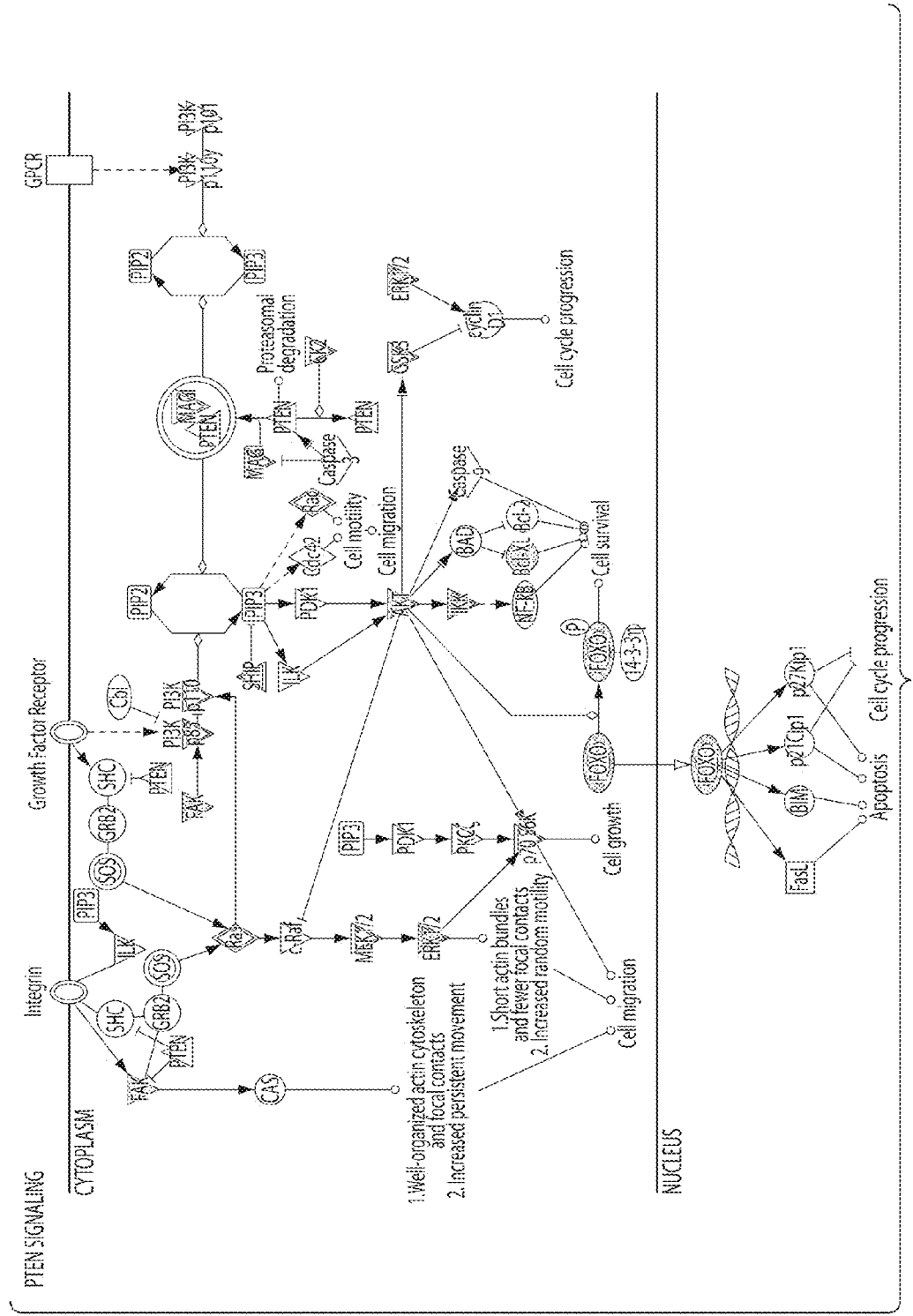

A strong down regulation of tumor protein p73 is also noted. Analyses of many tumors typically found in humans including breast and ovarian cancer show a high expression of p73 when compared to normal tissues in corresponding areas. Recent finding are suggesting that deregulated over expression of transcription factors within the body involved in cell cycle regulation and synthesis of DNA in mammalian cells (i.e.: E2F-1), induces the expression of p73. The suggestion is that p73 may be an oncoprotein, but may involve different mechanism that the related p53 protein. A schematic showing mapping of the apoptosis pathway is provided in FIG. 13.

SKMEL-28 Cells

From the survey of apoptotic related proteins it was observed multiple pro- and anti-apoptotic factors were in the BCL-2 family or that interact with these factors have modulated expression levels (BCL2L11, BNIP2, BAG1, HRK, BAK1, BCL2, BCL2L1). These proteins govern mitochondrial outer membrane permeabilization.

An early marker for apoptotic response is observed with the upregulation of Caspase-9 (16 hour) which is consistent with previous observations of apoptosis with caspase 3/7 proteins. Induction of stress signaling pathways causes release of cytochrome c from mitochondria and activation of apaf-1 (apoptosome), which in turn cleaves the pro-enzyme of caspase-9 into the active form. Once intiated caspase-9 goes on to cleave procaspase-3 & procaspase-7 to trigger additional apoptotic pathways.

TABLE 9

Changes in mRNA levels for SKMEL-28 cells treated with 100 µM A10, evaluated by RT-PCR arrays focused around apoptotic pathways.

| Refseq | Description | Symbol | 6 hr Q10 | 16 hr Q10 | 24 hr Q10 | 72 hr Q10 |
|---|---|---|---|---|---|---|
| NM_006538 | BCL2-like 11 (apoptosis facilitator) | BCL2L11 | 2.13 | 2.41 | 1.92 | 2.51 |
| NM_000875 | Insulin-like growth factor 1 receptor | IGF1R | 1.77 | 1.09 | 1.33 | 1.25 |
| NM_004048 | Beta-2-microglobulin | B2M | 1.74 | 1.76 | 1.58 | 3.11 |
| NM_003921 | B-cell CLL/lymphoma 10 | BCL10 | 1.55 | 1.87 | 1.48 | −3.11 |
| NM_004330 | BCL2/adenovirus E1B 19 kDa interacting protein 2 | BNIP2 | 1.46 | 1.51 | 1.57 | −1.61 |
| NM_005157 | C-abl oncogene 1, receptor tyrosine kinase | ABL1 | 1.42 | 2.77 | −1.22 | −2.03 |
| NM_004323 | BCL2-associated athanogene | BAG1 | 1.41 | 1.44 | −1.61 | −2.45 |
| NM_001229 | Caspase 9, apoptosis-related cysteine peptidase | CASP9 | 1.32 | 3.96 | 1.83 | 1.14 |
| NM_003806 | Harakiri, BCL2 interacting protein (contains only BH3 domain) | HRK | 1.18 | 4.52 | 2.73 | −1.14 |
| NM_001924 | Growth arrest and DNA-damage-inducible, alpha | GADD45A | 1.07 | 3.34 | 1.13 | −2.36 |
| NM_001188 | BCL2-antagonist/killer 1 | BAK1 | 1.06 | 2.73 | −1.00 | −4.54 |
| NM_004295 | TNF receptor-associated factor 4 | TRAF4 | −1.91 | 2.63 | −1.58 | −740.66 |
| NM_003842 | Tumor necrosis factor receptor superfamily, member 10b | TNFRSF10B | −2.07 | 1.53 | −1.81 | −710.49 |
| NM_000633 | B-cell CLL/lymphoma 2 | BCL2 | −2.98 | −1.63 | −2.82 | −11.36 |
| NM_001242 | CD27 molecule | CD27 | −3.40 | −2.38 | −1.35 | −12.72 |
| NM_014430 | Cell death-inducing DFFA-like effector b | CIDEB | −3.48 | 1.56 | −3.69 | −2.59 |
| NM_001065 | Tumor necrosis factor receptor superfamily, member 1A | TNFRSF1A | −4.53 | 2.28 | −3.30 | 1.22 |
| NM_005427 | Tumor protein p73 | TP73 | −4.66 | −9.80 | −8.71 | −26.96 |
| NM_003844 | Tumor necrosis factor receptor superfamily, member 10a | TNFRSF10A | −4.84 | −5.26 | −4.33 | −11.84 |
| NM_138578 | BCL2-like 1 | BCL2L1 | −4.94 | −1.80 | −6.17 | −7.04 |
| NM_001165 | Baculoviral IAP repeat-containing 3 | BIRC3 | −13.68 | −1.98 | −2.42 | −3.42 |

There is a consistent linkage to the tumor necrosis factor receptor family of proteins being modulated.

A strong down regulation of tumor protein p73 is also noted. Analyses of many tumors typically found in humans including breast and ovarian cancer show a high expression of p73 when compared to normal tissues in corresponding areas. Recent finding are suggesting that deregulated over expression of transcription factors within the body involved in cell cycle regulation and synthesis of DNA in mammalian cells (i.e.: E2F-1), induces the expression of p73. The suggestion is that p73 may be an oncoprotein, but may involve different mechanism that the related p53 protein Experiment 2

Real-Time PCR Arrays Using Oxidative Stress and Antioxidant Defense Array

To identify proteins that were involved in the Q10 response, real-time polymerase chain reaction (RT-PCR) methods were employed to identify changes in the level of mRNA's for genes/proteins involved in targeted pathway arrays for oxidative stress and antioxidant defense.

Table 10 below lists the genes that are regulated in SK-MEL28 cells with 100 µM Q10 treatment. Results are given only for those genes that are regulated in two independent experiments. Although there is a significant amount of gene regulation seen at 6 hours, most significant changes in RNA levels are seen at 48 hours.

TABLE 10

Genes in SK-MEL-28 cells that are regulated by 100 μM Q10 treatement as seen in the Oxidative Stress and Antioxidant Defense Arrays.

| Symbol | Description | Regulation | Location | Possible Functions. |
|---|---|---|---|---|
| ALB | Albumin | Down Regulation at 48 hours | Extracellular space | Carrier protein, anti-apoptotic |
| AOX1 | Aldehyde oxidase 1 | Up regulation from 16 hours | Cytoplasm | Produces free radicals, drug metabolic process. |
| APOE | Apolipoprotein E | Down Regulation at 48 hours | Extracellular space | Lipid metabolism |
| ATOX1 | ATX1 antioxidant protein 1 homolog (yeast) | Down Regulation at 48 hours | Cytoplasm | Copper metabolism |
| BNIP3 | BCL2/adenovirus E1B 19 kDa interacting protein 3 | Down Regulation at 48 hours | Cytoplasm | Anti-apoptotic |
| CSDE1 | Cold shock domain containing E1, RNA-binding | Down Regulation at 48 hours | Cytoplasm | Transcriptional regulation. |
| CYBA | Cytochrome b-245, alpha polypeptide | Down Regulation at 48 hours | Cytoplasm | Apoptotic, |
| CYGB | Cytoglobin | Down Regulation at 48 hours | Cytoplasm | Peroxidase, Transporter. |
| DHCR24 | 24-dehydrocholesterol reductase | Down Regulation at 6 hours | Cytoplasm | Electron carrier, binds to TP53, involved in apoptosis. |
| DUOX1 | Dual oxidase 1 | Up Regulation at 48 hours | Plasma Membrane | Calcium ion binding, electron carrier. |
| DUOX2 | Dual oxidase 2 | Down Regulation at 48 hours | Unknown | Calcium ion binding. |
| EPHX2 | Epoxide hydrolase 2, cytoplasmic | Down Regulation at 48 hours | Cytoplasm | Arachidonic acid metabolism. |
| EPX | Eosinophil peroxidase | Down Regulation at 48 hours | Cytoplasm | Phenyl alanine metabolism, apoptosis. |
| GPX2 | Glutathione peroxidase 2 (gastrointestinal) | Down Regulation at 48 hours | Cytoplasm | Electron carrier, binds to TP53, involved in apoptosis. |
| GPX3 | Glutathione peroxidase 3 (plasma) | Up Regulation at 48 hours | Extracellular space | Arachidonic acid metabolims, up regulated in carcinomas. |
| GPX5 | Glutathione peroxidase 5 (epididymal androgen-related protein) | Up Regulation at 48 hours | Extracellular space | Arachidonic acid metabolism. |
| GPX6 | Glutathione peroxidase 6 (olfactory) | Down Regulation at 48 hours | Extracellular space | Arachidonic acid metabolism. |
| GSR | Glutathione reductase | Down Regulation at 48 hours | Cytoplasm | Glutamate and glutathione metabolism, apoptosis. |
| GTF2I | General transcription factor II, i | Down Regulation at 6 hours | Nucleus | Transcriptional activator, transcription of fos. |
| KRT1 | Keratin 1 (epidermolytic hyperkeratosis) | Up Regulation at 48 hours | Cytoplasm | Sugar Binding. |
| LPO | Lactoperoxidase | Down Regulation at 48 hours | Extracellular space | Phenyl alanine metabolism. |
| MBL2 | Mannose-binding lectin (protein C) 2, soluble (opsonic defect) | Down Regulation at 48 hours | Extracellular space | Complement signaling, pattern recognition in receptors. |
| MGST3 | Microsomal glutathione S-transferase 3 | Upregulation at 16 hours | Cytoplasm | Xenobiotic metabolism. |
| MPO | Myeloperoxidase | Down Regulation at 48 hours | Cytoplasm | Anti-apoptotic, phenyl alanine metabolism. |
| MPV17 | MpV17 mitochondrial inner membrane protein | Down Regulation at 6 hours | Cytoplasm | Maintenance of mitochondrial DNA. |
| MT3 | Metallothionein 3 | Down Regulation at 48 hours | Cytoplasm | Copper ion binding. |
| NCF1 | Neutrophil cytosolic factor 1, (chronic granulomatous disease, autosomal 1) | Down Regulation from 6 hours | Cyoplasm | Produces free radicals. |
| NCF2 | Neutrophil cytosolic factor 2 (65 kDa, chronic granulomatous disease, autosomal 2) | Up Regulation at 48 hours | Cytoplasm | Electron carrier. |
| NME5 | Non-metastatic cells 5, protein expressed in (nucleoside-diphosphate kinase) | Down Regulation at 48 hours | Unknown | Kinase, Purine and pyrimidine metabolism. |
| NOS2A | Nitric oxide synthase 2A (inducible, hepatocytes) | Down Regulation at 48 hours | Cytoplasm | Glucocorticoid receptor signaling, apoptosis. |
| OXR1 | Oxidation resistance 1 | Down Regulation at 48 hours | Cytoplasm | Responds to oxidative stress. |
| PDLIM1 | PDZ and LIM domain 1 (elfin) | Up Regulation at 48 hours | Cytoplasm | Transcriptional activator. |
| PIP3-E | Phosphoinositide-binding protein PIP3-E | Down Regulation at 48 hours | Cytoplasm | Peroxidase. |
| PRDX2 | Peroxiredoxin 2 | Down Regulation at 6 hours | Cytoplasm | Role in phenyl alanine metabolism. Role in cell death. |

TABLE 10-continued

Genes in SK-MEL-28 cells that are regulated by 100 µM Q10 treatement as seen in the Oxidative Stress and Antioxidant Defense Arrays.

| Symbol | Description | Regulation | Location | Possible Functions. |
|---|---|---|---|---|
| PRDX4 | Peroxiredoxin 4 | Down Regulation from 24 hours | Cytoplasm | Thioredoxin peroxidase. |
| PREX1 | Phosphatidylinositol 3,4,5-trisphosphate-dependent RAC exchanger 1 | Down Regulation at 48 hours | Cytoplasm | Forms oxygen free radicals. |
| PRG3 | Proteoglycan 3 | Down Regulation at 48 hours | Extracellular space | Role in cell death. |
| PTGS1 | Prostaglandin-endoperoxide synthase 1 (prostaglandin G/H synthase and cyclooxygenase) | Down Regulation at 48 hours | Cytoplasm | arachidonic acid metabolism, prostaglandin synthesis. |
| PTGS2 | Prostaglandin-endoperoxide synthase 2 (prostaglandin G/H synthase and cyclooxygenase) | Up Regulation at 48 hours | Cytoplasm | arachidonic acid metabolism, prostaglandin synthesis. |
| PXDN | Peroxidasin homolog (*Drosophila*) | Up Regulation at 48 hours | Unknown | binds to TRAF4, calcium ion binding, iron ion binding. |
| PXDNL | Peroxidasin homolog (*Drosophila*)-like | Down Regulation at 48 hours | Unknown | peroxidase, calcium ion binding, iron ion binding. |
| RNF7 | Ring finger protein 7 | Up Regulation at 16 hours | Nucleus | apoptotic, copper ion binding, ubiquitin pathway. |
| SGK2 | Serum/glucocorticoid regulated kinase 2 | Down Regulation at 48 hours | Cytoplasm | Kinase, potassium channel regulator. |
| SIRT2 | Sirtuin (silent mating type information regulation 2 homolog) 2 (*S. cerevisiae*) | Up regulation at 16 hours | Nucleus | Transcription factor. |
| SOD1 | Superoxide dismutase 1, soluble (amyotrophic lateral sclerosis 1 (adult)) | Up Regulation at 16 hours | Cytoplasm | Apoptotic, Caspase Activator. |
| SOD2 | Superoxide dismutase 2, mitochondrial | Up regulation at 16 hours | Cytoplasm | Apoptotic, Regulated by TNF. |
| SOD3 | Superoxide dismutase 3, extracellular | Down Regulation at 48 hours | Extracellular space | Pro-apoptotic |
| SRXN1 | Sulfiredoxin 1 homolog (*S. cerevisiae*) | Down Regulation at 48 hours | Cytoplasm | DNA binding, oxidoreductase |
| TPO | Thyroid peroxidase | Down Regulation at 48 hours | Plasma Membrane | iodination of thyroglobulin, tyrosine metabolism, phenylalanine metabolism. |
| TTN | Titin | Down Regulation at 48 hours | Cytoplasm | Actin cytoskeleton signaling, integrin signaling |
| TXNDC2 | Thioredoxin domain-containing 2 (spermatozoa) | Down Regulation at 48 hours | Cytoplasm | Pyrimidine metabolism |

The Neutrophil cytosolic factor 2 (NCF2, 65 kDa, chronic granulomatous disease, autosomal 2) was one of the initial top induced mRNA's (observed at 6 hours). Subsequently at the 16 hour time point and onward, Neutrophil cytosolic factor 1 (NCF1) (chronic granulomatous disease, autosomal 1) was induced at very high levels after an initial lag phase.

Neutrophil cytosolic factor 2 is the cytosolic subunit of the multi-protein complex known as NADPH oxidase commonly found in neutrophils. This oxidase produces a burst of superoxide which is delivered to the lumen of the neutrophil phagosome.

The NADPH oxidase (nicotinamide adenine dinucleotide phosphate-oxidase) is a membrane-bound enzyme complex. It can be found in the plasma membrane as well as in the membrane of phagosome. It is made up of six subunits. These subunits are: a Rho guanosine triphosphatase (GTPase), usually Rac1 or Rac2 (Rac stands for Rho-related C3 botulinum toxin substrate)

Five "phox" units. (Phox stands for phagocytic oxidase.)
P91-PHOX (contains heme)
p22phox
p40phox
p47phox (NCF1)
p67phox (NCF2)

It is noted that another NADPH oxidase levels do not change. The enzyme is NOX5, which is a novel NADPH oxidase that generates superoxide and functions as a H+ channel in a Ca(2+)-dependent manner In addition Phosphatidylinositol 3,4,5-trisphosphate-dependent RAC exchanger 1(PREX1) was also upregulated. This protein acts as a guanine nucleotide exchange factor for the RHO family of small GTP-binding proteins (RACs). It has been shown to bind to and activate RAC1 by exchanging bound GDP for free GTP. The encoded protein, which is found mainly in the cytoplasm, is activated by phosphatidylinositol-3,4,5-trisphosphate and the beta-gamma subunits of heterotrimeric G proteins.

The second major early induced protein was Nitric oxide synthase 2A (inducible, hepatocytes) (NOS2A). Nitric oxide is a reactive free radical which acts as a biologic mediator in several processes, including neurotransmission and antimicrobial and antitumoral activities. This gene encodes a nitric oxide synthase which is expressed in liver and is inducible by a combination of lipopolysaccharide and certain cytokines.

Superoxide dismutase 2, mitochondrial (SOD2) is a member of the iron/manganese superoxide dismutase family. It encodes a mitochondrial protein that forms a homotetramer and binds one manganese ion per subunit. This protein binds to the superoxide byproducts of oxidative phosphorylation and converts them to hydrogen peroxide and diatomic oxygen. Mutations in this gene have been associated with idiopathic cardiomyopathy (IDC), premature aging, sporadic motor neuron disease, and cancer.

An example of a down regulated protein is Forkhead box M1 (FOXM1), which is known to play a key role in cell cycle progression where endogenous FOXM1 expression peaks at S and G2/M phases. Recent studies have shown that FOXM1, regulates expression of a large array of G2/M-specific genes, such as Plk1, cyclin B2, Nek2 and CENPF, and plays an important role in maintenance of chromosomal segregation and genomic stability. The FOXM1 gene is now known as a human proto-oncogene. Abnormal upregulation of FOXM1 is involved in the oncogenesis of basal cell carcinoma (BCC). FOXM1 upregulation was subsequently found in the majority of solid human cancers including liver, breast, lung, prostate, cervix of uterus, colon, pancreas, and brain. Further studies with BCC and Q10 should evaluate FOXM1 levels.

SKMEL-28 Cells

Further experiments were carried out using SKMEL-28 cells. The level of mRNA present in SKMEL-28 cells treated with 100 μM Q10 were compared to the levels in untreated cells at various time points using real-time PCR methods (RT-PCR). The PCR array (SABiosciences) is a set of optimized real-time PCR primer assays on 96-well plates for pathway or disease focused genes as well as appropriate RNA quality controls. The PCR array performs gene expression analysis with real-time PCR sensitivity and the multi-gene profiling capability of a microarray.

TABLE 11

Listing and classification of mRNA levels evaluated in the Oxidative Stress and Antioxidant Defense PCR Array.

Antioxidants:

Glutathione Peroxidases (GPx): GPX1, GPX2, GPX3, GPX4, GPX5, GPX6, GPX7, GSTZ1.
Peroxiredoxins (TPx): PRDX1, PRDX2, PRDX3, PRDX4, PRDX5, PRDX6.
Other Peroxidases: CAT, CSDE1, CYGB, DUOX1, DUOX2, EPX, GPR156, LPO MPO, PIP3-E, PTGS1, PTGS2, PXDN, PXDNL, TPO, TTN.
Other Antioxidants: ALB, APOE, GSR, MT3, SELS, SOD1, SOD3, SRXN1, TXNDC2, TXNRD1, TXNRD2.

Genes Involved in Reactive Oxygen Species (ROS) Metabolism:

Superoxide Dismutases (SOD): SOD1, SOD2, SOD3.
Other Genes Involved in Superoxide Metabolism: ALOX12, CCS, CYBA, DUOX1, DUOX2, CSDE1, MT3, NCF1, NCF2, NOS2A, NOX5, PREX1, PRG3.
Other Genes Involved in ROS Metabolism: AOX1, BNIP3, EPHX2, MPV17, SFTPD.
Oxidative Stress Responsive Genes: ANGPTL7, APOE, ATOX1, CAT, CCL5, CSDE1, CYGB, DGKK, DHCR24, DUOX1, DUOX2, DUSP1, EPX, FOXM1, GLRX2, GPR156, GPX1, GPX2, GPX3, GPX4, GPX5, GPX6, GPX7, GSS, KRT1, LPO, MBL2, MPO, MSRA, MT3, NME5, NUDT1, OXR1, OXSR1, PDLIM1, PIP3-E, PNKP, PRDX2, PRDX5, PRDX6, PRNP, RNF7, SCARA3, SELS, SEPP1, SGK2, SIRT2, SOD1, SOD2, SRXN1, STK25, TPO, TTN, TXNRD2.

After six hours of treatment with 100 μM Q10 on SKMEL-28 cells, the largest changes to the mRNA levels are indicated by highlighting the protein code (increased—bold; decreased—underlined; or no change—grey).

TABLE 12

Time course evaluation of 100 μM treatment of SKMEL-28.

| Refseq | Symbol | Description | 6 hr Q10 | 16 hr Q10 | 24 hr Q10 | 48 hr Q10 | 72 hr Q10 |
|---|---|---|---|---|---|---|---|
| NM_000265 | NCF1 | Neutrophil cytosolic factor 1, (chronic granulomatous disease, autosomal 1) | 0 | high | 3.3829 | 15.7838 | 31.5369 |
| NM_012423 | RPL13A | Ribosomal protein L13a | −0.9025 | 3.1857 | 2.5492 | 4.9253 | 7.82 |
| NM_020820 | PREX1 | Phosphatidylinositol 3,4,5-trisphosphate-dependent RAC exchanger 1 | −3.2971 | 2.867 | 0.3222 | 6.3719 | 7.476 |
| NM_012237 | SIRT2 | Sirtuin (silent mating type information regulation 2 homolog) 2 (*S. cerevisiae*) | −0.9025 | 4.0829 | 4.4766 | 5.7166 | 6.6257 |
| NM_005125 | CCS | Copper chaperone for superoxide dismutase | −0.6206 | 3.0077 | 3.452 | 2.9801 | 6.1539 |
| NM_181652 | PRDX5 | Peroxiredoxin 5 | −2.995 | 3.0454 | 3.5381 | 4.7955 | 6.0169 |
| NM_016276 | SGK2 | Serum/glucocorticoid regulated kinase 2 | 0 | 0 | 0 | 0.5995 | 5.937 |
| NM_003551 | NME5 | Non-metastatic cells 5, protein expressed in (nucleoside-diphosphate kinase) | −0.6652 | 3.1138 | 3.3694 | 3.1549 | 5.782 |
| NM_004417 | DUSP1 | Dual specificity phosphatase 1 | −0.6998 | 0.5902 | 2.7713 | 3.321 | 5.5375 |
| NM_001752 | CAT | Catalase | −0.8589 | 2.8424 | 0.1046 | 3.8557 | 5.3988 |
| NM_000041 | APOE | Apolipoprotein E | −0.8212 | 3.2069 | −0.9543 | 3.7694 | 5.3315 |
| NM_000101 | CYBA | Cytochrome b-245, alpha polypeptide | −0.3945 | 4.3475 | 3.9208 | 6.2452 | 5.0762 |

TABLE 12-continued

Time course evaluation of 100 µM treatment of SKMEL-28.

| Refseq | Symbol | Description | 6 hr Q10 | 16 hr Q10 | 24 hr Q10 | 48 hr Q10 | 72 hr Q10 |
|---|---|---|---|---|---|---|---|
| NM_000433 | NCF2 | Neutrophil cytosolic factor 2 (65 kDa, chronic granulomatous disease, autosomal 2) | 1.2266 | 3.0077 | 0.0954 | 5.476 | 0 |
| NM_000963 | PTGS2 | Prostaglandin-endoperoxide synthase 2 (prostaglandin G/H synthase and cyclooxygenase) | −0.6912 | 2.7046 | 2.6552 | 4.0553 | −3.3022 |
| NM_183079 | PRNP | Prion protein (p27-30) (Creutzfeldt-Jakob disease, Gerstmann-Strausler-Scheinker syndrome, fatal familial insomnia) | −0.2144 | 3.5236 | 2.9086 | 5.0837 | −3.9396 |
| NM_004052 | BNIP3 | BCL2/adenovirus E1B 19 kDa interacting protein 3 | −2.9376 | 3.3288 | 4.312 | −18.2069 | −4.8424 |
| NM_000242 | MBL2 | Mannose-binding lectin (protein C) 2, soluble (opsonic defect) | −0.3622 | −1.9072 | −3.0142 | −1.1854 | −6.4544 |
| NM_021953 | FOXM1 | Forkhead box M1 | −0.8135 | 0.068 | −0.9216 | 3.3655 | −10.0953 |

The mRNA level changes were monitored by RT-PCR methods and oxidative stress and antioxidant defense proteins array was evaluated.

The Neutrophil cytosolic factor 2 (NCF2, 65 kDa, chronic granulomatous disease, autosomal 2) was one of the initial top induced mRNA's (observed at 6 hours). Subsequently at the 16 hour time point and onward, Neutrophil cytosolic factor 1 (NCF1) (chronic granulomatous disease, autosomal 1) was induced at very high levels after an initial lag phase.

Neutrophil cytosolic factor 2 is the cytosolic subunit of the multi-protein complex known as NADPH oxidase commonly found in neutrophils. This oxidase produces a burst of superoxide which is delivered to the lumen of the neutrophil phagosome. The NADPH oxidase (nicotinamide adenine dinucleotide phosphate-oxidase) is a membrane-bound enzyme complex. It can be found in the plasma membrane as well as in the membrane of phagosome. It is made up of six subunits. These subunits are:

a Rho guanosine triphosphatase (GTPase), usually Rac1 or Rac2 (Rac stands for Rho-related C3 botulinum toxin substrate)

Five "phox" (phagocytic oxidase) units.
P91-PHOX (contains heme)
p22phox
p40phox
p47phox (NCF1)
p67phox (NCF2)

It is noted that another NADPH oxidase levels do not change. The enzyme is NOX5, which is a novel NADPH oxidase that generates superoxide and functions as a H+ channel in a Ca(2+)-dependent manner In addition Phosphatidylinositol 3,4,5-trisphosphate-dependent RAC exchanger 1(PREX1) was also upregulated. This protein acts as a guanine nucleotide exchange factor for the RHO family of small GTP-binding proteins (RACs). It has been shown to bind to and activate RAC1 by exchanging bound GDP for free GTP. The encoded protein, which is found mainly in the cytoplasm, is activated by phosphatidylinositol-3,4,5-trisphosphate and the beta-gamma subunits of heterotrimeric G proteins.

The second major early induced protein was Nitric oxide synthase 2A (inducible, hepatocytes) (NOS2A). Nitric oxide is a reactive free radical which acts as a biologic mediator in several processes, including neurotransmission and antimicrobial and antitumoral activities. This gene encodes a nitric oxide synthase which is expressed in liver and is inducible by a combination of lipopolysaccharide and certain cytokines.

An example of a down regulated protein is FOXM1, which is known to play a key role in cell cycle progression where endogenous FOXM1 expression peaks at S and G2/M phases. Recent studies have shown that FOXM1, regulates expression of a large array of G2/M-specific genes, such as Plk1, cyclin B2, Nek2 and CENPF, and plays an important role in maintenance of chromosomal segregation and genomic stability. The FOXM1 gene is now known as a human proto-oncogene. Abnormal upregulation of FOXM1 is involved in the oncogenesis of basal cell carcinoma (BCC). FOXM1 upregulation was subsequently found in the majority of solid human cancers including liver, breast, lung, prostate, cervix, uterus, colon, pancreas, and brain.

Experiment 3

Real-Time PCR Arrays Using Heat Shock Array

Heat Shock Arrays were run for SCC cells and the data of regulated genes is summarized below in Table 13.

TABLE 13

Genes from the Heat Shock Protein array regulated with 100 µM Q10 treatment in SCC cells.

| Symbol | Description | Regulation. | Location. | Possible functions. |
|---|---|---|---|---|
| CCT6B | Chaperonin containing TCP1, subunit 6B (zeta 2) | Down regulated at 24 hours | Cytoplasm | Protein folding and protein complex assembly. |

TABLE 13-continued

Genes from the Heat Shock Protein array regulated with 100 μM Q10 treatment in SCC cells.

| Symbol | Description | Regulation. | Location. | Possible functions. |
|---|---|---|---|---|
| DNAJA1 | DnaJ (Hsp40) homolog, subfamily A, member 1 | Up regulated at 6 hours. | Nucleus | Responds to DNA damage and changes in protein folding. |
| DNAJB13 | DnaJ (Hsp40) related, subfamily B, member 13 | Down regulated at 6 hours. | Unknown | Protein folding and apoptosis. |
| DNAJB5 | DnaJ (Hsp40) homolog, subfamily B, member 5 | Down regulated at 6 hours. | Unknown | Binds to HSP, involved in protein folding and in protein complex assembly. |
| DNAJC12 | DnaJ (Hsp40) homolog, subfamily C, member 12 | Down regulated at 6 hours. | Unknown | Binds to HSP, involved in protein folding and in protein complex assembly. |
| DNAJC4 | DnaJ (Hsp40) homolog, subfamily C, member 4 | Down regulated at 6 hours. | Cytoplasm | Binds to HSP, involved in protein folding and in protein complex assembly. |
| DNAJC5B | DnaJ (Hsp40) homolog, subfamily C, member 5 beta | Down regulated at 6 hours. | Unknown | Involved in protein folding responds to changes in protein folding. |
| HSPA8 | Heat shock 70 kDa protein 8 | Up regulated at 6 hours. | Cytoplasm | Regulates TNF, binds BAG1, STUB1, TP53, involved in apoptosis. |
| HSPH1 | Heat shock 105 kDa/110 kDa protein 1 | Up regulated at 6 hours. | Cytoplasm | Binds to HSPA8, important for protein folding, responds to protein unfolding and stress. |

Experiment 4

Real-Time PCR Arrays Using Diabetes Array

The experiments described in this example were performed to test the overall hypothesis that Q10 would have an impact on multiple genes and alter the metabolic state of a cell. The mRNA from SKMEL-28 cells treated with 100 μM Q10 was evaluated by RT-PCR against a panel of target proteins involved in diabetes and related pathways. Results from this experiment demonstrate that several proteins involved in glycolyic pathways and insulin processing are altered in their mRNA expression levels (summarized in Table 14).

TABLE 14

Major mRNA level changes to SKMEL-28 cells treated with 100 μM Q10 for 16 hours.

| Refseq | Description | Symbol | Fold Change after 16 hours (100 μM Q10) |
|---|---|---|---|
| NM_000162 | Glucokinase (hexokinase 4) | GCK | 8.5386 |
| NM_178849 | Hepatocyte nuclear factor 4, alpha | HNF4A | 8.421 |
| NM_005249 | Forkhead box G1 | FOXG1 | 4.6396 |
| NM_000599 | Insulin-like growth factor binding protein 5 | IGFBP5 | 2.2721 |
| NM_001101 | Actin, beta | ACTB | −2.0936 |
| NM_002863 | Phosphorylase, glycogen; liver (Hers disease, glycogen storage disease type VI) | PYGL | −2.65 |
| NM_001065 | Tumor necrosis factor receptor superfamily, member 1A | TNFRSF1A | −2.8011 |
| NM_021158 | Tribbles homolog 3 (*Drosophila*) | TRIB3 | −2.8011 |
| NM_003749 | Insulin receptor substrate 2 | IRS2 | −2.9404 |
| NM_004578 | RAB4A, member RAS oncogene family | RAB4A | −3.1296 |
| NM_004176 | Sterol regulatory element binding transcription factor 1 | SREBF1 | −3.5455 |
| NM_004969 | Insulin-degrading enzyme | IDE | −4.4878 |
| NM_005026 | Phosphoinositide-3-kinase, catalytic, delta polypeptide | PIK3CD | −6.8971 |
| NM_000208 | Insulin receptor | INSR | −8.6099 |
| NM_003376 | Vascular endothelial growth factor A | VEGFA | −15.5194 |
| NM_001315 | Mitogen-activated protein kinase 14 | MAPK14 | −74.3366 |

The results of this initial experiment show that the mRNA levels for a variety of insulin related proteins were modulated in both directions. The results indicate that Q10 would have an impact on diabetic disease treatment and/or evaluation.

Further experiments were next conducted to confirm the results above obtained from SK-MEL-28 cells treated with Q10. Many of the genes in SK-MEL-28 cells are regulated as early as 6 hours after Q10 treatment. However, the initial regulation becomes less evident by 16 and 24 hours. Around 48 hours, we find that many of the genes in the Diabetes array are again strongly regulated. Results that are consistent from two or more or independent experiments are summarized below in Table 15. SCC cells also appeared to exhibit regulation in some genes, both at 6 and 24 hours after Q10 treatment. These results from SCC cells are summarized in Table 16 while genes that are regulated both in SK-MEL-28 cells and in SCC cells are summarized in Table 17.

TABLE 15

Genes in SK-MEL-28 cells regulated by 100 μM Q10 treatment when analyzed by the Diabetes Array.

| Symbol | Description | Regulation. | Location | Possible Function |
|---|---|---|---|---|
| ADRB3 | Adrenergic, beta-3-, receptor | Down Regulated at 48 hours | Plasma membrane | cAMP signaling, G-protein signaling |
| CEACAM1 | Carcinoembryonic antigen-related cell adhesion molecule 1 (biliary glycoprotein) | Down Regulated at 48 hours | Extracellular space | Anti-apoptotic, positive regulation of angiogenesis. |
| CEBPA | CCAAT/enhancer binding protein (C/EBP), alpha | Up regulated at 48 hours | Nucleus | Glucocorticoid receptor signaling, VDR/RXR activation. |
| CTLA4 | Cytotoxic T-lymphocyte-associated protein 4 | Down Regulated at 48 hours | Plasma Membrane | T cell receptor signaling, activates CASP8. |
| DUSP4 | Dual specificity phosphatase 4 | Down Regulated at 48 hours | Nucleus | Phosphatase |
| ENPP1 | Ectonucleotide pyrophosphatase/phosphodiesterase 1 | Down Regulated at 48 hours | Plasma membrane | Negative regulator of the insulin receptor pathway |
| FOXC2 | Forkhead box C2 (MFH-1, mesenchyme forkhead 1) | Down Regulated at 48 hours | Nucleus | Anti-apoptotic, transcription factor |
| G6PD | Glucose-6-phosphate dehydrogenase | Up regulated at 48 hours, then down regulated | Cytoplasm | Pentose Phosphate Pathway, Glutathione metabolism. |
| HMOX1 | Heme oxygenase (decycling) 1 | Down Regulated at 48 hours | Cytoplasm | Heme oxygenase decycling |
| ICAM1 | Intercellular adhesion molecule 1 (CD54), human rhinovirus receptor | Down Regulated at 48 hours | Plasma membrane | Regulated by atorvastatin, processes some caspases. |
| IL4R | Interleukin 4 receptor | Down Regulated at 48 hours | Plasma membrane | Up regulation by TP73, binds to IRS1 and IRS2 |
| IRS1 | Insulin receptor substrate 1 | Up regulated at 48 hours then down regulated | Plasma membrane | Binds Insulin receptor |
| IRS2 | Insulin receptor substrate 2 | Down Regulated at 48 hours | Plasma membrane | IGF-1 signaling |
| NSF | N-ethylmaleimide-sensitive factor | Down Regulated at 48 hours | Cytoplasm | GABA signaling |
| PIK3CD | Phosphoinositide-3-kinase, catalytic, delta polypeptide | Down Regulated at 48 hours | Cytoplasm | Kinase |
| PPARG | Peroxisome proliferator-activated receptor gamma | Down Regulated at 48 hours | Nucleus | Transcriptional factor |
| PRKCB1 | Protein kinase C, beta 1 | Down Regulated at 48 hours | Cytoplasm | PKC family |
| SELL | Selectin L (lymphocyte adhesion molecule 1) | Down Regulated at 48 hours | Plasma membrane | Activates RAS, MAPK |
| SREBF1 | Sterol regulatory element binding transcription factor 1 | Up regulated at 48 hours then down regulated | Nucleus | Transcriptional factor |
| STXBP1 | Syntaxin binding protein 1 | Down Regulated at 48 hours | Cytoplasm | Present in myelin enriched fraction. |
| TGFB1 | Transforming growth factor, beta 1 | Up regulated at 48 hours then down regulated | Extracellular space | Pro-apoptotic |
| NKX2-1 | NK2 homeobox 1 | Down Regulated at 48 hours | Nucleus | Transcriptional activator |
| TNF | Tumor necrosis factor (TNF superfamily, member 2) | Up regulated at 48 hours | Extracellular space | Pro-apoptotic |
| TNFRSF1A | Tumor necrosis factor receptor superfamily, member 1A | Down Regulated at 72 hours | Plasma membrane | Pro-apoptotic |

TABLE 15-continued

Genes in SK-MEL-28 cells regulated by 100 µM
Q10 treatment when analyzed by the Diabetes Array.

| Symbol | Description | Regulation. | Location | Possible Function |
| --- | --- | --- | --- | --- |
| VEGFA | Vascular endothelial growth factor A | Up regulated at 58 hours then down regulated | Cytoplasm | Kinase |

TABLE 16

Genes in SCC cells regulated by 100 µM Q10
treatment when analyzed by the Diabetes Array.

| Symbol | Description | Regulation. |
| --- | --- | --- |
| G6PD | Glucose-6-phosphate dehydrogenase | Down regulated at 6 hours. |
| ICAM1 | Intercellular adhesion molecule 1 (CD54), human rhinovirus receptor | Down regulated at 6 hours. |
| INPPL1 | Inositol polyphosphate phosphatase-like 1 | Down regulated at 6 hours. |
| NOS3 | Nitric oxide synthase 3 (endothelial cell) | Down regulated at 6 hours. |
| PIK3CD | Phosphoinositide-3-kinase, catalytic, delta polypeptide | Down regulated at 6 hours. |
| PPARA | Peroxisome proliferative activated receptor, alpha | Down regulated at 6 hours. |
| PYGL | Phosphorylase, glycogen; liver (Hers disease, glycogen storage disease type VI) | Down regulated at 6 hours. |
| SREBF1 | Sterol regulatory element binding transcription factor 1 | Down regulated at 6 hours. |
| STXBP2 | Syntaxin binding protein 2 | Down regulated at 6 hours. |
| TNF | Tumor necrosis factor (TNF superfamily, member 2) | Down regulated at 6 hours. |
| TNFRSF1A | Tumor necrosis factor receptor superfamily, member 1A | Down regulated at 6 and 24 hours. |
| VEGFA | Vascular endothelial growth factor A | Down regulated at 6 hours. |

TABLE 17

Genes from the diabetes array regulated with 100 µM
Q10 treatment for both SK-MEL-28 and SCC cells.

| Symbol | Description. |
| --- | --- |
| G6PD | Glucose-6-phosphate dehydrogenase |
| ICAM1 | Intercellular adhesion molecule 1 (CD54), human rhinovirus receptor |
| PIK3CD | Phosphoinositide-3-kinase, catalytic, delta polypeptide |
| SREBF1 | Sterol regulatory element binding transcription factor 1 |
| TNF | Tumor necrosis factor (TNF superfamily, member 2) |
| TNFRSF1A | Tumor necrosis factor receptor superfamily, member 1A |
| VEGFA | Vascular endothelial growth factor A |

The mRNA levels for a variety of insulin related proteins were modulated in both directions. Q10 has an impact on regulation of cellular metabolism, and thus influences metabolic disregluation diseases such as diabetes. Two proteins that were significantly modulated are further discussed below.

Mitogen-Activated Protein Kinase 14 (MAPK14):

Mitogen-activated protein kinase 14 (MAPK14) is a member of the MAP kinase family. MAP kinases act as an integration point for multiple biochemical signals, and are involved in a wide variety of cellular processes such as proliferation, differentiation, transcription regulation and development. Results from this experiment show that the MAPK14 was significantly down-regulated.

Hepatocyte Nuclear Factor 4, Alpha (HNF4A):

HNF4 (Hepatocyte Nuclear Factor 4) is a nuclear receptor protein mostly expressed in the liver, gut, kidney, and pancreatic beta cells that is critical for liver development. In humans, there are two isoforms of NHF4, alpha and gamma encoded by two separate genes HNF4A and HNF4G respectively. (See, e.g., Chartier F L, Bossu J P, Laudet V, Fruchart J C, Laine B (1994). "Cloning and sequencing of cDNAs encoding the human hepatocyte nuclear factor 4 indicate the presence of two isoforms in human liver". *Gene* 147 (2): 269-72.)

HNF4 was originally classified as an orphan receptor. However HNF4 was found later to be constitutively active by virtue of being continuously bound to a variety of fatty acids. (See, e.g., Sladek F (2002). "Desperately seeking . . . something". *Mol Cell* 10 (2): 219-221 and Jump D B, Botolin D, Wang Y, Xu J, Christian B, Demeure O (2005). "Fatty acid regulation of hepatic gene transcription". *J Nutr* 135 (11)). The ligand binding domain of HNF4, as with other nuclear receptors, adopts a canonical alpha helical sandwich fold (see, e.g., Wisely G B, Miller A B, Davis R G, Thornquest A D Jr, Johnson R, Spitzer T, Sefler A, Shearer B, Moore J T, Miller A B, Willson T M, Williams S P (2002). "Hepatocyte nuclear factor 4 is a transcription factor that constitutively binds fatty acids". *Structure* 10 (9): 1225-34 and Dhe-Paganon S, Duda K, Iwamoto M, Chi Y I, Shoelson S E (2002). "Crystal structure of the HNF4 alpha ligand binding domain in complex with endogenous fatty acid ligand". *J Biol Chem* 277 (41): 37973-6) and interacts with co-activator proteins. (See, e.g., Duda K, Chi Y I, Shoelson S E (2004). "Structural basis for HNF-4-alpha activation by ligand and coactivator binding". *J Biol Chem* 279 (22): 23311-6).

Mutations in the HNF4-α gene have been linked to maturity onset diabetes of the young (MODY). (See, e.g., Fajans S S, Bell G I, Polonsky K S (2001). "Molecular mechanisms and clinical pathophysiology of maturity-onset diabetes of the young". *N Engl J Med* 345 (13): 971-80.)

Hepatocyte nuclear factor 4 (HNF4) is a tissue-specific transcription factor known to regulate a large number of genes in hepatocytes and pancreatic cells. Although HNF4 is highly expressed in some sections of the kidney, little is known about its role in this organ and about HNF4-regulated genes in the kidney cells. The abundance and activity of HNF4 are frequently reduced in renal cell carcinoma (RCC) indicating some tumor suppressing function of HNF4 in renal cells. Interestingly, many of the genes regulated by HNF4 have been shown to be deregulated in RCC microarray studies. These genes (ACY1, WT1, SELENBP1, COBL, EFHD1, AGXT2L1, ALDH5A1, THEM2, ABCB1, FLJ14146, CSPG2, TRIM9 and HEY1) are good candidates for genes whose activity is changed upon the decrease of HNF4 in RCC.

Figure 28:
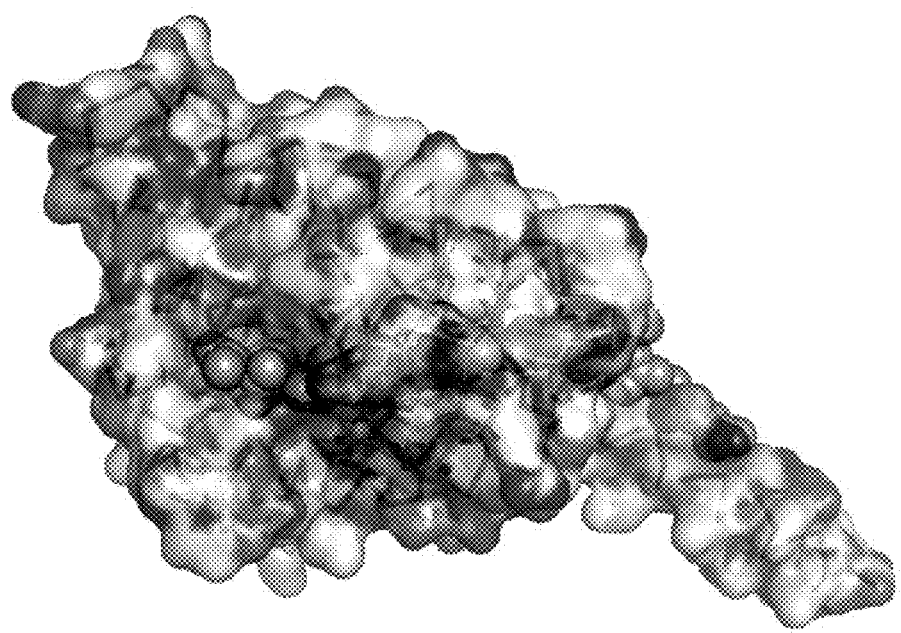
FIG. 28: Theoretical model of Q10 (spheres) inserted into the lipid binding channel of HNF4alpha (1M7W.pdb) in the Helix 10 open conformation.

In the structure of the ligand binding domain of HNF4alpha (1M7W.pdb; Dhe-Paganon (2002) JBC, 277, 37973); a small lipid was observed and which co-purified from *E. coli* production. The crystal contains two conformations of the protein, where the elongated helix 10 and short helix 12 have alternate conformations. Upon examination of the lipid binding region, it was interesting to observe that there are two exits regions. One exit region holds the small lipids head group, and it is noted that several pocket regions are co-localized with this exit port. A hypothesis would be that Q10 binds specifically to this transcription factor. When Q10 in modeled into this lipid binding tunnel, the Q10 ring would fit into the surface pocket (FIG. 28). A known loss-of-function mutation (E276Q) would have the potential to order the residues lining this surface pocket, and thus have a negative impact on the putative Q10 binding.

In addition, with this Q10 binding model, the hydrophobic tail would extend out of the internal cavity and would then interact with the elongated helix 10. Thus, this interaction could potential alter the conformation of the helix 10/12 group. This may then alter the activation/inactivation equilibrium of the transcription factor activity.

Example 7

Antibody MicroArray Analysis

The evaluation of protein concentration due to the presence of Q10 was evaluated through the utilization of antibody microarray methods. The microarray contained antibodies for over 700 proteins, sampling a broad range of protein types and potential pathway markers.

An initial experiment to assess changes at the protein concentration level in cells treated with Q10 was conducted with an antibody microarray (Panorama XP725 Antibody Array, Sigma) and SK-MEL-28 cells treated for 6 or 24 hour. The cells were harvested and extracted to obtain a soluble protein supernatant. Two portions of protein (~1 mg total) from each sample (at 1 mg/mL) were each label with fluorescent dye (Cy3 and Cy5, respectively). The excess dye was removed from the protein and the material utilized for the microarray incubations. To compare two time point samples, equal amounts of protein were mixed, with each sample being of the different label type (e.g., 3 hour extract labeled with Cy3 was mixed with the 24 hour extract labeled with Cy5). After incubation with the microarray chip (according to manufactures recommended protocols), the chips were washed and dried. The microarrays were scanned with a fluorescent laser scanner to measure the relative fluorescence intensity of the Cy3 and Cy5 dyes.

TABLE 18

Proteins with increased levels in SK-MEL-28 cells after 24 hour treatment with 50 µM Q10

| Name | Ratio |
| --- | --- |
| Cdk1 | 0.1 |
| DcR1 | 0.1 |
| Protein Kinase Cb2 | 0.1 |
| Tumor Necrosis Factor Soluble Receptor II | 0.1 |
| BAD | 0.1 |
| Caspase13 | 0.2 |
| FBI1 PAKEMON | 0.2 |
| Zyxin | 0.2 |
| Cdc25A | 0.3 |
| PIASx | 0.3 |
| Nerve Growth Factor b | 0.3 |
| Protein Tyrosine Phosphatase PEST | 0.3 |
| hBRM hSNF2a | 0.4 |
| GRP94 | 0.4 |
| Calmodulin | 0.4 |
| Serine Threonine Protein Phosphatase 2C a b | 0.4 |
| ARC | 0.4 |
| NeurabinII | 0.4 |
| Nitric Oxide Synthase bNOS | 0.4 |
| Serine Threonine Protein Phosphatase 1b | 0.4 |
| Heat Shock Protein 110 | 0.4 |
| Serine Threonine Protein Phosphatase 1g1 | 0.4 |
| COX II | 0.5 |
| HSP70 | 0.5 |
| BLK | 0.5 |
| Cytokeratin 8 12 | 0.5 |
| BUBR1 | 0.5 |
| FOXC2 | 0.5 |
| Serine Threonine Protein Phosphatase 2 A Bg | 0.5 |
| MSH6 | 0.5 |
| DR6 | 0.5 |
| Rad17 | 0.5 |
| BAF57 | 0.5 |
| Transforming Growth Factorb pan | 0.5 |
| BTK | 0.5 |
| SerineThreonine Protein Phosphatase 2 A/B pan2 | 0.5 |
| CNPase | 0.5 |
| SynCAM | 0.5 |
| Proliferating Cell Nuclear Antigen | 0.5 |

TABLE 19

Proteins with increased levels in SK-MEL-28 cells after 24 hour treatment with 50 µM Q10

| Name | Ratio |
| --- | --- |
| BclxL | 4.2 |
| BID | 3.7 |
| Bmf | 3.7 |
| PUMA bbc3 | 3.0 |
| Zip Kinase | 2.8 |
| Bmf | 2.8 |
| DcR2 | 2.7 |
| E2F1 | 2.7 |
| FAK pTyr577 | 2.5 |
| FKHRL1 FOXO3a | 2.5 |
| MTBP | 2.5 |

TABLE 19-continued

Proteins with increased levels in SK-MEL-28
cells after 24 hour treatment with 50 μM Q10

| Name | Ratio |
|---|---|
| Connexin 32 | 2.5 |
| Annexin VII | 2.4 |
| p63 | 2.4 |
| SUMO1 | 2.4 |
| IAfadin | 2.3 |
| MDMX | 2.3 |
| Pyk2 | 2.3 |
| RIP Receptor Interacting Protein | 2.3 |
| RICK | 2.3 |
| IKKa | 2.3 |
| Bclx | 2.3 |
| Afadin | 2.2 |
| Proliferating Cell Protein Ki67 | 2.2 |
| Histone H3 pSer28 | 2.2 |
| CASK LIN2 | 2.2 |
| Centrin | 2.2 |
| TOM22 | 2.1 |
| Nitric Oxide Synthase Endothelial eNOS | 2.1 |
| Protein Kinase Ba | 2.1 |
| Laminin | 2.1 |
| Myosin Ib Nuclear | 2.1 |
| Caspase 7 | 2.1 |
| MAP Kinase 2 ERK2 | 2.1 |
| KIF17 | 2.1 |
| Claspin | 2.1 |
| GRP75 | 2.1 |
| Caspase 6 | 2.1 |
| ILP2 | 2.1 |
| aActinin | 2.1 |
| Vitronectin | 2.1 |
| DRAK1 | 2.1 |
| PTEN | 2.1 |
| Grb2 | 2.1 |
| HDAC4 | 2.0 |
| HDAC7 | 2.0 |
| Nitric Oxide Synthase bNOS | 2.0 |
| HDAC2 | 2.0 |
| p38 MAPK | 2.0 |
| Reelin | 2.0 |
| Protein Kinase Cd | 2.0 |
| cerbB3 | 2.0 |
| hSNF5 INI1 | 2.0 |
| Protein Kinase Ca | 2.0 |
| Glutamate receptor NMDAR 2a | 2.0 |
| Leptin | 2.0 |
| Dimethyl Histone H3 diMeLys4 | 2.0 |
| BID | 2.0 |
| MeCP2 | 2.0 |
| Nerve growth factor receptor p75 | 2.0 |
| Myosin Light Chain Kinase | 2.0 |
| cRaf pSer621 | 2.0 |
| GRP78 BiP | 2.0 |
| cMyc | 2.0 |
| Raf1 | 2.0 |
| MTA2 MTA1L | 2.0 |
| Sir2 | 2.0 |
| ATF2 pThr69 71 | 2.0 |
| Protein Kinase C | 2.0 |
| Protein Kinase Cb2 | 2.0 |

In order to confirm the previously observed apoptosis proteins, and to expand the evaluation into a larger number of pro-apoptosis and anti-apoptosis proteins, two assay methods were chosen which were capable of screening the broad family of proteins potentially involved.

First, an antibody micro array (Panorama XP725 Antibody Array, Sigma) was utilized to screen over 700 protein antibodies to assess changes at the protein concentration level in SK-MEL-28 cells treated for 24 hours with 50 μM Q10.

From the Antibody array experiments, on SKMEL-28 with Q10 (24 hr), the following are some of the identified proteins with altered levels: Bcl-xl, Bmf, BTK, BLK, cJun (pSer63), Connexin 32, PUMA bbc3, BID, Par4, cCbl. The key conclusion from this initial study was that the expected pro-apoptosis proteins are altered.

Antibody Microarray for SK-MEL-28

An antibody micro array (Panorama XP725 Antibody Array, Sigma) was utilized to screen over 700 protein antibodies to assess changes at the protein concentration level in SK-MEL-28 cells treated for 24 hours with 50 μM Q10.

TABLE 20

Changes in protein levels in SKMEL-28 treated with 50 μM Q10

| Name | Antibody Number (Sigma) | SKMEL28 Q10/ SKMEL28 control | SKMEL28/ HEKa control | HEKa Q10/ HEKa control |
|---|---|---|---|---|
| BclxL | B9429 | 2.46 | 1.04 | 1.83 |
| PUMA bbc3 | P4743 | 2.31 | 1.14 | 2.14 |
| Bmf | B1559 | 2.23 | 1.12 | 2.11 |
| Bmf | B1684 | 2.09 | 1.13 | 1.74 |
| cJun pSer63 | J2128 | 1.99 | 1.14 | 1.85 |
| BLK | B8928 | 1.94 | 1.05 | 1.51 |

From the Antibody array experiments, on SKMEL-28 with Q10 (24 hr), the following are some of the identified proteins with altered levels: Bcl-xl, Bmf, BTK, BLK, cJun (pSer63), Connexin 32, PUMA bbc3, BID, Par4, cCbl. These data confirm that the levels of pro-apoptosis proteins are altered upon incubation with elevated levels of exogenously added Q10.

Bcl-xl ("Basal cell lymphoma-extra large") is a transmembrane molecule in the mitochondria. It is involved in the signal transduction pathway of the FAS-L and is one of several anti-apoptotic proteins which are members of the Bcl-2 family of proteins. It has been implicated in the survival of cancer cells. However, it is known that alternative splicing of human Bcl-x mRNA may result in at least two distinct Bcl-x mRNA species, Bcl-xL and Bcl-xS. The predominant protein product (233 amino acids) is the larger Bcl-x mRNA, Bcl-xL, which inhibits cell death upon growth factor withdrawal (Boise et al., 1993. *Cell* 74, 597-608). Bcl-xS, on the other hand, inhibits the ability of Bcl-2 to inhibit cell death and renders cells more susceptible to apoptotic cell death.

TABLE 21

Proteins with increased levels in SCC cells
after 24 hour treatment with 100 μM Q10.

| Name | Ratio |
|---|---|
| PUMA bbc3 | 3.81 |
| HDAC7 | 3.21 |
| BID | 3.12 |
| MTBP | 3.00 |
| p38 MAP Kinase NonActivated | 2.93 |
| PKR | 2.87 |
| TRAIL | 2.86 |
| DR5 | 2.86 |
| Cdk3 | 2.82 |

TABLE 21-continued

Proteins with increased levels in SCC cells after 24 hour treatment with 100 μM Q10.

| Name | Ratio |
|---|---|
| NCadherin | 2.71 |
| Reelin | 2.68 |
| p35 Cdk5 Regulator | 2.63 |
| HDAC10 | 2.60 |
| RAP1 | 2.59 |
| PSF | 2.56 |
| cMyc | 2.55 |
| methyl Histone H3 MeLys9 | 2.54 |
| HDAC1 | 2.51 |
| F1A | 2.48 |
| ROCK1 | 2.45 |
| Bim | 2.45 |
| FXR2 | 2.44 |
| DEDAF | 2.44 |
| DcR1 | 2.40 |
| APRIL | 2.40 |
| PRMT1 | 2.36 |
| Pyk2 pTyr580 | 2.34 |
| Vitronectin | 2.33 |
| Synaptopodin | 2.32 |
| Caspase13 | 2.30 |
| Syntaxin 8 | 2.29 |
| DR6 | 2.29 |
| BLK | 2.28 |
| ROCK2 | 2.28 |
| Sir2 | 2.25 |
| DcR3 | 2.24 |
| RbAp48 RbAp46 | 2.21 |
| OGlcNAc Transferase | 2.21 |
| GRP78 BiP | 2.20 |
| Sin3A | 2.20 |
| p63 | 2.20 |
| Presenilin1 | 2.19 |
| PML | 2.18 |
| PAK1pThr212 | 2.17 |
| HDAC8 | 2.16 |
| HDAC6 | 2.15 |
| Nitric Oxide Synthase Inducible iNOS | 2.15 |
| Neurofibromin | 2.15 |
| Syntaxin 6 | 2.13 |
| Parkin | 2.12 |
| Rad17 | 2.11 |
| Nitric Oxide Synthase bNOS | 2.10 |
| TIS7 | 2.09 |
| OP18 Stathmin (stathmin 1/oncoprotein 18) | 2.08 |
| phospho-b-Catenin pSer45 | 2.07 |
| NeurabinII | 2.07 |
| e Tubulin | 2.07 |
| PKB pThr308 | 2.07 |
| Ornithine Decarboxylase | 2.07 |
| P53 BP1 | 2.06 |
| Pyk2 | 2.05 |
| HDAC5 | 2.05 |
| Connexin 43 | 2.05 |
| a1Syntrophin | 2.04 |
| MRP1 | 2.04 |
| cerbB4 | 2.03 |
| S Nitrosocysteine | 2.03 |
| SGK | 2.02 |
| Rab5 | 2.01 |
| Ubiquitin Cterminal Hydrolase L1 | 2.01 |
| Myosin Ib Nuclear | 2.00 |
| Par4 Prostate Apoptosis Response 4 | 2.00 |

TABLE 22

Proteins with reduced levels in SCC cells after 24 hour treatment with 100 μM Q10.

| Name | Ratio |
|---|---|
| AP1 | 0.68 |
| Centrin | 0.55 |
| CUGBP1 | 0.67 |
| Cystatin A | 0.69 |
| Cytokeratin CK5 | 0.60 |
| Fibronectin | 0.63 |
| gParvin | 0.70 |
| Growth Factor Independence1 | 0.63 |
| Nerve Growth Factor b | 0.60 |
| ProCaspase 8 | 0.72 |
| Rab7 | 0.62 |
| Rab9 | 0.73 |
| Serine Threonine Protein Phosphatase 1g1 | 0.71 |
| Serine Threonine Protein Phosphatase 2 A Bg | 0.73 |
| SKM1 | 0.70 |
| SLIPR MAGI3 | 0.67 |
| Spectrin a and b | 0.70 |
| Spred2 | 0.66 |
| TRF1 | 0.74 |

Example 8

Western Blot Analysis

The first experiment processed and evaluated by Western blot and 2-D gel electrophoresis was carried out on the skin cancer cell line SKMEL-28. This experimental set involved SK-MEL-28 cells treated at 3, 6, 12, and 24 hours with 50 or 100 μM Q10.

Figure 14:
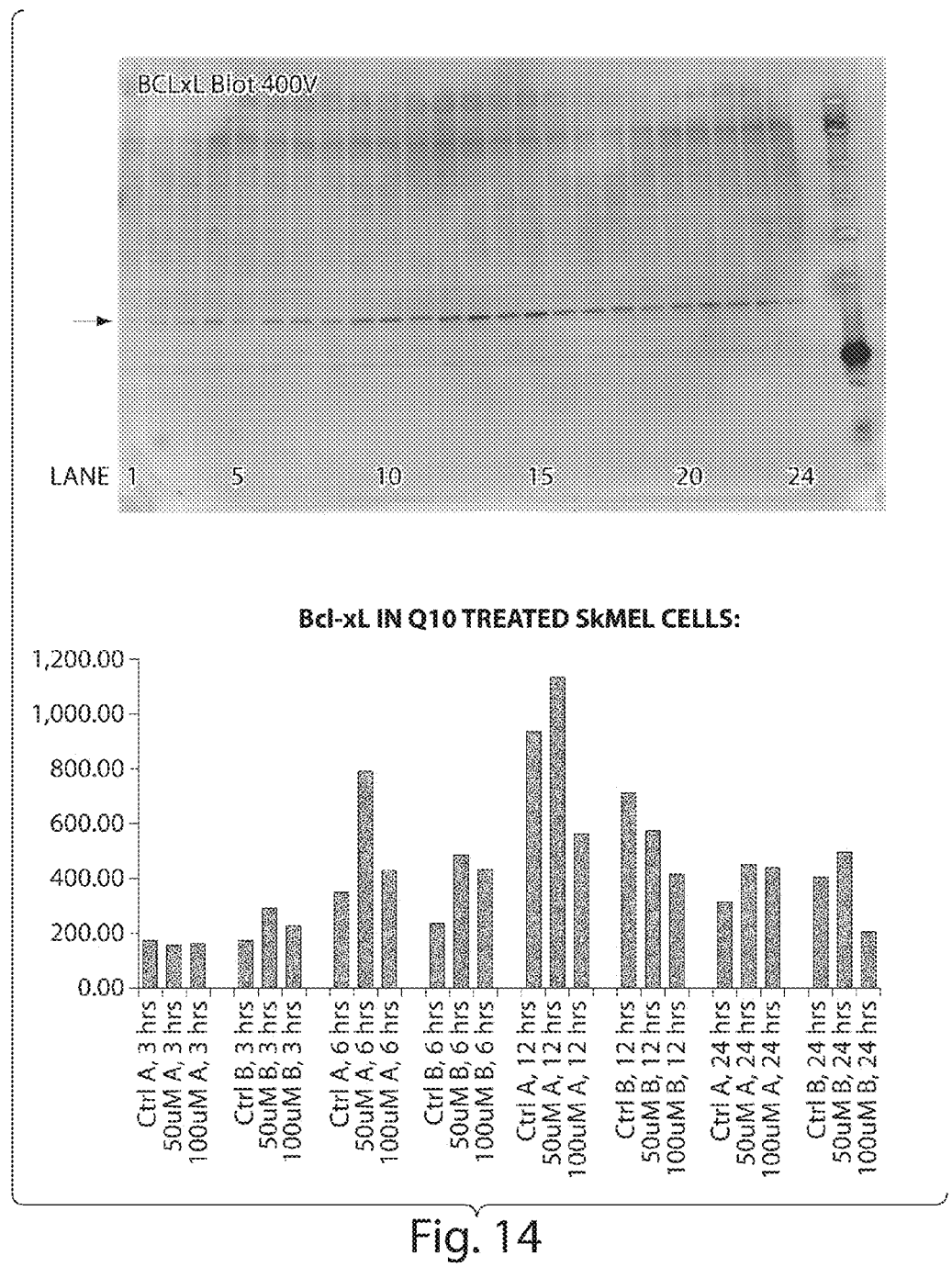
FIG. 14: Western blot analysis of Bcl-xl.
Figure 15:
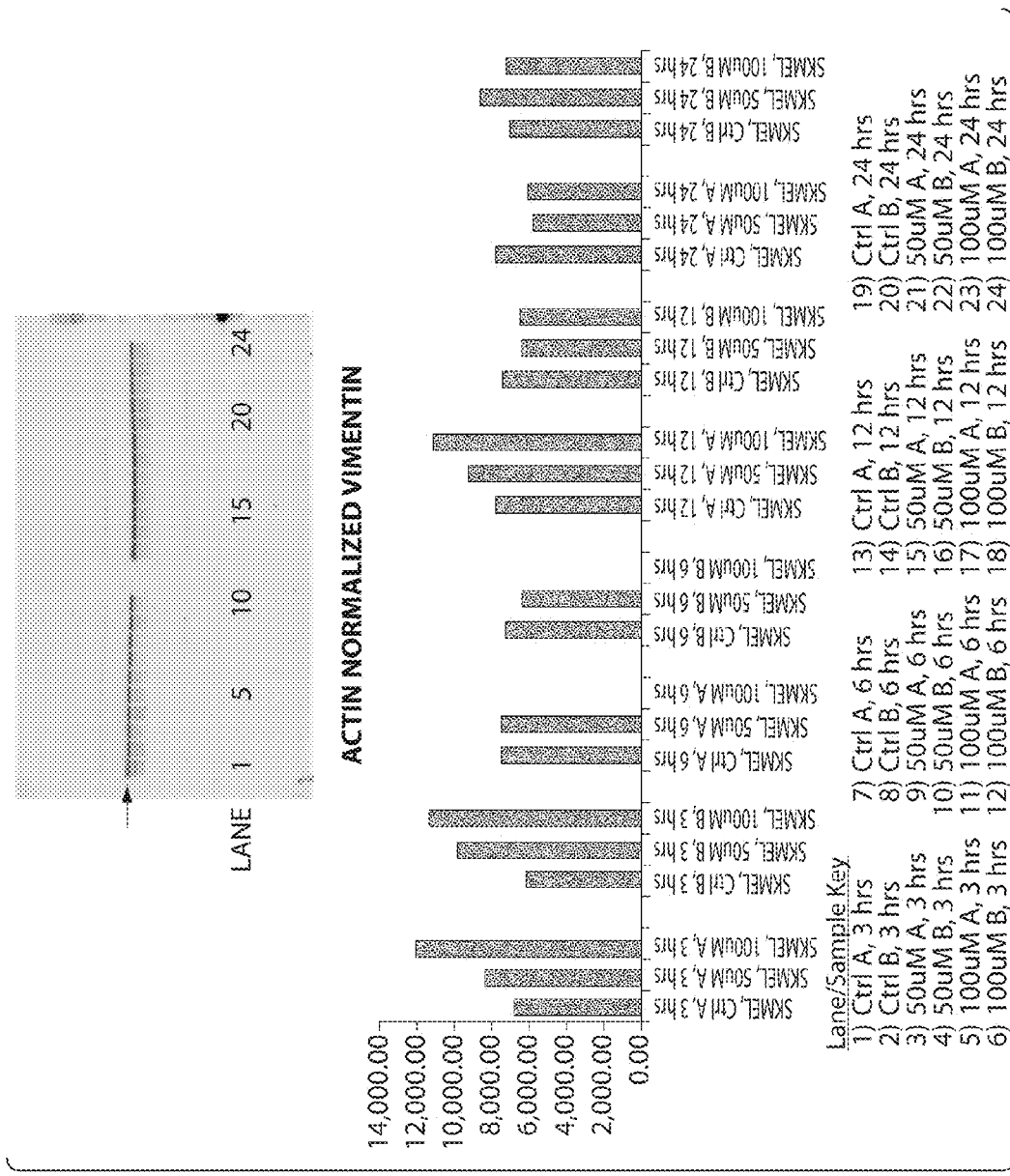
FIG. 15: Western blot analysis of SK-MEL-28 sample set proved with a Vimentin antibody.
Figure 16:
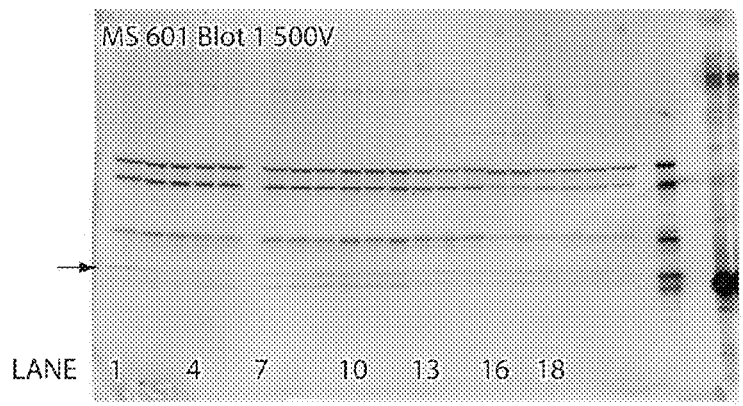
FIG. 16: Western blot analysis of cell lysis from a number of cell lines, evaluated with five antibodies targeting oxidative phosphorylation complexes (MitoSciences #MS601).
Figure 17:
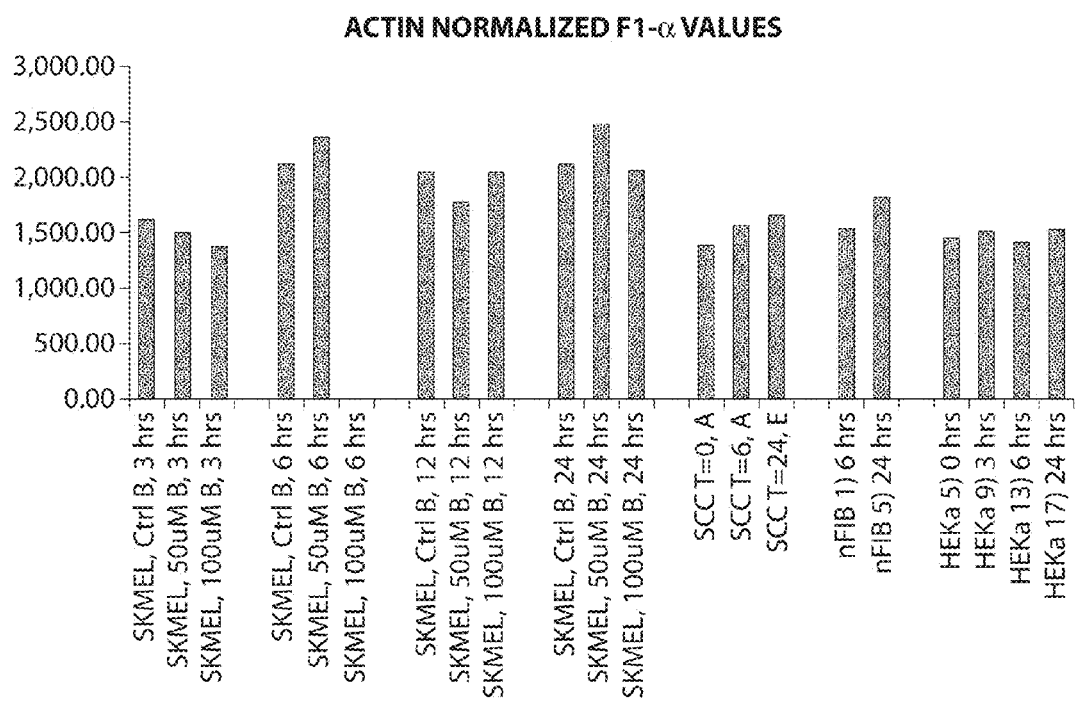
FIG. 17: Western blot comparison of F1-alpha levels.
Figure 18:
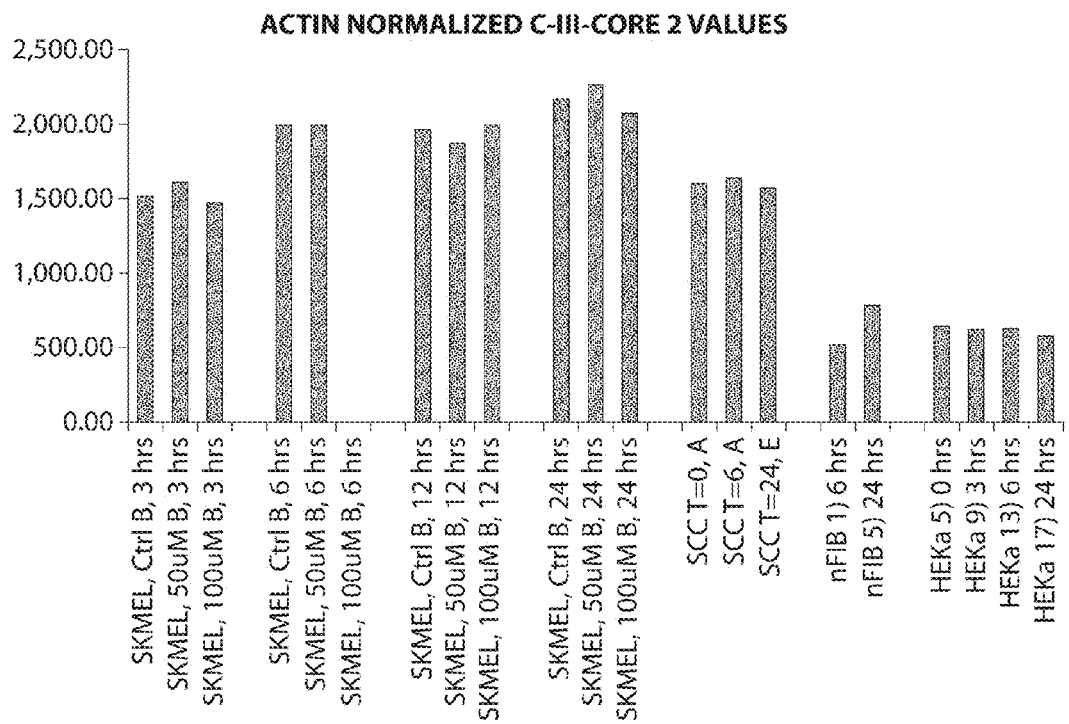
FIG. 18: Western blot comparison of Q10 response with C-III-Core 2.
Figure 19:
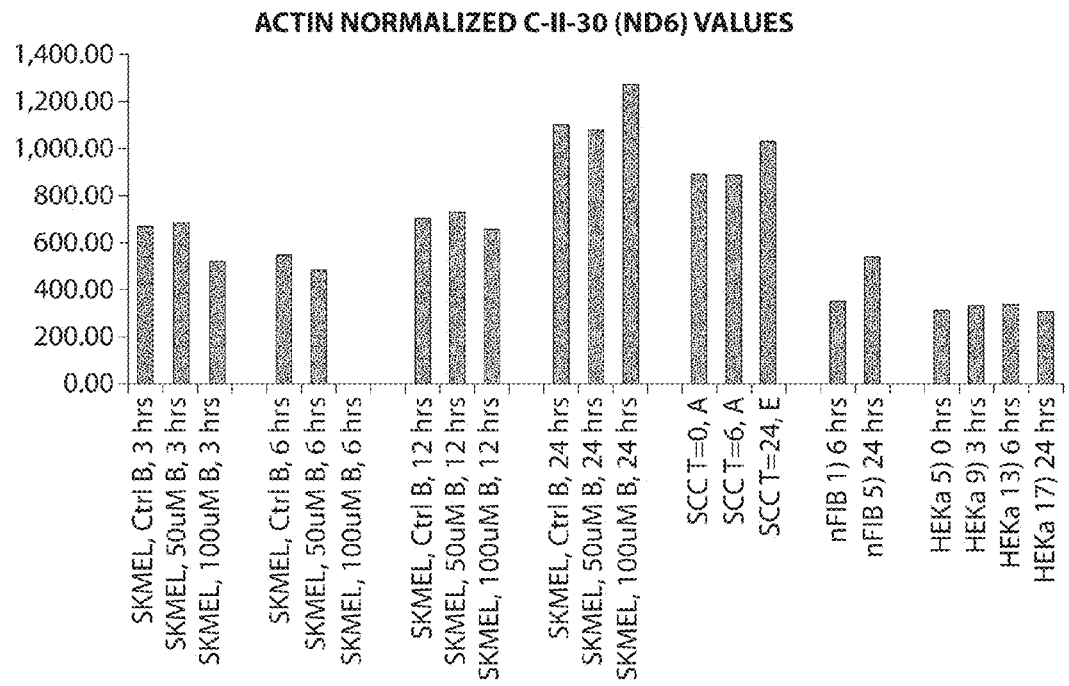
FIG. 19: Western blot comparison of Q10 response with C-II-30.
Figure 20:
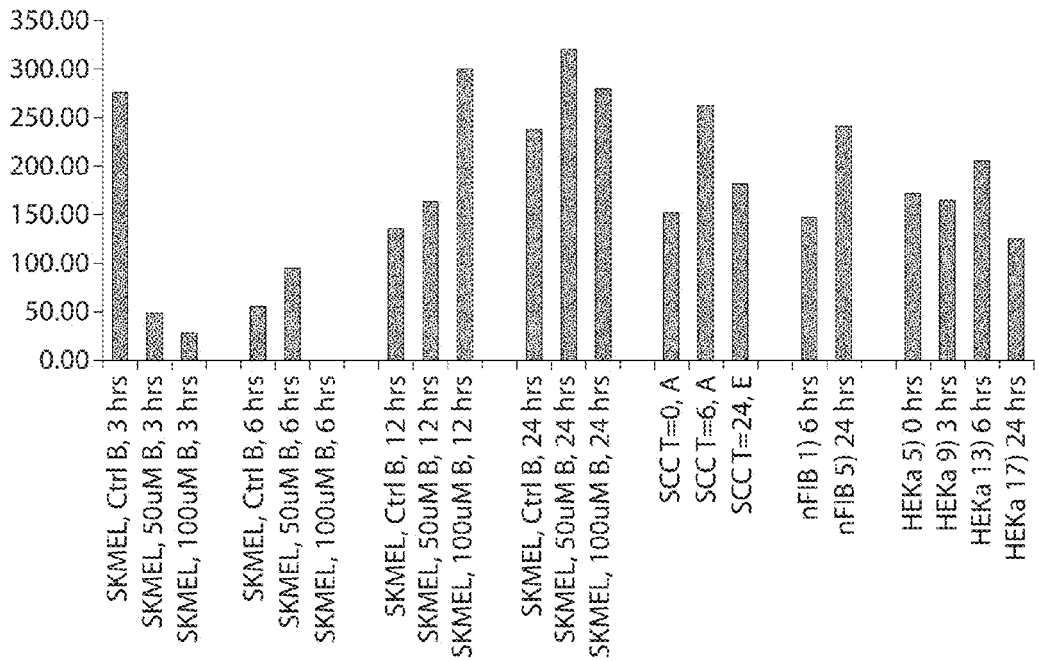
FIG. 20: Western blot comparison of Q10 response with C-IV-COX II.
Figure 21:
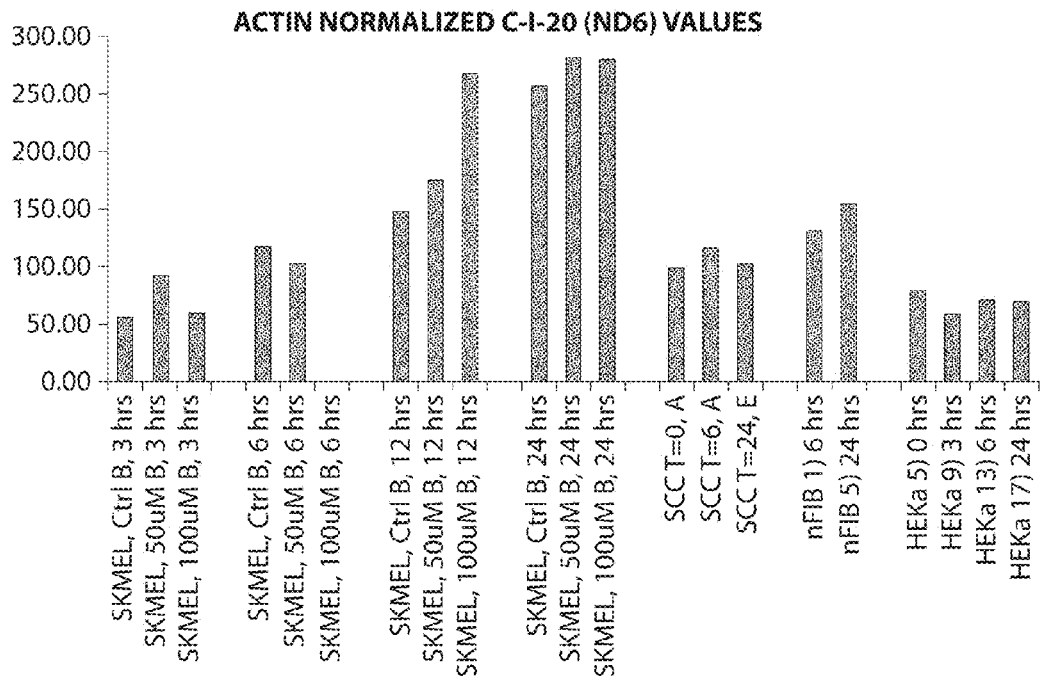
FIG. 21: Western blot comparison of Q10 response with C-I-20 (ND6).
Figure 22:
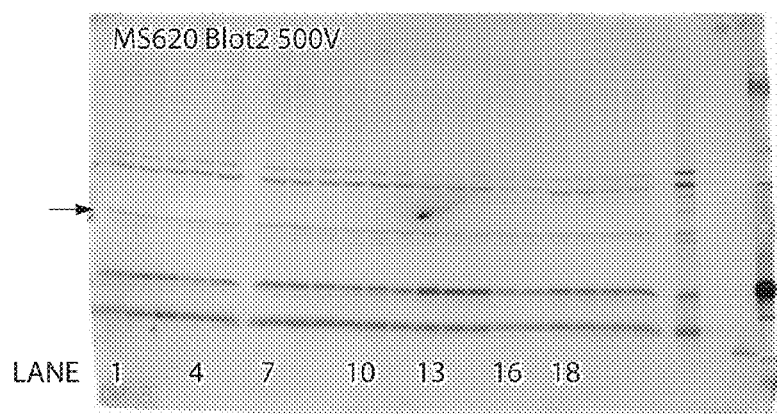
FIG. 22: Western blot analysis of a variety of cell types against five mitochondrial protein.
Figure 23:
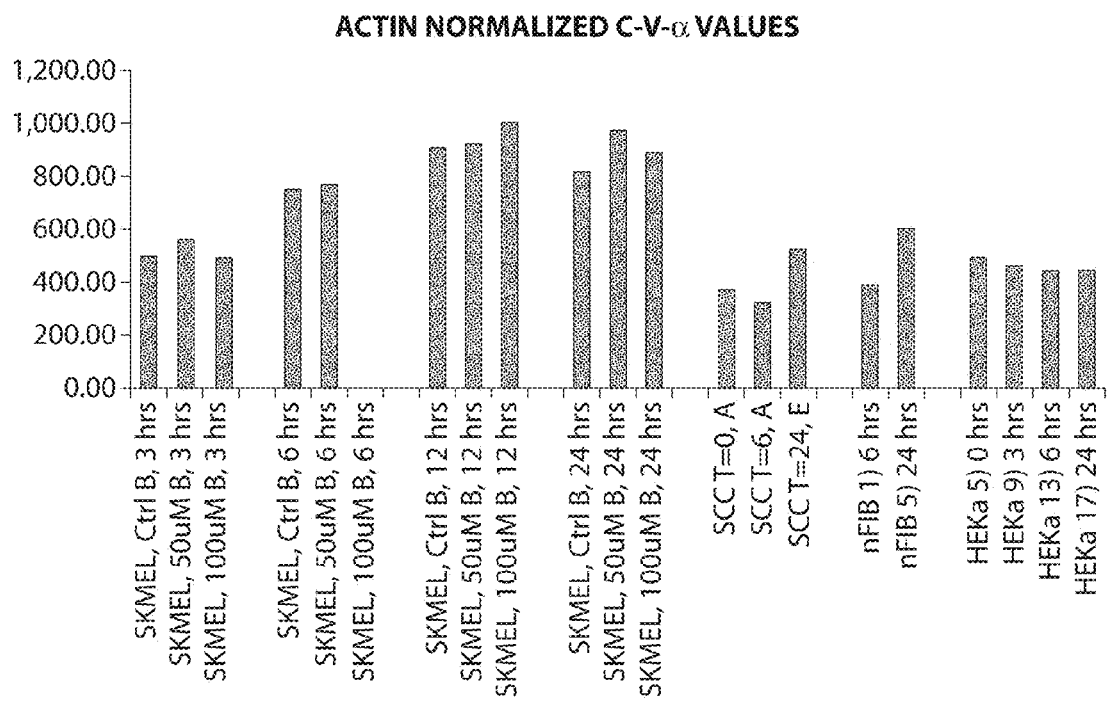
FIG. 23: Western blot comparison of Q10 response with Complex V protein C-V-α.
Figure 24:
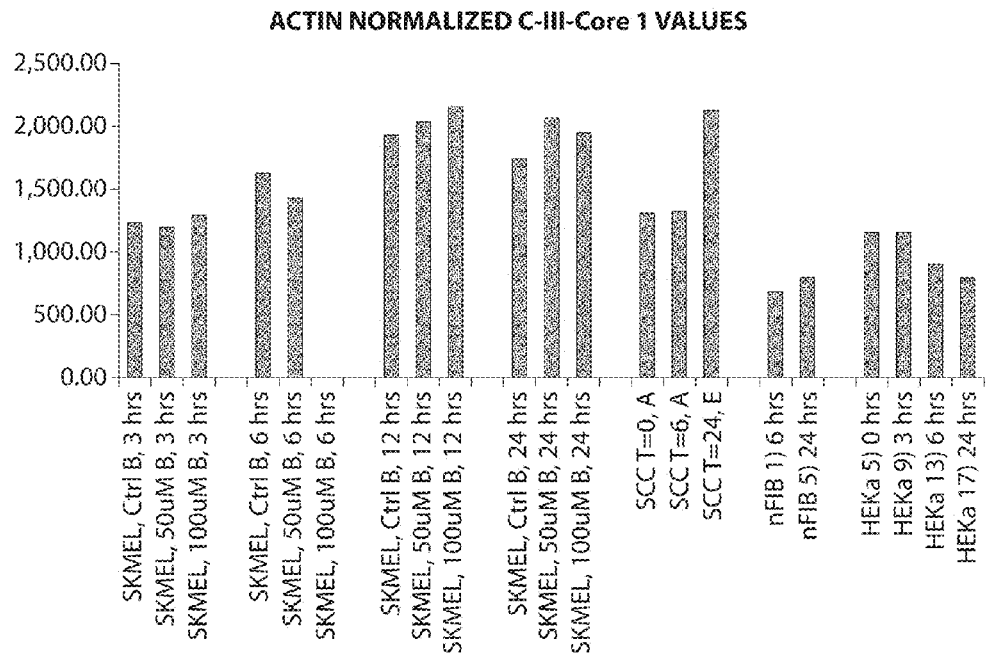
FIG. 24: Western blot comparison of Q10 response with C-III-Core 1.
Figure 25:
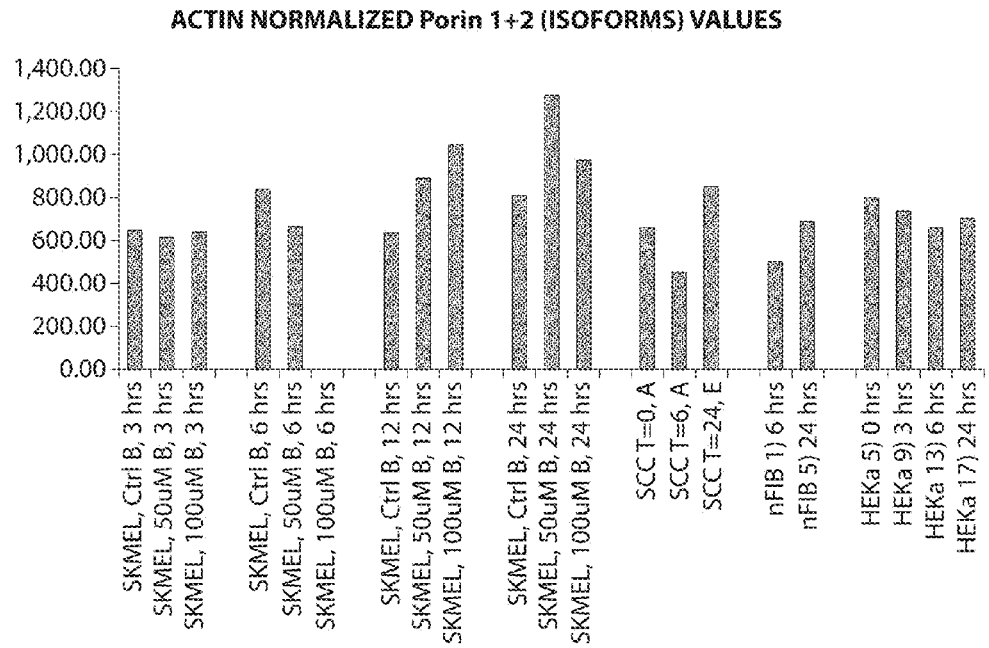
FIG. 25: Western blot comparison of Q10 response with Porin (VDAC1).
Figure 26:
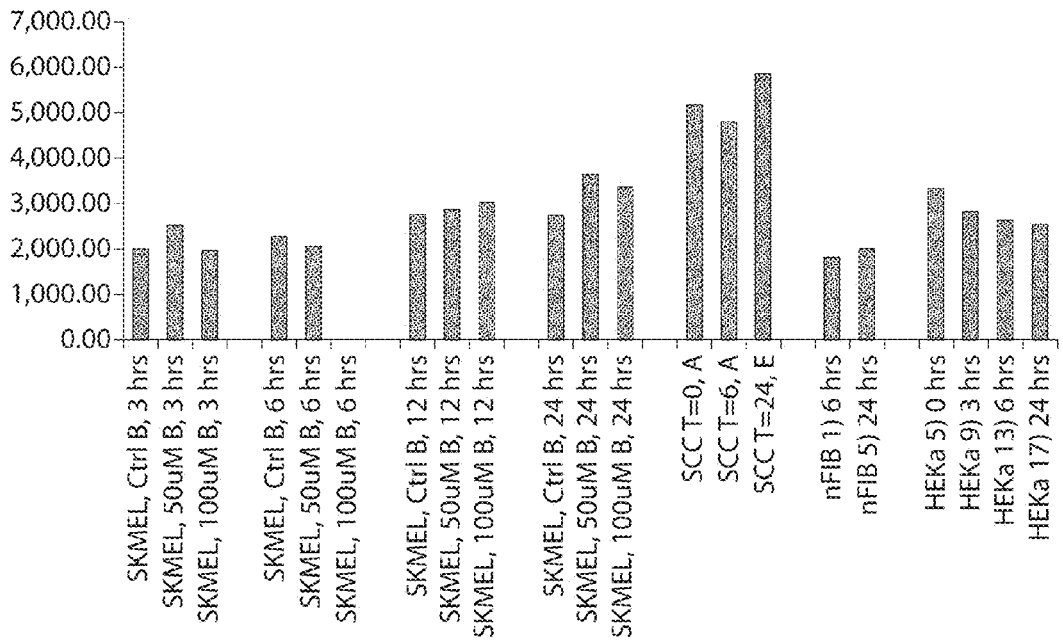
FIG. 26: Western blot comparison of Q10 response with Cyclophilin D.
Figure 27:
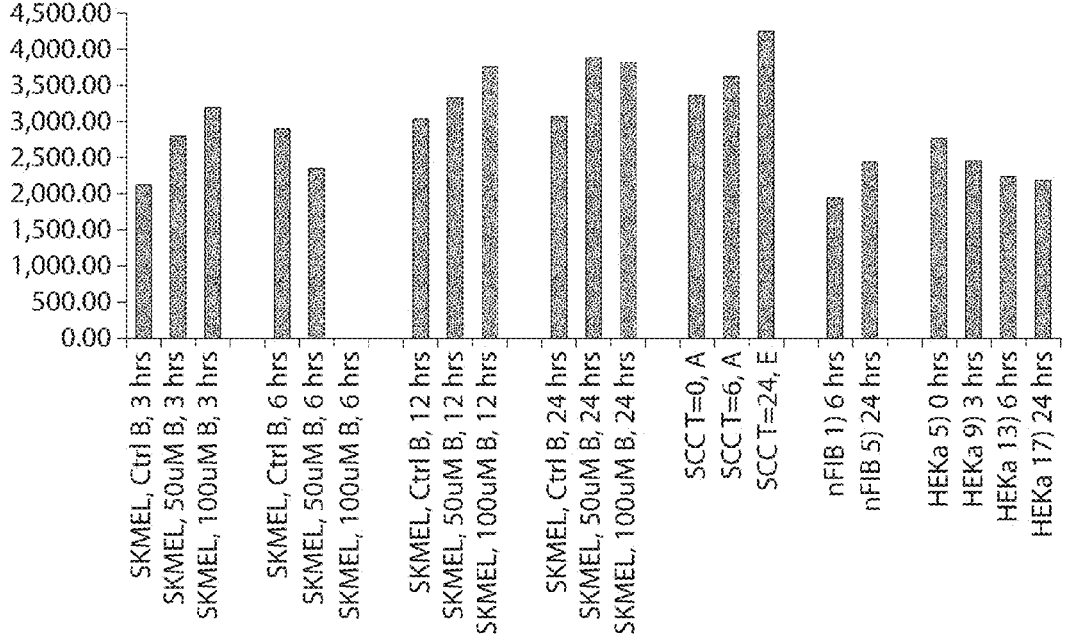
FIG. 27: Western blot comparison of Q10 response with Cytochrome C.

A variety of cell types were evaluated by Western blot analysis against an antibody for Bcl-xL (FIG. 14), an antibody for Vimentin (FIG. 15), a series of antibodies for mitochondrial oxidative phosphorylation function (FIGS. 16-21) and against a series of antibodies related to mitochondrial membrane integrity (FIGS. 22-27). The results from these experiments demonstrated that several of the examined proteins were upregulated or downregulated as a result of cell treatment with Q10.

Example 9

Diabetes Related Genes Identified as being Modulated at the mRNA Level by Treatment of Pancreatic Cancer Cells (PaCa2) with 100 um Q10

Diabetes arrays were run for samples treated with 100 uM Q10 at various times after treatment. Experiments were carried out essentially as described above. The various genes found to be modulated upon Q10 treatment are summarized in Table 23 below. The results showed that the following genes are modulated by Q10 treatment: ABCC8, ACLY, ADRB3, CCL5, CEACAM1, CEBRA, FOXG1, FOXP3, G6PD, GLP1R, GPD1, HNF4A, ICAM1, IGFBP5, INPPL1, IRS2, MAPK14, ME1, NFKB1, PARP1, PIK3C2B, PIK3CD, PPARGC1B, PRKAG2, PTPN1, PYGL, SLC2A4, SNAP25, HNF1B, TNRFSF1A, TRIB3, VAPA, VEGFA, IL4R and IL6.

TABLE 23

Genes from the diabetes array whose expression
is regulated with 100 µM Q10 and their possible functions in a cell.
Up-regulated (grey) and down-regulated (white).

| Gene Name | Gene Function. |
|---|---|
| ADRB | cAMP signaling, G-protein signaling |
| CCL5 | Natural ligands for CCR5 and is regulated by TNF. |
| CEACAM1 | Anti-apoptotic, positive regulation of angiogenesis. |
| GLPR1 | Increases Insulin and decreases glucagon secretion from the pancreas. |
| GPD1 | Carbohydrate metabolism, NADH oxidation. |
| ICAM1 | Regulated by atorvastatin, processes some caspases. |
| MAPK14 | DNA damage checkpoint, angiogenesis, glucose metabolic process. |
| PARP1 | DNA repair, regulates TP53, NOS2A, NFKB, telomere maintenance. |
| PIK3C2B | Phosphoinositide mediated signaling, regulates AKT and AKT1. |
| PIK3CD | Kinase |
| PYGL | carbohydrate metabolism, regulates glycogen and glycogen synthase. |
| SLC2A4 | regulates glucose and is regulated by INS and insulin. |
| SNAP25 | regulation of insulin secretion, nerotransmitter uptake. |
| CEBPA | Glucocorticoid receptor signaling, VDR/RXR activation. |
| FOXP3 | Regulates IL4, IL2. |
| G6PD | Pentose Phosphate Pathway, Glutathione metabolism. |
| IGFBP5 | Regulation of cell growth, regulated by IGF1 |
| INPPL1 | Regulates Akt and glycogen. |
| IRS2 | IGF-1 signaling |
| ME1 | Regulates malic acid and is regulated by T3. |
| NFKB1 | Regulates IL6 and TNF. |
| PPARGC1B | Regulated by MAPK14 |
| PRKAG2 | Fatty acid, cholesterol biosynthesis. |
| PTPN1 | dephosphorylates JAK2 and EGFreceptor kinase. |
| VEGFA | Kinase, angiogenesis. |
| IL4R | Up regulation by TP73, binds to IRS1 and IRS2 |
| HNF1B | HNF4A |
| TNFRSF1A | Pro-apoptotic |
| TRIB3 | Regulates AKT1 and negative regulator of NFkB. |
| VAPA | Regulates NFkB, vesicle trafficking. |

Example 10

Angiogenesis Related Genes Identified as being
Modulated at the mRNA Level by Treatment of
Pancreatic Cancer Cells (PaCa2) with 100 µM Q10

Angiogenesis arrays were run for samples treated with 100 uM Q10 at various times after treatment. Experiments were carried out essentially as described above. The various genes found to be modulated upon Q10 treatment are summarized in Table 24 below. The results showed that the following genes are modulated by Q10 treatment: AKT1, ANGPTL4, ANGPEP, CCL2, CDH4, CXCL1, EDG1, EFNA3, EFNB2, EGF, FGF1, ID3, IL1B, 1L8, KDR, NRP1, PECAM1, PROK2, SERPINF1, SPHK1, STAB1, TGFB1, VEGFA and VEGFB.

TABLE 24

A list of genes from the angiogenesis array whose expression
is regulated with 100 µM Q10 and their possible functions in a cell.
Up-regulated (grey) and down-regulated (white).

| Gene | Gene Function. |
|---|---|
| ANGPTL4 | antiangiogenesis, negative regulator of apoptosis, lipid metabolism. |
| CDH5 | blood vessel maturation, cell-adhesion, negative regulator of cell proliferation. |
| FGF1 | Cell adhesion, cell proliferation. |
| AKT1 | carbohydrate metabolic process, glycogen biosynthetic process, glucose metabolic process, insulin receptor signaling pathway, activation of pro-apoptotic gene products, apoptotic mitochondrial changes |
| ANPEP | proteolysis, multicellular organismal development, cell differentiation |
| CCL2 | chemotaxis, anti-apoptosis, JAK-STAT cascade, organ morphogenesis, viral genome replication |
| CXCL1 | chemotaxis, inflammatory response, immune response, negative regulation of cell proliferation, actin cytoskeleton organization and biogenesis. |
| EDG1 | positive regulation of cell proliferation, transmission of nerve impulse, regulation of cell adhesion, neuron differentiation, positive regulation of cell migration, positive regulation of Ras |
| EFNB2 | cell-cell signaling, regulated by VEGFA. |
| EGF | activation of MAPKK activity, positive regulation of mitosis, DNA replication |
| IL1B | response to glucocorticoid stimulus, apoptosis, signal transduction, cell-cell signaling, negative regulation of cell proliferation |
| IL8 | cell cycle arrest |
| KDR | VEGF pathway, regulated by AKT. |
| NRP1 | cell adhesion, signal transduction, cell-cell signaling, cell proliferation, regulated by VEGFA |
| PECAM1 | cell adhesion, regulated by TNF. |
| PROK2 | activation of MAPK, anti-apoptosis, cell proliferation, regulates AKT, |
| SPHK1 | anti-apoptosis, cell proliferation, regulates mitosis, cell migration. |
| STAB1 | inflammatory response, cell adhesion, receptor-mediated endocytosis, cell-cell signaling, negative regulation of angiogenesis, defense response to bacterium |
| VEGFA | anti-apoptosis, regulates TNF, regulated by HIF1. |

Example 11

Apoptosis Related Genes Identified as being Modulated at the mRNA Level by Treatment of Pancreatic Cancer Cells (PaCa2) with 100 µM Q10

Apoptosis arrays were run for samples treated with 100 uM Q10 at various times after treatment. Experiments were carried out essentially as described above. The various genes found to be modulated upon Q10 treatment are summarized in Table 25 below. The results showed that the following genes are modulated by Q10 treatment: ABL1, AKT1, Bcl2L1, BclAF1, CASP1, CASP2, CASP6, CIDEA, FADD, LTA, TNF, TNFSF10A and TNFSF10.

TABLE 25

A list of genes from the apoptosis array whose expression
is regulated with 100 µM Q10 and their possible functions in a cell.
Up-regulated (Grey) and down-regulated (white).

| Gene | Gene Function. |
|---|---|
| CASP1 | Pro-Apoptotic, Regulates IL1B, regulated by TNF. |
| CASP6 | Pro-Apoptotic, regulates PARP, MCL1, APP |
| TNF | cell proliferation, differentiation, apoptosis, lipid metabolism, and coagulation |
| TNFSF10 | Pro-Apoptotic, regulates caspases. |
| ABL1 | Regulates Bcl2L1, TP53, Pro-apoptotic, actin cytoskeleon organization and biogenesis. |
| AKT1 | Prop-apoptotic, apoptotic mitochondrial changes, carbohydrate transport, response to heat, glucose metabolism, IGF signaling pathway. |
| BclAF1 | Pro-Apoptotic. |
| Bcl2L1 | Anti-Apoptotic. release of cytochrome c from mitochondria, regulates Caspases, binds to BAD, BAX, BCl2L11 |
| CASP2 | Anti-Apoptotic. |
| CIDEA | Pro-Apoptotic |
| FADD | Pro-Apoptotic |
| LTA | Pro-Apoptotic |
| TNFSF10A | Caspase Activator |

Example 12

PCR Diabetes Arrays on Liver Cancer (HepG2) Cells

HepG2 (liver cancer) cells were treated with either the vehicle for 24 hours or 100 µM Q10 for different times. The treatment was initiated on 1×105 cells per well, following the procedure utilized in the PaCa2 cells (above, Examples 9-11). However, the total amount of RNA that was extracted from these samples was lower than expected. Reverse transcription is normally done using 1 µg of total RNA (determined by measurement at 260 nm). The maximum volume that can be used per reverse transcription is 8 µl. Since the RNA concentration was low, the RT-PCR array analysis using the vehicle, and Q10 treated samples from 16 hours and 48 hours was performed using 0.44 µg of RNA. The arrays provided an initial analysis of trends and patterns in HepG2 gene regulation with 100 µM Q10 treatment, as summarized in Table 26 below. The results showed that each of the genes PPARGC1A, PRKAA1 and SNAP25 were downregulated at 16 hours following treatment (by approximately 20 fold, 6 fold and 5 fold, respectively). At 48 hours following treatment, PPARGC1A and PRKAA1 had normalized or were slightly upregulated, while SNAP25 was downregulated by approximately 2 fold.

TABLE 26

List of genes regulated in the Diabetes Arrays
when HepG2 cells were treated with 100 µM Q10.

| Gene | Gene name | Gene Function. |
|---|---|---|
| PPARGC1A | peroxisome proliferator-activated receptor gamma, coactivator 1 alpha | Involved in cell death, proliferation, cellular respiration and transmembrane potential. |
| PRKAA1 | protein kinase, AMP-activated, alpha 1 catalytic subunit | Regulates TP53 and is involved in apoptosis, regulates glycolysis, regulates metabolic enzyme activities. |
| SNAP25 | synaptosomal-associated protein, 25 kDa | Plays in transport, fusion, exocytosis and release of molecules. |

Example 13

PCR Angiogenesis Array on Liver Cancer (HEPG2) Cells

HepG2 (liver cancer) cells were treated with either the vehicle for 24 hours or 100 µM Q10 for different times. The treatment was initiated on 1×105 cells per well, following the procedure utilized in the PaCa2 cells (above Examples 9-11). However, the total amount of RNA that was extracted from these samples was lower than expected. Reverse transcription is normally done using 1 µg of total RNA (determined by measurement at 260 nm). The maximum volume that can be used per reverse transcription is 8 µl. Since the RNA concentration was low, the RT-PCR array analysis using the vehicle, and Q10 treated samples from 16 hours and 48 hours was performed using 0.44 µg of RNA. The arrays provided an initial analysis of trends and patterns in HepG2 gene regulation with 100 µM Q10 treatment, as summarized in Table 27 below. The various genes found to be modulated upon Q10 treatment are summarized in Table 27 below. The results showed that each of the genes ANGPTL3, ANGPTL4, CXCL1, CXCL3, CXCL5, ENG, MMP2 and TIMP3 were upregulated at 16 hours following treatment (by approximately 5.5, 3, 3, 3.2, 3, 3, 1 and 6.5 fold, 6 fold and 5 fold, respectively, over that of control). ID3 was downregulated at 16 hours following Q10 treatment, by approximately 5 fold over control. At 48 hours following treatment, ANGPTL3, CXCL1, CXCL3, ENG and TIMP3 were still upregulated (by approximately 3.5, 1.5, 3.175, 2 and 3 fold, respectively, over control), while ANGPTL4, CXCL5, ID3 and MMP2 were downregulated by approximately 1, 1, 2 and 18 fold, respectively, over control.

TABLE 27

List of genes regulated in the Angiogenesis Arrays
when HepG2 cells were treated with 100 µM Q10.

| Gene | Gene Name. | Gene Function. |
|---|---|---|
| ANGPTL3 | angiopoietin-like 3 | Predominantly expressed in live, role in cell migration and adhesion, regulates fatty acid and glycerol metabolism. |
| ANGPTL4 | angiopoietin-like 4 | Regulated by PPARG, apoptosis inhibitor for vascular endothelial cells, role lipid and glucose metabolism and insulin sensitivity. |
| CXCL1 | chemokine (C-X-C motif) ligand 1 (melanoma growth stimulating activity, alpha) | Role in cell proliferation and migration |
| CXCL3 | chemokine (C-X-C motif) ligand 3 | Chemokine activation, hepatic stellar cell activation, migration, proliferation. |
| CXCL5 | chemokine (C-X-C motif) ligand 5 | Produced along with IL8 when stimulated with IL1 or TNFA. Role in chemotaxis, migration, proliferation. |
| ENG | endoglin | Binds to TGFBR and is involved in migration, proliferation, attachment and invasion. |
| ID3 | inhibitor of DNA binding 3, dominant negative helix-loop-helix protein | Regulates MMP2, Regulated by TGFB1, Vitamin D3, Retinoic acid, VEGFA, involved in apoptosis, proliferation, differentiation, migration. |
| MMP2 | matrix metallopeptidase 2 (gelatinase A, 72 kDa gelatinase, 72 kDa type IV collagenase) | Hepatic stellate cell activation, HIF signaling, binds to TIMP3, involved in tumorigenesis, apoptosis, proliferation, invasiveness, migration and chemotaxis. |
| TIMP3 | TIMP metallopeptidase inhibitor 3 | Regulates MMP2, ICAM1. Regulated by TGFB, EGF, TNF, FGF and TP53. Involved in apoptosis, cell-cell adhesion and malignancy. |

Proteins known to be involved in the process of angiogenesis were components in the RT-PCR array. Angiogenesis is a critical process by which cancer cells become malignant. Some of these proteins are also implicated in diabetes.

ANGPTL3 and ANGPTL4: The literature related to ANGPTL3 connects this protein to the regulation of lipid metabolism. In particular, the literature (Li, C. *Curr Opin Lipidol.* 2006 April; 17(2):152-6) teaches that both angiopoietins and angiopoietin-like proteins share similar domain structures. ANGPTL3 and 4 are the only two members of this superfamily that inhibit lipoprotein lipase activity. However, ANGPTL3 and 4 are differentially regulated at multiple levels, suggesting non-redundant functions in vivo. ANGPTL3 and 4 are proteolytically processed into two halves and are differentially regulated by nuclear receptors. Transgenic overexpression of ANGPTL4 as well as knockout of ANGPTL3 or 4 demonstrate that these two proteins play essential roles in lipoprotein metabolism: liver-derived ANGPTL3 inhibits lipoprotein lipase activity primarily in the fed state, while ANGPTL4 plays important roles in both fed and fasted states. In addition, ANGPTL4 regulates the tissue-specific delivery of lipoprotein-derived fatty acids. ANGPTL4 is thus an endocrine or autocrine/paracarine inhibitor of lipoprotein lipase depending on its sites of expression.

Lipoprotein lipase is an enzyme that hydrolyzes lipids in lipoproteins, such as those found in chylomicrons and very low-density lipoproteins (VLDL), into three free fatty acids and one glycerol molecule. Lipoprotein lipase activity in a given tissue is the rate limiting step for the uptake of triglyceride-derived fatty acids. Imbalances in the partitioning of fatty acids have major metabolic consequences. High-fat diets have been shown to cause tissue-specific overexpression of LPL, which has been implicated in tissue-specific insulin resistance and consequent development of type 2 diabetes mellitus.

The results in this Example indicate that Q10 is modulating proteins involved in lipid metabolism and thus warrants further investigation of ANGPTL3/ANGPTL4 and their related pathways. For example, ANGPTL3/ANGPTL4 have been implicated to play a role in the following pathways: Akt, cholesterol, fatty acid, HDL-cholesterol, HNF1A, ITGA5, ITGA5, ITGAV, ITG83, L-trilodothynonine, LIPG, LPL, Mapk, Nrth, NR1H3, PPARD, PTK2, RXRA, triacylglerol and 9-cis-retinoic acid.

Example 14

PCR Apoptosis Array on Liver Cancer (HEPG2) Cells

Apoptosis arrays were run for samples treated with 100 uM Q10 for 16 and 48 hours as described above. However, the array for 48 hours was run choosing FAM as the fluorophore instead of SYBR. Both FAM and SYBR fluoresce at the same wavelength.

The various genes found to be modulated upon Q10 treatment are summarized in Table 28 below. The results showed that CASP9 was upregulated at 16 hours following Q10 treatment, by approximately 61 fold over control, while BAG1 and TNFRSF1A were downregulated at 16 hours following treatment by approximately 6 and 4 fold, respectively, over that of control. At 48 hours following treatment, CASP9, BAG1 and TNFRSF1A were upregulated by approximately 55, 1 and 1 fold, respectively, over control.

TABLE 28

List of genes regulated in the Apoptosis Arrays
when HepG2 cells were treated with 100 µM Q10.

| Gene | Gene Name | Gene Function |
|---|---|---|
| BAG1 | BCL2-associated athanogene | Involved with Apoptosis |
| CASP9 | caspase 9, apoptosis-related cysteine peptidase | Apoptosis through release of cytochrome c. |

TABLE 28-continued

List of genes regulated in the Apoptosis Arrays
when HepG2 cells were treated with 100 μM Q10.

| Gene | Gene Name | Gene Function. |
|---|---|---|
| TNFRSF1A | tumor necrosis factor receptor superfamily, member 1A | anti-apoptosis, binds many cell death factors, regulates ICAM1 |

Example 15

Assessing Ability of MIM or Epi-Shifter to Treat Oncological Disorder

The ability of a selected MIM or Epi-shifter, e.g., CoQ10, to treat an oncological disorder, e.g., melanoma, is evaluated in a murine model. Melanoma tumors are induced in mice by SK-MEL28 injection into the subcutaneous layer. The animal study consists of both a control and treatment group each containing four mice. The mice are inoculated with two tumors. A topical formulation of the MIM or Epi-shifter is applied to the tumors in the treatment group daily for a period of 30 days, after which, the tumors are excised and the mass is determined. A MIM or Epi-shifter is identified as effective in treating the tumor when the difference in the overall mean mass of the treatment group is significant compared to the control.

Example 16

Identification of a MIM Associated with an Oncological Disorder

In order to evaluate a candidate molecule (e.g., environmental influencer) as a potential MIM, the selected candidate MIM is exogenously added to a panel of cell lines, including both diseased (cancer) cell lines and normal control cell lines, and the changes induced to the cellular microenvironment profile for each cell line in the panel are assessed. Changes to cell morphology, physiology, and/or to cell composition, including for example, mRNA and protein levels, are evaluated and compared for the diseased cells as compared to normal cells.

Changes to cell morphology/physiology are evaluated by examining the sensitivy and apoptotic response of cells to the candidate MIM. These experiments are carried out as described in detail in Example 3. Briefly, a panel of cell lines consisting of at least one control cell line and at least one cancer cell line are treated with various concentrations of the candidate MIM. The sensitivity of the cell lines to the potential MIM are evaluated by monitoring cell survival at various times, and over the range of applied concentrations. The apoptoic response of the cell lines to the potential MIM are evaluated by using, for example, Nexin reagent in combination with flow cytometry methodologies. Nexin reagent contains a combination of two dyes, 7AAD and Annexin-V-PE, and allows quantification of the population of cells in early and late apoptosis. An additional apoptosis assay that measures single-stranded DNA may be used, using for example Apostrand™ ELISA methodologies. The sensitivity and apoptotic response of the disease and control cell lines are evaluated and compared. A molecule that displays differential cytotoxicity and/or that differentially induces the apoptotic response in the diseased cells as compared to the normal cells is identified as a MIM.

Changes in the composition of cells following treatment with the candidate MIM are evaluated. Changes in gene expression at the mRNA level are analyzed using Real-Time PCR array methodology. These experiments are carried out as described in detail in Examples 6 and 9-13. Briefly, the candidate MIM is exogenously added to one or more cell lines including, for example a diseased cell and a normal control cell line, and mRNA is extracted from the cells at various times following treatment. The level of mRNAs for genes involved in specific pathways are evaluated by using targeted pathway arrays, including, for example, arrays specific for apoptosis, oxidative stress and antioxidate defense, angiogenesis, heat shock or diabetes. The genes that are altered in their mRNA transcription by a two-fold level or greater are identified and evaluated. A molecule that induces changes in mRNA levels in cells and/or that induces differential changes in the level of one or more mRNAs in the diseased cells as compared to the normal cells is identified as a MIM.

In complementary experiments, changes in gene expression at the protein level are analyzed by using antibody microarray methodology, 2-dimensional gel electrophoresis followed by protein identificuation using mass spectrometry characterization, and by western blot analysis. These experiments are carried out as described in detail in Examples 7, 4 and 8, respectively. Briefly, the candidate MIM is exogenously added to one or more cell lines, including, for example a diseased cell and a normal control cell line, and soluble protein is extracted from the cells at various times, e.g., 6 hours or 24 hours, following treatment. Changes induced to protein levels by the candidate MIM are evaluated by using an antibody microarray containing antibodies for over 700 proteins, sampling a broad range of protein types and potential pathway markers. Further complementary proteomic analysis can be carried by employing 2-dimensional (2-D) gel electrophoresis coupled with mass spectrometry methodologies. The candidate MIM is exogenously added to one or more cell lines, including, for example a diseased cell and a normal control cell line, and cell pellets are lysed and subjected to 2-D gel electrophoresis. The gels are analyzed to identify changes in protein levels in treated samples relative to control, untreated samples. The gels are analyzed for the identification of spot changes over the time course of treatment due to increased levels, decreased levels or post-translational modification. Spots exhibiting statistically significant changes are excised and submitted for protein identification by trypsin digestion and mass spectrometry characterization. The characterized peptides are searched against protein databases with, for example, Mascot and MSRAT software analysis to identify the proteins. In addition to the foregoing 2-D gel analysis and antibody microarray experiments, potential changes to levels of specific proteins induced by the candidate MIM may be evaluated by Western blot analysis. In all of the proteomic experiments, proteins with increased or decreased levels in the various cell lines are identified and evaluated. A molecule that induces changes in protein levels in cells and/or that induces differential changes in the level of one or more proteins in the diseased cells as compared to the normal cells is identified as a MIM.

Genes found to be modulated by treatment with a candidate MIM from the foregoing experiments are subjected to cellular and biochemical pathway analysis and can thereby be categorized into various cellular pathways, including, for example apoptosis, cancer biology and cell growth, glycolysis and metabolism, molecular transport, and cellular signaling.

Experiments are carried out to confirm the entry of a candidate MIM into cells, to determine if the candidate MIM becomes localized within the cell, and to determine the level and form of the candidate MIM present in the cells. These experiments are carried out, for example, as described in detail in Example 5. For example, to determine the level and the form of the candidate MIM present in the mitochondria, mitochondrial enriched preparations from cells treated with the candidate MIM are prepared and analyzed. The level of the candidate MIM present in the mitochondria can thereby be confirmed to increase in a time and dose dependent manner with the addition of exogenous candidate MIM. In addition, changes in levels of proteins from mitochondria enriched samples are analyzed by using 2-D gel electrophoresis and protein identification by mass spectrometry characterization, as described above for total cell protein samples. Candidate MIMs that are found to enter the cell and to be present at increased levels, e.g., in the mitochondria, are identified as a MIM. The levels of the candidate MIM in the cell, or, for example, specifically in the mitochondria, over the time course examined can be correlated with other observed cellular changes, as evidenced by, for example, the modulation of mRNA and protein levels for specific proteins.

Candidate MIMs observed to induce changes in cell composition, e.g., to induce changes in gene expression at the mRNA or protein level, are identified as a MIM. Candidate MIMs observed to induce differential changes in cell morphology, physiology or cell composition (e.g., differential changes in gene expression at the mRNA or protein level), in a disease state (e.g., cancer) as compared to a normal (e.g., non-cancerous) state are identified as a MIM and, in particular, as having multidimensional character. Candidate MIMs found to be capable of entering a cell are identified as a MIM and, in particular, as having multidimensional character since the candidate MIM thereby exhibits a carrier effect in addition to a therapeutic effect.

Example 17

Identification of CoQ10 as an Epi-Shifter Associated with a Oncological Disorder A panel of skin cell lines consisting of a control cell lines (primary culture of keratinocytes and melanocytes) and several skin cancers cell lines (SK-MEL-28, a non-metastatic skin melanoma; SK-MEL-2, a metastatic skin melanoma; or SCC, a squamous cell carcinoma; PaCa2, a pancreatic cancer cell line; or HEP-G2, a liver cancer cell line) were treated with various levels of Coenzyme Q10. The cancer cell lines exhibited an altered dose dependent response when compared to the control cell lines, with an induction of apoptosis and cell death in the cancer cells only. Detailed exemplary experiments are presented in, e.g., Example 3 herein.

Assays were employed to assess changes in the mRNA and protein levels composition of the above-identified cells following treatment with CoQ10. Changes in mRNA expression were analyzed using real-time PCR microarrays specific for each of apoptosis, oxidative stress and antioxidants, angiogenesis and diabetes. Changes in protein expression were analyzed using antibody microarray analysis and western blot analysis. The results from these assays demonstrated that significant changes in gene expression, both at the mRNA and protein levels, were occurring in the cell lines due to the addition of the Coenzyme Q10. Numerous genes known to be associated with or involved in cellular metabolic processes were observed to be modulated as a result of treatment with CoQ10. For example, expression of the nuclear receptor protein HNF4A was found to be upmodulated in cells following Q10 treatment. Expression of transaldolase 1 (TAL) was also modulated in cells treated with Q10. TAL balances the levels of NADPH and reactive oxygen intermediate, thereby regulating the mitochondrial trans-membrande potentional, which is a critical checkpoint of ATP synthesis and cell survival. Of particular relevance to oncological disorders, numerous genes known to be associated with, e.g., apoptosis, cancer biology and cell growth, were identified as being regulated by Q10. Detailed exemplary experiments are presented in, e.g., Examples 4, 6, 7, 8 and 9 herein.

Q10 is an essential cofactor for exidative phosphorylation processes in the mitochondria for energy production. The level of Coenzyme Q10, as well as the form of CoQ10, present in the mitochondria was determined by analyzing mitochondrial enriched preparations from cells treated with CoQ10. The level of Coenzyme Q10 present in the mitochondria was confirmed to increase in a time and dose dependent manner with the addition of exogenous Q10. The time course correlated with a wide variety of cellular changes as observed in modulation of mRNA and protein levels for specific proteins related to metabolic and apoptotic pathways. Detailed exemplary experiments are presented in, e.g., Example 5 herein.

The results described herein identified the endogenous molecule CoQ10 as an epi-shifter. In particular, the results identified CoQ10 as inducing a shift in the metabolic state, and partially restoration of mitochondrial function, in cells. These conclusions are based on the following interpretation of the data described herein and the current knowledge in the relevant art.

Q10 is known to be synthesized, actively transported to, enriched in, and utilized in the mitochondrial inner membrane. Q10 is also known to be an essential cofactor for oxidative phosphorylation processes in the mitochondrial for energy production. However, most cancer cells predominantly produce energy by glycolysis followed by lactic acid fermentation in the cytosol, rather than by oxidation of pyruvate in mitochondria like most normal cells. The oxidative phosphorylation involves the electron transport complexes and cytochrome c. Apoptosis involves the disruption of the mitochondria, with permiabilization of the inter mitochondrial membrane by pro-apoptitic factors. By utilizing a different metabolic energy synthesis pathway, cancer cells are able to mitigate the normal apoptosis response to abnormalities in the cell. While not wishing to be bound by theory, Applicants propose that Q10 is functioning by upregulating the oxidative phosphorylation pathway proteins, thus switching the mitochondrial function back to a state that would recognize the oncogenic defects and trigger apoptosis. Thus, Q10 is acting as an Epi-shifter by shifting the metabolic state of a cell.

Example 18

Identification of an Epi-Shifter Associated with an Oncological Disorder

A panel of skin cell lines consisting of control cell lines (e.g., primary culture of keratinocytes and melanocytes) and cancer cell lines (e.g., SK-MEL-28, a non-metastatic skin melanoma; SK-MEL-2, a metastatic skin melanoma; or SCC, a squamous cell carcinoma; PaCa2, a pancreatic cancer cell line; or HEP-G2, a liver cancer cell line) are treated with various levels of a candidate Epi-shifter. Changes to cell morphology/physiology are evaluated by examining the sensitivy and apoptotic response of cells to the candidate Epi-shifter. These experiments are carried out as described in detail in Example 3. Briefly, the sensitivity of the cell lines to the candidate Epi-shifter are evaluated by monitoring cell survival at various times, and over a range of applied concentrations. The apoptoic response of the cell lines to the candidate Epi-shifter are evaluated by using, for example, Nexin reagent in combination with flow cytometry methodologies. Nexin reagent contains a combination of two dyes, 7AAD and Annexin-V-PE, and allows quantification of the population of cells in early and late apoptosis. An additional apoptosis assay that measures single-stranded DNA may be used, using for example Apostrand™ ELISA methodologies. The sensitivity and apoptotic response of the disease and control cell lines are evaluated and compared. Candidate Epi-shifters are evaluated based on their ability to inhibit cell growth preferentially or selectively in cancer cells as compared to normal or control cells. Candidate Epi-shifters are further evaluated based on their ability to preferentially or selectively induce apoptosis in cancer cells as compared to normal or control cells.

Assays are employed to assess changes in the mRNA and protein level composition of the above-identified cells following treatment with the candidate Epi-shifter. Changes in mRNA levels are analyzed using real-time PCR microarrays. These experiments are carried out as described in detail in Examples 6 and 9-13. Briefly, mRNA is extracted from the cells at various times following treatment. The level of mRNAs for genes involved in specific pathways are evaluated by using targeted pathway arrays, including, arrays specific for apoptosis, oxidative stress and antioxidate defense, angiogenesis, heat shock or diabetes. The genes that are altered in their mRNA transcription by a two-fold level or greater are identified and evaluated.

Changes in protein expression are analyzed using antibody microarray analysis, 2-D gel electrophoresis analysis coupled with mass spectrometry characterization, and western blot analysis. These experiments are carried out as described in detail in Examples 7, 4 and 8, respectively. Briefly, soluble protein is extracted from the cells at various times, e.g., 6 hours or 24 hours, following treatment with the candidate Epi-shifter. Changes induced to protein levels by the candidate Epi-shifter are evaluated by using an antibody microarray containing antibodies for over 700 proteins, sampling a broad range of protein types and potential pathway markers. Further complementary proteomic analysis can be carried out by employing 2-dimensional (2-D) gel electrophoresis coupled with mass spectrometry methodologies. The candidate Epi-shifter is exogenously added to the cell lines and cell pellets are lysed and subjected to 2-D gel electrophoresis. The gels are analyzed to identify changes in protein levels in treated samples relative to control, untreated samples. The gels are analyzed for the identification of spot changes over the time course of treatment due to increased levels, decreased levels or post-translational modification. Spots exhibiting statistically significant changes are excised and submitted for protein identification by trypsin digestion and mass spectrometry characterization. The characterized peptides are searched against protein databases with, for example, Mascot and MSRAT software analysis to identify the proteins. In addition to the foregoing 2-D gel analysis and antibody microarray experiments, potential changes to levels of specific proteins induced by the candidate MIM may be evaluated by Western blot analysis. In all of the proteomic experiments, proteins with increased or decreased levels in the various cell lines are identified and evaluated.

Candidate Epi-shifters are evaluated based on changes induced to gene expression, at the mRNA and/or protein levels, in the cell lines due to the addition of the candidate Epi-shifter. In particular, candidate Epi-shifters are evaluated based on their ability to modualate genes known to be associated with or involved in cellular metabolic processes. Of particular relevance to oncological disorders, candidate Epi-shifters are evaluated based on their ability to modulate genes known to be associated with, for example, apoptosis, cancer biology and cell growth.

The level of the candidate Epi-shifter, as well as the form of the candidate Epi-shifter, present in the cell or a particular cell location is determined using routine methods known to the skilled artisan. For example, the level of the candidate Epi-shifter in mitochondria over time and over a range of doses is determined by analyzing mitochondrial enriched preparations from cells treated with the candidate Epi-shifter. The levels of the candidate Epi-shifter in the mitochondria over the time course can be compared and correlated with other cellular changes observed, such as modulation of mRNA and protein levels for specific proteins related to metabolic and apoptotic pathways.

Candidate Epi-shifters observed to induce a shift in the metabolic state of a cell based on the results obtained from the foregoing experiments are identified as Epi-shifters. For example, a candidate Epi-shifter that displays cytotoxicity and/or that induces apoptosis in a cell is identified as an Epi-shifter. Preferably, a candidate Epi-shifter that displays differential cytotoxicity and/or that differentially induces the apoptotic response in diseased (cancer) cells as compared to normal cells (e.g., Epi-shifters that differentially modulate expression of proteins involved in apoptosis in cancer cells as compared to normal cells) is identified as an Epi-shifter.

Example 19

Identification of Vitamin D3 as an Epi-Shifter

Vitamin D3, or 1α, 25-dihydroxyvitamin D3 (also known as calcitriol), is a vitamine D metabolite that is synthesized from vitamin D by a two-step enzymatic process. Vitamin D3 interacts with its ubiquitous nuclear vitamin D receptor (VDR) to regulate the transcription of a wide spectrum of genes involved in calcium and phosphate homeostasis as well as in cell division and differentiation. Vitamin D3 has been reported to have anticancer effects in numerous model systems, including squamous cell carcinoma, prostate adenocarcinoma, cancers of the ovary, breast and lung (reviewed in Deeb et al. 2007 Nature Reviews Cancer 7:684-700).

The anticancer effects of vitamin D3 are reported to involve multiple mechanisms, including growth arrest at the G1 phase of the cell cycle, apoptosis, tumor cell differentiation, disruption of growth factor-mediated cell survival signals, and inhibition of angiogenesis and cell adhesion (reviewed in Deeb et al. 2007 Nature Reviews Cancer 7:684-700). For example, with particular respect to apoptosis, Vitamin D3 has been reported to induce apoptosis by regulating key mediators of apoptosis, such as repressing the expression of the anti-apoptotic, pro-survival proteins BCL2 and BCL-XL, or inducing the expression of pro-apoptotic proteins (e.g., BAX, BAK and BAD) (Deeb et al. 2007). In a further example, with particular respect to angiogenesis, Vitamin D3 has been reported to inhibit the proliferation of some tumor-derived endothelial cells and to inhibit the expression of vascular endothelial growth factor (VEGF) that induces angiogenesis in tumors (reviewed in Masuda and Jones, 2006 Mol. Cancer Ther. 5(4): 797-8070). In another example, with particular respect to cell cycle arrest, Vitamin D3 has been reported to induce gene transcription of the cyclin-dependent kinase inhibitor p21WAFI/CIPI and to induce the synthesis and/or stabilization of the cyclin-dependent kinase inhibiotor p27KIPI protein, both of which are critical for induction of G1 arrest. (Deeb et al. 2007).

Based on the foregoing observations, Vitamin D3 is identified as an Epi-shifter, i.e., owing to its ability to shift the metabolic state of a cell. Vitamin D3 is an Epi-shifter owing to its ability to induce apoptosis in a cell and, in particular, based on its ability to differentially inhibit cell growth and induce the apoptotic response in diseased (cancer) cells as compared to normal cells (e.g., differentially modulate expression of proteins, such as BCL-2, BCL-XL, and BAX, involved in apoptosis in cancer cells as compared to normal cells).

Example 20

Summary of Key Proteins

In summary, based on the results of experiments described in the foregoing Examples, the key proteins modulated by Q10 are summarized in the Table below.

TABLE 29

Key proteins modulated by Q10.

| Pathway | Examples |
|---|---|
| Transcription factors | HNF4alpha |
| Apoptotic response | Bcl-xl, Bcl-xS, BNIP-2, Bcl-2, Birc6, Bcl-2-L11 (Bim), XIAP, BRAF, Bax, c-Jun, Bmf, PUMA, cMyc |
| Pentose Phosphate Pathway | transaldolase 1 |
| Biosynthetic pathway | COQ1, COQ3, COQ6, prenyltransferase, 4-hydroxybenzoate |
| Oxidative stress (pro-oxidant) | Neutrophil cytosolic factor 2, nitric oxide synthase 2A, superoxide dismutase 2 (mitochondrial) |
| Membrane Alterations | VDAC, Bax channel, ANT, |
| Oxidative phosphorylation metabolism | Cytochrome c, complex I, complex II, complex III, complex IV, |

Example 21

Relative Sensitivities of Oncogenic and Normal Cells to Coenzyme Q10

The effects of Coenzyme Q10 treatment on a variety of oncogenic and normal cell lines were examined and compared. The sensitivity of cells to Coenzyme Q10 was assessed by monitoring induction of apoptosis. CoQ10 treatment of cells was carried out as described in detail below in the Materials and Methods. Induction of apoptosis was assessed in the treated cells by monitoring indicators of early apoptosis (e.g., Bcl-2 expression, caspase activation and by using annexin V assays) as described below. From these studies, the minimal CoQ10 dosage, e.g., concentration of CoQ10 and time of treatment, required to induce apoptosis in the panel of cell lines was determined.

In an unexpected and surprising result, the data demonstrated that efficacy of Coenzyme Q10 treatment was greater in cell types that exhibited increased oncogenicity and/or greater metastatic potential, i.e., cell types that were derived from more aggressive cancers or tumors. The results of these studies are summarized below in Table 30. The data demonstrates that CoQ10 is more effective in both a time and concentration dependent manner on cells in a more aggressive cancer state. Moreover, a surprising divergent effect was observed on normal cells as compared to oncogenic cells. Specifically, Coenzyme Q10 was unexpectedly found to exhibit a slightly supportive role in a normal tissue environment, wherein increased proliferation and migration was observed in normal cells, including keratinocytes and dermal fibroblasts.

The effect of Coenzyme Q10 on gene regulatory and protein mechanisms in cancer is different in a normal cell. Key cellular machinery and components, such as membrane fluidity, transport mechanisms, immunomodulation, angiogenesis, cell cycle control, genomic stability, oxidative control, glycolytic flux, metabolic control and integrity of extracellular matrix proteins, are dysregulated and thus the genetic and molecular fingerprint of the cell is altered. The disease environment favors governance of cellular control processes. The data provided herein suggests that CoQ10 exerts a greater level of efficacy (e.g., in cancer cells vs. normal cells, and in cells of a more aggressive cancer state as compared to cells of a less aggressive or non-aggressive cancer state) by normalizing some of the key aforementioned processes in a manner that allows for restored apoptotic potential.

TABLE 30

Minimal CoQ10 concentration and treatment time required for induction of early apoptosis in various cell types.

| Tissue Origin (Cell type) | Indication of Early apoptosis (Bcl-2, annexin V, or caspase activation) | Concentration (µM) | Time (hr) | Level of aggressiveness: 1 = normal tissue 2 = malignant 3 = metastatic |
|---|---|---|---|---|
| SKIN: | | | | |
| Keratinocytes (Heka, Hekn) | None | N/A | N/A | 1 |
| Fibroblasts (nFib) | None | N/A | N/A | 1 |
| Melanocytes (Hema, LP) | None | N/A | N/A | 1 |
| Melanoma (Skmel 28) | Strong | 20 | 24 | 2 |
| Melanoma (Skmel 2) | Very Strong | 25 | 24 | 3 |
| SCC, Squamous cell carcinoma | Very Strong | 25 | 24 | 3 |

TABLE 30-continued

Minimal CoQ10 concentration and treatment time required for induction of early apoptosis in various cell types.

| Tissue Origin (Cell type) | Indication of Early apoptosis (Bcl-2, annexin V, or caspase activation) | Concentration (μM) | Time (hr) | Level of aggressiveness: 1 = normal tissue 2 = malignant 3 = metastatic |
|---|---|---|---|---|
| BREAST: | | | | |
| MCF-7 | Strong | 50 | 48 | 2 |
| SkBr-3 | Very Strong | 50 | 24 | 3 |
| BT-20 | Strong | 100 | 48 | 2 |
| ZR-75 | Slight | 200 | 72 | 2 |
| MDA MB 468 | Strong | 100 | 48 | 2 |
| Mammary fiboblasts: 184A1 and 184B5) (Lawrence Berkeley) | None | N/A | | 1 |
| PROSTATE: | | | | |
| PC3 | Very Strong | 25 | 24 | 3 |
| LIVER: | | | | |
| HepG2 | Very Strong | 50 | 24 | 3 |
| Hep3B | Very Strong | 50 | 24 | 3 |
| BONE: | | | | |
| Osteosarcoma (143b) | Very Strong | 50 | 48 | 2 |
| Ewing's sarcoma (NCI) | Extremely strong | 5 | 1 | 3 |
| PANCREAS: | | | | 3 |
| PaCa2 | Very Strong | 25 | 24 | |
| Heart: | | | | |
| Aortic smooth muscle (HASMC) | None | N/A | N/A | 1 |

Materials and Methods
Cell Preparation and Treatment
Cells Prepared in Dishes or Flasks Cells were cultured in T-75 flasks with relevant medium supplemented with 10% Fetal Bovine Serum (FBS), 1% PSA (penicillin, streptomycin, amphotericin B) (Invitrogen and Cellgro) in a 37° C. incubator with 5% $CO_2$ levels until 70-80% confluence was reached. To harvest cells for treatment, flasks were primed with 1 mL Trypsin, aspirated, trypsinized with an additional 3 mL, and incubated at 37° C. for 3-5 minutes. Cells were then neutralized with an equal volume of media and the subsequent solution was centrifuged at 10,000 rpm for 8 minutes. The supernatant was aspirated and the cells were resuspended with 8.5 ml of media. A mixture of 500 ul of the resuspension and 9.5 ml of isopropanol was read twice by a coulter counter and the appropriate number of cells to be seeded into each dish was determined Control and concentration ranging from 0-200 μM groups were examined in triplicate. From a 500 μM CoQ-10 stock solution, serial dilutions were performed to achieve desired experimental concentration in appropriate dishes. Dishes were incubated in a 37° C. incubator with 5% $CO_2$ levels for 0-72 hours depending on cell type and experimental protocol.

Protein Isolation and Quantification
Cells Prepared in Dishes

Following cell treatment incubation period was complete, protein isolation was performed. Dishes of all treatment groups were washed twice with 2 ml, and once with 1 ml of ice cold 1× Phosphate Buffered Saline (PBS). The PBS was aspirated from the dishes after the initial 2 washes only. Cells were gently scraped and collected into microcentrifuge tubes using the final volume from the third wash and centrifuged at 10,000 rpm for 10 minutes. After centrifugation, the supernatant was aspirated and the pellet was lysed with 50 uL of lysis buffer (1 uL of protease and phosphotase inhibitor for every 100 uL of lysis buffer). Samples were then frozen overnight at −20° C.

Cells Prepared in Flasks

After the cell treatment incubation period was complete, protein isolation was performed. Flasks of all treatment groups were washed twice with 5 mL, and once with 3 mL of ice cold 1×PBS. The PBS was aspirated from the flasks after the first 2 washes only. Cells were gently scraped and collected into 15 mL centrifuge tubes using the final volume from the third wash and centrifuged for at 10,000 rpm for 10 minutes. After centrifugation, the supernatant was aspirated and the pellet was lysed with an appropriate amount of lysis buffer (1 uL of protease and phosphotase inhibitor for every 100 uL of lysis buffer). Lysis buffer volume was dependent on pellet size. Samples were transferred in microcentrifuge tubes and frozen overnight at −20° C.

Protein Quantification

Samples were thawed at −4° C. and sonicated to ensure homogenization the day following protein isolation. Protein quantification was performed using the micro BCA protein assay kit (Pierce). To prepare samples for Immuno-blotting, a 1:19 solution of betamercaptoethanol (Sigma) to sample buffer (Bio-Rad) was prepared. Samples were diluted 1:1 with the betamercaptoethanol-sample buffer solution, boiled at 95° C. for 5 minutes, and frozen overnight at −20° C.

Immuno-Blotting
Bcl-2, Caspase, 9, Cyotochrome c

The volume of sample to load per well was determined using the raw mean concentration of protein obtained from the BCA protein assay. Approximately 30-60 μg of protein were loaded for each treatment time point. Proteins were run in triplicate on 12% Tris-HCl ready gels (Bio-Rad) or hand cast gels in 1× running buffer at 85 and 100 volts. Proteins were then transferred onto nitrocellulose paper for an hour at 100 volts, and blocked for another hour in a 5% milk solution. Membranes were placed in primary antibody (1 uL Ab:1000 uL TBST) (Cell Signaling) overnight at −4° C. The following day, membranes were washed three times for ten minutes each with Tris-Buffered Saline Tween-20 (TBST), and secondary antibody (anti-rabbit; 1 uL Ab: 1000 uL TBST) was applied for an hour at −4° C. Membranes were washed again three times for ten minutes with TBST and chemoluminescence using Pico or Femto substrate was completed (Pierce). Membranes were then developed at time intervals that produced the best visual results. After developing, membranes were kept in TBST at −4° C. until Actin levels could be measured.

Actin

Membranes were placed in primary Actin antibody (1 uL Ab:5000 uL TBST) (cell signaling) for 1 hour at −4° C., washed three times for ten minutes each with TBST, and secondary antibody (anti-mouse; 1 uL Ab: 1000 uL TBST) was applied for an hour at −4° C. Membranes were washed again three times for ten minutes each with TBST and chemoluminescence using Pico substrate was completed (Pierce). Membranes were then developed at time intervals that produced the best visual results.

Annexin V Assay

Cells were washed twice in PBS10X and resuspended in Binding Buffer (0.1 M HEPES, pH 7.4; 1.4 M NaCl; 25 mM CaCl2). Samples of 100 μl were added to a culture tube with 5 μl of annexin-PE dye or 7-ADD. The cells were mixed and incubated without light at room temperature for 15 minutes. After which, 400 μl of 1× Binding Buffer was added to each sample and they were subjected to analysis by flow cytometry.

Example 21

Western Analysis of Cells Treated with Coenzyme Q10

Over the past five decades enormous volume of information has been generated implicating endogenous/exogenous factors influencing specific processes as the underlying cause of malignant transformations. Clinical and basic literature provides evidence that changes in the DNA structure and function play a significant role in the initiation and progression of cancer, defining cancer as a genetic disease (Wooster, 2010; Haiman, 2010). In the early 1920s, Otto Warburg and other investigators involved in characterizing fundamental changes in etiology of oncogenesis described two major observations (a) the ability of cells to transport and utilize glucose in the generation of ATP for energy production in the presence of oxygen—also known as Warburg Effect and (b) alterations in the mitochondrial structure and function—including changes in the electron transport leading to a decrease in the production of mitochondrial ATP. The past few years has seen a resurgence in the investigating the central role of cellular bioenergetics in the etiology of cancer i.e. viewing cancer as a metabolic disease.

Historically, although mutations in genes has been thought to be responsible for changes in gene expression, there is accumulating literature in support of epigenetic processes playing a critical role in influencing gene expression in supporting carcinogenesis. This is evidenced by the observation that mutation rate for most genes is low and cannot account for the numerous (spectrum of) mutations found in the cancer cells. Epigenetic alteration is regulated by methylation and modification of histone tails, both changes inherently linked to the energy (nutrient) status of the cells since they require the availability of co-factors e.g. acetyl CoA requirement for histone acetylation (ref). The biosynthesis of acetyl CoA depends on glycolysis and Kreb's Cycle, directly linking the intracellular energy status to regulation of gene expression and activity.

In normal cells, mitochondrial oxidative phosphorylation generates sufficient ATP to meet the energy demands for maintaining normal physiological activities and cell survival. A consequence of mitochondrial energy production is the generation of reactive oxygen species (ROS), aberrant production of which leads to damage of mitochondria (refs). It is well established that chronic ROS generation by the mitochondria leads to cumulative accumulation of genetic mutations, a phenomenon that has been implicated in the etiology of carcinogenesis. It has been suggested that cancer cells decrease mitochondrial respiration to minimize ROS generation, and switch to glycolysis to sustain energy production. Thus, a progressive shift of energy generation from oxidative phosphorylation to glycolysis would be essential for a cell to maintain energy production to maintain physiological functions and could be associated with the progression of a normal cell phenotype to that of a cancer cell. The progressive shift in cellular energy (bioenergetic) profile in tandem with accumulated alteration (mutations) in mitochondrial genetic make-up alters the cellular metabolome. Changes in the whole cell metabolomic profile as a consequence of mitochondrial phosphorylation to glycolysis transition corresponds to an abnormal bioenergetic induced metabolomic profile and is the underlying cause supporting carcinogenesis. Targeted intervention using an endogenous molecule to elicit a cellular metabolomic shift towards conditions of a non-cancerous normal mitochondrial oxidative phosphorylation associated cellular bioenergetic state represents a therapeutic endpoint in the treatment of cancer.

Coenzyme Q10 as a MIM Causing an Epi-Metabolomic Shift

The data presented herein demonstrates that treatment of normal and cancer cells with Coenzyme Q10 is associated with changes in the expression of proteins that regulate key biochemical terminals within the glycolysis-mitochondrial oxidative stress continuum. The combination of data describing assessment of protein expression by western blotting and oxygen consumption rates demonstrates that in normal cells, there is no significant alteration in normal glycolytic and mitochondrial respiration rates following exposure to Coenzyme Q10. Thus, the values for expression of the proteins and mitochondrial respiration rates in normal cell lines e.g. HDFa (normal human adult fibroblast), HASMC (normal human aortic smooth muscle cell), nFib (normal fibroblast) and HeKa (normal human keratinocytes) can be considered as representatives of baseline physiological state. Any deviation in expression of proteins and mitochondrial respiration rates in cancer cell lines, e.g. HepG2 (liver cancer), PaCa-2 (pancreatic cancer), MCF7 (breast cancer), SK-MEL (melanoma) and SCC-25 (squamous cell carcinoma), is representative of alteration due to initiation/progression of the disease, in this case cancer. The experimental evidence provides support to the hypothesis that exposure of Coenzyme Q10 to cancer cells is associated with cellular pathophysiological reorganization that is reminiscent of normal cells. Specifically, the data provided herein demonstrates that Coenzyme Q10 exposure in cancer cells is associated with a shift in the glycolytic pathways and mitochondrial oxidative phosphorylation responsible for induction of global reorganization of cellular architecture to that observed in normal cells.

In normal cells, the end-points of glycolytic output are linked to mitochondrial oxidative phosphorylation (OXPHOS), i.e. generation of pyruvate from glucose via the glycolytic pathway for the entry into the Kreb's Cycle (also known as Tricarboxylic acid cycle, TCA, or Citric Acid Cycle) to generate reducing equivalents to support the mitochondrial OXPHOS for ATP production. Thus, in normal cells the expression and functional orientation of gene products involved in glycolysis is primed towards adequate generation of pyruvate and its entry into the Kreb's Cycle. Dysregulated expression and function of key proteins participating in glycolysis and Kreb's Cycle pathways in cancer cells results in enhanced glycolysis with a significant decrease in mitochondrial function. Exposure of cancer cells to Coenzyme Q10, an endogenous molecule that selectively influences the mitochondrial respiratory chain, alters (normalizes) expression of proteins of the glycolyis and Kreb's Cycle pathways to facilitate a bioenergetic shift such that energy production (i.e. ATP generation) is restored to the mitochondria.

Experimental Procedure
Western Blot Experiment 1

The cells that were used for the experiment were HDFa, and MCF-7 cells that were treated or not with Coenzyme Q10 at two different concentrations, 50 μM and 100 μM, and harvested after 24 hours of treatment. The whole cell pellets were resuspended one at a time in 1 mL of C7 buffer and transferred to labeled 15 mL tubes. The samples were then sonicated in the cold room on ice using 6 sonic pulses with the setting at #14. The samples were spun for a short time to 2500 g after sonication and the samples transferred to 2 ml tubes. The pH was verified of each sample (pH should be 9.0) using the foam remaining in the 50 mL sample tubes.

Alkylation and reduction of samples was performed for each sample by adding 10 ul of 1M acrylamide, 25 ul of tributylphoshene and incubation for 90 mins with intermittent mixing. After incubation, 10 ul of 1M DTT was added and the tubes were spun at 20,000 g at 20 deg C. for 10 minutes and transferred the supernatant to labeled Amicon Ultra centrifugal filter units with a 10 k cut off (Millipore catalog #UFC 801024). The samples were spun for 15 minutes at 2500 g in 2 intervals. The conductivity was measured for Chaps alone as well as the samples using a conductivity meter. If the conductivity of samples is high, then 1 ml of chaps was added for buffer exchange and spun again at 2500 g until the volume was down to 250 ul. When the conductivity was 200 or less the samples were spun in 5 min intervals at 2500 g until the volume of the supernatant was between 150-100 ul. The sample supernatants were transferred to eppendorf tubes and Bradford assay was performed using BSA as standard.

The samples were processed as per standard protocols as described above and the amount of protein in each of the samples was determined by Bradford assay. Sample volumes equivalent to 10 ug of protein were prepared as shown below with Lamelli Loading dye (LDS) and MilliQ water were run on a 4-12% Bis-Tris Novex NuPAGE gel (Invitrogen, cat #NP0323Box)

The gels were run for 50 minutes using 1×MOPS buffer using a NOVEX Xcell Surelock system at 200 V. The gels were then transferred for 1 hour using a NOVEX Xcell Surelock wet transfer protocol at 30 V. The blots were stained with Simply Blue Safestain from Invitrogen (LC6065).

IDH1 and ATP Citrate Lyase Levels in HDFa and MCF-7 Samples.

After transfer each of the blots was placed in between 2 Whatman Filter papers and dried for 15-20 minutes. After drying the blots were labeled with the date, the type of samples and either blot 1 or blot 2 using a HB pencil. The molecular weight markers were outlined with the pencil and with single lines for the blue and a doublet for the colored markers. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each). Blot 1 was probed with the primary antibody for IDH1 (Cell Signaling #3997) in TBST with 5% BSA (at 1:1000 dilutions) and blot 2 with the rabbit polyclonal antibody for ATP Citrate Lyase in 5% BSA (Cell Signaling #4332) at 1:1000 dilution by incubation overnight at 4 deg C. with shaking. After the overnight incubation with primary antibodies, the blots were washed 3 times with TBS-T (1×-15'; 2×5' each) and probed with the secondary antibody (antirabbit; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 mins and then each blot scanned with 5100 Fuji Laser scanner at 25 uM resolution, 16 bit, green laser, at 400V and at 500 V.

Actin Levels in HDFa and MCF-7 Samples.

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The 2 blots were scanned in laser scanner to check for complete stripping. The blots were then activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the antibody for Actin in 5% BSA (Sigma catalog #A5316, clone AC-74) at 1:5000 dilutions for 1 hour at room temperature with shaking. After 1 hour of incubation with primary antibody for Actin, the membranes were washed 3 times with TBS-T (1×-15'; 2×5' each) and probed with the secondary antibody (antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Western Blot Experiment 2

The cells used in this experiment were SKMEL28, SCC-25, nFib and Heka that were treated or not with coenzyme Q10 at two different concentrations, 50 μM or 100 μM, and harvested after 3, 6 and/or 24 hours of treatment. The samples were processed and run on a 4-12% Bis-Tris Novex NuPAGE gel as described above. The gels were run, transferred and stained essentially as described above.

Levels of IDH1 for the 4 Cell Lines

After transfer the blot was dried for 15-20 minutes, activated with methanol for 5 seconds, washed with water for 5 minutes, and TBST for 15 minutes. The blot was blocked for 1 hour with 5% blocking reagent in TBS-T at room temperature and then washed 3 times with TBS-T (1×-15'; 2×5' each). This was then probed with the primary antibody for IDH1

(Cell Signaling #3997) in TBST with 5% BSA (at 1:1000 dilutions) by incubation overnight at 4 deg C. with shaking. After the overnight incubation with primary antibody for IDH1, the blot was washed 3 times with TBS-T (1×-15'; 2×5' each) and probed with the secondary antibody (antirabbit; 1:10,000 dilution) for 1 h at room temperature. After 1 h of incubation with secondary antibodies, the blot was washed 3 times with TBS-T (1×-15'; 2×5' each) and then incubated with ECF reagent for 5 mins and then each blot scanned with 5100 Fuji Laser scanner at 25 uM resolution, 16 bit, green laser, at 400V and at 500 V.

ATP Citrate Lyase Levels in 4 Different Cell Lines.

The Isocitrate dehydrogenase blot was stripped by incubating for 30 minutes with methanol, followed by two 10 minute washes with TBS-T, then 30 minutes of incubation with stripping buffer at 50 deg C., and followed by two washes with 100 ml or more of TBS-T for 30' each. The blot was scanned in laser scanner to check for complete stripping. The blot was activated with methanol for 5 seconds, washed with water for 5 minutes, and TBST for 15 minutes. The blot was blocked for 1 hour with 5% blocking reagent in TBS-T at room temperature and then washed 3 times with TBS-T (1×-15'; 2×5' each). This was then probed with the rabbit polyclonal antibody for ATP Citrate Lyase in 5% BSA (Cell Signaling #4332) at 1:1000 dilution overnight at 4 deg C. with shaking. After the overnight incubation with primary antibody for ATP Citrate Lyase, the membrane was washed 3 times with TBS-T (1×-15'; 2×5' each) and probed with the secondary antibody (antirabbit; 1:10,000 dilution) for 1 h on the orbital tilting shaker at room temperature. After 1 h of incubation with secondary antibodies, the blot was washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Actin Levels in 4 Different Cell Lines.

The ATP Citrate Lyase blot was stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blot was scanned in laser scanner to check for complete stripping. The blot was activated with methanol for 5 seconds, washed with water for 5 minutes, and TBST for 15 minutes. The blot was blocked for 1 hour with 5% blocking reagent in TBS-T at room temperature and then washed 3 times with TBS-T (1×-15'; 2×5' each) and probed with the antibody for Actin in 5% BSA (Sigma catalog #A5316, clone AC-74) at 1:5000 dilutions for 1 hour at room temperature with shaking. After 1 hour of incubation with primary antibody for Actin, the membranes were washed 3 times with TBS-T (1×-15'; 2×5' each) and probed with the secondary antibody (antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Western Blot Experiment 3

The cells used in this experiment were HepG2, HASMC, and PACA2 cells that were treated or not with Coenzyme Q10 at two different concentrations (50 µM and 100 µM) and harvested 48 hours of treatment. In this experiment (western blot experiment 3), and in all of the experiments described below in this Example (i.e., western blot experiments 4 through 9), the cells were additionally treated with either 5 mM glucose ("5G") or 22 mM glucose ("22G"). The samples derived from the cells were processed and run on a 4-12% Bis-Tris Novex NuPAGE gel as described above. The gels were run, transferred and stained essentially as described above.

IDH1, ATP Citrate Lyase and Actin Levels in HASMC vs. PACA2 and HepG2.

The levels of IDH1, ATP citrate lyase and actin levels were determined by probing the blots with primary antibodies for IDH1, ATP citrate lyase and actin, essentially as described above.

Western Blot Experiment 4

The cells used in this experiment were HepG2 cells that were treated or not with Coenzyme Q10 at two different concentrations, 50 or 100 µM, and harvested after 24 or 48 hours of treatment. The samples were processed and run on a 4-12% Bis-Tris Novex NuPAGE gel as described above. The gels were run, transferred and stained essentially as described above.

Lactate Dehydrogenase Levels in HepG2 Cells.

After transfer each blot was dried for 15-20 minutes, activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Lactate Dehydrogenase (abcam ab2101; polyclonal) in 5% BSA (at 1:1000 dilutions) by incubation overnight at 4 deg C. with shaking. After the overnight incubation with primary antibody for Lactate Dehydrogenase, the blots were washed 3 times with TBS-T (1×-15'; 2×5' each) and probed with the secondary antibody (rabbit antigoat; 1:10,000 dilution) for 1 h at room temperature. After 1 h of incubation with secondary antibodies, the blots were washed 3 times with TBS-T (1×-15'; 2×5' each) and then incubated with ECF reagent for 5 mins and then each blot scanned with 5100 Fuji Laser scanner at 25 uM resolution, 16 bit, green laser, at 400V and at 500 V.

Pyruvate Kinase Muscle Form (PKM2) Levels in HepG2 Cells.

The lactate dehydrogenase blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The 2 blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the rabbit polyclonal antibody for Pyruvate Kinase M2 in 5% BSA (NOVUS BIOLOGICALS catalog #H00005315-D01P) at 1:500 dilution overnight at 4 deg C. with shaking. After the overnight incubation with primary antibody for Pyruvate Kinase M2, the membranes were washed 3 times with TBS-T (1×-15'; 2×5' each) and probed with the secondary antibody (antirabbit; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Pyruvate Dehydrogenase Beta Levels in HepG2 Cells.

The pyruvate kinase blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The 2 blots were scanned in laser scanner to check for complete stripping. After making sure stripping of the antibody and the ECF reagent has worked, the blots were activated with methanol for 5 seconds, washed with water for 5 minutes, and TBST for 15 minutes. The blots are blocked for 1 hour with 5% blocking reagent in TBS-T at room temperature and then washed 3 times with TBS-T (1×-15'; 2×5' each) and probed with the antibody for Pyruvate Dehydrogenase in 5% BSA (ABNOVA catalog #H00005162-M03) at 1:500 dilutions) overnight at 4 deg C. with shaking. After the overnight incubation with primary antibody for Pyruvate Dehydrogenase, the membranes were washed 3 times with TBS-T (1×-15'; 2×5' each) and probed with the secondary antibody (antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Actin Levels in HepG2 Cells.

The Pyruvate Dehydrogenase blots were stripped and then reprobed for actin, essentially as described above.

Western Blot Experiment 5

The cells used in this experiment were MIAPACA2 (PACA2) cells that were treated or not with Coenzyme Q10 at two different concentrations, 50 or 100 µM, and harvested after 24 or 48 hours of treatment. The PACA2 samples were processed and the gels were run, transferred, stained and scanned essentially as described above.

Lactate Dehydrogenase (LDH) and Pyruvate Dehydrogenase (PDH) Levels in PaCa2 Cells The levels of LDH and PDH were determined by probing the blots successively with primary antibodies for LDH and PDH, essentially as described above.

Caspase 3 Levels in PaCa2 Cells.

The blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The 2 blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the antibody for Caspase 3 in 5% BSA (Santacruz Biotechnology #sc7272) at 1:200 dilutions) overnight at 4 deg C. with shaking. After the overnight incubation with primary antibody for Caspase 3, the membranes were washed 3 times with TBS-T (1×-15'; 2×5' each) and probed with the secondary antibody (antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Western Blot Experiment 6

The cells that were used for this Western blot experiment were PC-3, HepG2, MCF-7, HDFa and PACA2 that were treated or not with a Coenzyme Q10 IV formulation and harvested after 24 hours of treatment. The samples were processed and the gels were run, transferred, stained and scanned essentially as described above.

Capase 3 and Actin Levels in Different Cell Types.

The levels of Caspase 3 and actin were determined by probing the blots successively with primary antibodies for Caspase 3 and actin, essentially as described above.

Western Blot Experiment 7

The cells used in this experiment were Human Aortic Smooth Muscle (HASMC) cells that were treated or not with Coenzyme Q10 at two different concentrations, 50 µM or 100 µM, and harvested after 24 or 48 hours of treatment. The HASMC samples were processed and the gels were run, transferred, stained and scanned essentially as described above.

Experimental Protocol for Actin:

The levels of actin were determined by probing the blots with a primary antibody for actin, essentially as described above.

Experimental Protocol for Hif 1alpha, Caspase3 and PDHB:

The Actin blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Hif 1 alpha, Caspase 3 or PDHB in 5% BSA (at 1:200 by incubation overnight at 4 deg C. with gentle shaking. The primary antibody for Hif 1 alpha (Abcam ab2185; antirabbit) was at 1:500 dilution in 5% BSA. The primary antibody for Caspase 3 (Santacruz sc7272; antirabbit) was at 1:200 dilution in 5% BSA. The primary antibody for Pyruvate Dehydrogenase beta (PDHB) (Novus Biologicals H00005162-M03; antimouse) was at 1:500 dilution in 5% BSA. After incubation with primary antibodies, the membranes were washed 3 times with TBS-T (1×-15'; 2×5' each) and probed with the secondary antibody (PDHB antimouse; Hif1a and Caspase 3 antirabbit; 1:10,000 dilution) for 1 h at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Experimental Protocol for PKM2, SDHB and SDHC:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for PKM2, SDHB or SDHC in 5% BSA in TBS-T by incubation overnight at 4 deg C. with gentle shaking. The primary antibody for SDHC (ABNOVA H00006391-M02; antimouse) was at 1:500 dilution. The primary antibody for SDHB was from Abcam ab4714-200; antimouse; at 1:1000 dilution. The primary antibody for Pyruvate Kinase M 2 (PKM2) was from Novus Biologicals H00005315-D0IP; antirabbit; at 1:500 dilution. After incubation with primary antibodies, the membranes were washed 3 times with TBS-T (1×-15'; 2×5' each) and probed with the secondary antibody (SDHB & C antimouse; and PKM2 antirabbit; 1:10,000 dilution) for 1 h on the orbital tilting shaker at room temperature. After 1 h of incubation, the blots were washed 3 times with TBS-T (1×-15'; 2×5' each) and incubated with ECF reagent for 5 minutes and then each blot scanned with 5100 Fuji Laser scanner at 25 uM resolution, 16 bit, green laser, at 400V and at 500 V.

Experimental Protocol for LDH and Bik:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were scanned in laser scanner to check for complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for LDH or Bik in 5% BSA in TBS-T by incubation overnight at 4 deg C. with gentle shaking. The primary antibody for LDH was from Abcam ab2101; antigoat; at 1:1000 dilution. The primary antibody for Bik was from Cell Signaling #9942; antirabbit; at 1:1000 dilution. After incubation with primary antibodies, the membranes were washed 3 times with TBS-T (1×-15'; 2×5' each) and probed with the secondary antibody (LDH antigoat; Jackson Laboratories) and Bik antirabbit; 1:10,000 dilution) for 1 h on the orbital tilting shaker at room temperature. After 1 h of incubation, the blots were washed 3 times with TBS-T (1×-15'; 2×5' each) and incubated with ECF reagent for 5 minutes and then each blot scanned with 5100 Fuji Laser scanner at 25 uM resolution, 16 bit, green laser, at 400V and at 500 V.

Western Blot Experiment 9

The cells used were HepG2 cells that were treated or not with Coenzyme Q10 at two different concentrations, 50 μM or 100 μM, and harvested after 24 or 48 hours of treatment. The HepG2 samples processed and the gels were run, transferred, stained and scanned essentially as described above.

Experimental Protocol for Actin:

The levels of actin were determined by probing the blots with a primary antibody for actin, essentially as described above.

Experimental Protocol for Caspase3 and MMP-6:

The Actin blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Caspase 3 or MMP-6 in 5% BSA by incubation overnight at 4 deg C. with gentle shaking. The primary antibody for Caspase 3 (Abcam ab44976-100; antirabbit) was at 1:500 dilution in 5% BSA. The primary antibody for MMP-6 (Santacruz scMM0029-ZB5; antimouse) was at 1:100 dilution in 5% BSA. After incubation with primary antibodies, the membranes were washed 3 times with TBS-T (1×-15'; 2×5' each) and probed with the secondary antibody (MMP-6 antimouse; Caspase 3 antirabbit; 1:10,000 dilution) for 1 h at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Experimental Protocol for LDH:

The above blots were stripped by incubating for 30 minutes with methanol, followed by two 10 minute washes with TBS-T, then 30 minutes of incubation with stripping buffer at 50 deg C., and followed by two washes with 100 ml or more of TBS-T for 30' each. The blots were activated with methanol for 5 seconds, washed with water for 5 minutes, and TBST for 15 minutes. The blots ere blocked for 1 hour with 5% blocking reagent in TBS-T at room temperature and then washed 3 times with TBS-T (1×-15'; 2×5' each) and probed with the primary antibody for LDH in 5% BSA or 5% milk by incubation overnight at 4 deg C. with gentle shaking. The primary antibody for LDH 080309b1 (Abcam ab2101; antigoat) was at 1:1000 dilution in 5% BSA. The primary antibody for LDH 080309b2 (Abcam ab2101; antigoat) was at 1:1000 dilution in 5% milk. After incubation with primary antibodies, the membranes were washed 3 times with TBS-T (1×-15'; 2×5' each) and probed with the secondary antibody (Jackson Immuno Research antigoat; 1:10,000 dilution; 305-055-045) for 1 h. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400V and at 500 V.

Experimental Protocol for Transaldolase and Hif1a:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were activated with methanol for 5 seconds, washed with water for 5 minutes, and TBST for 15 minutes. The blots are blocked for 1 hour with 5% blocking reagent in TBS-T at room temperature and then washed 3 times with TBS-T (1×-15'; 2×5' each) and probed with the primary antibody for Transaldolase or Hif1a in 5% BSA by incubation overnight at 4 deg C. with gentle shaking. The primary antibody for Transaldolase (Abcam ab67467; antimouse) was at 1:500 dilution. The primary antibody for Hif1a (Abcam ab2185; antirabbit) was at 1:500 dilution. After incubation with primary antibodies, the membranes were washed 3 times with TBS-T (1×-15'; 2×5' each) and probed with the secondary antibody (antimouse or antirabbit; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400 & 500V.

Experimental Protocol for IGFBP3 and TP53:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were activated with methanol for 5 seconds, washed with water for 5 minutes, and TBST for 15 minutes. The blots are blocked for 1 hour with 5% blocking reagent in TBS-T at room temperature and then washed 3 times with TBS-T (1×-15'; 2×5' each) and probed with the primary antibody for IGFBP3 or TP53 in 5% BSA by incubation overnight at 4 deg C. with gentle shaking. The primary antibody for IGFBP3 (Abcam ab76001; antirabbit) was at 1:100 dilution. The primary antibody for TP53 (Sigma Aldrich AV02055; antirabbit) was at 1:100 dilution. After incubation with primary antibodies, the membranes were washed 3 times with TBS-T (1×-15'; 2×5' each) and probed with the secondary antibody (antirabbit; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400 & 500V.

Experimental Protocol for Transaldolase and PDHB:

The above blots were stripped by incubating for 30 minutes with methanol, followed by two 10 minute washes with TBS-T, then 30 minutes of incubation with Stripping buffer at 50 deg C., and followed by two washes with 100 ml or more of TBS-T for 30' each. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Transaldolase or PDHB in 5% BSA by incubation overnight at 4 deg C. with gentle shaking. The primary antibody for Transaldolase (Santacruz sc51440; antigoat) was at 1:200 dilution. The primary antibody for PDHB (Novus Biologicals H00005162-M03; antimouse) was at 1:500 dilution. After incubation with primary antibodies, the membranes were washed 3 times with TBS-T (1×-15'; 2×5' each) and probed with the secondary antibody (antigoat or antimouse; 1:10,000 dilution) for 1 h on the orbital tilting shaker at room temperature. After 1 h of incubation with secondary antibodies, the blots were washed 3 times with TBS-T (1×-15'; 2×5' each) and then incubated with ECF reagent for 5 minutes and then each blot scanned with 5100 Fuji Laser scanner at 25 uM resolution, 16 bit, green laser, at 400 & 500V.

Results

Isocitrate Dehydrogenase-1 (IDH-1)

Isocitrate dehydrogenase is one of the enzymes that is part of the TCA cycle that usually occurs within the mitochondrial matrix. However, IDH1 is the cytosolic form of the enzyme that catalyzes the oxidative decarboxylation of isocitrate to α-ketoglutarate and generates carbon dioxide in a two step process. IDH1 is the NADP$^+$ dependent form that is present in the cytosol and peroxisome. IDH1 is inactivated by Ser113 phosphorylation and is expressed in many species including those without a citric acid cycle. IDH1 appears to function normally as a tumor suppressor which upon inactivation contributes to tumorigenesis partly through activation of the HIF-1 pathway (Bayley 2010; Reitman, 2010). Recent studies have implicated an inactivating mutation in IDH1 in the etiology of glioblasotoma (Bleeker, 2009; Bleeker, 2010).

Treatment with Coenzyme Q10 increased expression of IDH1 in cancer cell lines including MCF-7, SKMEL28, HepG2 and PaCa-2 cells. There was a moderate increase in expression in the SCC25 cell lines. In contrast cultures of primary human derived fibroblasts HDFa, nFIB and the human aortic smooth muscle cells HASMC did not demonstrate significant changes in the expression pattern of the IDH1 in response to Coenzyme Q10. α-ketoglutarate (α-KG) is a key intermediate in the TCA cycle, biochemically synthesized from isocitrate and is eventually converted to succinyl coA and is a druggable MIM and EpiShifter. The generation of α-KG serves as a critical juncture in the TCA cycle as it can be used by the cell to replenish intermediates of the cycle, resulting in generation of reducing equivalents to increase oxidative phosphorylation. Thus, Coenzyme Q10 mediated increase in IDH1 expression would result in formation of intermediates that can be used by the mitochondrial TCA cycle to augment oxidative phosphorylation in cancer cells. The results are summarized in Tables 31-33, below.

TABLE 31

IDH1 in HDFa and MCF-7

| Composition | Average Normalized Intensity |
| --- | --- |
| HDF, Media | 346 |
| HDF24-50-Coenzyme Q10 | 519 |
| HDF24-100-Coenzyme Q10 | 600 |
| MCF, Media | 221 |
| MCF24-50-Coenzyme Q10 | 336 |
| MCF24-100-Coenzyme Q10 | 649 |

TABLE 32

IDH1 in HASMC vs. HepG2 after Treatment

| Amount - Composition | Normalized Intensity |
| --- | --- |
| HAS5g48-media | 20 |
| HAS5g48-50-Coenzyme Q10 | 948 |
| HAS5g48-100-Coenzyme Q10 | 1864 |
| HAS22G48-Media | 1917 |
| HAS22G48-50-Coenzyme Q10 | 1370 |
| HAS22G48-100-Coenzyme Q10 | 1023 |
| Hep5g48-Media | 14892 |
| Hep5g48-50-Coenzyme Q10 | 14106 |
| Hep5g48-100-Coenzyme Q10 | 15774 |
| Hep22G48-Media | 16558 |
| Hep22G48-50-Coenzyme Q10 | 15537 |
| Hep22G48-100-Coenzyme Q10 | 27878 |

TABLE 33

IDH1 in HASMC vs. PACA2 after Treatment

| Amount - Composition | Normalized Intensity |
| --- | --- |
| HAS5g48-media | 562 |
| HAS5g48-50-Coenzyme Q10 | 509 |
| HAS5g48-100-Coenzyme Q10 | 627 |
| HAS22G48-Media | 822 |
| HAS22G48-50-Coenzyme Q10 | 1028 |
| HAS22G48-100-Coenzyme Q10 | 1015 |
| PACA5g48-Media | 1095 |
| PACA5g48-50-Coenzyme Q10 | 1095 |
| PACA5g48-100-Coenzyme Q10 | 860 |
| PACA22G48-Media | 1103 |
| PACA22G48-50-Coenzyme Q10 | 1503 |
| PACA22G48-100-Coenzyme Q10 | 1630 |

ATP Citrate Lyase (ACL)

ATP citrate Lyase (ACL) is a homotetramer (~126 kd) enzyme that catalyzes the formation of acteyl-CoA and oxaloacetate in the cytosol. This reaction is a very important first step for the biosynthesis of fatty acids, cholesterol, and acetylcholine, as well as for glucogenesis (Towle et al., 1997). Nutrients and hormones regulate the expression level and phosphorylation status of this key enzyme. Ser454 phosphorylation of ACL by Akt and PKA has been reported (Berwick., D C M W et al., 2002; Pierce M W et al., 1982).

The data describes the effect of Coenzyme Q10 on ATP citrate Lyase is that in normal and cancer cells. It is consistently observed that in cancer cells there is a dose-dependent decrease in the expression of ACL enzymes. In contrast there appears to be a trend towards increased expression of ACL in normal cells. Cytosolic ACL has been demonstrated to be essential for histone acetylation in cells during growth factor stimulation and during differentiation. The fact that ACL utilizes cytosolic glucose derived citrate to generate Acetyl CoA essential for histone acetylation, a process important in the neoplastic process demonstrates a role of Coenzyme Q10 induced ACL expression in influencing cancer cell function. Acetyl CoA generated from citrate by cytosolic ACL serves as a source for biosynthesis of new lipids and cholesterol during cell division. Thus, Coenzyme Q10 induced changes in ACL expression alters Acetyl CoA availability for synthesis of lipids and cholesterol in normal versus cancer cells. The results are summarized in tables 34-37 below.

TABLE 34

ATPCL in HDFa and MCF-7

| Composition | Average Normalized Intensity |
| --- | --- |
| HDF-Media | ~15000 |
| HDF-50-Coenzyme Q10 | ~17500 |
| HDF-100-Coenzyme Q10 | ~25000 |
| MCF-Media | ~7500 |
| MCF-50-Coenzyme Q10 | ~7500 |
| MCF-100-Coenzyme Q10 | ~12500 |

TABLE 35

ATP Citrate Lysase ~kd band in HASMC vs. HepG2

| Amount - Composition | Normalized Intensity |
| --- | --- |
| HAS5g48-media | 24557 |
| HAS5g48-50-Coenzyme Q10 | 23341 |
| HAS5g48-100-Coenzyme Q10 | 25544 |
| HAS22G48-Media | 27014 |
| HAS22G48-50-Coenzyme Q10 | 21439 |
| HAS22G48-100-Coenzyme Q10 | 19491 |
| Hep5g48-Media | 28377 |
| Hep5g48-50-Coenzyme Q10 | 24106 |
| Hep5g48-100-Coenzyme Q10 | 22463 |
| Hep22G48-Media | 24262 |
| Hep22G48-50-Coenzyme Q10 | 31235 |
| Hep22G48-100-Coenzyme Q10 | 50588 |

TABLE 36

ATP Citrate Lysase ~kd band in HASMC vs. PACA2

| Amount - Composition | Normalized Intensity |
| --- | --- |
| HAS5g48-media | 11036 |
| HAS5g48-50-Coenzyme Q10 | 12056 |
| HAS5g48-100-Coenzyme Q10 | 15265 |
| HAS22G48-Media | 18270 |
| HAS22G48-50-Coenzyme Q10 | 15857 |
| HAS22G48-100-Coenzyme Q10 | 13892 |
| PACA5g48-Media | 11727 |
| PACA5g48-50-Coenzyme Q10 | 8027 |
| PACA5g48-100-Coenzyme Q10 | 4942 |
| PACA22G48-Media | 8541 |
| PACA22G48-50-Coenzyme Q10 | 9537 |
| PACA22G48-100-Coenzyme Q10 | 14901 |

TABLE 37

ATP Citrate Lysase in HepG2 and PACA2 as % of CTRL

| Amount - Composition | Normalized Intensity |
| --- | --- |
| PACA5g48-Media | 1.00 |
| PACA5g48-50-Coenzyme Q10 | 0.68 |
| PACA5g48-100-Coenzyme Q10 | 0.42 |
| PACA22G48-Media | 1.00 |
| PACA22G48-50-Coenzyme Q10 | 1.12 |
| PACA22G48-100-Coenzyme Q10 | 1.74 |
| Hep5g48-Media | 1.00 |
| Hep5g48-50-Coenzyme Q10 | 0.85 |

TABLE 37-continued

ATP Citrate Lysase in HepG2 and PACA2 as % of CTRL

| Amount - Composition | Normalized Intensity |
| --- | --- |
| Hep5g48-100-Coenzyme Q10 | 0.79 |
| Hep22G48-Media | 1.00 |
| Hep22G48-50-Coenzyme Q10 | 1.29 |
| Hep22G48-100-Coenzyme Q10 | 2.09 |

Pyruvate Kinase M2 (PKM2)

Pyruvate Kinase is an enzyme involved in the glycolytic pathway. It is responsible for the transfer of phosphate from phosphoenolpyruvate (PEP) to adenosine diphosphophate (ADP) to generate ATP and pyruvate. PKM2 is an isoenzyme of the glycolytic pyruvate kinase, expression of which is characterized by the metabolic function of the tissue i.e. M2 isoenzyme is expressed in normal rapidly proliferating cells with high energy needs such as embryonic cells and also expressed in few normal differentiated tissues such as lung and pancreatic islet cells that require high rate of nucleic acid synthesis. PKM2 is highly expressed in tumor cells due to their dependence on glycolytic pathway for meeting cellular energetic requirements. The PKM2 isoform normally thought to be embryonically restricted is re-expressed in cancerous cells. Cells expressing PKM2 favor a stronger aerobic glycolytic phenotype (show a shift in metabolic phenotype) with increased lactate production and decreased oxidative phosphorylation. Thus, decrease in expression of PKM2 in cancer cells would shift or down-regulate energy generation via the glycolytic pathway, a strategy that is useful in the treatment of cancer. Data demonstrates variable expression pattern of PKM2 in normal and cancer cells, with cancer cells demonstrating higher levels of expression compared to normal. Treatment of cells with Coenzyme Q10 altered expression pattern of the PKM2 upper and lower band levels in normal and cancer cells. In cancer cells tested, there was a dose-dependent decrease in the PKM2 expression, and no major changes in normal cells were observed. The results are summarized in tables 38-40, below.

TABLE 38

Pyruvate Kinase Muscle form 2 Upper Band in HepG2

| Amount - Composition | Normalized Volume (24 h) | Normalized Intensity (48 h) |
| --- | --- | --- |
| 5g-Media | 28386 | 413 |
| 5g-50-Coenzyme Q10 | 29269 | 303 |
| 5g-100-Coenzyme Q10 | 18307 | 354 |
| 22G-Media | 25903 | 659 |
| 22G-50-Coenzyme Q10 | 22294 | 562 |
| 22G-100-Coenzyme Q10 | 19560 | 601 |

TABLE 39

Pyruvate Kinase Muscle form 2 Lower Band (58 KD) in HepG2

| Amount - Composition | Normalized Volume (24 h) | Normalized Volume (48 h) |
| --- | --- | --- |
| 5g-Media | 10483 | 310 |
| 5g-50-Coenzyme Q10 | 11197 | 185 |
| 5g-100-Coenzyme Q10 | 7642 | 122 |
| 22G-Media | 9150 | 306 |
| 22G-50-Coenzyme Q10 | 6302 | 344 |
| 22G-100-Coenzyme Q10 | 6904 | 465 |

TABLE 40

Pyruvate Kinase Muscle form 2 Upper
Band in HASMC Cells after Treatment

| Amount - Composition | Normalized Intensity |
|---|---|
| 5g48-Media | 608 |
| 5g48-50-Coenzyme Q10 | 811 |
| 5g48-100-Coenzyme Q10 | 611 |
| 22G48-Media | 516 |
| 22G48-50-Coenzyme Q10 | 595 |
| 22G48-100-Coenzyme Q10 | 496 |
| 22G24-Media | 301 |
| 22G24-50-Coenzyme Q10 | 477 |
| 22G24-100-Coenzyme Q10 | 701 |

Lactate Dehydrogenase (LDH)

LDH is an enzyme that catalyzes the interconversion of pyruvate and lactate with the simultaneous interconversion of NADH and NAD$^+$. It has the ability to convert pyruvate to lactate (lactic acid) under low cell oxygen tension for generation of reducing equivalents and ATP generation at the expense of mitochondrial oxidative phosphorylation. Cancer cells typically demonstrate increased expression of LDH to maintain the glycolytic flux to generate ATP and reducing equivalents and reducing mitochondrial OXPHOS. Thus, reducing the expression of the LDH in cancer cells would shift metabolism from generation of lactate to facilitate entry of pyruvate into the TCA cycle. Treatment with Coenzyme Q10 reduced Lactate Dehydrogenase (LDH) expression in cancer with minimal effect on normal cells, supporting a role for Coenzyme Q10 in eliciting a shift in cancer cell bioenergtics for the generation of ATP from glycolytic to mitochondrial OXPHOS sources by minimizing the conversion of cytoplasmic pyruvate to lactic acid. The results are summarized in tables 41-43, below.

TABLE 41

Lactate Dehydrogenase in HepG2

| Amount - Composition | Normalized Volume (24 h) | Normalized Volume (48 h) |
|---|---|---|
| 5g-Media | 7981 | 5997 |
| 5g-50-Coenzyme Q10 | 7900 | 5188 |
| 5g-100-Coenzyme Q10 | 6616 | 7319 |
| 22G-Media | 9171 | 7527 |
| 22G-50-Coenzyme Q10 | 7550 | 6173 |
| 22G-100-Coenzyme Q10 | 7124 | 9141 |

TABLE 42

Lactate Dehydrogenase in HepG2
as % Control from 2 Experiments

| Amount - Composition | Average Volume as a % of Control |
|---|---|
| 5g24-Media | 1.00 |
| 5g24-50-Coenzyme Q10 | 0.64 |
| 5g24-100-Coenzyme Q10 | 1.06 |
| 5g48-Media | 1.00 |
| 5g48-50-Coenzyme Q10 | 1.12 |
| 5g48-100-Coenzyme Q10 | 1.21 |
| 22G24-Media | 1.00 |
| 22G24-50-Coenzyme Q10 | 1.21 |
| 22G24-100-Coenzyme Q10 | 1.44 |
| 22G48-Media | 1.00 |
| 22G48-50-Coenzyme Q10 | 0.95 |
| 22G48-100-Coenzyme Q10 | 0.67 |

TABLE 43

Lactate Dehydrogenase in PACA2

| Amount - Composition | Normalized Volume (24 h) | Normalized Volume (48 h) |
|---|---|---|
| 5g-Media | 2122 | 2360 |
| 5g-50-Coenzyme Q10 | 5068 | 2978 |
| 5g-100-Coenzyme Q10 | 3675 | 2396 |
| 22G-Media | 4499 | 2332 |
| 22G-50-Coenzyme Q10 | 10218 | 2575 |
| 22G-100-Coenzyme Q10 | 7158 | 3557 |

Pyruvate Dehydrogenase-B (PDH-E1)

Pyruvate Dehydrogenase beta (PDH-E1) is the first enzyme component that is part of the pyruvate dehydrogenase complex (PDC) that converts pyruvate to acetyl CoA. PDH-E1 requires thiamine as cofactor for its activity, performs the first two biochemical reactions in the PDC complex essential for the conversion of pyruvate to acetyl CoA to enter the TCA cycle in the mitochondria. Thus, concomitant decreases in PKM2 and LDH expression along with increase in expression of PDH-E1 in cancer cells would enhance the rate of entry of pyruvate towards augmenting the mitochondrial OXPHOS for generation of ATP. The data shows that for expression of PDH-E1 in normal and cancer cell lines, the baseline expressions of this enzyme is decreased in cancer compared to normal cells. Treatment with Coenzyme Q10 is associated with progressive increase in the expression of the PDH-E1 proteins in cancer cells with minimal changes in the normal cells. The results are summarized in tables 44-46, below.

TABLE 44

Pyruvate Dehydrogenase Beta in HepG2

| Amount - Composition | Normalized Volume (24 h) | Normalized Volume (48 h) |
|---|---|---|
| 5g-Media | 517 | 100 |
| 5g-50-Coenzyme Q10 | 921 | 123 |
| 5g-100-Coenzyme Q10 | 433 | 205 |
| 22G-Media | 484 | 181 |
| 22G-50-Coenzyme Q10 | 426 | 232 |
| 22G-100-Coenzyme Q10 | 340 | 456 |

TABLE 45

Pyruvate Dehydrogenase Beta in PACA2

| Amount - Composition | Normalized Volume (24 h) | Normalized Volume (48 h) |
|---|---|---|
| 5g-Media | 323 | 375 |
| 5g-50-Coenzyme Q10 | 492 | 339 |
| 5g-100-Coenzyme Q10 | 467 | 252 |
| 22G-Media | 572 | 276 |
| 22G-50-Coenzyme Q10 | 924 | 279 |
| 22G-100-Coenzyme Q10 | 1201 | 385 |

TABLE 46

Pyruvate Dehydrogenase Beta in HASMC after Treatment

| Amount - Composition | Normalized Volume |
|---|---|
| 5g48-Media | 140 |
| 5g48-50-Coenzyme Q10 | 147 |
| 5g48-100-Coenzyme Q10 | 147 |
| 22G48-Media | 174 |
| 22G48-50-Coenzyme Q10 | 149 |
| 22G48-100-Coenzyme Q10 | 123 |

TABLE 46-continued

Pyruvate Dehydrogenase Beta in HASMC after Treatment

| Amount - Composition | Normalized Volume |
| --- | --- |
| 22G24-Media | 140 |
| 22G24-50-Coenzyme Q10 | 145 |
| 22G24-100-Coenzyme Q10 | 150 |

Caspase 3

Control of the onset of apoptosis is often exerted at the level of the initiator caspases, caspase-2, -9 and -8/10. In the extrinsic pathway of apoptosis, caspase-8, once active, directly cleaves and activates executioner caspases (such as caspase-3). The active caspase-3 cleaves and activates other caspases (6, 7, and 9) as well as relevant targets in the cells (e.g. PARP and DFF). In these studies, the levels of effectors caspase-3 protein were measured in the cancer cell lines and in normal cell lines in response to Coenzyme Q10. It should be noted although control of apoptosis is through initiator caspases, a number of signaling pathways interrupt instead the transmission of the apoptotic signal through direct inhibition of effectors caspases. For e.g. P38 MAPK phosphorylates caspase-3 and suppresses its activity (Alvarado-Kristensson et al., 2004). Interestingly, activation of protein phosphates (PP2A) in the same study or protein kinase C delta (PKC delta) (Voss et al., 2005) can counteract the effect of p38 MAPK to amplify the caspase-3 activation and bolster the transmission of the apoptotic signal. Therefore, events at the level of caspase-3 activation or after Caspase 3 activation may determine the ultimate fate of the cell in some cases.

Caspase-3 is a cysteine-aspartic acid protease that plays a central role in the execution phase of cell apoptosis. The levels of caspase 3 in the cancer cells were increased with Coenzyme Q10 treatment. In contrast the expression of Caspase-3 in normal cells was moderately decreased in normal cells. The results are summarized in tables 47-49, below.

TABLE 47

Caspase 3 in PACA2

| Amount-Composition | Normalized Volume (24 h) | Normalized Volume (48 h) |
| --- | --- | --- |
| 5g-Media | 324 | 300 |
| 5g-50-Coenzyme Q10 | 325 | 701 |
| 5g-100-Coenzyme Q10 | 374 | 291 |
| 22G-Media | 344 | 135 |
| 22G-50-Coenzyme Q10 | 675 | 497 |
| 22G-100-Coenzyme Q10 | 842 | 559 |

TABLE 48

Caspase 3 in HepG2 cells as % Control from 2 Experiments

| Amount - Composition | Normalized Volume as a % of Control |
| --- | --- |
| 5g24-Media | 1..00 |
| 5g24-50-Coenzyme Q10 | 1.08 |
| 5g24-100-Coenzyme Q10 | 1.76 |
| 5g48-Media | 1.00 |
| 5g48-50-Coenzyme Q10 | 1.44 |
| 5g48-100-Coenzyme Q10 | 0.95 |
| 22G24-Media | 1.00 |
| 22G24-50-Coenzyme Q10 | 1.39 |
| 22G24-100-Coenzyme Q10 | 1.78 |
| 22G48-Media | 1.00 |
| 22G48-50-Coenzyme Q10 | 1.50 |
| 22G48-100-Coenzyme Q10 | 1.45 |

TABLE 49

Caspase 3 in HASMC after Treatment

| Amount - Composition | Normalized Volume |
| --- | --- |
| 5g48-Media | 658 |
| 5g48-50-Coenzyme Q10 | 766 |
| 5g48-100-Coenzyme Q10 | 669 |
| 22G48-Media | 846 |
| 22G48-50-Coenzyme Q10 | 639 |
| 22G48-100-Coenzyme Q10 | 624 |
| 22G24-Media | 982 |
| 22G24-50-Coenzyme Q10 | 835 |
| 22G24-100-Coenzyme Q10 | 865 |

Succinate Dehydrogenase (SDH)

Succinate dehydrogenase, also known as succinate-coenzyme Q reductase is a complex of the inner mitochondrial membrane that is involved in both TCA and electron transport chain. In the TCA, this complex catalyzes the oxidation of succinate to fumarate with the concomitant reduction of ubiquinone to ubiquinol. (Baysal et al., Science 2000; and Tomlinson et al., Nature Genetics 2002). Germline mutations in SDH B, C and D subunits were found to be initiating events of familial paraganglioma or leiomyoma (Baysal et al., Science 2000).

Western blotting analysis was used to characterize expression of SDH Subunit B in mitochondrial preparations of cancer cells treated with Coenzyme Q10. The results suggest that Coenzyme Q10 treatment is associated with increase SDH protein levels in the mitochondrion of the cells. These results suggest one of the mechanisms of action of Coenzyme Q10 is to shift the metabolism of the cell towards the TCA cycle and the mitochondrion by increasing the levels of mitochondrial enzymes such as SDHB. The results are summarized in table 50, below.

TABLE 50

Succinate Dehydrogenase B in NCIE0808 Mitopreps

| Composition - Time | Average Normalized Volume |
| --- | --- |
| Media | 531 |
| 50 uM Coezyme Q10, 3 h | 634 |
| 100 uM Coenzyme Q10, 3 h | 964 |
| 50 uM Coenzyme Q10, 6 h | 1077 |
| 100 uM Coenzyme Q10, 6 h | 934 |

Hypoxia Induced Factor-1

Hypoxia inducible factor (Hif) is a transcription factor composed of alpha and beta subunits. Under normoxia, the protein levels of Hif1 alpha are very low owing to its continuous degradation via a sequence of post translational events. The shift between glycolytic and oxidative phosphorylation is generally considered to be controlled by the relative activities of two enzymes PDH and LDH that determine the catabolic fate of pyruvate. Hif controls this crucial bifurgation point by inducing LDH levels and inhibiting PDH activity by stimulating PDK. Due to this ability to divert pyruvate metabolism from mitochondrion to cytosol, Hif is considered a crucial mediator of the bioenergetic switch in cancer cells.

Treatment with Coenzyme Q10 decreased Hif1 alpha protein levels after in mitochondrial preparations of cancer cells. In whole cell lysates of normal cells, the lower band of Hif1a was observed and showed a decrease as well. The results are summarized in tables 51-52, below.

TABLE 51

Hif1 alpha Lower Band in HASMC Cells after Treatment

| Amount - Composition | Normalized Volume |
| --- | --- |
| 5g48-Media | 22244 |
| 5g48-50-Coenzyme Q10 | 21664 |
| 5g48-100-Coenzyme Q10 | 19540 |
| 22G48-Media | 14752 |
| 22G48-50-Coenzyme Q10 | 17496 |
| 22G48-100-Coenzyme Q10 | 23111 |
| 22G24-Media | 21073 |
| 22G24-50-Coenzyme Q10 | 18486 |
| 22G24-100-Coenzyme Q10 | 17919 |

TABLE 52

Hif1 alpha Upper Band in HepG2 after Treatment

| Amount - Composition | Normalized Volume |
| --- | --- |
| 5g24-Media | 12186 |
| 5g24-50-Coenzyme Q10 | 8998 |
| 5g24-100-Coenzyme Q10 | 9315 |
| 5g48-Media | 8868 |
| 5g48-50-Coenzyme Q10 | 8601 |
| 5g48-100-Coenzyme Q10 | 10192 |
| 22G24-Media | 11748 |
| 22G24-50-Coenzyme Q10 | 14089 |
| 22G24-100-Coenzyme Q10 | 8530 |
| 22G48-Media | 8695 |
| 22G48-50-Coenzyme Q10 | 9416 |
| 22G48-100-Coenzyme Q10 | 5608 |

Example 22

Analysis of Oxygen Consumption Rates (OCR) and Extracellular Acidification (ECAR) in Normal and Cancer cCells Treated with CoQ10

This example demonstrates that exposure of cells to treatment by a representative MIM/epi-shifter of the invention—CoQ10—in the absence and/or presence of stressors (e.g., hyperglycemia, hypoxia, lactic acid), is associated with a shift towards glycolysis/lactate biosynthesis and mitochondrial oxidative phosphorylation (as measured by ECAR and OCR values) representative of values observed in a normal cells under normal physiological conditions.

Applicants have demonstrated in the previous section that treatment with CoQ10 in cancer cells is associated with changes in expression of specific proteins that enhance mitochondrial oxidative phosphorylation, with a concomitant decrease in glycolysis and lactate biosynthesis. This example shows that a direct measure of mitochondrial oxidative phosphorylation can be obtained by measuring the oxygen consumption rates (OCR) in cell lines using the SeaHorse XF analyzer, an instrument that measures dissolved oxygen and extracellular pH levels in an in vitro experimental model. (SeaHorse Biosciences Inc, North Billerica, Mass.).

The pH of the extracellular microenvironment is relatively acidic in tumors compared to the intracellular (cytoplasmic) pH and surrounding normal tissues. This characteristic of tumors serves multiple purposes, including the ability to invade the extracellular matrix (ECM), a hallmark attribute of tumor metastasis that subsequently initiates signaling cascades that further modulate:

tumor angiogenesis increased activation of arrest mechanisms that control cell cycle turn-over immuno-modulatory mechanisms that facilitate a cellular evasion system against immunosurveillance metabolic control elements that increase dependency on glycolytic flux and lactate utilization dysregulation of key apopototic gene families such as Bcl-2, IAP, EndoG, AIF that serve to increase oncogenicity While not wishing to be bound by any particular theory, the acidic pH of the external microenvironment in the tumor is a consequence of increase in hydrogen ion concentrations extruded from the tumor cells due to the increased lactate production from an altered glycolytic phenotype.

In this experiment, the OCR and extracellular acidification rate (ECAR) in normal cells lines were obtained in the presence and absence of CoQ10 to determine baseline values. It was observed that in its native nutrient environment, the basal OCR rates in normal cells lines are different, and are usually a function of the physiological roles of the cells in the body.

For example, one set of experiments were conducted using the non-cancerous cell line HDFa, which is a human adult dermal fibroblast cell line. Fibroblasts are cells that primarily synthesize and secrete extracellular matrix (ECM) components and collagen that form the structural framework (stroma) for tissues. In addition, fibroblasts are known to serve as tissue ambassadors of numerous functions such as wound healing and localized immunomodulation. Under normal physiological conditions, energy requirements in normal fibroblasts are met using a combination of glycolysis and oxidative phosphorylation—the glycolysis providing the necessary nutrients for synthesis of ECM.

In contrast to HDFa, the HASMC (human aortic smooth muscle cell) is found in arteries, veins, lymphatic vessels, gastrointestinal tracts, respiratory tract, urinary bladder and other tissues with the ability to undergo regulated excitation-contraction coupling. The ability of smooth muscles such as HASMC cells to undergo contraction requires energy provided by ATP. These tissues transition from low energy modes wherein ATP may be supplied from mitochondria to high energy modes (during exercise/stress) where energy is provided by switching to glycolysis for rapid generation of ATP. Thus, normal smooth muscle cells can use a combination of mitochondrial OXPHOS and glycolysis to meet their energy requirements under normal physiological environment.

Figure 29:
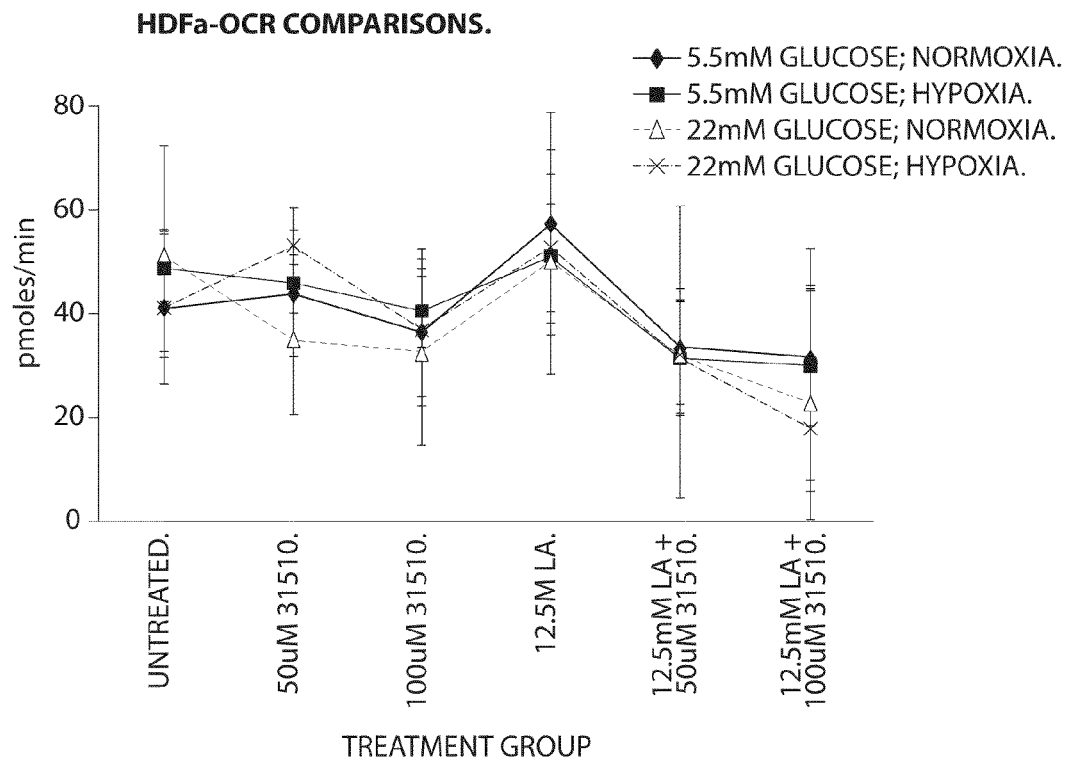
FIG. 29: OCR in HDFa cells in various glucose conditions in normoxic and hypoxic conditions.
Figure 30:
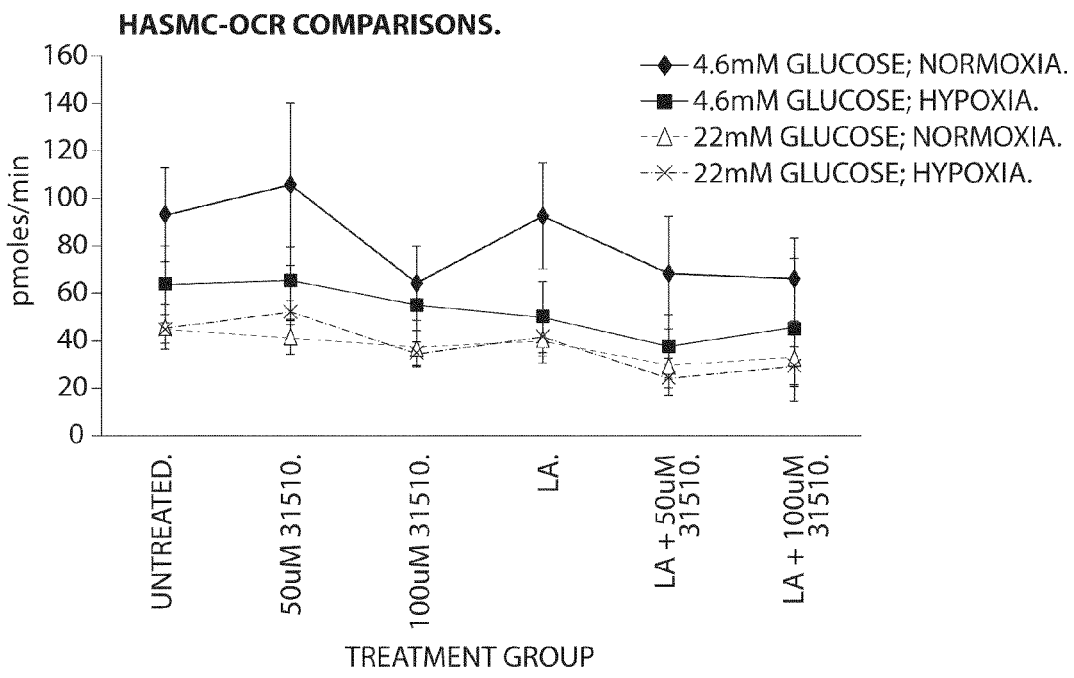
FIG. 30: OCR in HASMC cells in various glucose conditions in normoxic and hypoxic conditions.

The differences in their respective physiological roles (i.e., HDFa and HASMC) were observed in the resting OCR values measured in these cells lines using the SeaHorse XF analyzer. FIGS. 29 and 30 describe the OCR in HDFa and HASMC cells grown in physiologically normal glucose (about 4.6 mM) and high glucose (hyperglycemic) conditions.

The baseline OCR values for HDFa in the absence of any treatments under normal oxygen availability is approximately 40 pmoles/min (FIG. 29) in the presence of 5.5 mM glucose. This value was slightly elevated when the cells were maintained at 22 mM glucose. In contrast, in HASMC cells, the OCR values at 5.5 mM glucose is approximately 90 pmoles/min, and the OCR value declined to approximately 40 pmoles/min while at 22 mM glucose. Thus, under hyperglycemic conditions, there is a differential response between HDFa and HASMC, further demonstrating inherent differences in their respective physiological make-up and function.

Treatment with CoQ10 in cells is associated with changes in OCR that is representative of conditions observed at normal (5 mM) glucose conditions. The complexity of physiological response is compounded in the presence of low oxygen tension. Thus, CoQ10 exposure is associated with changes in OCR rates in normal cells towards a physiological state that is native to a particular cell.

Table 53, below, describes the ECAR values (mpH/min) in HDFa cells in the presence or absence of CoQ10 under normoxic and hypoxic conditions at 5.5 mM and 22 mM glucose. It can be observed that in normal cells, treatment with CoQ10 had minimal influence on ECAR values, even though it influenced OCR in these cells. In high glucose hypoxic conditions, treatment with CoQ10 was associated with lowering of elevated ECAR to a value that was observed in untreated normoxic conditions.

TABLE 53

ECAR values in HDFa cells in the absence and presence of CoQ10 under normoxic and hypoxic conditions at 5.5 mM and 22 mM glucose

| Treatment | Normoxia (5.5 mM) | | Hypoxia (5.5 mM) | | Normoxia (22 mM) | | Hypoxia (22 mM) | |
|---|---|---|---|---|---|---|---|---|
| | ECAR | SEM | ECAR | SEM | ECAR | SEM | ECAR | SEM |
| Untreated | 5 | 1.32 | 5 | 0.62 | 5 | 0.62 | 9 | 0.81 |
| 50 µM 31510 | 6 | 1.11 | 5 | 0.78 | 5 | 0.78 | 6 | 0.70 |
| 100 µM 31510 | 6 | 0.76 | 5 | 1.19 | 5 | 1.19 | 8 | 1.07 |

In Table 54 the measured baseline ECAR values (mpH/min) in HASMC were higher compared to that of HDFa. Induction of hypoxic conditions caused an increase in ECAR most likely associated with intracellular hypoxia induced acidosis secondary to increased glycolysis.

TABLE 54

ECAR values in HASMC cells in the absence and presence of CoQ10 under normoxic and hypoxic conditions at 5.5 mM and 22 mM glucose

| Treatment | Normoxic (5.5 mM) | | Hypoxic (5.5 mM) | | Normoxic (22 mM) | | Hypoxic (22 mM) | |
|---|---|---|---|---|---|---|---|---|
| | ECAR | SEM | ECAR | SEM | ECAR | SEM | ECAR | SEM |
| Untreated | 9 | 2.22 | 11 | 2.18 | 22 | 2.08 | 19 | 1.45 |
| 50 µM 31510 | 9 | 2.13 | 11 | 2.54 | 21 | 1.72 | 17 | 1.60 |
| 100 µM 31510 | 9 | 1.72 | 13 | 2.30 | 22 | 1.64 | 17 | 1.47 |

Treatment with CoQ10 was observed to be associated with a downward trend of ECAR rates in hyperglycemic HASMC cells in hypoxic conditions towards a value that would be observed in normoxic normal glucose conditions. These data demonstrate the presence of physiological variables that is inherent to the physiological role of a specific type of cell, alterations observed in abnormal conditions (e.g. hyperglycemia) is shifted towards normal when treated with CoQ10.

Figure 31:
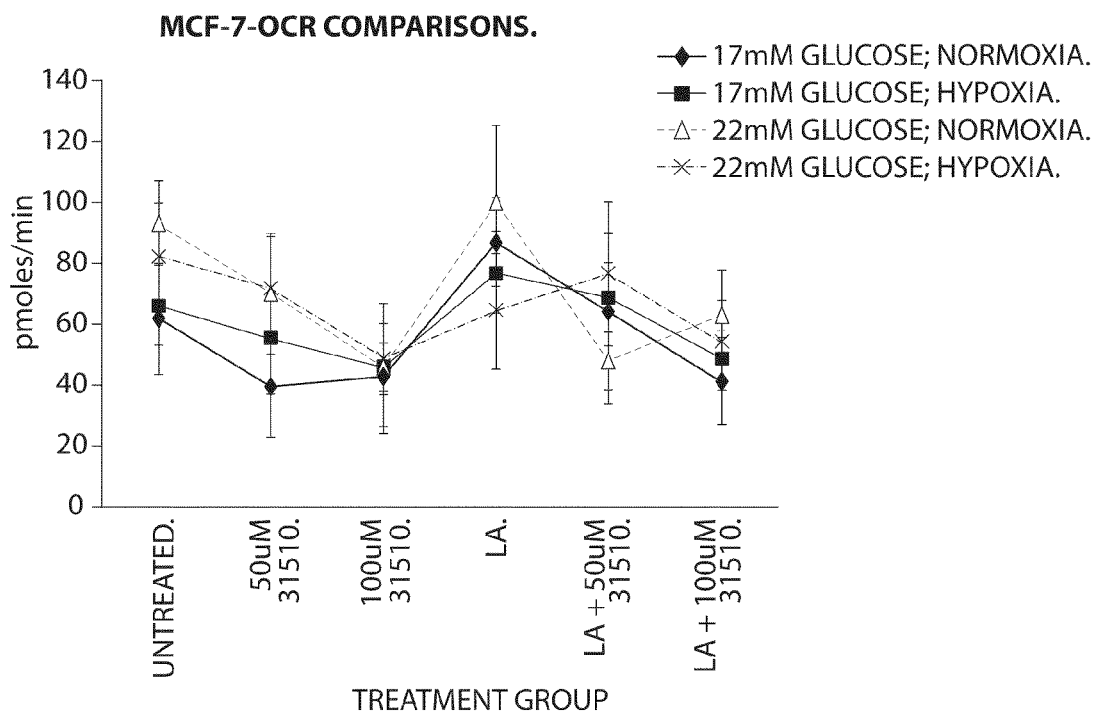
FIG. 31: OCR values in MCF-7 breast cancer cells in the absence and presence of CoQ10 and stressors.
Figure 32:
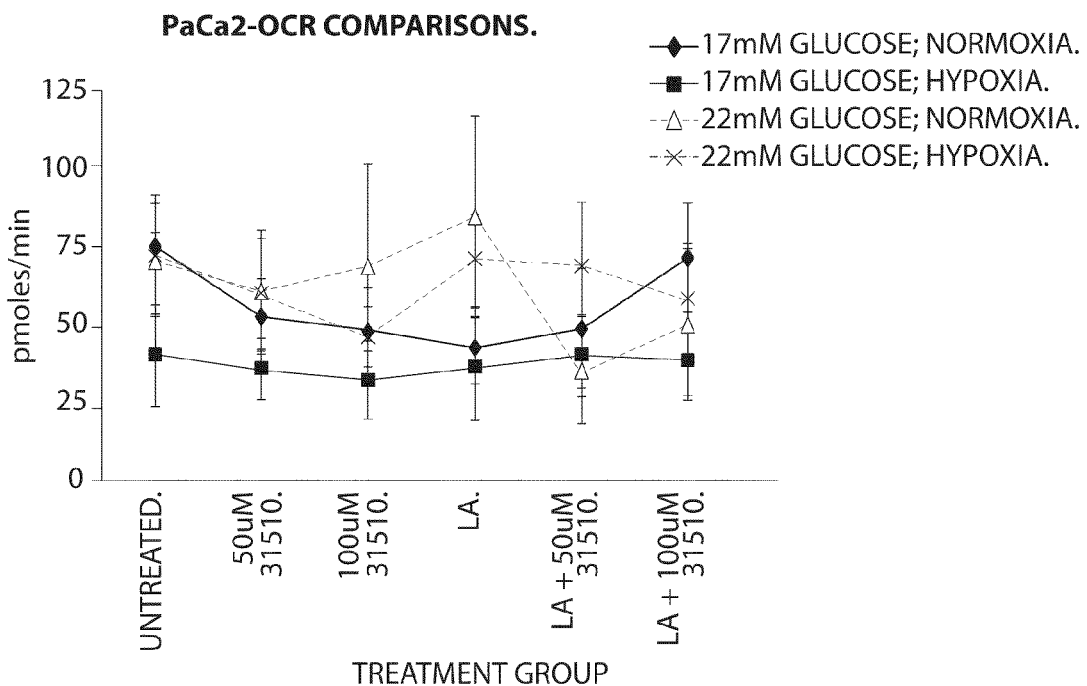
FIG. 32: OCR values in PaCa-2 pancreatic cancer cells in the absence and presence of CoQ10 and stressors.

In contrast, cancer cells (e.g., MCF-7, PaCa-2) are inherently primed to culture at higher levels of glucose compared to normal cells due to their glycolytic phenotype for maintenance in culture. Treatment with CoQ10 caused a consistent reduction in OCR values (FIG. 31 and FIG. 32).

The effects of CoQ10 on OCR values in MCF-7 and PaCa-2 cells was similar to that of the normal HDFa and HASMC cells, wherein the variable response was suggestive of a therapeutic response based on individual metabolic profile of the cancer cell line.

TABLE 55

ECAR values in PaCa-2 cells in the absence and presence of CoQ10 under normoxic and hypoxic conditions at 5.5 mM and 22 mM glucose

| Treatment | Normoxia (17 mM) | | Hypoxia (17 mM) | | Normoxia (22 mM) | | Hypoxia (22 mM) | |
|---|---|---|---|---|---|---|---|---|
| | ECAR | SEM | ECAR | SEM | ECAR | SEM | ECAR | SEM |
| Untreated | 21 | 5.97 | 16 | 3.41 | 24 | 4.35 | 36 | 5.65 |
| 50 µM 31510 | 13 | 3.08 | 12 | 1.66 | 20 | 5.15 | 25 | 4.58 |
| 100 µM 31510 | 14 | 2.14 | 17 | 2.59 | 19 | 3.38 | 30 | 5.62 |

Table 55 describes the ECAR values in PaCa-2 cells. In contrast to normal cells, cancer cells are phenotypically primed to use high glucose for ATP generation (enhanced glycolysis) resulting in higher ECAR (Table 55, ECAR for untreated normoxia 17 mM) at 21 mpH/min. Treatment with CoQ10 produces a significant decrease in ECAR rates under these conditions, most likely associated with a decrease in the glycolysis generated lactic acid. The associated decrease in OCR in these cells was likely associated with increased efficiency of the mitochondrial OXPHOS.

A similar comparison of OCR and ECAR values (data not shown) were determined in numerous other normal and cancer cells lines, including: HAEC (normal human aortic endothelial cells), MCF-7 (breast cancer), HepG2 (liver cancer) and highly metastatic PC-3 (prostate cancer) cell lines. In all of the cell lines tested, exposure to CoQ10 in the absence and/or presence of stressors (e.g., hyperglycemia, hypoxia, lactic acid) was associated with a shift in OCR and ECAR values representative of values observed in a normal cells under normal physiological conditions. Thus, the overall effect of CoQ10 in the treatment of cancer, including cell death, is an downstream effect of its collective influence on proteomic, genomic, metabolomic outcomes in concert with shifting of the cellular bioenergetics from glycolysis to mitochondrial OXPHOS.

Example 23

Building Block Molecules for the Biosynthesis of CoQ10

This example demonstrates that certain precursors of CoQ10 biosynthesis, such as those for the biosynthesis of the benzoquinone ring, and those for the biosynthesis of the isoprenoid repeats and their attachment to the benzoquinone ring ("building block components"), can be individually administered or administered in combination to target cells, and effect down-regulation of the apoptosis inhibitor Bcl-2, and/or up-regulation of the apoptosis promoter Caspase-3. Certain precursors or combinations thereof may also inhibit cell proliferation. The data suggests that such CoQ10 precursors may be used in place of CoQ10 to achieve substantially the same results as CoQ10 administration.

Certain exemplary experimental conditions used in the experiments are listed below.

Skmel-28 melanoma cells were cultured in DMEM/F12 supplemented with 5% Fetal Bovine Serum (FBS) and 1× final concentration of Antibiotics. The cells were grown to 85% confluency and treated with building block components for 3, 6, 12 and 24 hours. The cells were then pelleted and a Western blot analysis was performed.

The test building block components included L-Phenylylalanine, DL-Phenylyalanine, D-Phenylylalanine, L-Tyrosine, DL-Tyrosine, D-Tyrosine, 4-Hydroxy-phenylpyruvate, phenylacetate, 3-methoxy-4-hydroxymandelate (vanillylmandelate or VMA), vanillic acid, 4-hydroxy-benzoate, pyridoxine, panthenol, mevalonic acid, Acetylglycine, Acetyl-CoA, Farnesyl, and 2,3-Dimethoxy-5-methyl-p-benzoquinone.

In the Western Blot Analysis, the cells were pelleted in cold PBS, lysed, and the protein levels were quantified using a BCA protein assay. The whole cell lysate was loaded in a 4% loading 12% running Tris-HCl gel. The proteins were then transferred to a nitrocellulose paper then blocked with a 5% milk Tris-buffered solution for 1 hour. The proteins were then exposed to primary antibodies (Bcl-2 and Caspase-3) overnight. The nitrocellulose paper was then exposed to Pico Chemilluminescent for 5 min and the protein expression was recorded. After exposure, actin was quantified using the same method. Using ImageJ the levels of protein expression were quantified. A t-Test was used to analyze for statistical significance.

Illustrative results of the experiments are summarized below.

Western Blot Analysis of Building Block Component L-Phenylalanine:

Before proceeding to the synthesis pathway for the quinone ring structure, L-Phenylalanine is converted to tyrosine. A western blot analysis was performed to quantify any changes in the expression of the apoptotic proteins in the melanoma cells. The concentrations tested were 5 µM, 25 µM, and 100 µM. Initial studies added L-Phenylalanine to DMEM/F12 medium which contained a concentration of 0.4 M phenylalanine. For the 5 µM, 25 µM, and 100 µM the final concentration of the L-Phenylalanine in the medium was 0.405 M, 0.425 M, and 0.500 M, respectively. These final concentrations were tested on the Skmel-28 cells for incubation periods of 3, 6, 12 and 24 hours. The cells were grown to 80% confluency before adding the treatment medium and harvested using the western blot analysis procedure as described above. A statistically significant decrease in Bcl-2 was observed for the 100 µM L-Phenylalanine after 3 hours and 12 hours incubation. Fr the 5 µM L-phenylalanine, a statistically significant decrease in Bcl-2 was observed after 6 hours of incubation. For the 25 µM L-phenylalanine, a statistically significant decrease in Bcl-2 and a statistically significant increase in Caspase-3 were observed after 12 hours of incubation. A statistically significant decrease in Bcl-2 indicates a change in the apoptotic potential and a statistically significant increase in Caspase-3 confirms the cells are undergoing apoptosis. There was a constant trend for the decrease in Bcl-2 compared to the control even though, due to sample size and standard deviation, these time points were not statistically significant in this experiment.

Western Blot Analysis of Building Block Component D-Phenylalanine:

D-Phenylalanine, a chemically synthetic form of the bioactive L-Phenylalanine, was tested for comparison to L-phenylalanine. For all three concentrations (5 µM, 25 µM, and 100 µM of D-Phenylalanine, there was a significant reduction in Bcl-2 expression after 6 hours of incubation. In addition, for the 5 µM and 25 µM, there was a significant reduction after 3 hours of incubation. For the 5 µM and 100 µM concentrations, a significant increase in Caspase-3 expression was observed after 6 hours of incubation.

Western Blot Analysis of Building Block Component DL-Phenylalanine:

DL-Phenylalanine was also tested for comparison to L-Phenylalanine. Again, concentrations of 5 µM, 25 µM, and 100 µM were tested on Skmel-28 cells. The incubation periods were 3, 6, 12 and 24 hours. A statistically significant increase in Caspase-3 was observed after 3 hours of incubation. A statistically significant decrease in Bcl-2 was observed after 24 hours of incubation. Although a decreasing Bcl-2 and increasing Caspase-3 trend at all other concentrations and incubation time points, they were not statistically significant in this experiment.

Western Blot Analysis of Building Block Component L-Tyrosine:

L-Tyrosine is a building block component for the synthesis of quinone ring structure of CoQ10. Initial testing of L-Tyrosine did not result in a high enough protein concentration for western blot analysis. From this study concentrations under 25 µM were tested for Western Blot Analysis. The DMEM/F12 medium used contained L-Tyrosine disodium salt concentration of 0.398467 M. The initial concentration was increased by 500 nM, 5 µM, and 15 µM. A statistically significant increase in Caspase-3 was observed for the 500 nM concentration after 12 hours of incubation. A statistically significant increase in Caspase-3 was also observed for the 5A statistically significant decrease in Bcl-2 was observed for the 5 µM concentration after 24 hours of incubation. A statistically significant decrease in Bcl-2 was observed for the 500 µM and 5 µM concentrations after 24 hours of incubation.

Western Blot Analysis of Building Block Component D-Tyrosine:

D-Tyrosine, a synthetic form of L-Tyrosine, was tested for comparison against the L-Tyrosine apoptotic effect on the melanonal cells. Based on initial studies with L-Tyrosine, concentrations below 25 µM were chosen for the western blot analysis. The concentrations tested were 1 µm, 5 µM, and 15 µM. D-Tyrosine showed a reduction in Bcl-2 expression for the 5 µM and 15 µM concentrations for 12 and 24 hour time periods. Caspase-3 was significantly increased for the concentration of 5 µM for 3, 12 and 24 time periods. Also there was an increase in Caspase-3 expression for the 1 µM for 12 and 24 hour time period. In addition there is an increase in Caspase-3 expression for 5 µM for the 12 hour time period.

Western Blot Analysis of Building Block Component DL-Tyrosine:

DL-Tyrosine, a synthetic form of L-Tyrosine, was also tested for comparison against L-Tyrosine's apoptotic effect on the cells. There is a statistical decrease in Bcl-2 expression seen in the 1 µM and 15 µM concentrations after 12 hours incubation and for the 5 µM after 24 hour of incubation. An increase in Caspase-3 expression was also observed for the 5 µM and 15 µM after 12 hours of incubation.

Western Blot Analysis of Building Block Component 4-Hydroxy-Phenylpyruvate:

4-Hydroxy-phenylpyruvate is derived from Tyrosine and Phenylalanine amino acids and may play a role in the synthesis of the ring structure. The concentration of 1 µM, 5 µM, and 15 µM were tested for Bcl-2 and Caspase-3 expression. For the 5 µM and 15 µM concentrations there is a significant reduction in Bcl-2 expression after 24 hours of incubation and a significant increase in Caspase-3 expression after 12 hours of incubation.

Western Blot Analysis of Building Block Component Phenylacetate:

Phenylacetate has the potential to be converted to 4-Hydroxy-benzoate, which plays a role in the attachment of the side chain to the ring structure. The concentration tested were 1 µM, 5 µM, and 15 µM. For phenylacetate there was a decrease in Bcl-2 expression for the concentration of 5 µM and 15 µM after 12 hours and 24 hours of incubation. An increase in Caspase-3 expression was observed for the concentration of 5 µM and 15 µM after 12 hours and 24 hours of incubation.

Western Blot Analysis of Building Block Component 3-Methoxy-4-Hydroxymandelate (Vanillylmandelate or VMA):

VMA is an additional component for the synthesis of the CoQ10 quinone ring structure. The concentrations tested were 100 nM, 250 nM, 500 nM, 1 µM, 25 µM, 50 µM, and 100 µM. Though no statistically significant apoptotic effect was observed in this experiment, the data indicated a downward trend of Bcl-2 expression.

Western Blot Analysis of Building Block Component Vanillic Acid:

Vanillic is a precursor for the synthesis of the quinone ring and was tested at a concentration of 500 nm, 5 µM, and 15 µM. A western blot analysis measured Bcl-2 and Caspase-3 expression. Vanillic Acid was shown to significantly reduce Bcl-2 expression for the concentrations of 500 nM and 5 µM at the 24 hour incubation time point. For the 15 µM concentration there is a reduction in Bcl-2 expression after 3 hours of incubation. For the cells incubated with 15 µM for 24 hours there was a significant increase in Caspase-3 expression.

Western Blot Analysis of Building Block Component 4-Hydroxybenzoate:

4-Hydroxybenzoate acid plays a role in the attachment of the isoprenoid side chain to the ring structure. The concentrations tested were 500 nM, 1 µM, and 50 µM. There was a significant reduction in Bcl-2 expression for the 15 µM concentration after 24 hours of incubation.

Western Blot Analysis of Building Block Component 4-Pyridoxine:

Pyridoxine is another precursor building block for the synthesis of the quinone ring structure of CoQ10. The concentrations tested for this compound are 5 µM, 25 µM, and 100 µM. The cells were assayed for their levels of Bcl-2 and Caspase-3. Pyridoxine showed a significant reduction in Bcl-2 after 24 hours of incubation in melanoma cells.

Western Blot Analysis of Building Block Component Panthenol:

Panthenol plays a role in the synthesis of the quinone ring structure of CoQ10. The concentrations tested on melanoma cells were 5 µM, 25 µM, and 100 µM. This compound showed a significant reduction in Bcl-2 expression for the 25 µM concentration.

Western Blot Analysis of Building Block Component Mevalonic:

Mevalonic Acid is one of the main components for the synthesis of CoQ10. This compound was tested at the concentrations of 500 nM, 1 µM, 25 µm, and 50 µM. There was no significant reduction in Bcl-2 expression or an increase in Caspase-3 expression in this experiment.

Western Blot Analysis of Building Block Component Acetylglycine:

Another route for the synthesis of CoQ10 is the isoprenoid (side chain) synthesis. The addition of Acetylglycine converts Coenzyme A to Acetyl-CoA which enters the mevalonic pathway for the synthesis of the isoprenoid synthesis. The concentrations tested were 5 µM, 25 µM, and 100 µM. The testing of Acetylglycine showed significant decrease in Bcl-2 expression after 12 hours of incubation for the concentration of 5 µM and 25 µM. A significant decrease in Bcl-2 was recorded for the 100 µM concentration at the 24 hour incubation time point.

Western Blot Analysis of Building Block Component Acetyl-CoA:

Acetyl-CoA is a precursor for the mevalonic pathway for the synthesis of CoQ10. The concentrations tested were 500 nm, 1 µM, 25 µM, and 50 µM. There was no significant observed reduction in Bcl-2 or increase in Caspase-3 expression for the time points and concentrations tested.

Western Blot Analysis of Building Block Component L-Tyrosine in Combination with Farnesyl:

L-Tyrosine is one of the precursors for the synthesis of the quinone ring structure for CoQ10. Previous experiment tested the reaction of L-Tyrosine in medium with L-Phenylalanine and L-Tyrosine. In this study L-Tyrosine was examined in medium without the addition of L-Phenylalanine and L-Tyrosine. In this study the final concentrations of L-Tyrosine tested were 500 nM, 5 µM, and 15 µM. Farnesyl was tested at a concentration of 50 µM. There was no observed significant response for the 3 and 6 hour time points.

Western Blot Analysis of Building Block Component L-Phenylalanine in Combination with Farnesyl:

L-Phenylalanine, a precursor for the synthesis of the quinone ring structure, was examine in combination with farnesyl in medium free of L-Tyrosine and L-Phenylalanine. A western blot analysis was performed to assay the expression of Bcl-2 and Caspase-3. The final concentrations of L-Phenylalanine were: 5 µM, 25 µM, and 100 µM. Farnesyl was added at a concentration of 50 µM. This study showed a decrease in Bcl-2 expression for most of the concentrations and combinations tested as depicted in the table below.

| L-Phenylalanine | 3 hr | | 6 hr | | 12 hr | | 24 hr | |
|---|---|---|---|---|---|---|---|---|
| | Bcl-2 | Cas-3 | Bcl-2 | Cas-3 | Bcl-2 | Cas-3 | Bcl-2 | Cas-3 |
| 5 µM | X | | | | | | | |
| 5 µM w/ Farnesyl | | | | | | | X | X |
| 25 µM | X | | X | | | | | |
| 25 µM w/ Farnesyl | X | | | | | | X | |
| 100 µM | X | | X | | | X | | |
| 100 µM w/ Farnesyl | | | | X | | | | |

Cell Proliferation Assay of the Combination of 4-Hydroxy-Benzoate with Benzoquinone:

This set of experiments used a cell proliferation assay to assess the effect of combining different building block molecules on cell proliferation.

The first study examined the effect of combining 4-Hydroxy-Benzoate with Benzoquinone. Cells were incubated for 48 hours, after which a cell count was performed for the live cells. Each test group was compared to the control, and each combination groups were compared to Benzoquinone control. The compounds were statistically analyzed for the addition of Benzoquinone. The following table summarizes the cell count results wherein the X mark indicates a statistical decrease in cell number.

| 4-Hydroxy | Compared to Ctrl | Compared to 4-Hydroxy to compound w/o Benzoquinone | Compared to Benzoquinone Control |
|---|---|---|---|
| 500 nm | X | | |
| 500 nm w/Benzo (35 µM) | X | X | |
| 500 nm w/Benzo (70 µM) | X | X | |
| 1 µm | X | | |
| 1 µm w/Benzo (35 µM) | X | X | |
| 1 µm w/Benzo (70 µM) | X | X | |
| 50 µm | X | | |
| 50 µm w/Benzo (35 µM) | X | | |
| 50 µm w/Benzo (70 µM) | X | X | X |

There is a significant decrease in cell number for the cells incubated with 4-Hydroxybenzoic and benzoquinone and in combination. For the combination of 50 µM 4-Hydroxybenzoate in combination with 70 µM Benzoquinone there is significant reduction in cell number compared to the Benzoquinone control. This suggests a synergistic effect for this molar ratio.

Additional studies were performed testing additional molar ratios. For the first test 4-Hydroxybenzoic were tested at concentrations of 500 nM, 1 µM, and 50 µM. These concentrations were tested in combination with 2,3-Dimethoxy-5-methyl-p-benzoquinone (Benzo). The concentration of Benzo tested were 25 µM, 50 µM, and 100 µM. Melanoma cells were grown to 80% confluency and seeded in 6 well plates at a concentration of 40K cells per well. The cells were treated with CoQ10, 4-Hydroxybenzoate, Benzo, and a combination of 4-Hydroxybenzoate/Benzo.

A T-test was performed with $p<0.05$ as statistically significant. An X signifies a statistical decrease in cell number.

| | |
|---|---|
| Ctrl vs Benzo 25 µM | X |
| Ctrl vs Benzo (B) 50 µM | |
| Ctrl vs Benzo (B) 100 µM | X |
| Ctrl vs 4-Hydroxybenzoate (HB) 500 nm | X |
| Ctrl vs HB 1 µM | X |
| Ctrl vs HB 50 µM | X |
| 500 nM HB vs 500 nM HB w/25 B | X |
| 500 nM HB vs 500 nM HB w/50 B | X |
| 500 nM HB vs 500 nM HB w/100 B | X |
| 1 uM HB vs 1 µM HB w/25 B | X |
| 1 uM HB vs 1 µM HB w/50 B | X |
| 1 uM HB vs 1 µM HB w/100 B | |
| 50 uM HB vs 50 µM HB w/25 B | X |
| 50 uM HB vs 50 µM HB w/50 B | X |
| 50 uM HB vs 50 µM HB w/100 B | |
| 500 nM HB w/25 B vs 25 B | X |
| 500 nM HB w/50 B vs 50 B | X |
| 500 nM HB w/100 B vs 100 B | X |
| 1 µM HB w/25 B vs 25 B | X |
| 1 µM HB w/50 B vs 50 B | X |
| 1 µM HB w/100 B vs 100 B | |
| 50 µM HB w/25 B vs 25 B | X |
| 50 µM HB w/50 B vs 50 B | X |
| 50 µM HB w/100 B vs 100 B | |

There is a significant decrease in cell proliferation for the treatment medium containing HB. Moreover the combination of the HB with benzoquinone showed a significant reduction in cell number compare to the cells incubated with the corresponding benzoquinone concentrations.

A cell proliferation assay was also performed on neonatal fibroblast cells. The concentrations of HB tested were 500 nM, 5 µM, and 25 µM. HB was also tested in combination with benzoquinone at a concentrations of 25 µM, 50 µM, and 100 µM. Melanoma cells were seeded at 40 k cells per well and were treated for 24 hours. The cells were trypsinized and quantified using a coulter counter.

Statistical analysis did not show a significant reduction in fibroblast cells. This indicates minimal to no toxicity in normal cells.

Cell Proliferation Assay of the Combination of Phenylacetate and Benzoquinone:

Phenyl acetate is a precursor for the synthesis of 4-Hydroxybenzoic acid (facilitates the attachment of the ring structure. A cell proliferation assay was performed to assay the effect of incubating phenylacetate in combination with CoQ10 and Benzoquinone.

| | |
|---|---|
| Ctrl and 25/25 µM Ben | X |
| Ctrl and 25/50 µM Ben | X |
| Ctrl and 25/100 µM Ben | X |
| Ctrl and 25/25 µM Q-10 | X |
| Ctrl and 25/25 µM Q-10 | X |
| Ctrl and 25/50 µM Q-10 | X |
| Ctrl and 25/100 µM Q-10 | X |
| Ctrl and Ben 25 | X |
| Ctrl and Ben 50 | X |
| Ctrl and Ben 100 | X |
| Ctrl and Q-10 25 | |

-continued

| | |
|---|---|
| Ctrl and Q-10 50 | |
| Ctrl and Q-10 100 | X |
| Ben 25 µM and 500 nM/25 µM Ben | X |
| Ben 25 µM and 5 nM/25 µM Ben | X |
| Ben 25 µM and 25 nM/25 µM Ben | X |
| Ben 50 µM and 500 nM/50 µM Ben | X |
| Ben 50 µM and 5 nM/50 µM Ben | X |
| Ben 50 µM and 25 nM/50 µM Ben | X |
| Ben 100 µM and 500 nM/100 µM Ben | |
| Ben 100 µM and 5 nM/100 µM Ben | |
| Ben 100 µM and 25 nM/100 µM Ben | |
| Q-10 25 µM and 500 nM/25 µM Q-10 | X |
| Q-10 25 µM and 5 nM/25 µM Q-10 | X |
| Q-10 25 µM and 25 nM/25 µM Q-10 | X |
| Q-10 50 µM and 500 nM/50 µM Q-10 | X |
| Q-10 50 µM and 5 nM/50 µM Q-10 | X |
| Q-10 50 µM and 25 nM/50 µM Q-10 | X |
| Q-10 100 µM and 500 nM/100 µM Q-10 | X |
| Q-10 100 µM and 5 nM/100 µM Q-10 | X |
| Q-10 100 µM and 25 nM/100 µM Q-10 | X |

The data indicates the addition of phenylacetate in combination with benzoquinone significantly decreases the cellular proliferation. The combination with CoQ10 and phenylacetate significantly decrease the cell number compared to incubation with CoQ10 and benzoquinone alone.

Cell Proliferation Assay of the Combination of 4-Hydroxy-Benzoate with Farnesyl:

4-Hydroxy-Benzoate was incubated in combination with Farnesyl. The summary of the results are listed below. 4-Hydroxybenzoate groups were compared to the control and Farnesyl control groups. The X signifies a statistical decrease in cell number.

| 4-Hydroxy-Benzoate | Compared to Ctrl | Compared to 4-Hydroxy to compound w/o Farnesyl | Compared to Farnesyl Control |
|---|---|---|---|
| 500 nm | X | | |
| 500 nm w/Farnesyl (35 µM) | X | | |
| 500 nm w/Farnesyl (70 µM) | | X | |
| 1 µm | Error | | |
| 1 µm w/Farnesyl (35 µM) | Error | | |
| 1 µm w/Farnesyl (70 µM) | Error | | |
| 50 µm | X | | |
| 50 µm w/Farnesyl (35 µM) | X | | |
| 50 µm w/Farnesyl (70 µM) | | X | |

Cell Proliferation Assay of the Combination of L-Phenylalanine with Benzoquinone:

A cell proliferation assay was performed to test the combination of L-Phenylalanine combined with Benzoquinone. Below is a summary of the results of L-Phenylalanine compared to the control and Benzoquinone control. The X signifies a statistical decrease.

| L-Phenylalanine | Compared to Ctrl | Compared to L-Phenylalanine to compound w/o Benzoquinone | Compared to Benzoquinone Control |
|---|---|---|---|
| 5 µM | | | |
| 5 µm w/Benzo (50 µM) | | X | |
| 5 µm w/Benzo (100 µM) | | X | |
| 25 µm | | | |
| 25 µm w/Benzo (50 µM) | | X | |
| 25 µm w/Benzo (100 µM) | | X | |
| 100 µm | | | |
| 100 µm w/Benzo (50 µM) | X | X | X |
| 100 µm w/Benzo (100 µM) | X | X | X |

A similar synergistic role is seen for the L-Phenylalanine combined with Benzoquinone.

Cell Proliferation Assay of the Combination of L-Phenylalanine with Farnesyl:

Preliminary results for combination cell proliferation study of L-Phenylalanine incubated in combination with Farnesyl. The L-Phenylalanine were compared to the control and Farnesyl control group. An X signifies a statistical decrease in cell number.

| L-Phenylalanine | Compared to Ctrl | Compared to L-Phenylalanine to compound w/o Farnesyl | Compared to Farnesyl Control |
|---|---|---|---|
| 5 µM | | | |
| 5 µm w/Farnesyl (50 µM) | | | |
| 5 µm w/Farnesyl (100 µM) | | | |
| 25 µm | X | | |
| 25 µm w/Farnesyl (50 µM) | X | X | X |
| 25 µm w/Farnesyl (100 µM) | X | X | X |
| 100 µm | X | | |
| 100 µm w/Farnesyl (50 µM) | X | | X |
| 100 µm w/Farnesyl (100 µM) | X | | |

Cell Proliferation Assay of the Combination of L-Tyrosine with Benzoquinone:

L-Tyrosine was incubated in combination with Benzoquinone after which a cell count was performed. The groups were compared the control groups and Benzoquinone control group.

| L-Tyrosine | Compared to Ctrl | Compared to L-Tyrosine to compound w/o Benzoquinone | Compared to Benzoquinone Control |
|---|---|---|---|
| 500 nm | | | |
| 500 nm w/Benzo (50 µM) | | | |
| 500 nm w/Benzo (100 µM) | | | |
| 5 µm | X | | |
| 5 µm w/Benzo (50 µM) | X | | |
| 5 µm w/Benzo (100 µM) | X | | |
| 15 µm | X | | |

161

-continued

| L-Tyrosine | Compared to Ctrl | Compared to L-Tyrosine to compound w/o Benzoquinone | Compared to Benzoquinone Control |
|---|---|---|---|
| 15 μm w/Benzo (50 μM) | X | | |
| 15 μm w/Benzo (100 μM) | x | | |

The addition of Benzoquinone did not amplify the effect of L-Tyrosine on the cell number.

Cell Proliferation Assay of the Combination of L-Tyrosine with Benzoquinone:

This study examined the combination of L-Tyrosine with Farnesyl. The groups were compared to control and Farnesyl control groups.

| L-Tyrosine | Compared to Ctrl | Compared to L-Tyrosine to compound w/o Farnesyl | Compared to Farnesyl Control |
|---|---|---|---|
| 500 nm | | | |
| 500 nm w/Farnesyl (50 μM) | | | |
| 500 nm w/Farnesyl (50 μM) | | | |
| 5 μm | X | | |
| 5 μm w/Farnesyl (50 μM) | X | | |
| 5 μm w/Farnesyl (100 μM) | X | | |
| 15 μm | X | | |
| 15 μm w/Farnesyl (50 μM) | X | | |
| 15 μm w/Farnesyl (100 μM) | X | | |

Combining L-Tyrosine and Farnesyl does not appear to have a synergistic effect on reducing the cell number in this experiment.

The synthesis of the CoQ10 is divided into two main parts, which consist of the synthesis of the ring structure and synthesis of the side chain structure. Here, oncogenic cells were supplemented with compounds which are precursors for the synthesis of the side chain and the ring structure components. Our results have focused the study to 3 main components involved in the synthesis of the ring structure and two compounds that play a role in the attachment of the ring structure to the side chain structure. The three compounds that have shown a significant reduction in Bcl-2 and increase in Caspase-3 expression are: 1) L-Phenylalanine, 2) L-Tyrosine and 3) 4-Hydroxyphenylpyruvate. The two compounds involved with the attachment of the side chain to the ring structure are: 1) 4-hydroxy benzoate and 2) Phenylacetate.

Our results also showed that exogenous delivery of these compounds in combination with 2,3 Dimethoxy-5-methyl-p-benzoquinone (benzoquinone) significantly inhibits cell proliferation. This indicates a supplementation of the ring structure with compounds for the attachment of the side chain to the benzoquinone ring may supplement an impaired CoQ10 synthesis mechanism. This may also assist in the stabilization of the molecule to maintain the functional properties required by cellular processes. Phenylacetate is a precursor for the synthesis of 4-Hydroxybenzoate, which exogenous delivery in combination with benzoquinone has a similar effect in oncogenic cells.

162

EQUIVALENTS

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A method of assessing whether a subject is afflicted with an oncological disorder in a Coenzyme Q10 responsive state, the method comprising:
    (1) contacting a biological sample from a subject having an oncological disorder, wherein the subject has been administered Coenzyme Q10, with a panel of at least three detection reagents, wherein each detection reagent is an antibody or antigen-binding antibody fragment that specifically binds to one marker selected from the group consisting of APAF1, BAX, Calmodulin, CCT3, CTSD, GRB2, Heat Shock Protein 110, GRP78 Bip, IDH-1, neutrophil cytosolic factor 2, PDIA3, PECAM1, PRDX4, PSME3, RAB7, SOD3, and SRXN1, or an antigenic fragment thereof, such that at least three of said markers can be detected;
    (2) measuring the level of expression of the at least three markers present in the biological sample by detecting the detection reagents;
    (3) comparing the level of expression of each of the at least three markers in the biological sample to the level of expression of the markers present in a control sample to obtain three or more comparative results wherein the control sample is a biological sample from the subject prior to administration of Coenzyme Q10; and
    (4) combining at least three of the comparative results to determine whether or not the oncological disorder is in a Coenzyme Q10 responsive state,
    wherein the subject is determined to be afflicted with an oncological disorder in a Coenzyme Q10 responsive state when:
        (a) an increase in at least one of APAF1, BAX, Calmodulin, GRB2, Heat Shock Protein 110, GRP78 Bip, IDH-1, neutrophil cytosolic factor 2, and PDIA3 is detected; and decreases in at least two of CCT3, CTSD, PECAM1, PRDX4, PSME3, RAB7, SOD3, and SRXN1 are detected, as a result of administration of Coenzyme Q10;
        (b) increases in at least two of APAF1, BAX, Calmodulin, GRB2, Heat Shock Protein 110, GRP78 Bip, IDH-1, neutrophil cytosolic factor 2, and PDIA3 are detected; and a decrease in at least one of CCT3, CTSD, PECAM1, PRDX4, PSME3, RAB7, SOD3, and SRXN1 is detected, as a result of administration of Coenzyme Q10;
        (c) increases in at least three of APAF1, BAX, Calmodulin, GRB2, Heat Shock Protein 110, GRP78 Bip, IDH-1, neutrophil cytosolic factor 2, and PDIA3 are detected, as a result of administration of Coenzyme Q10; or
        (d) decreases in at least three of CCT3, CTSD, PECAM1, PRDX4, PSME3, RAB7, SOD3, and SRXN1 are detected, as a result of administration of Coenzyme Q10.

2. A method of assessing whether a subject is afflicted with an oncological disorder in a Coenzyme Q10 responsive state, the method comprising:
    (1) contacting a biological sample from a subject having an oncological disorder, wherein the subject has been administered Coenzyme Q10, with a panel of at least three detection reagents, wherein each detection reagent is specific for one marker selected from the group consisting of APAF1, BAX, Calmodulin, CCT3, CTSD, GRB2, Heat Shock Protein 110, GRP78 Bip, IDH-1, neutrophil cytosolic factor 2, PDIA3, PECAM1, PRDX4, PSME3, RAB7, SOD3, and SRXN1, such that at least three of said markers can be detected;
(2) measuring the level of expression of the at least three markers present in the biological sample by detecting the detection reagents while performing a technique selected from the group consisting of immunohistochemistry, immunocytochemistry, flow cytometry, and ELISA;
(3) comparing the level of expression of each of the at least three markers in the biological sample to the level of expression of the markers present in a control sample to obtain three or more comparative results wherein the control sample is a biological sample from the subject prior to administration of Coenzyme Q10; and
(4) combining at least three of the comparative results to determine whether or not the oncological disorder is in a Coenzyme Q10 responsive state,
wherein the subject is determined to be afflicted with an oncological disorder in a Coenzyme Q10 responsive state when:
(a) an increase in at least one of APAF1, BAX, Calmodulin, GRB2, Heat Shock Protein 110, GRP78 Bip, IDH-1, neutrophil cytosolic factor 2, and PDIA3 is detected; and decreases in at least two of CCT3, CTSD, PECAM1, PRDX4, PSME3, RAB7, SOD3, and SRXN1 are detected, as a result of administration of Coenzyme Q10;
(b) increases in at least two of APAF1, BAX, Calmodulin, GRB2, Heat Shock Protein 110, GRP78 Bip, IDH-1, neutrophil cytosolic factor 2, and PDIA3 are detected; and a decrease in at least one of CCT3, CTSD, PECAM1, PRDX4, PSME3, RAB7, SOD3, and SRXN1 is detected, as a result of administration of Coenzyme Q10;
(c) increases in at least three of APAF1, BAX, Calmodulin, GRB2, Heat Shock Protein 110, GRP78 Bip, IDH-1, neutrophil cytosolic factor 2, and PDIA3 are detected, as a result of administration of Coenzyme Q10; or
(d) decreases in at least three of CCT3, CTSD, PECAM1, PRDX4, PSME3, RAB7, SOD3, and SRXN1 are detected, as a result of administration of Coenzyme Q10.

3. A method of assessing whether a subject is afflicted with an oncological disorder in a Coenzyme Q10 responsive state, the method comprising:
(1) contacting a tumor sample or component thereof obtained from a subject having an oncological disorder with a panel of at least three detection reagents, wherein each detection reagent is an antibody or antigen-binding antibody fragment that specifically binds to one marker selected from the group consisting of APAF1, BAX, Calmodulin, CCT3, CTSD, GRB2, Heat Shock Protein 110, GRP78 Bip, IDH-1, neutrophil cytosolic factor 2, PDIA3, PECAM1, PRDX4, PSME3, RAB7, SOD3, and SRXN1, or an antigenic fragment thereof, such that at least three of said markers can be detected, and wherein the tumor sample or component thereof has been exposed to Coenzyme Q10 ex vivo;
(2) measuring the level of expression of the at least three markers present in the tumor sample or component thereof by detecting the detection reagents;
(3) comparing the level of expression of each of the at least three markers in the tumor sample after exposure to Coenzyme Q10 to the level of expression of the markers present in a control sample from the subject to obtain three or more comparative results, wherein the control sample is a tumor sample or component thereof not exposed to Coenzyme Q10; and
(4) combining at least three of the comparative results to determine whether the oncological disorder is in a Coenzyme Q10 responsive state,
wherein the subject is determined to be afflicted with an oncological disorder in a Coenzyme Q10 responsive state when:
(a) an increase in at least one of APAF1, BAX, Calmodulin, GRB2, Heat Shock Protein 110, GRP78 Bip, IDH-1, neutrophil cytosolic factor 2, and PDIA3 is detected; and decreases in at least two of CCT3, CTSD, PECAM1, PRDX4, PSME3, RAB7, SOD3, and SRXN1 are detected, as a result of exposure to Coenzyme Q10;
(b) increases in at least two of APAF1, BAX, Calmodulin, GRB2, Heat Shock Protein 110, GRP78 Bip, IDH-1, neutrophil cytosolic factor 2, and PDIA3 are detected; and a decrease in at least one of CCT3, CTSD, PECAM1, PRDX4, PSME3, RAB7, SOD3, and SRXN1 is detected, as a result of exposure to Coenzyme Q10;
(c) increases in at least three of APAF1, BAX, Calmodulin, GRB2, Heat Shock Protein 110, GRP78 Bip, IDH-1, neutrophil cytosolic factor 2, and PDIA3 are detected, as a result of exposure to Coenzyme Q10; or
(d) decreases in at least three of CCT3, CTSD, PECAM1, PRDX4, PSME3, RAB7, SOD3, and SRXN1 are detected, as a result of exposure to Coenzyme Q10.

4. A method of assessing whether a subject is afflicted with an oncological disorder in a Coenzyme Q10 responsive state, the method comprising:
(1) contacting a tumor sample or component thereof obtained from a subject having an oncological disorder with a panel of at least three detection reagents, wherein each detection reagent is specific for one marker selected from the group consisting of APAF1, BAX, Calmodulin, CCT3, CTSD, GRB2, Heat Shock Protein 110, GRP78 Bip, IDH-1, neutrophil cytosolic factor 2, PDIA3, PECAM1, PRDX4, PSME3, RAB7, SOD3, and SRXN1, or an antigenic fragment thereof, such that at least three of said markers can be detected, and wherein the tumor sample or component thereof has been exposed to Coenzyme Q10 ex vivo;
(2) measuring the level of expression of the at least three markers present in the tumor sample or component thereof by detecting the detection reagents while performing a technique selected from the group consisting of immunohistochemistry, immunocytochemistry, flow cytometry, and ELISA;
(3) comparing the level of expression of each of the at least three markers in the tumor sample after exposure to Coenzyme Q10 to the level of expression of the markers present in a control sample from the subject to obtain three or more comparative results, wherein the control sample is a tumor sample or component thereof not exposed to Coenzyme Q10; and
(4) combining at least three of the comparative results to determine whether the oncological disorder is in a Coenzyme Q10 responsive state,
wherein the subject is determined to be afflicted with an oncological disorder in a Coenzyme Q10 responsive state when:
(a) an increase in at least one of APAF1, BAX, Calmodulin, GRB2, Heat Shock Protein 110, GRP78 Bip, IDH-1, neutrophil cytosolic factor 2, and PDIA3 is detected; and decreases in at least two of CCT3, CTSD, PECAM1, PRDX4, PSME3, RAB7, SOD3, and SRXN1 are detected, as a result of exposure to Coenzyme Q10;
(b) increases in at least two of APAF1, BAX, Calmodulin, GRB2, Heat Shock Protein 110, GRP78 Bip, IDH-1, neutrophil cytosolic factor 2, and PDIA3 are detected; and a decrease in at least one of CCT3, CTSD, PECAM1, PRDX4, PSME3, RAB7, SOD3, and SRXN1 is detected, as a result of exposure to Coenzyme Q10;
(c) increases in at least three of APAF1, BAX, Calmodulin, GRB2, Heat Shock Protein 110, GRP78 Bip, IDH-1, neutrophil cytosolic factor 2, and PDIA3 are detected, as a result of exposure to Coenzyme Q10; or
(d) decreases in at least three of CCT3, CTSD, PECAM1, PRDX4, PSME3, RAB7, SOD3, and SRXN1 are detected, as a result of exposure to Coenzyme Q10.

5. The method of any one of claims 1, 2, 3 and 4, wherein the oncological disorder is an oncological disorder selected from the group consisting of: a leukemia, a lymphoma, a melanoma, a carcinoma and a sarcoma.

6. The method of any one of claims 1, 2, 3 and 4, wherein the sample comprises a fluid obtained from the subject.

7. The method of claim 6, wherein the fluid is selected from the group consisting of blood fluids, vomit, saliva, lymph, cystic fluid, urine, fluids collected by bronchial lavage, fluids collected by peritoneal rinsing, and gynecological fluids.

8. The method of claim 7, wherein the sample is a blood sample or a component thereof.

9. The method of any one of claims 1, 2, 3 and 4, wherein the sample comprises a tumor tissue or component thereof obtained from the subject.

10. The method of any one of claims 1, 2, 3 and 4, wherein the subject is a human.

11. The method of any one of claims 1, 2, 3 and 4, wherein the detection reagents are labeled.

12. The method of claim 1 or 3, wherein the level of expression of the markers in the sample is determined using a technique selected from the group consisting of immunohistochemistry, immunocytochemistry, flow cytometry and ELISA.

13. The method of any one of claims 1, 2, 3 and 4, further comprising continuing administration of Coenzyme Q10 to a subject determined to be afflicted with an oncological disorder in a Coenzyme Q10 responsive state.

14. The method of any one of claims 1, 2, 3 and 4, wherein the oncological disorder is an aggressive carcinoma or melanoma.

* * * * *